(12) United States Patent
Jiang

(10) Patent No.: US 7,498,404 B2
(45) Date of Patent: Mar. 3, 2009

(54) COMPOSITIONS, METHODS AND USES FOR A NOVEL FAMILY OF PEPTIDES

(75) Inventor: Yi Wei Jiang, College Station, TX (US)

(73) Assignee: The Texas A&M University System, College Station, TX (US)

( * ) Notice: Subject to any disclaimer, the term of this patent is extended or adjusted under 35 U.S.C. 154(b) by 208 days.

(21) Appl. No.: 11/046,560

(22) Filed: Jan. 28, 2005

(65) Prior Publication Data

US 2006/0228398 A1 Oct. 12, 2006

Related U.S. Application Data

(60) Provisional application No. 60/540,569, filed on Jan. 30, 2004.

(51) Int. Cl.
    *C07K 7/00* (2006.01)
(52) U.S. Cl. .......................... 530/327; 530/300; 514/2; 514/14
(58) Field of Classification Search .................. 514/2, 514/14; 530/300, 327
    See application file for complete search history.

(56) References Cited

U.S. PATENT DOCUMENTS

| | | | |
|---|---|---|---|
| 4,504,471 A | 3/1985 | Takagi et al. | |
| 5,863,574 A | 1/1999 | Julien | |
| 6,245,546 B1 | 6/2001 | Hansen et al. | |
| 6,503,544 B2 | 1/2003 | Nagai et al. | |
| 6,682,762 B2 | 1/2004 | Register | |
| 6,784,283 B2 * | 8/2004 | Andersen et al. | 530/327 |

FOREIGN PATENT DOCUMENTS

| | | |
|---|---|---|
| WO | 2000/52152 A1 | 9/2000 |
| WO | 03/044049 A1 | 5/2003 |

OTHER PUBLICATIONS

Voet et al. (1990), Biochemistry text book (John Wiley & Sons publisher) p. 1 116-117.*
Altschul, S. F., et al., (1997). Gapped BLAST and PSI-BLAST: a new generation of protein database search programs. Nucleic Acids Res 25(17), 3389-402.
Challis, G. L., et al., (2000). Predictive, structure-based model of amino acid recognition by nonribosomal peptide synthetase adenylation domains. Chem Biol 7(3), 211-24.
Conti, E., et al., (1997). Structural basis for the activation of phenylalanine in the non-ribosomal biosynthesis of gramicidin S. Embo J 16(14), 4174-83.
Gaitatzis, N., et al., (2001). In vitro reconstitution of the myxochelin biosynthetic machinery of *Stigmatella aurantiaca* Sg a15: Biochemical characterization of a reductive release mechanism from nonribosomal peptide synthetases. Proc Natl Acad Sci U S A 98(20), 11136-41. Epub 2001 Sep 18.
Hopwood, D. A. (1997). Genetic Contributions to Understanding Polyketide Synthases. Chem Rev 97(7), 2465-2498.
Keating, T. A., et al., (2001). Chain termination steps in nonribosomal peptide synthetase assembly lines: directed acyl-S-enzyme breakdown in antibiotic and siderophore biosynthesis. Chembiochem 2(2), 99-107.
Keating, T. A. & Walsh, C. T. (1999). Initiation, elongation, and termination strategies in polyketide and polypeptide antibiotic biosynthesis. Curr Opin Chem Biol 3(5), 598-606.
Kessler, N., et al., (2004). The linear pentadecapeptide gramicidin is assembled by four multimodular nonribosomal peptide synthetases that comprise 16 modules with 56 catalytic domains. J Biol Chem 279(9), 7413-9.
Konz, D., et al., (1999). Molecular and biochemical characterization of the protein template controlling biosynthesis of the lipopeptide lichenysin. J Bacteriol 181(1), 133-40.
Koumoutsi, A., et al., (2004), Structural and Functional Characterization of Gene Clusters Directing Nonribosomal Synthesis of Bioactive Cyclic Lipopeptides in *Bacillus amyloliquefaciens* Strain FZB42. J Bact 186(4):1084-1096.
Linne, U. & Marahiel, M. A. (2000). Control of directionality in nonribosomal peptide synthesis: role of the condensation domain in preventing misinitiation and timing of epimerization. Biochemistry 39(34), 10439-47.
Marahiel, M. A. (1997). Protein templates for the biosynthesis of peptide antibiotics. Chem Biol 4(8), 561-7.
Mootz, H. D. & Marahiel, M. A. (1997). The tyrocidine biosynthesis operon of *Bacillus brevis*: complete nucleotide sequence and biochemical characterization of functional internal adenylation domains. J Bacteriol 179(21), 6843-50.
Mootz, H. D., et al., (2002). Ways of assembling complex natural products on modular nonribosomal peptide synthetases. Chembiochem 3(6), 490-504.
Offenzeller, M., et al., (1996). Biosynthesis of the unusual amino acid (4R)-4-[(E)-2-butenyl]-4-methyl-L-threonine of cyclosporin A: enzymatic analysis of the reaction sequence including identification of the methylation precursor in a polyketide pathway. Biochemistry 35(25), 8401-12.
Offenzeller, M., et al., (1993). Biosynthesis of the unusual amino acid (4R)-4-[(E)-2-butenyl]-4-methyl-L-threonine of cyclosporin A. Identification of 3(R)-hydroxy-4(R)-methyl-6(E)-octenoic acid as a key intermediate by enzymatic in vitro synthesis and by in vivo labeling techniques. J Biol Chem 268(35), 26127-34.
Quadri, L. E., et al., (1998). Identification of a Mycobacterium tuberculosis gene cluster encoding the biosynthetic enzymes for assembly of the virulence-conferring siderophore mycobactin. Chem Biol 5(11), 631-45.
Stachelhaus, T., et al., (1998). Peptide bond formation in nonribosomal peptide biosynthesis. Catalytic role of the condensation domain. J Biol Chem 273(35), 22773-81.
Stachelhaus, T., et al., (1999). The specificity-conferring code of adenylation domains in nonribosomal peptide synthetases. Chem Biol 6(8), 493-505.
Eurasian Search Report for 200601408, dated May 16, 2007.

* cited by examiner

*Primary Examiner*—Chih-Min Kam
(74) *Attorney, Agent, or Firm*—Edwin S. Flores; Daniel J. Chalker; Chalker Flores, LLP

(57) ABSTRACT

The present invention includes compositions and methods for the characterization and use of novel peptide from *Brevibacillus* sp., and peptides related thereto, including an isolated and purified, heat stable, amino terminus-methylated, carboxy-terminus reduced peptide that have two or more D-amino acids used as, e.g., an antimicrobial or even a feed additive.

14 Claims, 29 Drawing Sheets

FIGURE 3E-1

```
ATTCGTTGGATCCAGTGTGGTGGAATTCAAACCCTCAGTGGGTAAAGATATTGCCAGAGTCTTGAAATGTACCAAACAGG
GAAATGGGTACCTTGAAGGCGACAAATATGTAGTAACCTGGGCATTTGGCCATCTGGTTACGCTGGCTGATCCTGAAGCC
TATGGAGAGACATATAAAGCTTGGAAGCTGGAGGATTTACCACTGTTGCCGTCTCGCCTGCAATTAACTGTCATCAGACA
GAGCTCCAAGCAATATCAGATTGTAAAAAAATTATTAGCGCGTCAGGATATTTCAGAAGTGATTATTGCTACTGATGCTG
GTCGTGAAGGTGAGCTGGTGGCGCGATGGATTTTAGAAAAGGCACATGTGAAAAAGCCTATTAAACGACTATGGATTTCC
TCTGTGACTGATAAAGCAATCAGTGATGGCTTCAGAAAGCTGCGAGATGGCAAGGAATACGAGAATCTCTATGCTTCTGC
TGTAGCTCGCGCTGAAGCTGACTGGTTTGTCGGGATCAATGCCACTCGTGCTCTTACAACGAAGCATAATGCCCAGCTCT
CCTGCGGGCGTGTACAAACTCCTACAGTGGCAATGATTGCCAAACGTGAGGAGGAGATTCAAAGGTTCGTTCCTCGCCCC
TATTATGGTGTTCAAGCGATCACAGGTAATGGATTAAAGCTTACGTGGCAGGATCAGCAAACCAAAGATATGAAGACGTT
TACCAAGGAGAAGGCTGAGAAAATTGTCGAAAGCAGTAAAAACAAGCAAGCTGAAATTATTGACATCAAGAAGGCTGACA
AGAAAAGCTTCGCCCCAGCTTTATATGATCTAACTGAGCTACAACGTGATGCGAATAAGCGTTTTGGTTTTTCGGCAAAG
GAAACCCTCTCCATTATGCAAGGGCTATACGAAACACATAAGGTACTCACATACCCGCGGACAGATTCTCGCTATTTGAC
ATCAGATATTGTCGAAACATTACCTGATCGATTGAGAGCGATATCTGTTAAGCCATACACTCCGTTTGCAGCTAAGCTGT
TAAAGCAACCGATTCGAGCTGGTAAACATGTAGTGGATAATAGCAAGGTATCTGATCACCATGCGATTATTCCAACTGAG
CAATCTGTGCTGTTAAATAAGCTTAGCGATAAGGAACGTAAAATTTATGACCTTGTGGTTAAACGCTTTCTGGCTGTGCT
ATATCCGCCTTTTGAATATGAACAAATTAGTATTCGTGCCCGAATTGGCAACGAGGAATTTCTAGCAAAAGGGAAGACGA
TAACGCATCAGGGCTGGAAGGAAATTTATGATAATCACTTTGATGAAGAGGATCAAGGAGATGGATTAAAAGAACAGCTT
TTACCAACGCTTGTACAAGGTGAGCAACTATCTGTACAAACCGTTTCTTTTACAAAAGGGGAAACAAAACCTCCAGAGCC
ATTTACGGAGGCTACACTCCTTTCAGCTATGGAGAATCCTGTCCGTTATATGGGACAGGTTGATAAGCAGCTAGCCAAAA
CATTAGGTGAGACAGGTGGATTAGGAACTGTTGCTACTCGCGCCGATATTATTGAAAAATTGTTTAATAGCTTCCTCATT
GAAAAGCGCAGCAAGCATATTCATATTACTTCTAAAGGAAGCAATTACTTGAGCTTGTACCAGAAGGACTTCGCTCACC
GGCTCTTACTGCTGAATGGGAAGTGAAGCTTGGAGCGATCTCGAAAGGAAGCCTGGCTAAAAACAGCTTCATACAGGAAA
TGAAGAAGTATGCAGAGCAAATCGTTCAACAGATCAAATTTAGTGAGCAAAAGTTTCGTCATGACAATCTGACTCGCTCC
AAATGCCCGGATTGTGGAAAGCTGATGCTTGAGGTAAATGGGAAAAAAGGAAAAATGTTAGTTTGTCAGGATCGTGAGTG
TGGTCACCGTAAGGCCGTATCCAAGGTTACAAATGCCAGATGCCCACAATGTCGAAAGAAGATGGAGATGCGTGGGGAAG
GAGAAGGAAAGATATTCGTATGCAAATGCGGACATCGTGAAAAACTGTCGACGTTTAACGACAGACGTAGCAAGGAGAAA
CAGACAAATGTTTCGAAACGAGATGTAGCCCAGTATATGAAAATCAGCAACGAGATCAAGAAGCTTAGGTAATCCAGC
CTTGATGGAGGCATTAAAGAATTTTAAGCTAGATCAGTAAGTCATTTTATATAGAAAAGATAGGCTCGAAAATAAGGCGC
CCGCTCTCTTTATTAGCTAAGAGAAAGGGCGTCTATTTTAGCTTCTCTTTTCTATATGGAAAAAAGGAATTAACAAAATC
TGAAGAAAATTTCAGAATTTATTATTTTTATGTTAAGAGATTTTGAAAGAAGTGCATCTATTTACTTTATCCATAAATGA
AAGCAAAAATGAGATTGTTATATTCCATAAAATGTAAATGTTTTTATATCTTGGAAAACATAGAGTCGAGAACGCTGTTC
ACTATACAAGAAGACTATAGATACGAGCTTTTACGGCTATTTTTACGATTTGATAACGCCTTCTTTTTTTAGTCTAATAA
AAAACAGTAACGAATCGAAAAAATAACAATAATTTGATTGGTAAATAACATTGTTACTAATTCACAGAAAACAAAATCAT
TATTTTTACATAATAAAAACATAATAATAAAATGTGATAGAAAAATATTGAAGAAAATGTCCATTATTGGTAGTATTGAA
AAATAAACCTGTAATTTTATGTATTATAATGCAATTATTTGTCGCATATTTACTAGCATAAATGTTAGCGATGATGTGAG
CAAATCGTTACCTGTTAGAAGGAAGATCAGCTACATATGATTCAAAATTTTTCGTTTTTTTATTTTAAAAGACAAAGAGG
TGGTCCTGATGGATTTATCTACATTAAATTTTTTGGGTGAAACAGAAAAGCATAAGTTATTGAATCAATTCAATGATACG
GACGCTAATTTTCCTCAGGAGATGACCATTCATGGGCTGTTTGAAAAGCAAGTCCAAGAAAGACCGAATCAAACTGCGGT
AATTTTTAATGAACAAAGTATGACGTATAAAGAAATGAATGAACGAGCCAATCAAGTAGCACATAGCTTACGGAAGCATG
GAGCTGCTCCAGATGAGATCGTTGGAATTCTAGCAGATCGCAACATGGACATGCTTATTTCCATTCTCGGCGTATTAAAG
GCTGGAGCTGCTTATATGCCTATTGATCCTACATACCCTACAGAACGTATTCTTTATATGATCCATGATAGCCAGACCAA
AATTGTCTTAGCTGAACATAGAGAGATGGTTCCGGAAGGCTGTAATGCAGAGCTGATCCTCTTGCACGATAGCTCCCTTT
TAAACGAAGAGACATCTGATCTAGAGCATGTAAATAAGCCTGAAGATTTGGCCTATATTATCTATACATCAGGTTCTACT
GGTAAACCAAAAGGGGTTATGATTGAACATCGAAATGTCATTCGCTTGCTATTTAATGACAGAAACCTATTTGATTTTAC
TAGTGATGATGTCTGGACCGTTTTCCATTCGTTCTGTTTTGACTTCTCTGTTTGGGAGATGTATGGGCTTTACTGTATG
GAGGAAAAATCGTTCTCGTCTCTTTTGAGATAGCTAGAGATCCTCAGGCCTTCCGAGATTTACTTCAGGAGCAAAAGGTT
ACGATTTTAAATCAAACCCCTACAGCTTTTTATCAGCTCTCGTCTCCAAGAGATGCAGCACTCAGACAGCAATCTATCGAT
TCGTAAATCATTTTTGGTGGAGAAGCGTTGACGCCATCACAGTTGAAAGCATGGAAACAAAAATATCCAAATACAGCCT
TGATTAATATGTACGGTATTACAGAAACAACTGTTCATGTGACTTATAAGGAGTTTCAATTACATGATATGGACAGCACA
GTTAGCAATATCGGAAAGCCTATCCCAACGCTTAGAACCTATGTTTTAGATTCCAAGAGAAACCTAGCTCCAATTGGAGT
GAAAGGTGAACTGTATGTGAGCGGCAAGGGAGTAGCCCGCGGTTATTTAAACAAACCTGAATTGACGGAAGAACGGTTTA
TGGATAACCCGTTTGTTGCTGGAGAAAGAATGTATCGCACAGGAGACCTAGCTAGATGGCTACCTGAAGGAGAGCTAGAA
TATCTAGGCAGGATTGACCATCAGGTAAAAATCAGAGGCTATCGCATTGAACTCGGAGAAATAGAAGCCGAGCTATTGAA
GCAAAAAGGGATTAAAGAAGCAGTAGTTTTAGTTACAAATGATAAAGATGCACAACCACAATTACATGCCTATTTAACAT
CTAAGGAAGATTTGGCAGCAGCAGATCTTCGTAATCAACTTACTACAACATTACCCTCTTACATGATTCCGGCTCATTTC
```

FIGURE 3E-2

```
ATTTTTGTGTCGCAAATGCCTGTTACGCCAAATGGAAAAATTGATAAAGAATCACTTCGTAAAATAGAACCATCACTTCA
AGAAAGCCCTACAGAAGCTTATGTAGCTCCACAAACACCTACAGAAAAGCAATTAGTCCACATATGGGAAGAAAATATTG
GAATGCAACCGATCAGCATAGACGATAATTATTTTGCTCTAGGTGGTGATTCCATCAAAGCGATTAAGCTATTGCATGCT
ATAAATAAAGAGTTTCAGATTAGTTTCCAAATTGGAGATTTGTATAAGCATGGAACCATTAGAGAAATGGGACAGCAAAT
CGGTGAAAAGGGCAAGCAATCTAGCAATCAAAAACTGTTGAAACTTCAGGAATTGGACCGTTTAAAAGAGAAAATTTTGG
GAAGTGAGAAATAGTCATGTCGGATAAGCTAAGCAACGCTAAAGACCTATTTCCAATGAGCGATATACAGCTAGGGATGG
TCTACCATTCGTTAAAACATGTACACGAAGCTGTATACCATGATCAATTTGTTTATCAAGTAGATGATGATTCATTTGAT
GTTCATGTGCTAGAGCAAGCGATGAATGATGGTTGATAAGCACGACATCTTAAAAACCAGCTTTCATATTGAGGAATT
TTCCACTCCAGTTCAAGTAGTGCACCAGGAGGTTTCTGTTCGAATTGATGAGACAGACATTACGCATCTGGGAGAAAAAC
AAAAAGAGTATATCCATCAGTATTTGGCACAGGATCGTCAATCCCCTTTTGATGTAACAACCGCTCCTCTATGGAGAATG
AGCGTTTTTAAACTGAATGCAAGCCAAGTTGCTTTAGTCTGGATCTTTCATCATGCTATTTTGGATGGATGGAGTGTTGC
ATCTTTTATTACGGAATTAATTGATGTTTATTTCAAATTAAAGCACAAAACTTGCACTTTGGAGCATTTGAACACGACCT
ATAAGGATTATGTGATTGATCAGATGCTATTATCTGAGCAAAATGAGCTGCGTGAATATTGGAAAGAAGAATTAAAAGAT
TACAAACGGCTACAGCTCCCAGTAAAAGTGGATGAAAATGGCGGTGTTCACGTTACCGTTGTTGAGAAGCTAGACCCTGA
CATTATAAATAAATGCAGAGAAATTGCACAAGCTCATCACATTCCATTAAAGACCGTATGCCTAACAGCCTTTCTTTCTA
TGATGCATATGATTTCTTATGAGAGAGACCTGACTGTGGGATTGATTGAGAACAACCGACCAATTATAGAAGATGCTGAA
AAGGTGTTGGGATGTTTTCTTAACTCAGTTCCATTCCGCGCCATTATAAAGAAAGATATGAGCTACAGAGAGCTATTAGA
GCAGACACAGCAAAAGCTTGTTGAGATTAAAACATATGGAAGACTTTCCTTTGCTAAGATTATTGAAGTAATTGGCGATA
CGGGAAGCGAGCGTAATCCAGTTTTTTGACTGTCTTTTTAACTTTGTCGACTTCCATGTATTTAAAGGGATAAAGGATCAT
AAAGTAAAGTTTTGGTTAGATGGATATGAAAAAACAAACACCATGTTTGACTTTTCTGTTTCGACCACAATGGATGACTA
TTTTGTTCGGGTTGTATCTGCACTGCCAAGAAGATACGATAAAACTAATTAACTATTATCAACGAATTTTAGAAAAGA
TTGCTCTTCACATAGATGAAAAATAGATAAACAAGCCAATCTTGATGAAAAGGAAAGCCACTTGCTGCTAGAGGAATGG
AATCAAACGTCAGTTGATTATCCAGACAAGCAAACATTGCATAAACGGTTTGAGGAGCAAGTAGCCAAAAATGAAGATCA
GGTAGCGCTGGAATATGAGGATAAGCAGCTTACCTATAGGGAATTGAACGCTAAAGCCAATCAATTGGCACGTGTTTTAC
AGAAGCATAATACGCTGCCAACTCAGGTAGTTGGTCTAATGGCAGAGCGTTCACTAGAGATGATAATAGGCATTCTTGGG
ATATTAAAAGCCGGCGGAGCTTATATGCCTATTGACCCTACGTATCCTGCGGAGCGTATCCAATATATGCTCGAAGATAG
TCGATCCTATCTCTTACTTGTACAAAAAGCAGAAATTGATTCCAGCCAATTATCAGGGGGAAGTACTTATCCTCACAGAGG
AACTTTGGGCAGATGAGAATACAGAGAACCTGGAACTAGTCAATCAGCCGCAGGATGTTGCCAATATCATGTATACATCT
GGGACTACAGGAAAGCCAAAAGGTATCCTGATCACTCATCGAAACATTATGACTACCATAATCAACAATGGCTATCTCGA
TATTTTTTCAACAGATCGAATATTGCAAATATCTAACTATGCTTTTGATGGTTCTACCTTTGATATATACAGTGCTTTGC
TAAACGGAGCTACTCTCGTGCTAGTTCCCAAGCAAACACTCATGAATACGACCGATCTGTTAGCAATCATCAAAGATAGC
AATATCACGGTAGCTTTAATGACAACCTCTCTATTCAATACGTTGGTTGATCTTGATGTAACCAGCTTCCAACATACACG
TAAGGTTTTATTTGGCGGGGAAAAGGCTTCATGTAAGCATGTAGAAAAAGCATTGGATTATTTGGGTGAAGGGCGCCTAG
TAAATGGATATGGTCCGACAGAAACAACGGTGTTCGCTACTACCTATACAGTCGATAACACGATTAAAAAGCTGGGAAGT
ATCCCGATCGGACGTCCTTTGAGCAACACTTCGGTATATATTTTTGGATTAGATGATCAATTACAACCACTTGGAGTACC
AGGGGAGTTATGTGTAGCAGGAGAATGCATTTCGCCTGGATATCTGAATCGTCCCGACTTAACGGCAGACAAATTTATTG
ATAATCCACTTAAACCAGGTGAGAGAATGTACCGTACAGGTGACCTAGTTCGTTGGCTGCCTGAAGGTGTCATGGAATAC
ATGGGGCGGATTGATGAACAAGTCAAGATTCGTGACATCGTATCGAGCTAGGGGAGATTGAGGCAAAGCTGCTTGAGCA
TCCTTCGATTCGAGAAACAGTGCTGGTGGCTAAACAGGATGCAAATGGCCATTCTTTTTTAGGTGCGTATCTTGTTACAG
ACAACTTCTGCCCTGTAACGGAATTACGGAATTATCTGATGGAAACCTTGCCAGAATATATGGTTCCTTCTTATTTTATC
GAGCTGGATAGCCTACCGCTTACTTCAAATGGAAAAGTAGATAAGCGAGCATTGCCCGAACCGGAATCTCAGGCTTTACA
CGCATATACCATGCCGGAGAATGAGACGGAAGAAAAATTGGTTCAGCTATTCCAGGAAGTGATGGATGTAGAGCGTGTTG
GTACTCAAGATAGCTTTTATGAATTAGGCGGTCATTCCTTAAAAGCAATGCTTTTGGTTTCACGAATTCATAAGGATTTT
GGAATAAAGATACCGTTGAAGGAAGTATTCAGTCGTCCGACCGTGAAGGAATTGGCTGCCTATCTGACTGGGTCAGAAGA
AGCAAACTATATTGAAATTGAAGCAGCAGAAGAGAAACCATACTATCCAGTTACTGCCGCCCAAAAACGGATGTATATCG
CCCAGCAATGGGAGGATGGGGAAGCCACTAGCAGTTATCACATGCCGTTTATGATGGAAATCACAGGGCCTCTTCAAGTA
GAAAAGCTACAACAAACAGTAAAGAGTCTTGTCGCAAGGCACGAGTCGTTGCGGACATCATTTCACATGATCAATGAAGT
ATTGATGCAAAAGATACATGCAGATGTATTGTGGGATTTAGACATTGATCTAGAGTCAGTTGTCGCTTCAGAGCAAGAAA
TTGATGAAAAATGTTCCAATTCCTCCGCAAATTTGATTTGAGTCAAGCTCCTCTCTTTAGAGCTAAGCTGATTCGTGTC
AATGCTAGTCGGCATGTATTGTTATTAGATATGCACCATATTATTTCGGATGGATTTTCATACCAGATATTTTTTGATGA
GCTTACCAGCTGTATCAGGGCGATGAACTGCCATCTCTCAAAATACAATAAAGGATTATGCCGTTTGGCAGCATTCGG
AAGAACAACAGAAGCGTTTGCAACAGCAAGGGATTATTGGTTAGGTCAATTCCAAGGGGAAATTCCTGTTCTGGAATTG
CCTACGGATTACCAGCGCCCCGGTTGATAAACAGTTTGCTGGAGCATTATTCACACACGGGTTATCTGCTGGTCTAACAGA
GAAGCTGAGAAAATTAGCGATTAAGGAAAAAACGACGTTATACACCGTACTGCTGACGGTCTATAACATTCTATTGAGCA
AATATACAAGTCAAGAGGACCTCATTGTAGGTACACCGATTGCTGGACGTCCACATGCTGATTTAGACAGAGTATTTGGG
ATGTTTGTAAACACGCTGGCCATCAGAACAGCTCCAAAAGTAGAGCATTCCTTCTTAACGTATCTATCTGAGGTCAAAGA
```

FIGURE 3E-3

```
AACAGTGCTAGGTGCTTATCAAAATCCAGACTATCCATTTGAGGAGCTGGTTGAAAAAACGCTAGTTCAGCGCGATGTAA
GCCGTAATCCTTTATTCGATGTAATGTTCTCCGTAGAGAAATTACCATCTGCTGTACAGTTCGATGATTTACGTTTCTGC
CCACGCTTATTTGATTGGAAGAAGGCAAAATTTGACTTGGATTGGACAGTGGTGGAAGGTGAATCATTGGAGGTTTTGGT
TGAATATAGCACGAGCTTGTTCGATCGGGCGACCATTGAGCGCATGGCTAAGCATTTTGAGCATATTTTGGAGCAAATCC
TTGATCAGCCAGACCTGTCTATTTCTGAGATTGAACTGCTGACCGAGGCAGAAAAACAACAAATTTTGATTGAGTTTAAT
CAATCGGATAAATCCTTTGACAGCGAAAAAACAATTCAGGAGCAATTTGAAGAATGGGCAGAAAAAGCCCCGCACAGCAT
TGCCTTAGTCTTTAAAGACAAGCAAATGACCTATCAGGAATTAAATCAACGTGCTAACCAAGTTGCGCATTTATTACGTG
GCAATGGGATTTCCGCAAATGATTTTATCGGTTTAATGGTGGATCGATCGTTTGAGATGATCATTAGTATGCTAGGTATT
TTGAAGGCGGGTGGAGCCTACCTACCTATTGATCCTGATTATCCTGAGGACCGTATCGATTATATGTTATCTGACAGCAA
AGCGAAGATTCTCTTAAAGCAAAGTGACCAAACTGCACCAGCTTCCTTTGAAGGTAAAGTCATCGCTATTGATACTCCAG
AATTGCTAGAGATGGATATAGAAAATATTCCTAAGGTGAATAACTCATCCGACTTGGCTTATATCATTTATACATCTGGA
TCAACCGGAAAACCAAAAGGAGTATTGATTAATCATCGATGCGTGATCAATATGCAGCTTACAGCTGAAACCTTTGGTAT
CTATCCTTCGAGTCGTATTCTACAGTTTGCATCCTTTAGTTTTGATTCATCTGTGGGCGAGATTTTTTATACATTATTAA
ACGGAGCATGCCTGTATTTGGTAGAAAAGGATTTGCTTTTATCCGGTAATGAATTCGTGGCATGGCTAAAGAAAAATCGG
ATTAGCTCGATTCCATTTATTTCACCGTCGGCTCTGCGGATGCTTCCTTATGAGGATTTACCTGATCTCGCATATATAAG
TACGGGTGGGGAGACATTGCCGGCTGACCTTGTTAAAGCGTGGGGAGAAAATCGTGTCTTCCTAAATGCATATGGCCCGA
CGGAAACAACTGTAGATGCCACTGTCGGTGTATGTACACCAGAAGGGAAACCGCATATCGGTAGACCCGTTACGAATAAA
AAGGTGTACGTAGTAAATAGTAACAATCAATTACAGCCGATTGGTGTTCCTGGCGAGCTTTGCATTGGCGGGAAGGGGT
TGCACTTGGCTATCTAAACAGACCTGATCTAACCCAAGAAAAATTCGTTTCCAATCCGTTTGCCCCGGGTGAAAGAATGT
ACCGCTCCGGAGACTTAGTCAGATGGCTACCTGATGGAACAATTGAGTACTTCGGAAGATTAGACGATCAAGTAAAAATT
AGAGGTCACCGTATTGAACTAGGAGAGATTGAAACAAGGCTACTAGAGCATCCATCCATTAAAGAAGCCATTGTCATTCC
ACGTTCTGATGAGTCAGAGGCTACATATTTATGCAGCTATTTGATTGCAGAAGGATCATGGAATGCGGCTGACTTACGTA
AGTATTTGAAGGCTTCTTTACCGGAATATATGATACCTTCGTATTTTGTGGAGCTGCACGAGCTACCGCTAACACCTAAT
GGAAAAGTTAATAAAAAAGCATTACCAAAACCAGAAAAGCAAATGCAGAGAGGGAAGGATTATGTAGCCCCTACTAACCC
TATCCAATCCATTTTATCTCAGATTTGGACTGATGTGCTTGGTGTTGAAAATATAGGAATTCACGACAATTTCTTTGAAT
TAGGTGGAGATTCAATTAAAGCCATCCAAATTTCAGCTCGACTTAATAAGCATAATCTCAAGGTTAAAATGCGGGAATTG
TTTAAGAACCCAACGATTGCTGAGCTAAGTCTGCTTGTACAACAGATCGTTCAGGAGATCGATCAAGGAGTAGTAGAAGG
AAATATTCCGCTTACACCGATCCAGCATTGGTTCTTTACCCAATCATTCCCGCAGGTCAACCATTACAATCAATCGGTTC
TTCTTTTTAATGCGGAGGGCTGGGATGAGCAGAAAGTAGACAAAGCTTTTGAGATGCTAACCCAGCACCATGATGCACTG
CGAATCGTATATAGCCTCGACGAGCAAGGGGTTGTACAGCGTAACCGGGGATTGGAAGGCTCGAACTATCATTTCGAAAT
CATTGATGCAAGACAAGATGGAAGGATCAGTCGAACTGGAAAGCAGCGGCGAATCGGATGCAGGCAAGTATGGATATCG
TAGAAGGACCTTTAGTGCAGATCGGATTGTTCCGTGCTAATGAAGGAGCTTATTTGTTAATTGCCATTCATCACTTAGTG
GTAGATGGGGTGTCTTGGCGTATCCTACTAGAAGACTTCTATCATTTATATAACGGAAACGACTCTTTGCCATTAAAAAC
GACCTCGTTCCAAGCATGGTCTCAAAAGCTCCAAGAGTACGCCCAAAGCAAGGAGCTAGAACATGAGCTTTCCTATTGGC
GCCATTTAGATGAAGCTATCACGGACTATACCTTACACAAAGATATAGAAGCCGCAACCTCAAATAAGACAACCTATGAG
GAATTTTTAACTGTATCGATGTCTTTATCAACTGAGGAACCCAACAGCTAGTAACAGAGGCTCATAAAGCGTACCAAAC
GGAAATAAATGATCTGCTACTCACGGCACTGGCTTTAGCTTTGAAGGAATGGACGAATAAAGACAGTTGCTAGTTAGTA
TGGAGGGGCATGGACGTGAAGAAATTCTAGATAACGTAGATATCTCCCGTACAGTTGGGTGGTTTACATCAGAGTATCCG
GTTGCTATTCATCTGACCAAAACAGACATTTCGTTTGCCATTAAACAAGTAAAGGAAACGTTGCGTCGTGTACCTAACAA
AGGGTTTGGCTATGGGATTCTTAAATATTTGGCAAAAGAGACGTTCAAGCTTAAGCCAGAAATCAGTTTTAACTATCTAG
GCCAATTTACAGATAAGGAAGAGGGGAACTCCTCTTTAATGGGTGATCTGATTAGCCCGGCAAATACCAGTGAGCTGTCC
CTAGATATCAATGGAAGTATAGAAGCTGACAGACTGCAAATGCACTTTAGTTATAACTCTCGTGCGTACTATCCAGAGAC
AATCGCAACCCTTGTTCAAAACTTCAAATCCTACTTGCTTGAGATTATCAATCATTGCCGGGCGAAAGAAGGAGTAGAGC
ATACACCAAGCGACTTTGATATCAATGATCTCACCATGGAAGAACTAGATGATATTTTGATGACCTGGAAGAAGAGGTA
TACAAATAACTAGGCAAAATATGGAGTGATTTAGATATGTTTAGCAGAAGTAATGTGCAAAATTTGTATCGCTTATCTC
CTATGCAAAAAGGGATCTTATTTCATTCCTTAAAAGATAAAGAAAATCATGCCTATTTTGATCAACTGATCTTCACTTTG
GAAGGTAAGGTAGAGCTTGAATATTTGGAAGAAGCCTTTACCCAATTAATCAAAAAGCATGATATTTTACGAACTGTTTT
TCGTTACAAAAAAGTAAAAGAACCTGTACAAATGGTATTAAAAGGAAAGAAGCTCCACTATTTATTTTGAAGATATTTCTC
ATCTGGAGCCAGAAGAAAAAGTGAATTACATTAAGCAGTTTAAAATGAGGGATCGGGAGAAGGGGTTTGACCTCTCCCGG
GACCTCCTCATCCGAATGTCATTATTTAAGCTTGATCAGGAGCAGTATCAGTTAATAATGAGTAATCACCATATCATTAT
GGATGGTTGGTGCCTTGGCATTATCCTTACTGATTTCTTACGTATGTATAAAGGAATCGTGAATCATACCCCTGTTCCAT
ACGAGCATGTGACACCTTACAGTAAGCATATTCAATGGCTAGAAAAACAGGATCATCAGGAAGCAAAGGATTTTTATCAA
CAGCTATTAGAGGGATACGACAAAGTAACAGGTGTTCCACAGCAATTAGTACGGGCGAATCACGAAGAATATACTCACGG
ACAATGCATCGTGAAATTAAATCAAGAACTGCCGACCGATTGATTGCCATAGCCAAAGCCTACCAGGTTACAGTCAATA
CCGTCTTCCAAACGATTTGGGGGATATTATTACAAAAATATAATAATACGGATGACATAGTATTTGGATCAGTTGTCTCG
GGGAGACCGGCAGAGATTCCTGATGTTGAAAAAATGGTTGGGCTATTTATCAATACAATTCCTGTGCGAATCAAAGCTGA
```

FIGURE 3E-4

```
TCAACAAGAGCGATTTGACACGCTAGTAGCCAAAGTACAGGAAATGGCCTTGGCTTCAGAATCATATGATTATCTTTCGT
TGGCA
GATATTCATCCAGAAGCTGGCGATTTTATCAATCATATTATTGCGTTTGAAAATTTTTATATCGATATGGACAGCTTTAA
TCAGCTAGCAGATAAAAAGAGCTTGGATTCTCGCTCGCATTCGCCACAGATCATCACGAGCAAACCAATTATGATCTAA
GTGTGCAGGCGCAGATTGGTGATGAATCTTCCATTAAAATTTTATATAATTCCAAGCTTTATACATCGGAATACATAGCA
AATGTAATTGATCATTTTGTTACTGTGGCTGACATAGTGGCTGCTAATCCTAGCATCCCTGTAAAGGAAATCGATATTTT
AACAAAAGATAAAAAAGATCAGATTCTCTATGGTTTTAACAATACCTATGCAGATTATCCAAGAGGAAGACCATCCATC
AGCTATTTGAAGAACAAGTAGATAAAAATCCGAATCAGATCGCACTTGTGTTTAAAGAAGAGAAGCTGACTTACGGTGAG
GTAAATGCGAAAGCAAATCAGTTGGCATACGTGTTAAGAAAGCAAGGTGTACAGCCTAATGATGTAATCGGCATCATCAC
CGAACGCTCCCCAGAAATGATCATAGGCATTTTGGCGATTTTTAAAGCAGGCGGAGCTTATATGCCAATTGATCCTTCTT
ATCCGGCTGAACGCATTCAATATATGCTACAGGATAATCAAACGAAGCTATTATTAGTGCAAAAACAAGAAATGATACCA
GCCAATTATCAGGGAGAGGTATTGTTCTTAACCCAAGAGAGTTGGATGCATGAGGAAACATCTAATCCGGCTCATATTAC
TCAAGCACAGGCTTTAGCATATGTGATGTATACCTCTGGTTCTACAGGAGAGCCTAAGGGCATTTTGACAACACATCAAA
ATATTATGAAGACCGTCATTCATAACGGTTATGTTGAGATTACGCCAGGAGATTGCTTGTCGCAGCTCTCCAATTATGCC
TTTGACGGCTCTACCTTTGAAATCTATGGGGCATTATTGCATGGAGCTACATTACTTTTAGTAACAAAAGAGGCTGTACT
CAATATGAATGAGCTGGCACGTCTTATTAAGAAGGAGCAAGTGACGGTTTCCTTCATGACGACTGCTCTGTTTAATACAC
TGGTGGATTTGGATATAACGTGCTTTCAATCGATACGAAAGGTGTTGTTCGGAGGAGAGCTTGCTTCGGTTAAGCATGTC
CTGAAAGCCCTTGATTATTTAGGCGAGCACCGGGTTATCAATGGTTATGGACCAACCGGAAACTACCGTGTATGCTACCTA
TTACTCTGTAGATCACTCCATGCTGACGAGGGCATCTGTTCCTATCGGAAGACCGATTAATAACACGAAAGCTTACATTG
TAAATACAGATGGACAGCCTCAGCCAATAGGAGTAGTCGGTGAGCTATGCATTGGCGGTGAGGGGGTAGCATGTGGTTAT
CTTAACCGTCCAGAGCTGACAAACAAACATTTCGTGGATAATCCGTTTGTCTTGGGTGAACGAATGTATTGTACCGGAGA
TTTAGCCCGCTTTTTACCAGACGGCAACATCGAATACATCGGGCGGATGGATGAACAGGTAAAGATTCGTGGTCACCGGA
TTGAGCTGGGCGAAATCGAAAAGGTTCTTTTACAGCACCCAGCTATCAGCGAGACAGTGCTTTTAGCAAAACGAGATGAG
CAAGGCCATTCCTATCTGTGTGCGTATATAGTAGGTCAGGTATTTTGGACTGTTACAGAGCTGCGTCAACACTTGATGGA
ATCCTTGCCAGAATACATGGTGCCTTCCTACTTTATCGAGATTGAGAAACATACCGCTTACGGCAAACGGGAAGGTAGATA
AGCGAGCGTTGCCTGAACCAGACAGAAAAATGGGCAGTGCTTACGTTGCTCCAGAGAACGAAACAGAGGAGAAGCTGGTT
CAATTTTTCCAAGAGATTTTGGGTGTTGAGCGAGTTGGCACGCAGGATACATTTTTCGAGCTTGGTGGTCACTCCCTTAA
GGCAATGATGCTCGTTTTACAGATTCATAAAGAAATGGGCATTGAAGTCCCGTTAAAGGAGATATTTACACGTCCTACCA
TCAAAGAATTAGCGGCGTATATTCATAAGATGGATCGCTCTGCCTACAGCATGATTGAGCCAACTGCCAAACAAGAGTAT
TATCCAGTCTCCCTTTGCCCAAAGACGAATGTTTGTAGTGCAGCAAATTAGAGATACGAATAACAACCAGCTACAATATGCC
GATTTTGCTAGAAATAGAAGGGGCTCTTGATAGGGAAAATGTGAGACAAACTCTGAAGAAATTGATAGAGCGTCATGAAT
CAATGAGAACGTCATTCCATATGATTGACGAGACCTTGCTACAAAAGGTGCATGATGATGTGACATGGGAAATGGAGGAG
ATGGAAGCGTCTGAGGAAGAAGTTTATGCTTTGACAAAATCCTTCATTCGTCCTTTTGATCTCGGTCAAGCTCCATTGTT
TAGAGCAGGATTAATTCGTGTTAATTCTGAGCGTCATTTGCTGCTGCTAGATACGCATCACATTATCTCAGATGGCGTAT
CTACTAACATACTCTTTCAAGATTTTACGCAATTATATCGTGGACGAGAGCTGCCTGCCCTGCGAATTCAATACAAGGAT
TTCGCCGTCTGGCAACAAGGAGAGGCTCAGCTTGCTCGTTTGCAAGAACAAGAAGAATACTGGCTGAAACAATTTTCAGA
GAGTGTGCCTGTACTAGAGCTTCCTACTGATTTTCCACGTCCAGCGATGCAGCAGTTTGATGGTGACGTATTGGACTTTG
CATTAAATCAGCAAGTATGGCAGGAATTCAACAGCTCATTGTTAAAGAGGGCTGTACGGCTTACATGATATTGCTGGCG
GCTTATCATGTCTTGCTTTCCAAGTATTCGTCGCAAAACGATATTGTGATAGGTTCCCGATAGCAGGCCGAACAAATGC
TGATTTGCAATCGATTGTCGGGATGTTTGTTAACACGCTGGCTATCCGCACCAAATCAGAGGGAACTCAGACATTCCGCG
AGTTTCTCTCTACGATTAAACAACTGGTTCTTCAAGCTCAATCCAATGCAGAGTATCCATTTGAAGAGCTGGTTGATAAG
GTAAATCCAAGTCGCGATCTAAGTCGCCAGCCTTTATTTGACACAATCTTTGTCATGCAAAACATGGATATTACCGAGGT
TGCGATACAAGGTCTTTCAATCGTAACGAAGGACATGGAATGGAAGCATTCAAAATTTGATCTTACATGGGCGGCTGTAG
AGAAAGAATCCTTGCATTTTTCAGTTGAATATAGTACCCGCTTATTTAAGAAAGAAACAATCGAGCGGATGGCGAAGCAT
TTTGCCCATTTGCTAAATCAAGTGGCGGAAAATCCTGACTTGAGCCTTTCAGATATGGAATTGGCAACGGATGAAGAAGT
GTACCAGCTTTTGGAGGAGTTTAATAATACAGAAGCTGATTATCCGAGTGATAAAACGATTCACCAGCAGTTTGAGCAGA
AGGTAGAGGAAAACCCTGATCAGATAGCGTTGTTATTTAAAGATAAGGAAATTACTTACGGACAGTTGAATGCAAAAGCA
AATCAATTTGCTCGCGTATTAAGAAAGCATGGGTACAGCCGGATCAAGTGGTTGGATTAATCACTGATCGTTCCATTGA
AATGATGATAGGAATTTTGGCAATCTTAAAAGCTGGCGGAGCCTATTTGCCAATTGATCCTTCTTATCCATTAGAACCGA
TTACCTACATGCTAGAGGATAGTCAGGCACAGCTTTTGATTGTGCAGGAAGCTGCTATGATTCCAGAGGGGTATCAGGGC
AAAGTATTGCTTCTAGCAGAAGAGTGTTGGATGCAGGAGGAAGCGTCCAACTTAGAGTTGATTAATGATGCCCAGGATTT
GGCGTATGTGATGTATACCTCAGGGTCTACTGGTAAGCCAAAGGGCAATCTGACGACTCACCAAAACATTTTGAGAACCA
TCATCAACAATGGATTTATCGAGATTGTACCAGCAGACCGTCTATTACAGCTATCGAACTACGCCTTTGATGGCTCTACC
TTCGATATCTACAGCGCGCTATTAAATGGAGCCACTCTTGTACTGGTGCCAAAAGAGGTCATGCTAAATCCAATGGAGCT
GGCGAGGATCGTCCGCGAGCAGGATATTACGGTTTCGTTTATGACCACGTCCTGTTCATACGCTAGTGAGCTTGACG
TGACTAGTATGAAATCCATACGCAAGGTTGTATTTGGTGGGAAAAGGCTTCATACAAGCATGTAGAAAAGGCTCTGGAT
```

FIGURE 3E-5

```
TATCTCGGAGAAGGCCGTTTAGTAAATGGATACGGCCCTACAGAAACAACCGTTTTTGCTACCACATACACGGTGGATTC
TAGTATCAAGGAAACGGGAATTGTACCGATTGGCCGTCCGTTAAACAATACGAGTGTCTATATTTTGAATGAGAATAATC
AACCACAGCCGATTGGAGTACCAGGGGAATTGTGCGTTGGCGGAGCAGGAATTGCACGTGGATATTTAAACCGTCCAGAG
CTGACAGCAGAGCGCTTTGTGGATAATCCGTTTCTTGTAGGAGATAGAATGTATCGGACGGGAGATATGGCTAGATTCTT
ACCAGATGGCAACATTGAGTACATCGGACGAATGGATGAACAAGTGAAGATTCGCGGACATCGAATTGAACTGGGCGAAA
TTGAAAAAGTCTCCTGGAGTACCCTGCTATCAGTGAAGCAGTACTTGTCGCAAAACGTGATGAACAAGGTCATTCCTAT
CTGTGCGCTTATGTTGTAAGCACGGATCAATGGACGGTGGCTAAGGTACGTCAACACATACTGGAGGCTCTGCCAGAGTA
CATGGTACCATCCTATTTCGTTGAGCTTGAAAAGCTACCTCTTACTTCTAATGGCAAGGTAGACAAGCGTGCATTGCCTG
AACCAGATCGAGTGATTACCAATGAGTATGTGGCGGCAGTCAATGAGACAGAGGAGAAGCTAGTTCAGTTTTTCCAAGAG
ATCTTAGCTGTAGACCGAGTCGGAACGCAGGATACATTCTTTGAATTGGGTGGTCATTCCCTAAAAGCAATGATGCTGGT
TTCAAGAATACACAAGGAATTAGAAATAGAGGTTCCGTTAAAAGAAGTATTCGCCAGACAAACCGTTAAAGAATTAGCAG
CCTATATCAGACAGGCTGAACAGTCGGATTACAGCGAAATCCAACCGGCCATGGAGCAAGAATACTACCCGGTATCTAAT
GCACAGCGACGGATGTATGTGGTTCAGCAAATGAGAGATGTAGAAACAACAGGCTACAATATGCCGTTCTATTTAGAAAT
GGAGGGTGCTCTTGAGGTAGAAAAGCTATCTCTAGCTTTTGAAACAACTAATTGAGCGTCATGAGTCATTGCGAACCTCCT
TCCATATGGTTGAAGATGAACTGATGCAAAAGGTACATGCAGAAGTCGCATGGGAGATGGAAATGATTCATGCCGTAGAG
GAAGAAGTTCAACAGCTGACCGATTCCTTTATGCGTCCTTTCGATCTTGCTAAGGCGCCATTATTCCGAGCGAGACTCAT
TCAAATCAATCCGAAGCGACATTTATTGATGCTGGATATGCATCATATCATCTCAGATGGGGTATCGATGAATGTATTGT
TCCAGGATATAACGCAGTTGTATCAAGGGATAGAGCTGAGTCCTCTCAAGATTCAATCAAGGATTTTGCGGTGTGGCAA
CAAGGCATCGCTCAGGTTGTCCGTTTTCAGGAGCAGGAAAGGTATTGGTTAAACCAATTCTCTGGTGACCTACCAATTTT
GGAAATGGTAACTGATTATCCACGACCAGCCATACAGCAGTTCGACGGAGATTCCTGGTCATTTGAAATTGATGCCAAAG
TATTGGACAGCATAAAGCAATTGTCAGCTAAGCAAGGCACTACGTTGTATATGACTCTATTGGCGATTTATCAAATCCTG
TTAGCCAAGTATACCCGTCAAGATGACATCATTGTCGGAACTCCGATCGCAGGAAGACCTCATGCAGACACAGAGAGCAT
TGTGGGGATGTTTGTCAATACACTAGCCCTACGTGGTCAACCAAAAGAAGAGCAATCTTTCATCTCTTACTTATCAGAAG
TGAAAGAAAACGTACTACAAGCCTATGCCAACGCTGATTATCCATTTGAAGAGTTGGTAGAGAAGCTGCATTTGCAAAGA
GATATGAGTCGTCATCCATTGTTTGATACGATGTTTGTTTTACAAAACATGGATATGTCCGATATAAATATTTCTGGTCT
AAAGCTTCATTCGCGTGATTTAAACTGGAAAAATGCAAAATTTGATATGACCTGGATGATAGCCGAACAAAATAATCTAT
TGATTTCGGTTGAGTACAGTACCAACCTGTTTAAACATGAAACCATTCAAAGGCTAGAAAAGCATTTCACTTATTTAGTA
GAACAAGTGGCTAAGCATCCGGATTGCTTACTCAGAGATTTAGAACTCACAACAGACGAAGAAAAACAGCAAATACTGAC
GGTATTTAACGATACTGCTACTGATGATTTACAGGATTTATCCATTTGCCATCTATTCGAACAACAAGTGCAGCGTTTTC
CAGATCGGCCGGCACTTGTGTTTAAAGAAAAGCAGCTCACATACAGTGAGTTCCATGCAAAAGTAAATCAATTAGCCCGG
GTACTCAGAAGAAAGGTGTGCAGCCGGATCAAGCGGTTGGATTAATCACCGATCGTTCCATTGAGATGATGATAGGGAT
TTTCGCCATCCTAAAAGCAGGCGGAGCTTATATGCCAATTGATCCTTCCTATCCAATCGATCGGATCGAGCACATGCTAG
AGGACAGCCGGACTAAGTTGTTATTCGTGCAAAAAACAGAAATGATCCCTGCTAGCTATCAGGGGGAGGTATTACTCCTA
GCGGAAGAGTGCTGGATGCATGAAGATTCATCGAATTTGGAGCTGATCAATAAAACACAGGATTTGGCATATGTCATGTA
TACCTCAGGTTCTACTGGTAAACCAAAGGGCAACCTGACAACGCACCAAAACATTTTGACCACCATCATCAACAATGGCT
ATATCGAGATCGCGCCAACAGACGGTCTATTACAGCTATCTAACTATGCTTTTGATGGCTCTACCTTCGATATCTACAGT
GCGCTATTAAATGGAGCCACTCTTGTACTGGTGCCAAAAGAGGTCATGTTAAATCCAATGGAGCTGGCGAAGATCGTCCG
CGAGCAGGATATTACGGTTTCGTTTATGACCACGTCCCTGTTCCATACGCTAGTGGAGCTTGACGTGACTAGTATGAAAT
CCATGCGCAAGGTTGTATTTGGCGGGGAAAAGGCTTCATACAAGCATGTAGAAAAGGCTCTGGATTATCTCGGAGAAGGC
CGTTTAGTAAATGGATACGGCCCTACAGAAACAACCGTTTTCGCTACCACATACACCGTGGATTCTAGCATCAAGGAAAC
GGGAATCGTACCGATTGGACGTCCGTTAAACAATACGAGTGTCTATGTCTTAAATGAGAATAATCAGCTTCAGCCGATTG
GAGTACCAGGGGAATTGTGCGTTGGCGGAGCAGGAATTGCACGGGCTATTTAAATCGTCCAGAGCTAACAGCAGAGCGC
TTTGTGGAAAATCCTTTCGTGTCAGGAGATAGAATGTATCGTACCGGTGATTTAGCACGTTGGTTGCCGGATGGAAGCAT
GGAGTATTTAGGACGGATGGATGAGCAGGTTAAGGTACGCGGTTACCGAATTGAGCTGGGAGAAATAGAGACAAGATTAT
TGGAGCATCCTTCTATAAGCGCAGCGGTTTTACTAGCAAAGCAAGATGAGCAAGGGCATTCGTACCTATGTGCTTACATC
GTTGCAAATGGGGTATGGACGGTTGCGGAACTACGTAAGCATCTAAGCGAGGCTTTGCCAGAATACATGGTGCCTACTTA
TTTTGTTGAACTAGAGCAGATACCATTCACTTCTAATGGAAAGGTGAACAAACGCGCTTTACCAGAGCCAGAAGGACAAA
TGACCAGTGTATATGTGGCCCCAGAAACGGAGACAGAAGCAAAAGTAGCAGCGTTATTCAAGAGATTTTGGGTGTCGAG
AGAGTTGGTACACAGGACATGTTCTTTGAGCTGGGTGGTCATTCGCTAAAAGCGATGATGCTCGTTTTTACGAATGAATAA
AGAACTGGGCATCGAGGTGCCTTTGAAAGAGGTATTCGCCCATCCTACTGTCAAGGAATTGGCAGCAACGATCGACCTTC
TTGATCGATCAGGCCACTCAGAGATTGAGCCTGCCCCAAGGCAGGAATTCTATCGGTATCTTCCGCGCAGAGACGGATG
TACGTGGTGCAGCATTTAGGAAATGTCCAAACAACCAGCTACAATATGCCGCTTTTCCTTGAAGTGGAGGGAGCTTTAGA
AATTGATAAGCTTCATCTAGCACTTGAGAAATTGGTCGAAAGACACGAGTCGCTACGAACCTCCTTTCATATGGTTGACG
AAGAGCTGATGCAGCAGGTGCATGAAGAGGTGGCCTGGATTTAGAGATCATGGATGGAACGGAAGGAGACCTTGCAAGC
ATCACAGCAGGATTTATACGTCCGTTTGATCTCAGCCAAGCTCCATTGTTCCGTGCAGGCATCGTGCGGATTAGCCCTGA
GAGATTCCTTTTCATGCTAGATATGCACCATATCATCTCAGACGGAGTTTCTACCAATGTATTGTTCAAGGATATAACGC
```

FIGURE 3E-6

```
AGCTCTATCAAGGAAAGGACCTGCCCCCTCTTCCGATACAGTACAAGGACTACGCTGTGTGGCAACAAGCTGATGCTCAA
GTGACTCGCTTACAAGATCAGGAAAGCTATTGGTTACATCAATTTGCTGGAGAAGCTTCTGTCTTGGAAATGCCGACAGA
TTTCCCGCGTCCTGCAGTCCAGCAGTTCGAAGGAGATGTATGGACCTTTGAGATTGATGCTGACATTCTCAGCCAGTTGA
AAAAATTATCAGTGAGTCAGGGTTCTACTCTATATATGACTTTATTGGCGGTTTATCAGGTGTTGCTGGCTAAGTATACC
GGTCAAGATGATATTATTGTCGGTTCACCAATTGCCGGACGCCCTCATGCGGATGTAGAGAGCATCGTCGGTATGTTCGT
CAACACGCTAGCTTTACGTGGACAGCCTGTAGGAGAGCAGACGTTTATTACCTATCTGGCACAAGTTAAGGAACAGGTTT
TACAAGCTTATGCCAATGCAGAGTATCCATTTGAGAAATTGGTAGAGAAGCTCGATTTACAACGAGATATGAGTCGCCAT
CCACTCTTCGATACGATGTTTACTTTTGCAAAACATGGAGATGACTGATATTGATTTGGCAGGCTTGACCTTCAAGCCATT
TGATTTTGAATGGAAAAATGCCAAGTTTGACATGGATTGGACAATGCTTGAGGAAGAAACACTCAAGGTAGCTATTGAAT
ACAGTACAAGCCTGTATACAAAAGAAACCATTAGCAGAATGGCTCAACATTTCACCTATGTTTTACAACAAATTATTGAG
CATCCAGCCATTCGTTTGGCTGAAATCAAAATTGCTACTCTACCAGAAATTGAACAGATTTTAACGCAATTTAATGATAC
TAGGGCCAATTACCCTGATAACCAAACCATTCATAGTCTATTCGAGCAACAAGTGGAGCGTACACCAGAACAGATAGCTG
TTGTCTATCAGGATCAATCCATCACGTATCGTGAGCTTAATGAACGTGCAAATAGATTGGCACGTTGCTTGATCGACAAA
GGGATACAGAGAAATCAATTTGTTGCAATCATGGCGGATCGTTCCATAGAAACCGTTATTGGAATGATGGGAATTCTCAA
AGCAGGAGGAGCTTATGTTCCAATTGATCCTGATTACCCTCTAGATCGAAAGCTGTATATTCTTGAAGACAGCCATGCAT
CACTATTATTGTTCCAGCAAAAGCATGAGGTCCCCTCAGAATTCACAGGTGATCGGATATTAATTGAGCAGATGCAGTGG
TACCAAGCGGCTGATACGAATGTGGGGATCGTCAATACAGCTCAAGATTTGGCGTATATGATCTATACCTCAGGTTCTAC
AGGTCAACCAAAAGGGGTAATGATTGATCATCAAGCAGTATGTAACCTATGCTTAATGGCCCAAACCTATGGAATCTTTG
CGAATAGTCGCGTTCTACAGTTTGCCTCCTTTAGCTTTGACGCTTCCGTAGGAGAGGTTTTCCATACCCTTACAAATGGA
GCCACTCTCTATCTGATGGATCGCAATTTGCTCATGGCTGGCGTTGATTTGTTGAATGGTTACGAGTAAATGAAATAAC
TTCTATTCCGTTTATCTCGCCTTCTGCATTGCGTGCATTGCCGTATGAGGATTTACCAGCATTGAAATATATCAGTACAG
GTGGGGAAGCATTACCTGTAGATTTAGTCAGACTATGGGGAACTGAGCGAATCTTCTTAAATGCATATGGCCCGACTGAA
ACAACAGTAGATGCAACGATTGGCTTATGTACGCCAGAGGATAAGCCACATATTGGTAAGCCTGTGTTGAATAAAAAAGC
CTACATTATTAATCCAAATTATCAACTTCAGCCAATTGGGGTACCGGGTGAGTTATGCATCGGTGGAGTAGGGATTGCTC
CTGGATATTGGAACCGCCCTGAACTAACTAGAGAGAAATTGTGGATAATCCATTTGCCCAAGGCGAAAGAATGTATAAG
ACGGGGACTTAGTACGTTGGCTTCCAGATGGAAATATTGAGTTTTTAGGACGTATTGATGATCAGGTGAAAATTCGTGG
ACACCGAATTGAATTGGGTGAAATTGAGACGCGGCTTCTTGAGCATGAGCAGGTAATAGAGGCGGTTGTGCTGGCGCGTG
AAGATGAACAAGGTCAAGCTTATCTGTGTGCTTATCTGGTAGCAGCAGATGAATGGACGGTAGCAGAACTGCGCAAACAT
CTAGGAAAAACACTGCCCGATTATATGATTCCTGCTTATTTTATCGAGCTTGAGGAGTTTCCTTTGACACCAAGCGGGAA
GGTGAATAAAAAAGCTTTTACCAGAGCCTGATGGACAAATACAAACGGGAGTGGAGTACGTAGAGGCTACTACCGAAAGCC
AAAAAATCCTTGTTGAGCTTTGGCAAGAGGTGTTACGTGTCGAGCGGATCGGTATTTACGATAACTTCTTTGAGCTGGGC
GGTGACTCCATCAAAGCAATTCAAATCACAGCAAGATTCGTCGCCACCACCGCAAGCTGGAAATCAGCCATCTGTTTAA
GCACCCAACGATTGCAGAGCTTGCTCCATGGATGCAAACCAGTCAGGCATTACTTGAACAAGGAACTGTTGAAGGCGAAG
TTATGCTCACGCCAATTCAAAAAGCATTCTTTGAAGAAAATCAGGAACAGCCGCAGCATTTTAATCAGGATTCGTTACTG
TACAGCTCGAATGGCTGGAACCAAGATGCGATCGAGCAGGTATTTGAAAAAATAACGGAGCATCACGATGCCCTGCGAAT
GGTGTATCCGCATACCGAGGGCAAGGTGACTCAGATCAACAGGGGACTTGAGGACAAGGCGTTCACATTGCAGGTGTTCG
ATTTTACCCAAGAACCAACTGATACGCAGGCAACAGTAATTGAGCAAATCGCTACTCAATTGCAAGCGAGCTTTGATTTA
AAAAAGGGACCTCTGGTACGACTTGGCTTATTTACCACCAAGGCTGGGGATTATTTACTGATCGTGATCCATCACCTAGT
GATTGACGGCGTCTCTTGGCGTATATTGCTTGAGGATTTTTCATAATGCTTATCAGCAAGTCATTCAAGGTCAAGCAATTG
TACTTCCTGAAAAAACGACCTCCTTTAAAACATGGAGTGAGCGCTTGAATGAATATGCAAATAGTCATGCTCTTTTACAC
GAGATTCCATATTGGAAGCAGATGGAAGAAATATCGATCGCCCCTCTTCCTAAAAAAGGAAACAATGACGGTAGATATTA
TGTGAAGGACAGCGAATATGCCACGATGAGTCTAACAGAAGAAGAAACCCAAAATCTTCTTACTCGTGTACATCGAGCTTT
ATCGAACGGAGATTAATGATCTGTTGCTTGCCATTAGGATTAGGAACGTAAGGAATGGACAAAAGAGAATCGAGTGGCT
ATCCACTTAGAGGGTCATGGTCGTGAGGAAATAGGTGAAGGGGTAGATGTCAACCGCACTGTTGGATGGTTTACCTCCCT
GTTCCCATTCGTGATTGATTTAGAAAATGACGAATTGCCTCTCATCATTAAATCGGTAAAAGAAACCTTGCGCCGAGTTC
CTAATAAAGGCATGGGCTACGGCATACTCAAGCATCTGACAAGCGATGCGAACAAACAGGAGATAACCTTCTCGCTTCGC
CCAGAGATCAGCTTTAACTATCTGGGGGTATTTGATCAACAAGAGGAGGAAAGCGAATCTGCTGGGATTCCTACTGGTCA
GCCGATCAGCCCGCAATATTATGACACGCACCTGCTGGAGTTTAATGGAGCGGTCTCGAATAACCAGTTGCATGTAAATT
GCCGATTTGCTCCTGCAGCCGTTGATCGAGCGATTGTTGAAATTTTGATGGAGCGCTTCAAGCACCATTTACTTCTAATT
AGTAAGCATTGCTTGGAAAAGGATACCGTAGATTTACACCTACTGATTTTTACAGAAAAGGAATTAAGCCAAGAACAGCT
TGACGATCTATTAGATGATTTGTTTGAAGACATAGATGATCTGTAATCGCAATGAGATAGGTGGTGCCACACATCGTGCA
AAAAAAAGACAAGATCAAAGATATCTATTCACTTTCTCCGTTGCAAAAGGGTATGCTATTTCATTCCATGAAAGACCCGC
AGAGCGATGCCTATTTCGAGCAGGTTACCCTTTTGCTGGAGGGGGTTGTAAACCCAACCTATTTGGCTGAAAGTATTCAG
GGACTCGTACAAAAATACGACATGTTCCGAAGTGTGTTCCGCTATAAAAAAGTAGACCCTGTTCAGGTTGTGCTTAGTGA
ACGAAAAATAGATTTACAGATTGAGGACCTTACTCAAATCAATGAAGAAGAGCAACGGAAATTCATTGAGGAATATAGAA
AAAAGGACCGGGAAAGAGGCTTCGACCTTTCCCGGGATATCCTGCTACGTTTTACATTGTTTCAAACAGCCGCCAATCGG
```

FIGURE 3E-7

```
TATGAATTACTGTGGAGTCATCATCATATCCTGATGGATGGCTGGTGTACGGGTATCGTTTTTCAGGATTTATTTCAAAT
GTACCAACGTCGCTTGTCAGGACAGGCCTTACTTCCAGAGGTGGCCCCTCAATATAGCGAATATATACGCTGGTTAAAGA
AACAAGATGACCAACAAGCATTGGCATTTTGGAAGGAGTATCTACAGGGGTTTGAAAACCTTACGGGAATCCCGCGTCTA
AGGTCAGGCAATCATCCCTACAAGCAAGAGGAATTCATTTTCTCCTTGGGAGAGGAAGCTACACAAAAACTAACGCAAAC
GGCTCAAAAGTATCAGGTGACCTTAAATACTGTTGTGCAAACAATTTGGGGAGCGTTATTGCAAAAATACAATAACACGA
ATGACGCGGCCTACGGTGTGGTTGTCTCCGGACGACCCGCCGAGGTGCCAAATGTTGAACAAATGGTGGGGTTATTTAGT
AATACCATTCCTATTCGTATTAAAAAAGAAGCAGGAAAAACGTTTGGGGAAGTGCTGAAAAACGTACAGCA
AACAGCGCTGGAGGCAGAAAAATACGGATATCTTTCTTTAGCCGATATTCAGGCGAGCGCAGCTTATACGCATCAATTGC
TTGATCATATTTTAGCGTTTGAAAATTTCCCGATGGATCAAGAAACATTTAATCAAGAAAACGTTCTCGGATTTGCCGTG
AAGGATGCCCACACGTTTGAGCAGACGCACTATGATCTGACCGTGCTAGTCATTCCTGGCAAGGAATTAATCTTTAAGTT
TATGTATAACGAAAGTGTTCATTCAAAAGAGTACCTCAATCTTTTAGAGCTGAATATGAAAAAGCTGGTCTCTTTGGTTA
TTGAGCAGCAGGATATCTTTGACCCAGCTACCGAGTTTGTATCTGATTTGGAAAAGGATAAGCTTTTAACCATTTTTAAT
CGTACGGATGCAAAGTACCCAAGAGAAAAAACGATTCATGAGCTGTTTCAAGAGCAGGTTGACAAGAACCCTGATCAAGT
GGCACTCGTATTTGGCGAGGCTCAACTAACATACCGCGAGCTGAACGAAAAGGCGAATCAAATGGCCCGCGGTTTGCGCA
AACAAGGGGTTTTACCTGATCAGGTGATAGGGTTACTTACGGATCGTTCCTTAGAGATGATCATAGCCATTCTAGCGATC
TTTTAAAGCTGGTGGCGCTTATATGCCTATCGACCCATCTTATCCGAGTGAACGCATTCAATACATGCTAGCAGATAGTCG
TACCCATTTGCTATTGGTGCAAAAAGCTGAAATGATCCCAGCTAATTATCAGGGTGAGGTACTACTGTTAACAGAAGATA
GCTGGATGGACGAGAATACAGATAATTTAGATTTGGTCAACCAAGCACAAGACCTTGCTTATGTCATGTATACCTCAGGT
TCAACAGGTAAACCAAAGGGAAATCTGACACCCATCAAAATATCGTCAAGACCATCATGAACAATGGTTACATGGAGAT
TACGCCAAATGATCGTCTTCTCCAGTTGTCCAATTACGCGTTTGATGGATCAACCTTTGATATATACAGCGCATTGTTAA
ACGGAGCTTCTCTTATTTTAGTACCAACGCATGTACTGATGAATCCGACTGATTTGGCATCGGTCATTCAAGACCAGCAT
ATTACCGTGTCCTTTATGACAACATCTCTATTTAACACTCTGGTTGAGCTGGATGTGACTAGTCTCAAACACATGCGTAA
GGTGGTGTTTGGAGGAGAAAAGGCTTCGATCAAGCACGTAGAAAAAGCGCTGGATTATTTGGGAGCTGGACGTTTGGTCA
ATGGGTATGGACCAACAGAAACTACTGTTTTTGCCACTACCTATACGGTGGACCATCGATCAAGGAGACGGGGATTATG
CCGATAGGTCGCCCGTTGAACAATACGAAGGTGTTTATTTTAGGAGCAGACAATCAACTACAGCCGATAGGTGCATTAGG
CGAGCTATGTCTGTGAGCGGGGAAGGGCTTGCCCGCGGGTATCTCAATCTTCCAGAGCTGACTGCTGATCGTTTCGTTGAAA
ATCCTTTTATGCGGGGAGAGAGAATGTATCGCACAGGGGATTTAGCGCGTTGGTTACCGGATGGAAGCATTGAGTACGTA
GGTAGAATAGATGAACAAGTTAAGATTCGGGGACATCGGATCGAATTAGGTGAAATTGAAGCTAGATTACTAGAGCATCC
TGCTATTAGCGAGACCGTTTTGCTGGCGAAGCAGGATGAGCAGGGGCATTCCTTCCTATGTGCCTATCTAGTGACAAATG
GTGCCTGGTCAGTCGCAGAGCTTCGCAAGCATATCAAGGAAACATTGCCGGATTCTATGGTGCCATCTTATTTTATCGAG
ATAGATAAAATGCCGCTCACTTCAAATGGCAAGGCAGACAAGCGTGCATTGCCAGAGCCAGATGTTCAACAAGTAAGCTC
TTATATTGCTCCTGAGACCGAAACAGAGGAAAAGCTGGTTCAATTATTTCAAGAAATCCTAAGTGTTGAACAAGTCGGTA
CGCAGGATAATTTCTTCGAGCTGGGCGGACATTCGTTAAAAGCGATGATGCTGGTTTCAAGAATGCACAAGGAATTAGAT
ATAGAAGTACCGCTCAAGGACGTGTTTGCTCGACCTTCAGTAAAAGAATTGGCCGCATTTCTTACAAACACAGAAGTGTC
GGATTATATAGCGATTGAACCGGCGGCAAAACAGGAATTTTATCCGGTTTCTTCTGCACAGCGCCGAATGTATGTAGTAG
AGCAAATCGGTAGCAGTAATACAACCAGCTACAATATGCCTTTTTTGCTTGAAAATAGGAGGAGCCCTCGATGTAGTAGGG
TTACAAAAAGCATTAAAGAAACTGGTCATAAGACATGAATCGTTGAGAACGTCCTTTCACATGGTTGATGAGGTATTAAT
GCAGAAGATCCATCCTGACGTGGAATGGGATTTAATGGTCATGGAAGCAAAAGACGAGGACCTTCCGCAAATCATTGATG
GTTTTATCCAGCCGTTTGATTTAAGTGACGCTTCTTTATTTAGAGCGGGACTCGTACGAATGGAAGCTGATCGACATCTA
CTGATGCTTGATATGCACCATATTATTTCAGATGGGGTATCAACCAATGTATTATTCCAAGACCTGATGCAAATCTATCA
GGGCAAGGAGCTCCCTTCTCTTAGAATTCAATACAAGGATTATGCTGTTTGGCAGCAGGCAGAAGCCCAGGTTAATCGTT
TACGAGAACAGGAGCAGTATTGGCTTAACCAATTTTCGGGAGAGTTACCTGTACTGGAAATGCCTACCGATTACACTCGT
CCATCTATTCAGCAGTCAGAAGGGATATATGGTCATTTGAAATTAGTGCCGGATCATAAACAAGTAAAGAAACTGTC
CTCCTCGCAGGGTACAACCTTGTATATGACATTGCTGGCCGCCTACCAAGTATTATTGTCAAAATATACGGGGCAAGAGG
ACGTTATTGTGGGTTCTCCTATTGCTGGCCGACCTCATGCGGATGTAGAAAAGATTGTTGGTATGTTCGTGAACACGTTA
GCCTTCAGAGGGCAGCCAAAATCAACTCAAACCTTTAGTACATATCTGTCCGAGGTTAAGGAGCAGGTATTGCACGCCTA
TGACAATGCAGAATATCCGTTTGAGGAATTACTTGAAAAGCTTGATTTAGAAAGAGATCTAAGTCGTCATCCACTGTTTG
ATACCATGTTTGCTTTGCAGAATATGGAAATCAATATCATGGATCTCTCCTTTCAGCCGCGGGATTTAACA
TGGAAAAATGCAAAATTCGACCTGACATGGATGATGCGGAAGCGGAAAATTTGTATGTCACCATTGAGTATGTACCTC
GCTCTTTAAGCCAGAAACAATTGAGCGATTAGGTAAACGATTCACCCATTTACTAAAACAGATCGGGGATGCTCCTGAAC
GTTTGATTGCTGACTTAGAAGTAGCGACGGAGGATGAAAAACATCAGATTTTATCGGTATTTAATTTGACTCAATCGGAT
TATCCAGTAAATAAAACCGTTCATCAGCTCTTTGAGGAGCAAGTGCAAAATATGCCTGATCAAAAGGCGATAGTATTTGG
TGAAGAGCAAGTAACATACAAAGAATTAAACGCCAAAGCCAACCATCTGGCTACCCTCTTAAAACAAAAGGCATAACAA
ACGAGCAACTTGTGGCTGTTATGATTGAGCCTTCCATCGAGTTTTTTGTAGGCATTCTAGCTGTTCTAAAAGCAGGAGGG
GCTTATCTACCAATTGACCCAACTTATCCGACGGAACGAATTGCCTATATTTTGGAGGATAGTCAATCAAAGGTTCTGTT
AGTGAGAGGTCATGAACAGGTACAGACACAATTTGCTGGGGAAATCTTGGAAATTGATAGCAAGAAGTTGTCTACCGAAG
```

FIGURE 3E-8

```
AGCTGAAAGACGTACCTATGAATAACAAAGTAACCGATCTAGCCTATGTCATTTATACATCGGGTTCCACTGGGCAACCA
AAAGGTGTCATGGTGGAGCATAGATCGTTGATGAATCTTTCAGCTTGGCACGTTCAGTATTTTGGCATCACAAAGGATGA
TCGAAGCACCAAATACGCAGGGGTTGGATTTGATGCATCTGTATGGGAGGTCTTCCCTTACTTAATAGCTGGTGCAACGA
TTTACGTCATCGATCAAGAGACAAGATACGATGTAGAAAAACTGAATCAGTACGTAACAGATCAAGGGATTACGATCAGC
TTTTTACCTACGCAATTTGCTGAACAGTTTATGCTGACAGATCATACGGATCATACTGCCCTACGCTGGTTGCTTATCGG
CGGTGATAAAGCCCAGCAAGCCGTTCAGCAGAACAGTATCAGATGGTATTAAATAACTATGGGCCTACTGAGAACACGTTG
TAACAACCAGCTATATAGTGAGTCCTGAGGATAAAAAAATCCCGATAGGGCGTCCAATTGCTAATAATCAGGTATTTATC
CTGAATAAAGAGAATCAATTACAGCCAGTAGGGATTCCAGGTGAACTATGCGTTAGCGGCGACAGCCTAGCACGCGGCTA
TCTGCATCGTCCAGAGTTAACGAGTGAGCGTTTTGTAGCTAATCCGTTTGTCCCTGGCGAACGCATGTATAAAACCGGAG
ATATTGCCCGCTGGTTACCAGATGGAAATATTGAGTATCTAGGTAGATTGGATGATCAAATTAAGATCAGAGGATACCGG
GTTGAATTAGGTGAGATAGAATCCGCTATTTTGGAGCATGAAGCAATTCATGAGACAGTAGTGCTCGCAAGACAAGACGA
TCAGAATCAGACATATCTATGTGCTTATGTTGTACCGAAAAAATCTTTTGATGTAGCCGAGCTTCGTCAATATCTAGGCA
GAAAGCTACCTCACTTTATGATTCCGGCCTTTTTTACGGAAATGACAGAGTTCCCAATTACATCGAATGGGAAAGTAGAT
AAAAAAGCACTCCCACTACCGGATTTGTCCAAGCAATCAGAGATCGATTACGTTGCCCCAACCACCACGTTAGAAGAAAC
GCTGGCGGAACTATGGACAGAAGTGCTAGGAGTTTCCCAAGTGGGAATCCATGATAACTTCTTTAAACTGGGTGGGGATT
CGATCAAGGCTATTCAGATTGCAGCAAGATTAAATACGAAGCAATTAAAATTGGAAGTTAAGGATTTATTCCAGGCACAA
ACGATTGCTCAGGTTATTCCATACATCAAAACCAAGGAAAGTAAAGCTGAGCAAGGAATTGTTCAAGGAAAGGTAGAGCT
AACCCCTATACAGGAATGGTTTTTCCAGCAATCCTTCGATATTCGATCATCATTGGAATCAGTCCATGATGTTTTATCGAA
AGGAAGGGTGGGATCAGCACGTTGTACAAAGGGTGTTCCAAAAAATTGCAGAACACCATGATGCCTTGCGAATGGCTTAT
CAGCAGGAAAATGGCAAAACGATTCAGATCAATCGCGGAGTGGAAGGCAAGTTGTTTGAGCTAAGCATTTTTGACTTTAA
ACAACAGGCGAATGTGCCAGAGCTGATCGAGCAAGCAGCTAATCGTCTACAATCCGCAATGAACTTGCAGGACGGTCCAT
TGGTTCAACTGGGACTCTTTCAGACATCTGAGGGGATCATCTTTTGATAGCAATTCATCACTTAGTGGTCGATGCCGTT
TCATGGCGAATCATTACGGAGGATTTCATGAATGGCTATCAACAAGATTTGCAGGGAGAGCCGATTGCATTTACGAGCAA
AACAGACTCCTACCAAAAATGGGCCAAGAGCCTGCTAGAGTACGCTACTAGTGAAGAAATTCAATCAGAGCTGAAATACT
GGCAAAGCATGATTGCAAAAGGGTTACCTGCATTGCCAAGAGATTCAAAAGTAGGTGCCCCGTATCTACTCAAGGATATA
CAAGAGGTCGCTATCCAATTGACAAAAGAGCAAACGAATAAACTATTAACGGATGCCCATAACGCCTACAACACACAGAT
TAACGATCTTTTGTTGACAGCATTAGCTCTAACTATTCAGGAATGGGCACAAACCAATTCAATCGCAATTACACTAGAAG
GACATGGACGCGAGGATATTGGGGTGGACATTGACATTAACCGTACAGTTGGTTGGTTTACGTCCATGTATCCAGTGGTA
TTTGATTTGCAGAAGCAAGGGATTGCAAATACGGTTAAGCAAGTAAAAGAAGAGCTGCGACAAATACCGAATAAAGGGAT
TGGCTATGGGGTTGTTAGATACCTATCGAATCAAGGAAGTACAGAGCTGAGTCTAAGCTCCCATGCGATAAATCCAGAGA
TTAGCTTCAATTACCTTGGGCAAATGGATCAATCTGGACAGGAAGAGGAGTATCAATTGTCCCCATTGTCTTCCGGTCAA
CAGATTAGTCAGATGAATCAAGGCTTGTTCCCGATAAATGTGAGTGGAATTGTAGTGGAAAATCAGTTGTCCATTCAAAT
ATCTTATGATAGCCAAGCTTATCATGATTCTACTATGGAAAAGCTGATTCAACGTTATCAATATCACTTGTTGGAGATTA
TTAATCATTGTGTTCAGCAGACAGAAACAGAATTAACCCCGAGTGATTTTTCCACCAAAGAGCTTTCGATGGAGGATTTA
GAATCAGTATTTGAGTTACTAGATGAATAAACTTTGGTTATGTCATTAGGAGGCTTTATATGTTAAGTAAAGCAAATATT
AAAGCATCTATACATTATCTCCGCTACAAAAAGGCATGTTATTCAGCATTTAAAAGAAGAAGCACGGCTTATTTTGA
GCAATTACACTTTACGATTAAGGGACAACTATATGTAGATAGCTTTGAAGCAAGCTTTCAGCATCTCATAAACAAATATG
ATGTGCTACGAACCGTTTTTTCTGTATAAAAATATGACCCAGCCCATGCAAATGGTTTTAAAAGAAAGAAAAACAAGTGTG
CATTTTGAAGATATCTCCCACCTAGATTCTAAAGCCGTGAGTGAATATGTTGAAGAGTTTAAAAATCAGGATCGGGAGAA
GGGATTTGAACTCTCGAAGGACATTCTCATGCGTTTTGCTATTTTGAAGGCTGGTGCTGAGTCCTATCATTTAATTTGGA
GCTTCCATCATATTTTAATGGACGGCTGGTGCATGGGCATTGTGTTACAGGATTTGTTCAGAATGTATCAGCAGCATCGT
CAAAATATACCGATTACCGTTGAGAGCGTTCCTGCCTATAGCGATGTATCCGTTGCGTTGAGAAGCAGATATGTAACAAA
GGCGAGGGATTACTGGAAAAATTACTTAGAGGGCTATGAGGAATTAACAGGTATCATTCGTCTCGATACGAAGCATACGA
GTCACAACAACGAGGTACAGGAATGCGCCTTTACACTGGATAAGGACATAACGGAAGGACTTACTCAGCTTGCTCGTCAT
TATTCAGTGACAGTAAATACGCTTTTTCAAACAATTTGGGGCATGCTGTTGCAAAAGTATAACAATAAGGATGATGTTGT
GTTTGGTGCGGTCGTATCTGGCCGCCCCTCTGAAATCCATGGCGTAGAAAACATGGTTGGCTTGTTTATCAACACTGTCC
CTATTCGTATTCAAAAACAAATGAATGATACCTTTAGCCATTTATTAAAAGAGTTCACGAATCTACGCTATTGTCTAAA
CAGTATGAGTTTGTATCCTTGGCAGATATTCAAACCGATCAGGATTTTCTGGTCAATTGCTAGATCACATCTTAGTTTT
TGAAAACTATCCGATAAGTGAAGGTTCTTTTGAGGAAGAAGAATTTTACGATGGATAGTATAAAAACCTATGAGAAAACAA
GCTATGACCTAAACGTGATGATTCGGCCTAATGAGGATCAGCTTGATATTGCCTTCCAATTCAACGATGACGTGTACTCA
AGCGAAAATGTAAAAAGACTGTTCCAGCATATGAAGCAACTGGCTCTAGCTGTAATCAAGAATCCGATGTGCGCTTGGA
AGAAATAGCAATGATCACAGAAGAGGAACGCTATCAAATCTTGCACGATTTCCAAGGGGAGATAGTTGATTTTGTAACAG
AAAAAACGCTTCCTGAACTGTTTGAAGACCAGGTGAAACGAACTCCAGAAGCAATTGCACTTCGATTTGAAGATCAACAA
TTGACCTATCAGGAGCTAAATCAGCGAGTAAATCAATTAGCTTGGACACTAAGAATGAAGGGCTTGCAGCAAGAAGAACT
CGTTGGAATTATGGTGCAGCGCTCATTAGAAATGATCGTTGGTGTGCTAGCCGTTATAAAAGCAGGCGGCGCATACGTAC
CAATTGATCCGGAATATCCGCTTGACCGAATCCAATATATGCTGGAAGACAGTGGAACCAATTGGCTGTTAACCACGAAA
```

FIGURE 3E-9

```
CAGAGCGAAATTCCTTCCATCTATCTAGGGCATGTCCTGTATCTTGAGGAAGATACGGTGTATCACGAGCGGTCTTCAGA
TGTAGAGATTGTAAATCAATCCAGCGACTTAGCTTATATTATCTACACGTCCGGTTCTACTGGTCAGCCTAAGGGTGTCA
TGATTGATCATCGTGCTGTTCATAATTTGCATTTGTCAGCAGGAATCTATGGAATCGCACAGGGAAGCCAGGTTTTGCAG
TTTGCCTCTTTAAGCTTTGATGCTTCGGTGGGTGATATCTTCCACAGCCTATTAACGGGAGCTACCTTGCATCTTGTAAA
AAAAGAGCAATTGCTATCCGGACACGCCTTTATGGAGTGGTTAGACGAAGCTGGCATTACGACTATTCCGTTTATTCCAC
CAAGCGTCCTAAAAGAATTACCATATGCAAAACTGCCTAAGCTCAAAACAATCAGTACTGGCGGGGAAGAATTACCGGCT
GATTTAGTAAGGATTTGGGGAGCAAACCGCACATTTTTAAATGCATATGGTCCGACAGAAACGACGGTTGATGCTTCGAT
TGGTAATTGTGTAGAGATGACGGATAAGCCTTCGATTGGTACGCCAACCGTTAATAAGCGAGCGTATATTTTGGATCAAT
ACGGTCATATTCAGCCAATCGGTGTTCCCGGGGAATTATGCGTAGGTGGAGAAGGCGTAGCTCGTGGATATTTACATAGA
CCTGAGCTTACAGATGAAAAGTTCGTGAACGATCCTTATGTACCAAACGGGAGAATGTATAAAACGGGAGACTTAGCTAG
ATGGTTGCCGGATGGAACAATCGAATTTTTAGGCCGTATGGATGGCCAAGTAAAAATTCGTGGATTTAGGATTGAGCTTG
GAGAAATTGAAGCTCGGCTAAACCAAGCCCCATCTGTAAAGCAAGCTGTGGTTCTAGCTCGTTCAGGAGAACAAAAGCAG
GTATACCTATGCGCATATTTGGTGACGGACAACGATTTAAAGGTTTCTGCCCTACGTAAGGAATTAAGTCAAACGTTACC
AGACTATATGATTCCATCGTTTTTTATAAAAGTCGAAAAGATTCCAGTCACAGTAAACGGCAAGATAGACAAGAAAGCCT
TGCCAGAACCAGAAAAGAAGTAGAGCTGCAAACCGAATATGTAGCTCCAACGAACCCAACAGAGGAGATTCTTGTACAG
ATTTGGCAAAAGGTGCTGGGAATGGAGCGAGTAGGGATAGAGGATAACTTCTTTGAGCTAGGTGGTCACTCTATCAAGGC
AATGATGCTTGCTTCCAATATTTATAAGGAATTAAAGATTGATCTGCCTTTGCGTGAGATTTTTAAGCATACGACAGTAA
AAGAAATGGCGCGTTTTATCGACGGTCGGGATGAGGAAGAATACGTCGGAATTCAACCCGCAGCCAAACAAGAATACTAC
CCTGTCTCTTCTGCACAAAAAGGATGTATGTCATTCAATCATTGGAAGATAAGGCTCAAGGCACGAGCTATAATATGCC
GTCTTTCTATAAAATGAAGGGCTCGGTAGATGCAGAGAAATTAGAGAAGGTATTCCAAACATTATTGGATCGGCACGAAT
CATTACGAACCTCCTTTCATATGATCGAGGAGCAGCTAGTTCAAAAGGTTCACGAACAGGTTTCATGGAAAATGGACATG
AAAACCGTCAGCGCCAATGATGTTTCAAGATTAAAGGATTCGTTTGTCCAACCGTTTGACATCAGTACAGCTCCTTTGTT
CCGAGCCAGTCTTCTTACGATTCATAAAGATGAGCACATTCTTATGATGGATGTACACCATATTGTAGGAGACGGTGTTT
CGACCACGATCTTGTTCCAGGAGCTTATCCAGTTGTATCAAGGGCAAGCGCTACCTGAAGTGAAGGTACACTATAAAGAT
TACGCTGTGTGGCAATTGTCCCAGCAGGATCGTTTGAAAGAAAGTGAAAATTTCTGGTTGCAGCAATTTTCTGGAGAGTT
GCCGGTGTTGGAGCTACCTACTGATTATTCTCGTCCCCAATTCGCCGATTGGAAGGAGAATATGTAAGCCAAAGCCTAC
GTGGTGATCTCCATGAAAGCGTAAAAGCCTTCATGAAAAATCACGAAGTAACGCTATATATGGTACTGCTTGCACATAT
AACGTTCTTCTGCACAAATACACGAATCAGCACGACATTATTGTTGGTACGCCTGTTTCGGACCGACCGCATCCAGATGT
CATGTCCACTGTCGGTATGTTTGTAAATACGCTGGCAGTCCGAAATCAGTTGGAGTCTGAGCAAACCTTCGAAAAGTTTT
TAGCAAATGTGAAAAATAAAATGCTAGAGGTCTATGGTCATCAGGAGTATCCGTTTGAAGATGTAATTGAAAAAGTAAAG
GTTCAAAGGGATACAAGCAGACATCCGCTATTTGACACAATGTTTGGTGTACAAAATCTGGAGATATCCCACGTGGAGCT
ACCCGATTGGGGTATAGAAGCATTGGATATTGACTGGACTAACTCCAAGTTTGATATGAGCTGGATGGTATTTGAAGCAG
ACGGTCTAGAAATTGGCGTGGAGTATAGCACAAGCCTATTTGAGCGCAATACGATTCAGCGAATGATCGGACACTTTGAA
CATATCATCGAGCAGATTATGGAAAATCCTCAAATTCGTTTAGCTGATATTCAGTTGACGACAGAAGATGAGAGAATCCA
AATCTTAGAGGAATTCAATCATCAACCAACAAAAATAACCTACGATCAGGCAATCCAAAACAGATTTGAAGAACAGGCTA
TGAAGCACCTGATGCAGTGGCACTTGTATATAAAGGTCAGGAGTTAACCTATCGTGAGCTTAACCAAAGATCAAATCAG
ATGGCTCGTACATTAAGAGAGCATGGGGTCGGGCGTGATCAAATAATTGCGGTCATGATTAATCGTTCACATGAGCTGAT
CATTAGTATCCTAGCCGTATTAAAGGCAGGAGGAGCATACCTGCCAATTGATCCAACGTACCCGCTTGATCGGATTGAAC
ACATGCTAGAGGATAGCCAGACTGCAATGCTGTTAACTCAAAAAGAAATCCAAATACCTACAGGATATTCAGGGGAAGTT
CTCTTCGTTGATCAAGCTGATATTTATCATGAGGATGCTACGGATTTATCTAGTATGAATCAGCCTGCGGATTTGGCCTA
TATTATTTACACATCAGGCTCTACTGGAAAGTCCAAGGGAGTAATGATCGAGCATCGTTCATTACATAATCTGATTCATA
TTTCTCACCCCTATAAAATGGGAGCAGGAAGCAGAGTCCTTCAATTTGCCTCTAGCAGCTTTGATGCCTCGGTAGCAGAG
ATCTTTCCAGCTCTTTTAACTGGATCAACTTTTATATATAGAAGAGAAAGAGGAGCTATTAACCAATTTAGTTCCCTACTT
ACTTGAGAATCAAATAACAACAGTAGCATTGCCGCCATCTTTATTAAGATCCGTTCCTTATAGGGAACTGCCAGCTTTAG
AGTGCATAGTTAGTGTCGGAGAAGCTTGCACATTTGACATTGTACAAACTTGGGGCAAAACCGCACCTTTATAAACGGA
TACGGCCCTACAGAATCAACTGTTTGCAGTGCCTTTGGTGTGGTTACAGCAGAGGACAAGCGTATCACGATTGGTAAACC
GTTCCCTAATCAAAAGGTCTATATCATCAATGAAAATCAACAGCTACAACCAATCGGGGTTCCAGGTGAGCTTTGCATAG
CAGGGGCTGGATTAAGCCGTGGGTACTTGAATCGTCCAGAGCTGACACAGGAAAATTTGTAAACAACCCCTTTGCACCT
GGTGAGCGTATGTATAAAACAGGAGACGTAGCTCGCTGGTTGCCTGATGGCAATATCGAATATGCCGGTCGTATGGATGA
TCAGGTTAAAGTACGCGGAAATCGGGTCGAGCTTGGGGAGGTTACCAGCCAATTACTTACGCATCCTTCGATTACAGAAG
CTGTTGTTGTACCAATAGTCGATACACATGGAGCAACGACACTATGCGCCTATTTCATCGAGGATAAAGAAGTGAAGGTC
AACGATTTGCGCCATCATTTGGCTAAAGCTCTACCTGAGTTTATGATTCCTACTTACTTTATTAAAGTAGATCATATTCC
ATTGCACGGAAACGGAAAGGTAAATAAACAAGCATTACCTGACCCTTCCGAATTCATTTCAGCACAAACAGGCCATGAAA
TCGTTGCCCCTTCTTCTCAGGACGAGGAAATACTGGTTCAGGTATGGGAAGAAGTCCTGCAGTTCAAACCGATTGGGGTA
GAGGACAACTTCTTTGAACGAGGCGGAGACTCCATTAAGGCATTGCAAATCGTAGCTAGACTTAGTAAATATAATCGGAA
ATTGGATAGTAGACATATTTTTAAAAATCCAACGATTTCCATGCTGGCTCCTTACCTTGAACAAAGAGGTGCTTTGATTG
```

FIGURE 3E-10

```
AACAAGATTCAATTGAAGGCGAAGTGCCGCTTACACCGATTCAATCCTGGTTCTTTGAACAACCCTTTGTGTATCCACAC
CACTTTAATCAATCTATGCTTCTACCAAATGAACAAGGCTGGGATCGTCAACGAATAGAACAAGCATTTACAACCATTGT
TAGACACCATGATGCCTTAAGAATGAAGTACCAGTTTAGAGAGAAGATCATTCAAGAAAATCAGGGTATCGAGGGAGAGT
TTTTTACCCTGCATGAGGTGGATGTAACCAAGGAAAGAGACTGGCAAATGCGCATCGAACAAGAAGCGAATCAACTCCAA
GCAAGCTTTGATTTGACAACAGGCCCTCTTGTAAAGCTTGGCTTATACCATACGGCATATGGCGATTATCTTCTGATTGT
TGTACATCATCTCTTAATTGATGGTGTCTCATGGCGCATCCTGCTGGAGGATTTCCAGACGCTTTATGAGCAAAAGGGTG
AGTTGCCAGCGAAAACCACTTCCTTTAAGGCGTGGGCTGTACAACTGGAGGGGTATGCTCGCAGCAAAAAGCTACAAGAC
GAGGCAAGCTACTGGAAAGGGTTGTTGAATAAATCGATAAGAGAGCTGCCTGCGGATAAGGAATCAAGCGATACATTCCT
CTTTGGAGATACAAAAGAAGTACAGCTTACCTTTGATATAAATGAAACCCAAGACCTGCTTACGGATGCCCACCATGCTT
ATAAGACAAAAGCGGATGATTTATTGCTGGCAGCGTTGGTTCTTAGCATAAATGAGTGGACGAAGCAAAGCGATATCATA
GTGAATTTGGAAGGTCATGGCCGTGAGACGATCGGCGAAGGCATTGATTTGAGCCGTACAATTGGCTGGTTTACTACAAT
TTATCCAGTTCTGTTTGAAGTAGAGAACCATCAACTTTCCAGCGTGATTAAACATGTAAAAGAAACGCTGCGCAATGTAC
CGAATAATGGTATTGGTTTTGGGATCTTACAACACATGTCTCATTCTGATGTAAGCCAGAGCCAATTAAGTTCTCATCAC
ATAAGCTTCAACTACCTAGGTCAGATGGGAGAAGATTCCGCTAGTCAGTCTGAGACGGATAATGGAGTCCTTATCAATAC
AGGAGACCAGATAAGCCCAATGAACGCAAATCCGGGCTCGCTTAATATGACTTGCCTTGTAATGAATAATACGTTGCTTG
TTACTTTTGATTATAATCCGCAACGTTACGAACAGGAGACAATTCAACGTCTGGCAGATCGTTATAAGAGCAATTTAAAA
GCAGTCCTCGATCATTGTGTTCAACGAGAGCAGACAGAGCGAACACCTAGTGATTTTAGTACGAAGAAGCTTTCTTTAGA
GGACTTAGACGACGTGTTTGCAACACTTAAAAATCTATAAAGGTATCCTGAGGAGGAGAAGATTAACTTGATTAATACCT
CAGACGTCAAAGACATTTATAGTTTATCCCCGATGCAACGAGGAATGTTATTTCATACATTAAAAGACAAAGAAAACCTT
GCCTATTTTGATCAGACAACTTTTCAAATAGAAGGTGACATATGTGTCGAATCCCTTGAGAAAAGTTTTAACGAGCTGAT
TCGCAAGTATGATGTTCTGCGTACGATCTTTTTATATCAGAAATTAAAAGAGCCGATGCAGGTTGTGTTAAAGGAGAGAA
CAGCAAACATTCATTATGAGGATTTCTCTATGAAGAGCGAGTCGGATAAAGCAAAGGCTCTTCGTGTAGCAAAACAGAGG
GACCGGGACGAGGGCTTTGACCTCTCCCGGGACATCCTCATGCGGTTATCTTTATTAAAAGTCGCCCCTAACCAATACGA
ATTAGTGATCAGTAGCCACCATATTATCATTGATGGATGGTGTACAGGAATTTTGTATCAGGAGCTGTTTTATTTTTATC
AATGCTTCGTAGCAAATCAACCTATCCCTGCTGAGAAATCGATTCCGTATAGCAGATATATTCGTTGGCTTGAAGAACAG
GATGAAGAGGAAGGAAAAGCCTATTGGGGTGAATATCTACAAGATTTCGAGGGGGCATCTGTTATCCCTAAGCAAAACGC
TAAGGGAGAGAAGGAAGTATGCTCCATTGATAAGGTAACCTTCCACTTTGATAAAAAGCTGACGGAGGAACTGGTGCAGG
TAGCAAAAACTTGCCAAGTAACAATAAGTACCTTGTTTCAAACAATGTGGGGCATCCTGCTCCAAAAGTATAATAACTCG
CAGGAAGCTATATTTGGATCGGTTATTTCAGGAAGATCACCAGAGATTCCTGATGTGGAAAAAATAGTTGGAATTTTTAT
TAATACCATTCCTGTTCGCATTCGTACATTGGACAAGCAAACCTTCAAGGAATTGCTGATCCAGGTTCAGGAGGCATCTG
TCAACTCTGAAAAATATAATTATCTAACATTGGCTGATATTCAAGCGGTTACCGGATCGAATCATGCACTTATCCATCAT
ATTGTGGCATTTGAAAATTTCCCGATTGCCTCGGACAGCTTCGTAGATTCGAGCGATTCCGATTCAGAAGAATTGAAAGT
TGTGAACGTCATAGACGATCATGAAAAGACCAACTTTGATTTAGTGTGCAAGTTCAGCTTGATACAGAGTTACTAGTAA
AAATCTCTTATAATCAACATCTTTATCATAGAAGCTTTATTGAAAATATCTTTCATCACCTGCAACAGATTGCCGGGTCT
ATCACTCATAACCCAGATATTCAAATAAATGAGATAGCTATTGTTTCTAAGGAAGAGAGAGGCAACTATTACGTCTATTC
CACTCCAGCCAAGTCAGATTTTCCAATGGATAAAACCATTCATCAGCTATTTGAGGAGCAGGTATCACGGACACCAGAGC
AGATGCGCGGTCGTTTTTAAAGGGGAGTCCTTCACCTATCGCGAGTTAAATGAAAAGGCAAATCAATTGGCATGGGTGCTA
AGAAAACGGGAGGTAAGACCTAACGAGATCGTTGCGATCATGGCAGAGCACTCTCTAGAGATGCTGGTTGGGGTGATTGG
GACTTTAAAGGCAGGTGCGGCCTATCTTCCTATTGACCCATCCTACCCAGAAAAAGAATCGCTCATATGCTACAAGATA
GCAAAGCGGAGCAACTACTTATCCAGCCTCATTTGAATATGCCACAGGACTTTAAGGGAAGTGTCTTATGGTTAACAGAA
GAGAGCTGGCGAAGGAGAGTACGACCGATCTGCCGCTTGCAACGAGTGCAAATGATCTAGCATACATGATTTATACCTC
AGGCTCAACAGGACTGCCGAAGGGAGTTATGGTTGAGCATCAAGCCTTGGTTAATTTAGTTATGTGGCATAACGAGGCAT
TTGGCGTAACCATGACTGATCAATGCACGAAATTGGCGGGATTTGGATTCGATGCGTCGGTGTGGGAGACCTTCCCTCCG
CTTATACAGGGAGCGACGCTTCATGTGTTAGAGGAATCGAGACGTGGAGATATTTATGCTCTGCATGAATACTTTGAAAA
GAATGCGATCACCATTAGCTTCTTGCCTACTCAATTAGCCGAACAATTTATGGAGCTTACAAGCAGTACATTACGTGTGT
TACTCATTGGCGGTGACCGAGCCCAAAAGGTTAAAGAGACATCGTATCAAATCATAAACAACTACGGTCCAACCGAAAAT
ACAGTAGTCACGACGAGCGGTCAACTGCATCCTGAGCAGGATGTCTTCCCTATTGGAAAGCCGATCACCAATCACAGCGT
TTATATTTTAGATCAGAACAGACATCTACAGCCGATCGGAATACCTGGCGAGCTGTGCGTCAGTGGTGCAGGGCTTGCTA
GAGGCTACCTTAATCAGCCTGAACTCACCGTAGAACGCTTTGTTGATAATCCCTTTGTACCTGGAGAGAGAATGTATCGC
ACAGGGGACTTAGTTCGTTGGAGAATCGATGGTAGCATCGAATATCTGGGAAGGATTGACGAGCAAGTCAAGATTCGAGG
ATACAGAATTGAGTTAGGTGAGATCGAAACAAAGCTTCTTGAGCATCCTTCCATTAGTGAGGCGCTCGTCGTGGCTCGAA
ATGACGAGCAAGGTTATACCTATCTATGCGCTTATGTGGTAGCAACTGGGGCCTGGAGCGTATCTTCATTACGTGAGCAT
TTAATCGAAACATTGCCCGAATATATGATTCCAGCTTACATGATGGAAGTGGAAAAAATGCCGCTTACTGCAAACGGAAA
GATAGATAAGCGAGCGTTACCAGTGCCTGATAGGCAAAGAATGAACGAATATGTGGCACCTGCAACAGAGACAGAGGAAA
AGCTAGTTCTACTGTTCCAAGAGATTTTAGGACTTGAGCGTATTGGTACTAAAGATCACTTCTTTGAATTAGGGGACAT
TCGCTGAAGGCGATGATGCTTGTGTCTCGTATGCACAAGGAGCTAGGTGTGGATGTGCAGTTAAATGAGATGTTTGCTCG
```

FIGURE 3E-11

```
TCCAACGGTTAAAGATCTATCTGCTTACATAGATCAGATGAACGGCTCTGCTTACACAGCAATTCAACCAGTGGAGGAAC
AGCCTTATTATCCTGTTTCTTTTGCCCAAAGAAGAATGTATGTTGTACAGCAAATGAGAGATAGTGAAACGACGAGCTAT
AACATGCCGTTTACGTTTGAGCTAAAAGGAAAGCTACATCTGGACAAGCTGCGAGAAGCGTTACAGATTCTGGTTCTACG
ACATGAAAGTCTGCGTACATCCTTTCATATGATTGATGAAAATCTTGTTCAAAAAGTGAATAAAGATATTTCATGGGATT
TAGAAGTAATAGAAGCTCAGGAGTCAGGAGATAGAAGTAAAACTGGAGGAATTTATCAGACCGTTCCATTTAAGTGAGGCT
CCGCTTTTCAGAGCTCGTTTAATTTGCTTGAATCCACAGCATCATCTTTTGAGCTTAGACATGCATCATATTATTTCAGA
TGGAGTATCTATGAACCTGTTCCTACAGGAATTCATGACACTCTATCAGGGAGAAGCATTGCCAGCGCTCTCTATTCAAT
ACAAGGATTACGCCGTATGGCAACAATCAGACAAGCAGCGAGCTAGATTAAAAGAGCAGGAAAAATATTGGTTACATCAT
TTTTCTGGAGAGCTGCCTACCTTAGAATTGCCAACAGATTTTCCACGCCCTGCAATACAGCAATTTGATGGAGATGAATG
GGCGTTTGAAATGAATGCTGATCTTTTAGCGAAGGTCAAACAGATCTGCTCTAGCCAAGGCACGACGTTATATATGACGC
TTCTCGCTGCTTATCAGGTGTTCTTAGCCAGATATACCGGGCAGGAGGATATCATTGTAGGTTCTCCAATTGCTGGACGT
TCTCATGCTGATTTGGAAAACATGATAGGTATGTTTGTCAATACATTAGCTTTGCGCGGTAAGCCAAAGGCAGATCAATC
CTTCCTCTCCTATTTAAAACAGGTAAAAGAGACCGTATTCCAAGCATACGCGAACGCAGAATATCCATTTGAAGAGTTGA
TTGAGAAACTCGATTTAGAACGAGATATGAGCCGTCATCCGCTATTTGATACCTTGTTCTCTTTGCAAAATATGGAAATA
TCTGAGTTCCAAATGAATAATCTAGAGATTTTTCCTTATGAAACGGGACAAAAGAATGCAAAATTCGCTCTTAGCTGGTT
AATAGCAGAAGGAGAGTCCCTTTATGTAACAATCGAATACAGCACCAAATGCTTTAAGCGAGAAACCATTAAACGCATGG
CAAGTCATTTTGAACAACTGCTAGCCCAAATTGTTGAGCAACCGGAAGCGCGCATTGGCCAACTGGAGTTAGTAGCAGAT
GCCGAAAGAAAAATGTTACTGGAAGACTTTAATCTGACAAAAGTCGACTATCCACGGGAAAAACAATTCAAGAATTATT
TGAAGAGCAGGTGGACAAAAACCCTGATCAAATCGCGCTTATATGTGGAGAGCAACAGTTTACCTACGAACAATTAAATG
TGAAATTTAACCAATTAGCTCACGTATTAAGAAGAGAAGGCGTTCAACCCAATCAGGTAATAGGGCTAATTACGGATCGA
TCGCTGTCGATGATTGTAGGTATTTTTGGAATTATAAAAGCAGGTGGGGGCTATCTGCCAATCGATCCGACCTATCCTAC
CGAAAGAATTGAATACATGCTTGAAGATAGTCAAACTCACCTATTGTTGGTACAACACAGAGACATGGTTCCAGCAGGTT
ATCAGGGAGAGGTTTTGATAATAGAGGATGAGATAAGTCGAGATGAACAAGTAGCTAACATAGAATTGATCAATCAGCCG
CAAGACTTGGCTTATGTCATGTACACATCTGGCTCTACAGGTAAACCAAAGGGGAACCTGACTACTCATCGAAACATTAT
CAAAACGGTATGCAATAACGGATATATTGAGATAACGACTGAGGATCGTCTTTTGCAGTTATCTAATTATGCTTTTGACG
GCTCTACCTTTGATATATTCAGCTCGTTATTACACGGAGCAACGCTGGTACTGGTACCAAAAGAAGTGATCTTGAATCCA
ACAGACTTGATTACATTGATACGCGAACAGCAGATCACTGTATCGTTTATGACTACCTCATTGTTTAATGCATTAGTGGA
ACTGGATGTAAGCAGTTTCCAAAACATGCGCAAGATCGCATTTGGAGGAGAAAAGGCTTCCTTTAAGCATGTGGAAAAGG
CATTGGATTTCCTCGGAAATGGACGATTGGTGAATGGATATGGTCCCACAGAAACAACCGTTTTTGCTACAACCTACACT
GTGGATGAGCGCATAAAGGAATGGGGGATTATACCGATTGGTCGACCGCTACATAATACTACGGTCCACATTTTAAGCGC
TGATGACAAGCTACAGCCAATTGGAGTCATTGGAGAACTGTGCGTAAGCGGTGAAGGATTGGCACGCGGTTACCTTAATC
TACCAGAGTTGACGATGGAGCGATTTGTTGAAAATCCATTTAGACCTGGTGAAGAATGTACCGCACAGGGGACTTGGCT
CGTTGGTTACCGGATGGGGTTCTTGAATATGTAGGACGCAAGGATGAACAAGTGAAAATTCGCGGACATCGCATTGAGCT
TAGTGAAATTGAAACAAGGATATTGGAGCATCCTGCGATCAGTGAAACGGTTCTGCTAGCCAAGCGAAATGAGCAAGGCA
GCTCATACCTGTGCGCTTATATTGTTGCCCATGGCCAATGGAATATCCAAGAATTGCGCAAACATGTAAGAGATGTTTTG
CCAGAACACATGGTGCCTTCTTATTTTATTGGCTTAGACAAACTTCCACTTACCTCCAATGGTAAAGTCGACAAACGAGC
ATTGCCAGAACCAGAGGGCAGCCTGCAACTGACTAGGAGAATTGTTGCTCCACGCAATGAATCTGAAAAACAGTTAGTTG
AAATTGTTGCTGAGGTTCTGGGACTAGAAGCTAGTGAAATAAGTATTACCGATAATCTTTTTGAGCTAGGTGGACATTCC
CTAACGATTCTGAGAATCCTTGCTAAGGTTCATACATGTAACTGGAAGCTTGAAATGAAAGACTTCTATAATTGCAAGAA
CCTTGAGGAAATAGCAAGCAAGGCAACTGATATGCAGGAAAATCAAATCTGTCTGGCAGTGGCTCAGTCTTTAAAAAGG
GTGGGAAGAAATCAATCCCGGTAGTACCCGTCCACGATAGACAAAAAGAAATGGAGCATGTTTTATTGCTCGGCTCCACT
GGTTTCTTAGGTATTCATTTGCTACATGAGCTGCTACAGAAAACAGAAGCGACAATTCTTTGCGTCATTCGTGCAGAAAA
TGATGAGGCTGCTATGCAACGACTACGCAAAAAAATTGATTTTTACTTTACCTCACAGTACAGTAGCTCTCAAATTGATG
AGTGGTTTACCCGCATCCAAATCATTCACGGTGATATTACGCAAGCCAACTTTGGATTAGAGGCAAAACATTACGAGTCG
CTAGGAGCTATCGTTGACACTGTCATTCATACGGCTGCATTGGTGAAGCACTACGGGCACTATGAAGAGTTTGAAAGAGC
AAATGTACATGGAACTCAGCAAGTAGTTACCTTTTGCTTGAACAATAAATTACCAATGCACTATGTTTCAACCCTGAGCG
TTTCGGGAACCACCGTTGAAGAAGCAACAGAGCTTGTAGAATTTACCGAGAAGGACTTTTATGTTGGTCAAAACTATGAG
TCAAATGTATATCTGAGAAGTAAATTTGAAGCCGAAGCCGTACTTGTTGGCGGAATGGAAAACGGACTCGATGCACGTAT
CTACCGGGTTGGCAATTTAACAGGACGCTTTCAGGATGGATGGTTCCAGGAAAATATCAATGAAATATGTTTTATCTCC
TATCGAAAGCCTTCCTTGAGCTTGGAGGTTTTGATCAGGAAATTATGCAGGGTATGGTTGATTTAACCCCTATTGATATA
TGTGCACAAGCTATTATACACATCATCAACAGCAAAGGAATTGAGGAAAGAGTCTTCCATTTACGAATCCGCACTTGGT
AACATACGATGATATGTATCGTGTATTTGAAGGGCTTGGCTTTTCTAGACGGGTACAAAGTCGAGAAGATGTTACACGTG
AACTAGATGTAATGATGTCTCAGGGTAATGAAAAGCTATTTTTGGCTGGGATTCTGACCA
CGATGTTGGATGATGTAGAGCGTGCTGAACAATTTAATGTTGCAGTCGATTCAAGTAGGACAATGCAGCTATTAGAGGAT
ACCTCGTTTACCTATCCTGTTCCTGATGATGAGTATTTGCGCAAGCTGGCTATGCATATGATCAAAGTTGGGTTTGTTAC
TCCTAATCATACTGTTGCTGAAAGATAGGAACTAGTCGTTAGCGCTATGCTAGCGACTGGTTCCCAACCTAAATGAATA
```

FIGURE 3E-12

```
GCTAAAGGAAGGAGAGGGAACCCATGGCAGTCATTGAACTAAAAAACCTTACGAAAAAGTATAATGAGGTCTATGCTGTT
GATCATCTAAATATAGAAGTACCTCAAGGACATATTTATGCGTTTTTAGGTAGCAATGGGGCGGGAAAGACAACCACAAT
TAAAATGATGACGGGCCAATTGAACCCTTCAGAGGGAGAGGTTCTATTTCTAGGGCGCAATATTTGGCAGGATCGTGAGG
CAAGAAGAATTGCGGGCTATGCTCCAGACGTTCCACTTCTTCATGAAGGATTGACAGTCAGAGAAATGGTACGCTTTGTG
GGGGCTCTTTATGGTAGTGACGAAGATCTGAATAAACGTGTTGACACGTTGTTAGAACATTTTGAGCTGGCAGATAAAGC
AGACCAGCTTATTAAAGAATACTCATTAGGAATGAAACGAAAGGTTTCGATTGCTTGCGCATTGATTCATCGCCCCAAAA
TCTTGCTATTAGACGAAGTTACGAATGGGTTGGACCCAAAGGCGACCCGTGAAGTGAAAAATTATATTCGACATTTTGCC
AAAGAAGAGGGTGGTACTGTTTTTATTACGACCCATATTTTGGACATTGTTGAAGAATTAGCCGATACCATTTCCATCCT
GCATAAAGGAAAAATCAAAGTGACGGGAAGCATGGAAGAATTGCGTCATGTGGCAGGCAATGAAGAAGGTCGATTGGAAG
ATATCTTTTTATCCGCTATCGAGTAGTAGGAGGTGACAGAATTGTATGTGGGCACAAACGAAATGGATTAGTTTCTTTTA
CACAAGACCCTTCTTTAATCGCTTTTTTATCCATAGTCCTTCTAAATGGATCATTTATGTGGGCTTGGGAACCATTGCTA
TTGCCATGTACTTTTCGGAGAATTTTGGGCAGCTTCTCTTACATGCCAGTCTCAGTGCTAGATTGATGCTTCTCATAGGG
GAATGTATTTTGTCGGTTTGCTTCGTGGCATGAATACGTTGACACAACAAATGTACGCTGATCGATTACTGACATTGTT
TTATGTATCGGGAGTTTCTCCGTTTCGGATGATCCTTGGGCAATCTACTTCAAGTCTACCTCTGTACACGTGGTCATCCA
TTATGATTGCTATTCCATTAACGATTGGCTATTCCGCCATGGAAAGAGTTCTGTATGTTTTGTTATTCCTAGTCGTTTCT
CTATTGATGATTTGGTTAACAGACATCTTAAGCCGATTTTTAATGGTTCTGACCATGCGGTTTTTCCCTATTATTGTCAA
AACATTCGTAGGTATCTCCTCGCTTGCCTATGTTGCTTTAATTGGCCTATTGGTTTGGGCATTGATTGAGGTTGAAACAA
TTTCTCCAGAAGCTTGGCAGAGCTTAGAGCGTTTTATGGTATATGTTTTGTGCATTTTCGCGGTCGGTCTTGGAGCGTTG
TTTCTATTCTCTGAACAAATTGGAGGGTTTTATTACGAAAGCTGGCTGAACCATGCGGAGTCGCAAGATAGGACCAGACC
AGAAACACAGGAAAATCTATCGAATTTGGTCAAAAACGCTCATGATGCCATCGTTTTT
```

FIGURE 3F

MDLSTLNFLGETEKHKLLNQFNDTDANFPQEMTIHGLFEKQVQERPNQTA
VIFNEQSMTYKEMNERANQVAHSLRKHGAAPDEIVGILADRNMDMLISIL
GVLKAGAAYMPIDPTYPTERILYMIHDSQTKIVLAEHREMVPEGCNAELI
LLHDSSLLNEETSDLEHVNKPEDLAYIIYTSGSTGKPKGVMIEHRNVIRL
LFNDRNLFDFTSDDVWTVFHSFCFDFSVWEMYGALLYGGKIVLVSFEIAR
DPQAFRDLLQEQKVTILNQTPTAFYQLSSQEMQHSDSNLSIRKIIFGGEA
LTPSQLKAWKQKYPNTALINMYGITETTVHVTYKEFQLHDMDSTVSNIGK
PIPTLRTYVLDSKRNLAPIGVKGELYVSGKGVARGYLNKPELTEERFMDN
PFVAGERMYRTGDLARWLPEGELEYLGRIDHQVKIRGYRIELGEIEAELL
KQKGIKEAVVLVTNDKDAQPQLHAYLTSKEDLAAADLRNQLTTTLPSYMI
PAHFIFVSQMPVTPNGKIDKESLRKIEPSLQESPTEAYVAPQTPTEKQLV
HIWEENIGMQPISIDDNYFALGGDSIKAIKLLHAINKEFQISFQIGDLYK
HGTIREMGQQIGEKGKQSSNQKLLKLQELDRLKEKILGSEK

FIGURE 3G

MSDKLSNAKDLFPMSDIQLGMVYHSLKHVHEAVYHDQFVYQVDDDSFDVH
VLEQAMRMMVDKHDILKTSFHIEEFSTPVQVVHQEVSVRIDETDITHLGE
KQKEYIHQYLAQDRQSPFDVTTAPLWRMSVFKLNASQVALVWIFHHAILD
GWSVASFITELIDVYFKLKHKTCTLEHLNTTYKDYVIDQMLLSEQNELRE
YWKEELKDYKRLQLPVKVDENGGVHVTVVEKLDPDIINKCREIAQAHHIP
LKTVCLTAFLSMMHMISYERDLTVGLIENNRPIIEDAEKVLGCFLNSVPF
RAIIKKDMSYRELLEQTQQKLVEIKTYGRLSFAKIIEVIGDTGSERNPVF
DCLFNFVDFHVFKGIKDHKVKFWLDGYEKTNTMFDFSVSTTMDDYFVRVV
SALPEEDTIKLINYYQRILEKIALHIDEKIDKQANLDEKESHLLLEEWNQ
TSVDYPDKQTLHKRFEEQVAKNEDQVALEYEDKQLTYRELNAKANQLARV
LQKHNTLPTQVVGLMAERSLEMIIGILGILKAGGAYMPIDPTYPAERIQY
MLEDSRSYLLLVQKAEMIPANYQGEVLILTEELWADENTENLELVNQPQD
VANIMYTSGTTGKPKGILITHRNIMTTIINNGYLDIFSTDRILQISNYAF
DGSTFDIYSALLNGATLVLVPKQTLMNTTDLLAIIKDSNITVALMTTSLF
NTLVDLDVTSFQHTRKVLFGGEKASCKHVEKALDYLGEGRLVNGYGPTET
TVFATTYTVDNTIKKLGSIPIGRPLSNTSVYIFGLDDQLQPLGVPGELCV
AGECISPGYLNRPDLTADKFIDNPLKPGERMYRTGDLVRWLPEGVMEYMG
RIDEQVKIRGHRIELGEIEAKLLEHPSIRETVLVAKQDANGHSFLGAYLV
TDNFCPVTELRNYLMETLPEYMVPSYFIELDSLPLTSNGKVDKRALPEPE
SQALHAYTMPENETEEKLVQLFQEVMDVERVGTQDSFYELGGHSLKAMLL
VSRIHKDFGIKIPLKEVFSRPTVKELAAYLTGSEEANYIEIEAAEEKPYY
PVTAAQKRMYIAQQWEDGEATSSYHMPFMMEITGPLQVEKLQQTVKSLVA
RHESLRTSFHMINEVLMQKIHADVLWDLDIDLESVVASEQEIDEKMFQFL
RKFDLSQAPLFRAKLIRVNASRHVLLLDMHHIISDGFSYQIFFDELTKLY
QGDELPSLKIQYKDYAVWQHSEEQQKRLQQQEDYWLGQFQGEIPVLELPT
DYQRPVDKQFAGALFTHGLSAGLTEKLRKLAIKEKTTLYTVLLTVYNILL
SKYTSQEDLIVGTPIAGRPHADLDRVFGMFVNTLAIRTAPKVEHSFLTYL
SEVKETVLGAYQNPDYPFEELVEKTLVQRDVSRNPLFDVMFSVEKLPSAV
QFDDLRFCPRLFDWKKAKFDLDWTVVEGESLEVLVEYSTSLFDRATIERM
AKHFEHILEQILDQPDLSISEIELLTEAEKQQILIEFNQSDKSFDSEKTI
QEQFEEWAEKAPHSIALVFKDKQMTYQELNQRANQVAHLLRGNGISANDF
IGLMVDRSFEMIISMLGILKAGGAYLPIDPDYPEDRIDYMLSDSKAKILL
KQSDQTAPASFEGKVIAIDTPELLEMDIENIPKVNNSSDLAYIIYTSGST
GKPKGVLINHRCVINMQLTAETFGIYPSSRILQFASFSFDSSVGEIFYTL
LNGACLYLVEKDLLLSGNEFVAWLKKNRISSIPFISPSALRMLPYEDLPD
LAYISTGGETLPADLVKAWGENRVFLNAYGPTETTVDATVGVCTPEGKPH
IGRPVTNKKVYVVNSNNQLQPIGVPGELCIGGEGVALGYLNRPDLTQEKF
VSNPFAPGERMYRSGDLVRWLPDGTIEYFGRLDDQVKIRGHRIELGEIET
RLLEHPSIKEAIVIPRSDESEATYLCSYLIAEGSWNAADLRKYLKASLPE
YMIPSYFVELHELPLTPNGKVNKKALPKPEKQMQRGKDYVAPTNPIQSIL
SQIWTDVLGVENIGIHDNFFELGGDSIKAIQISARLNKHNLKVKMRELFK
NPTIAELSLLVQQIVQEIDQGVVEGNIPLTPIQHWFFTQSFPQVNHYNQS
VLLFNAEGWDEQKVDKAFEMLTQHHDALRIVYSLDEQGVVQRNRGLEGSN
YHFEIIDARQDGEDQSNWKAAANRMQASMDIVEGPLVQIGLFRANEGAYL
LIAIHHLVVDGVSWRILLEDFYHLYNGNDSLPLKTTSFQAWSQKLQEYAQ
SKELEHELSYWRHLDEAITDYTLHKDIEAATSNKTTYEEFLTVSMSLSTE
ETQQLVTEAHKAYQTEINDLLLTALALALKEWTNKEQLLVSMEGHGREEI
LDNVDISRTVGWFTSEYPVAIHLTKTDISFAIKQVKETLRRVPNKGFGYG
ILKYLAKETFKLKPEISFNYLGQFTDKEEGNSSLMGDLISPANTSELSLD
INGSIEADRLQMHFSYNSRAYYPETIATLVQNFKSYLLEIINHCRAKEGV
EHTPSDFDINDLTMEELDDIFDDLEEEVYK

FIGURE 3H-1

MFSRSNVQNLYRLSPMQKGILFHSLKDKENHAYFDQLIFTLEGKVELEYL
EEAFTQLIKKHDILRTVFRYKKVKEPVQMVLKERSSTIYFEDISHLEPEE
KVNYIKQFKMRDREKGFDLSRDLLIRMSLFKLDQEQYQLIMSNHHIIMDG
WCLGIILTDFLRMYKGIVNHTPVPYEHVTPYSKHIQWLEKQDHQEAKDFY
QQLLEGYDKVTGVPQQLVRANHEEYTHGQCIVKLNQETADRLIAIAKAYQ
VTVNTVFQTIWGILLQKYNNTDDIVFGSVVSGRPAEIPDVEKMVGLFINT
IPVRIKADQQERFDTLVAKVQEMALASESYDYLSLADIHPEAGDFINHII
AFENFYIDMDSFNQLADKKELGFSLAFATDHHEQTNYDLSVQAQIGDESS
IKILYNSKLYTSEYIANVIDHFVTVADIVAANPSIPVKEIDILTKDKKDQ
ILYGFNNTYADYPREKTIHQLFEEQVDKNPNQIALVFKEEKLTYGEVNAK
ANQLAYVLRKQGVQPNDVIGIITERSPEMIIGILAIFKAGGAYMPIDPSY
PAERIQYMLQDNQTKLLLVQKQEMIPANYQGEVLFLTQESWMHEETSNPA
HITQAQALAYVMYTSGSTGEPKGILTTHQNIMKTVIHNGYVEITPGDCLS
QLSNYAFDGSTFEIYGALLHGATLLLVTKEAVLNMNELARLIKKEQVTVS
FMTTALFNTLVDLDITCFQSIRKVLFGGELASVKHVLKALDYLGEHRVIN
VYGPTETTVYATYYSVDHSMLTRASVPIGRPINNTKAYIVNTDGQPQPIG
VVGELCIGGEGVACGYLNRPELTKKHFVDNPFVLGERMYCTGDLARFLPD
GNIEYIGRMDEQVKIRGHRIELGEIEKVLLQHPAISETVLLAKRDEQGHS
YLCAYIVGQVFWTVTELRQHLMESLPEYMVPSYFIEIEKLPLTANGKVDK
RALPEPDRKMGSAYVAPENETEEKLVQFFQEILGVERVGTQDTFFELGGH
SLKAMMLVLQIHKEMGIEVPLKEIFTRPTIKELAAYIHKMDRSAYSMIEP
TAKQEYYPVSFAQRRMFVVQQIRDTNTTSYNMPILLEIEGALDRENVRQT
LKKLIERHESMRTSFHMIDETLLQKVHDDVTWEMEEMEASEEEVYALTKS
FIRPFDLGQAPLFRAGLIRVNSERHLLLLDTHHIISDGVSTNILFQDFTQ
LYRGRELPALRIQYKDFAVWQQGEAQLARLQEQEEYWLKQFSESVPVLEL
PTDFPRPAMQQFDGDVLDFALNQQVWQELQQLIVKEGCTAYMILLAAYHV
LLSKYSSQNDIVIGSPIAGRTNADLQSIVGMFVNTLAIRTKSEGTQTFRE
FLSTIKQLVLQAQSNAEYPFEELVDKVNPSRDLSRQPLFDTIFVMQNMDI
TEVAIQGLSIVTKDMEWKHSKFDLTWAAVEKESLHFSVEYSTRLFKKETI
ERMAKHFAHLLNQVAENPDLSLSDMELATDEEVYQLLEEFNNTEADYPSD
KTIHQQFEQKVEENPDQIALLFKDKEITYGQLNAKANQFARVLRKHGVQP
DQVVGLITDRSIEMMIGILAILKAGGAYLPIDPSYPLERITYMLEDSQAQ
LLIVQEAAMIPEGYQGKVLLLAEECWMQEEASNLELINDAQDLAYVMYTS
GSTGKPKGNLTTHQNILRTIINNGFIEIVPADRLLQLSNYAFDGSTFDIY
SALLNGATLVLVPKEVMLNPMELARIVREQDITVSFMTTSLFHTLVELDV
TSMKSIRKVVFGGEKASYKHVEKALDYLGEGRLVNGYGPTETTVFATTYT
VDSSIKETGIVPIGRPLNNTSVYILNENNQPQPIGVPGELCVGGAGIARG
YLNRPELTAERFVDNPFLVGDRMYRTGDMARFLPDGNIEYIGRMDEQVKI
RGHRIELGEIEKSLLEYPAISEAVLVAKRDEQGHSYLCAYVVSTDQWTVA
KVRQHILEALPEYMVPSYFVELEKLPLTSNGKVDKRALPEPDRVITNEYV
AAVNETEEKLVQFFQEILAVDRVGTQDTFFELGGHSLKAMMLVSRIHKEL
EIEVPLKEVFARQTVKELAAYIRQAEQSDYSEIQPAMEQEYYPVSNAQRR
MYVVQQMRDVETTGYNMPFYLEMEGALEVEKLSLALKQLIERHESLRTSF
HMVEDELMQKVHAEVAWEMEMIHAVEEEVQQLTDSFMRPFDLAKAPLFRA
RLIQINPKRHLLMLDMHHIISDGVSMNVLFQDITQLYQGIELSPLKIQYK
DFAVWQQGIAQVVRFQEQERYWLNQFSGDLPILEMVTDYPRPAIQQFDGD
SWSFEIDAKVLDSIKQLSAKQGTTLYMTLLAIYQILLAKYTRQDDIIVGT
PIAGRPHADTESIVGMFVNTLALRGQPKEEQSFISYLSEVKENVLQAYAN
ADYPFEELVEKLHLQRDMSRHPLFDTMFVLQNMDMSDINISGLKLHSRDL
NWKNAKFDMTWMIAEQNNLLISVEYSTNLFKHETIQRLEKHFTYLVEQVA
KHPDCLLRDLELTTDEEKQQILTVFNDTATDDLQDLSICHLFEQQVQRFS
DRPALVFKEKQLTYSEFHAKVNQLARVLRKKGVQPDQAVGLITDRSIEMM
IGIFAILKAGGAYMPIDPSYPIDRIEHMLEDSRTKLLFVQKTEMIPASYQ
GEVLLLAEECWMHEDSSNLELINKTQDLAYVMYTSGSTGKPKGNLTTHQN
ILTTIINNGYIEIAPTDRLLQLSNYAFDGSTFDIYSALLNGATLVLVPKE
VMLNPMELAKIVREQDITVSFMTTSLFHTLVELDVTSMKSMRKVVFGGEK

FIGURE 3H-2
ASYKHVEKALDYLGEGRLVNGYGPTETTVFATTYTVDSSIKETGIVPIGR
PLNNTSVYVLNENNQLQPIGVPGELCVGGAGIARGYLNRPELTAERFVEN
PFVSGDRMYRTGDLARWLPDGSMEYLGRMDEQVKVRGYRIELGEIETRLL
EHPSISAAVLLAKQDEQGHSYLCAYIVANGVWTVAELRKHLSEALPEYMV
PTYFVELEQIPFTSNGKVNKRALPEPEGQMTSVYVAPETETEAKVAALFQ
EILGVERVGTQDMFFELGGHSLKAMMLVLRMNKELGIEVPLKEVFAHPTV
KELAATIDLLDRSGHSEIEPAPRQEFYPVSSAQRRMYVVQHLGNVQTTSY
NMPLFLEVEGALEIDKLHLALEKLVERHESLRTSFHMVDEELMQQVHEEV
AWDLEIMDGTEGDLASITAGFIRPFDLSQAPLFRAGIVRISPERFLFMLD
MHHIISDGVSTNVLFKDITQLYQGKDLPPLPIQYKDYAVWQQADAQVTRL
QDQESYWLHQFAGEASVLEMPTDFPRPAVQQFEGDVWTFEIDADILSQLK
KLSVSQGSTLYMTLLAVYQVLLAKYTGQDDIIVGSPIAGRPHADVESIVG
MFVNTLALRGQPVGEQTFITYLAQVKEQVLQAYANAEYPFEKLVEKLDLQ
RDMSRHPLFDTMFTLQNMEMTDIDLAGLTFKPFDFEWKNAKFDMDWTMLE
EETLKVAIEYSTSLYTKETISRMAQHFTYVLQQIIEHPAIRLAEIKIATL
PEIEQILTQFNDTRANYPDNQTIHSLFEQQVERTPEQIAVVYQDQSITYR
ELNERANRLARCLIDKGIQRNQFVAIMADRSIETVIGMMGILKAGGAYVP
IDPDYPLDRKLYILEDSHASLLLFQQKHEVPSEFTGDRILIEQMQWYQAA
DTNVGIVNTAQDLAYMIYTSGSTGQPKGVMIDHQAVCNLCLMAQTYGIFA
NSRVLQFASFSFDASVGEVFHTLTNGATLYLMDRNLLMAGVEFVEWLRVN
EITSIPFISPSALRALPYEDLPALKYISTGGEALPVDLVRLWGTERIFLN
AYGPTETTVDATIGLCTPEDKPHIGKPVLNKKAYIINPNYQLQPIGVPGE
LCIGGVGIAPGYWNRPELTREKFVDNPFAQGERMYKTGDLVRWLPDGNIE
FLGRIDDQVKIRGHRIELGEIETRLLEHEQVIEAVVLAREDEQGQAYLCA
YLVAADEWTVAELRKHLGKTLPDYMIPAYFIELEEFPLTPSGKVNKKALP
EPDGQIQTGVEYVEATTESQKILVELWQEVLRVERIGIYDNFFELGGDSI
KAIQITARLRRHHRKLEISHLFKHPTIAELAPWMQTSQALLEQGTVEGEV
MLTPIQKAFFEENQEQPQHFNQDSLLYSSNGWNQDAIEQVFEKITEHHDA
LRMVYPHTEGKVTQINRGLEDKAFTLQVFDFTQEPTDTQATKIEQIATQL
QASFDLKKGPLVRLGLFTTKAGDYLLIVIHHLVIDGVSWRILLEDFHNAY
QQVIQGQAIVLPEKTTSFKTWSERLNEYANSHALLHEIPYWKQMEEISIA
PLPKKGNNDGRYYVKDSEYATMSLTEEETQNLLTRVHRAYRTEINDLLLA
ALGLASKEWTKENRVAIHLEGHGREEIGEGVDVNRTVGWFTSLFPFVIDL
ENDELPLIIKSVKETLRRVPNKGMGYGILKHLTSDANKQEITFSLRPEIS
FNYLGVFDQQEEESESAGIPTGQPISPQYYDTHLLEFNGAVSNNQLHVNC
RFAPAAVDRAIVEILMERFKHHLLLISKHCLEKDTVEFTPTDFTEKELSQ
EQLDDLLDDLFEDIDDL

FIGURE 31

MQKKDKIKDIYSLSPLQKGMLFHSMKDPQSDAYFEQVTLLLEGVVNPTYL
AESIQGLVQKYDMFRSVFRYKKVDPVQVVLSERKIDLQIEDLTQINEEEQ
RKFIEEYRKKDRERGFDLSRDILLRFTLFQTAANRYELLWSHHHILMDGW
CTGIVFQDLFQMYQRRLSGQALLPEVAPQYSEYIRWLKKQDDQQALAFWK
EYLQGFENLTGIPRLRSGNHPYKQEEFIFSLGEEATQKLTQTAQKYQVTL
NTVVQTIWGALLQKYNNTNDAAYGVVVSGRPAEVPNVEQMVGLFSNTIPI
RIKKEAGKTFGEVLKNVQQTALEAEKYGYLSLADIQASAAYTHQLLDHIL
AFENFPMDQETFNQENVLGFAVKDAHTFEQTHYDLTVLVIPGKELIFKFM
YNESVHSKEYLNLLELNMKKLVSLVIEQQDIFDPATEFVSDLEKDKLLTI
FNRTDAKYPREKTIHELFQEQVDKNPDQVALVFGEAQLTYRELNEKANQM
ARGLRKQGVLPDQVIGLLTDRSLEMIIAILAIFKAGGAYMPIDPSYPSER
IQYMLADSRTHLLLVQKAEMIPANYQGEVLLLTEDSWMDENTDNLDLVNQ
AQDLAYVMYTSGSTGKPKGNLTTHQNIVKTIMNNGYMEITPNDRLLQLSN
YAFDGSTFDIYSALLNGASLILVPTHVLMNPTDLASVIQDQHITVSFMTT
SLFNTLVELDVTSLKHMRKVVFGGEKASIKHVEKALDYLGAGRLVNGYGP
TETTVFATTYTVDHTIKETGIMPIGRPLNNTKVFILGADNQLQPIGALGE
LCVSGEGLARGYLNLPELTADRFVENPFMRGERMYRTGDLARWLPDGSIE
YVGRIDEQVKIRGHRIELGEIEARLLEHPAISETVLLAKQDEQGHSFLCA
YLVTNGAWSVAELRKHIKETLPDSMVPSYFIEIDKMPLTSNGKADKRALP
EPDVQQVSSYIAPETETEEKLVQLFQEILSVEQVGTQDNFFELGGHSLKA
MMLVSRMHKELDIEVPLKDVFARPSVKELAAFLTNTEVSDYIAIEPAAKQ
EFYPVSSAQRRMYVVEQIGSSNTTSYNMPFLLEIGGALDVVGLQKALKKL
VIRHESLRTSFHMVDEVLMQKIHPDVEWDLMVMEAKDEDLPQIIDGFIQP
FDLSDASLFRAGLVRMEADRHLLMLDMHHIISDGVSTNVLFQDLMQIYQG
KELPSLRIQYKDYAVWQQAEAQVNRLREQEQYWLNQFSGELPVLEMPTDY
TRPSIQQSEGDIWSFEISAEIINKVKKLSSSQGTTLYMTLLAAYQVLLSK
YTGQEDVIVGSPIAGRPHADVEKIVGMFVNTLAFRGQPKSTQTFSTYLSE
VKEQVLHAYDNAEYPFEELLEKLDLERDLSRHPLFDTMFALQNMEMAEIN
IMDLSFQPRDLTWKNAKFDLTWMMAEAENLYVTIEYSTSLFKPETIERLG
KRFTHLLKQIGDAPERLIADLEVATEDEKHQILSVFNLTQSDYPVNKTVH
QLFEEQVQNMPDQKAIVFGEEQVTYKELNAKANHLATLLKQKGITNEQLV
AVMIEPSIEFFVGILAVLKAGGAYLPIDPTYPTERIAYILEDSQSKVLLV
RGHEQVQTQFAGEILEIDSKKLSTEELKDVPMNNKVTDLAYVIYTSGSTG
QPKGVMVEHRSLMNLSAWHVQYFGITKDDRSTKYAGVGFDASVWEVFPYL
IAGATIYVIDQETRYDVEKLNQYVTDQGITISFLPTQFAEQFMLTDHTDH
TALRWLLIGGDKAQQAVQQKQYQIVNNYGPTENTVVTTSYIVSPEDKKIP
IGRPIANNQVFILNKENQLQPVGIPGELCVSGDSLARGYLHRPELTSERF
VANPFVPGERMYKTGDIARWLPDGNIEYLGRLDDQIKIRGYRVELGEIES
AILEHEAIHETVVLARQDDQNQTYLCAYVVPKKSFDVAELRQYLGRKLPH
FMIPAFFTEMTEFPITSNGKVDKKALPLPDLSKQSEIDYVAPTTTLEETL
AELWTEVLGVSQVGIHDNFFKLGGDSIKAIQIAARLNTKQLKLEVKDLFQ
AQTIAQVIPYIKTKESKAEQGIVQGKVELTPIQEWFFQQSFDIPHHWNQS
MMFYRKEGWDQHVVQRVFQKIAEHHDALRMAYQQENGKTIQINRGVEGKL
FELSIFDFKQQANVPELIEQAANRLQSAMNLQDGPLVQLGLFQTSEGDHL
LIAIHHLVVDAVSWRIITEDFMNGYQQDLQGEPIAFTSKTDSYQKWAKSL
LEYATSEEIQSELKYWQSMIAKGLPALPRDSKVGAPYLLKDIQEVAIQLT
KEQTNKLLTDAHNAYNTQINDLLLTALALTIQEWAQTNSIAITLEGHGRE
DIGVDIDINRTVGWFTSMYPVVFDLQKQGIANTVKQVKEELRQIPNKGIG
YGVVRYLSNQGSTELDLSSHAINPEISFNYLGQMDQSGQEEEYQLSPLSS
GQQISQMNQGLFPINVSGIVVENQLSIQISYDSQAYHDSTMEKLIQRYQY
HLLEIINHCVQQTETELTPSDFSTKELSMEDLESVFELLDE

FIGURE 3J

MLSKANIKDIYTLSPLQKGMLFQHLKEESTAYFEQLHFTIKGQLYVDSFE
ASFQHLINKYDVLRTVFLYKNMTQPMQMVLKERKTSVHFEDISHLDSKAV
SEYVEEFKNQDREKGFELSKDILMRFAILKAGAESYHLIWSFHHILMDGW
CMGIVLQDLFRMYQQHRQNIPITVESVPAYSEYIRWLEKQNVTKARDYWK
NYLEGYEELTGIIRLDTKHTSHNNEVQECAFTLDKDITEGLTQLARHYSV
TVNTLFQTIWGMLLQKYNNKDDVVFGAVVSGRPSEIHGVENMVGLFINTV
PIRIQKQMNDTFSHLLKRVHESTLLSKQYEFVSLADIQTDAGFSGQLLDH
ILVFENYPISEGSFEEEEFTMDSIKTYEKTSYDLNVMIRPNEDQLDIAFQ
FNDDVYSSENVKRLFQHMKQLALAVIKNPDVRLEEIAMITEEERYQILHD
FQGEIVDFVTEKTLPELFEDQVKRTPEAIALRFEDQQLTYQELNQRVNQL
AWTLRMKGLQQEELVGIMVQRSLEMIVGVLAVIKAGGAYVPIDPEYPLDR
IQYMLEDSGTNWLLTTKQSEIPSIYLGHVLYLEEDTVYHERSSDVEIVNQ
SSDLAYIIYTSGSTGQPKGVMIDHRAVHNLHLSAGIYGIAQGSQVLQFAS
LSFDASVGDIFHSLLTGATLHLVKKEQLLSGHAFMEWLDEAGITTIPFIP
PSVLKELPYAKLPKLKTISTGGEELPADLVRIWGANRTFLNAYGPTETTV
DASIGNCVEMTDKPSIGTPTVNKRAYILDQYGHIQPIGVPGELCVGGEGV
ARGYLHRPELTDEKFVNDPYVPNGRMYKTGDLARWLPDGTIEFLGRMDGQ
VKIRGFRIELGEIEARLNQAPSVKQAVVLARSGEQKQVYLCAYLVTDNDL
KVSALRKELSQTLPDYMIPSFFIKVEKIPVTVNGKIDKKALPEPEKEVEL
QTEYVAPTNPTEEILVQIWQKVLGMERVGIEDNFFELGGHSIKAMMLASN
IYKELKIDLPLREIFKHTTVKEMARFIDGRDEEEYVGIQPAAKQEYYPVS
SAQKRMYVIQSLEDKAQGTSYNMPSFYKMKGSVDAEKLEKVFQTLLDRHE
SLRTSFHMIEEQLVQKVHEQVSWKMDMKTVSANDVSRLKDSFVQPFDIST
APLFRASLLTIHKDEHILMMDVHHIVGDGVSTTILFQELIQLYQGQALPE
VKVHYKDYAVWQLSQQDRLKESENFWLQQFSGELPVLELPTDYSRPPIRR
LEGEYVSQSLRGDLHESVKAFMKNHEVTLYMVLLATYNVLLHKYTNQHDI
IVGTPVSDRPHPDVMSTVGMFVNTLAVRNQLESEQTFEKFLANVKNKMLE
VYGHQEYPFEDVIEKVKVQRDTSRHPLFDTMFGVQNLEISHVELPDWGIE
ALDIDWTNSKFDMSWMVFEADGLEIGVEYSTSLFERNTIQRMIGHFEHII
EQIMENPQIRLADIQLTTEDERIQILEEFNHQPTKITYDQAIQNRFEEQA
MKTPDAVALVYKGQELTYRELNQRSNQMARTLREHGVGRDQIIAVMINRS
HELIISILAVLKAGGAYLPIDPTYPLDRIEHMLEDSQTAMLLTQKEIQIP
TGYSGEVLFVDQADIYHEDATDLSSMNQPADLAYIIYTSGSTGKSKGVMI
EHRSLHNLIHISHPYKMGAGSRVLQFASSSFDASVAEIFPALLTGSTLYI
EEKEELLTNLVPYLLENQITTVALPPSLLRSVPYRELPALECIVSVGEAC
TFDIVQTWGQNRTFINGYGPTESTVCSAFGVVTAEDKRITIGKPFPNQKV
YIINENQQLQPIGVPGELCIAGAGLSRGYLNRPELTQEKFVNNPFAPGER
MYKTGDVARWLPDGNIEYAGRMDDQVKVRGNRVELGEVTSQLLTHPSITE
AVVVPIVDTHGATTLCAYFIEDKEVKVNDLRHHLAKALPEFMIPTYFIKV
DHIPLTGNGKVNKQALPDPSEFISAQTGHEIVAPSSQDEEILVQVWEEVL
QFKPIGVEDNFFERGGDSIKALQIVARLSKYNRKLDSRHIFKNPTISMLA
PYLEQRGALIEQDSIEGEVPLTPIQSWFFEQPFVYPHHFNQSMLLPNEQG
WDRQRIEQAFTTIVRHHDALRMKYQFREKIIQENQGIEGEFFTLHEVDVT
KERDWQMRIEQEANQLQASFDLTTGPLVKLGLYHTAYGDYLLIVVHHLLI
DGVSWRILLEDFQTLYEQKGELPAKTTSFKAWAVQLEGYARSKKLQDEAS
YWKGLLNKSIRELPADKESSDTFLFGDTKEVQLTFDINETQDLLTDAHHA
YKTKADDLLLAALVLSINEWTKQSDIIVNLEGHGRETIGEGIDLSRTIGW
FTTIYPVLFEVENHQLSSVIKHVKETLRNVPNNGIGFGILQHMSHSDVSQ
SQLSSHHISFNYLGQMGEDSASQSETDNGVLINTGDQISPMNANPGSLNM
TCLVMNNTLLVTFDYNPQRYEQETIQRLADRYKSNLKAVLDHCVQREQTE
RTPSDFSTKKLSLEDLDDVFATLKNL

FIGURE 3K

```
MINTSDVKDIYSLSPMQRGMLFHTLKDKENLAYFDQTTFQIEGDICVESL
EKSFNELIRKYDVLRTIFLYQKLKEPMQVVLKERTANIHYEDFSMKSESD
KAKALRVAKQRDRDEGFDLSRDILMRLSLLKVAPNQYELVISSHHIIIDG
WCTGILYQELFYFYQCFVANQPIPAEKSIPYSRYIRWLEEQDEEEGKAYW
GEYLQDFEGASVIPKQNAKGEKEVCSIDKVTFHFDKKLTEELVQVAKTCQ
VTISTLFQTMWGILLQKYNNSQEAIFGSVISGRSPEIPDVEKIVGIFINT
IPVRIRTLDKQTFKELLIQVQEASVNSEKYNYLTLADIQAVTGSNHALIH
HIVAFENFPIASDSFVDSSDSDSEELKVVNVIDDHEKTNFDFSVQVQLDT
ELLVKISYNQHLYHRSFIENIFHHLQQIAGSITHNPDIQINEIAIVSKEE
KKQLLRYSTPAKSDFPMDKTIHQLFEEQVSRTPEQIAVVFKGESFTYREL
NEKANQLAWVLRKREVRPNEIVAIMAEHSLEMLVGVIGTLKAGAAYLPID
PSYPEKRIAHMLQDSKAEQLLIQPHLNMPQDFKGSVLWLTEESWAKESTT
DLPLATSANDLAYMIYTSGSTGLPKGVMVEHQALVNLVMWHNEAFGVTMT
DQCTKLAGFGFDASVWETFPPLIQGATLHVLEESRRGDIYALHEYFEKNA
ITISFLPTQLAEQFMELTSSTLRVLLIGGDRAQKVKETSYQIINNYGPTE
NTVVTTSGQLHPEQDVFPIGKPITNHSVYILDQNRHLQPIGIPGELCVSG
AGLARGYLNQPELTVERFVDNPFVPGERMYRTGDLVRWRIDGSIEYLGRI
DEQVKIRGYRIELGEIETKLLEHPSISEALVVARNDEQGYTYLCAYVVAT
GAWSVSSLREHLIETLPEYMIPAYMMEVEKMPLTANGKIDKRALPVPDRQ
RMNEYVAPATETEEKLVLLFQEILGLERIGTKDHFFELGGHSLKAMMLVS
RMHKELGVDVQLNEMFARPTVKDLSAYIDQMNGSAYTAIQPVEEQPYYPV
SFAQRRMYVVQQMRDSETTSYNMPFTFELKGKLHLDKLREALQILVLRHE
SLRTSFHMIDENLVQKVNKDISWDLEVIEAQESEIEVKLEEFIRPFHLSE
APLFRARLICLNPQHHLLSLDMHHIISDGVSMNLFLQEFMTLYQGEALPA
LSIQYKDYAVWQQSDKQRARLKEQEKYWLHHFSGELPTLELPTDFPRPAI
QQFDGDEWAFEMNADLLAKVKQICSSQGTTLYMTLLAAYQVFLARYTGQE
DIIVGSPIAGRSHADLENMIGMFVNTLALRGKPKADQSFLSYLKQVKETV
FQAYANAEYPFEELIEKLDLERDMSRHPLFDTLFSLQNMEISEFQMNNLE
IFPYETGQKNAKFALSWLIAEGESLYVTIEYSTKCFKRETIKRMASHFEQ
LLAQIVEQPEARIGQLELVADAERKMLLEDFNLTKVDYPREKTIQELFEE
QVDKNPDQIALICGEQQFTYEQLNVKFNQLAHVLRREGVQPNQVIGLITD
RSLSMIVGIFGIIKAGGGYLPIDPTYPTERIEYMLEDSQTHLLLVQHRDM
VPAGYQGEVLIIEDEISRDEQVANIELINQPQDLAYVMYTSGSTGKPKGN
LTTHRNIIKTVCNNGYIEITTEDRLLQLSNYAFDGSTFDIFSSLLHGATL
VLVPKEVILNPTDLITLIREQQITVSFMTTSLFNALVELDVSSFQNMRKI
AFGGEKASFKHVEKALDFLGNRLVNGYGPTETTVFATTYTVDERIKEWG
IIPIGRPLHNTTVHILSADDKLQPIGVIGELCVSGEGLARGYLNLPELTM
ERFVENPFRPGERMYRTGDLARWLPDGVLEYVGRKDEQVKIRGHRIELSE
IETRILEHPAISETVLLAKRNEQGSSYLCAYIVAHGQWNIQELRKHVRDV
LPEHMVPSYFIGLDKLPLTSNGKVDKRALPEPEGSLQLTREIVAPRNESE
KQLVEIVAEVLGLEASEISITDNLFELGGHSLTILRILAKVHTCNWKLEM
KDFYNCKNLEEIASKATDMQENQNLSGSGSVFKKGGKKSIPVVPVHDRQK
EMEHVLLLGSTGFLGIHLLHELLQKTEATILCVIRAENDEAAMQRLRKKI
DFYFTSQYSSSQIDEWFTRIQIIHGDITQANFGLEAKHYESLGAIVDTVI
HTAALVKHYGHYEEFERANVHGTQQVVTFCLNNKLPMHYVSTLSVSGTTV
EEATELVEFTEKDFYVGQNYESNVYLRSKFEAEAVLVGGMENGLDARIYR
VGNLTGRFQDGWFQENINENMFYLLSKAFLELGGFDQEIMQGMVDLTPID
ICAQAIIHIINSKGIEERVFHLQNPHLVTYDDMYRVFEGLGFSRRVQSRE
DVTRELDVMMSQGNEKLFLAGILTTMLDDVERAEQFNVAVDSSRTMQLLE
DTSFTYPVPDDEYLRKLAMHMIKVGFVTPNHTVAEKIGTSR
```

FIGURE 3L
MAVIELKNLTKKYNEVYAVDHLNIEVPQGHIYAFLGSNGAGKTTTIKMMT
GQLNPSEGEVLFLGRNIWQDREARRIAGYAPDVPLLHEGLTVREMVRFVG
ALYGSDEDLNKRVDTLLEHFELADKADQLIKEYSLGMKRKVSIACALIHR
PKILLLDEVTNGLDPKATREVKNYIRHFAKEEGGTVFITTHILDIVEELA
DTISILHKGKIKVTGSMEELRHVAGNEEGRLEDIFLSAIE

FIGURE 4A. ALIGNMENT OF ADENYLATION (A-) DOMAINS OF THE BT NRPS

```
MODULE        A1              A2              A3              A4       A5
    5       ITYGQL       LKAGGAYLPID     LAYVMYTSGSTGKPKG     FDGS    NGYGPTE
    6       LTYSEF       LKAGGAYMPID     LAYVMYTSGSTGKPKG     FDGS    NGYGPTE
    2       LTYREL       LKAGGAYMPID     VANIMYTSGTTGKPKG     FDGS    NGYGPTE
    8       LTYREL       FKAGGAYMPID     LAYVMYTSGSTGKPKG     FDGS    NGYGPTE
   13       FTYEQL       IKAGGGYLPID     LAYVMYTSGSTGKPKG     FDGS    NGYGPTE
    4       LTYGEV       FKAGGAYMPID     LAYVMYTSGSTGEPKG     FDGS    NVYGPTE
    9       TYKELN       LKAGGAYLPID     LAYVIYTSGSTGQPKG     FDAS    NNYGPTE
   12       FTYREL       LKAGAAYLPID     LAYMIYTSGSTGLPKG     FDAS    NNYGPTE
    3       MTYQEL       LKAGGAYLPID     LAYIIYTSGSTGKPKG     FDSS    NAYGPTE
    7       ITYREL       LKAGGAYVPID     LAYMIYTSGSTGQPKG     FDAS    NAYGPTE
   10       LTYQEL       IKAGGAYVPID     LAYIIYTSGSTGQPKG     FDAS    NAYGPTE
   11       LTYREL       LKAGGAYLPID     LAYIIYTSGSTGKSKG     FDAS    NGYGPTE
    1       MTYKEM       LKAGAAYMPID     LAYIIYTSGSTGKPKG     FDFS    NMYGITE
CONSENSUS   LTYREL       LKAGGAYLPID     LAYVIYTSGSTGKPKG     FDGS    NGYGPTE

MODULE          A6            A7              A8                A9         A10
    5       GELCVGGAGIARGYL  YRTGDM    GRMDEQVKIRGHRIELGEIE   LPEYMVP    NGKVDK
    6       GELCVGGAGIARGYL  YRTGDL    GRMDEQVKVRGYRIELGEIE   LPEYMVP    NGKVNK
    2       GELCVAGECISPGYL  YRTGDL    GRIDEQVKIRGHRIELGEIE   LPEYMVP    NGKVDK
    8       GELCVSGEGLARGYL  YRTGDL    GRIDEQVKIRGHRIELGEIE   LPDSMVP    NGKADK
   13       GELCVSGEGLARGYL  YRTGDL    GRKDEQVKIRGHRIELSEIE   LPEHMVP    NGKVDK
    4       GELCIGGEGVACGYL  YCTGDL    GRMDEQVKIRGHRIELGEIE   LPEYMVP    NGKVDK
    9       GELCVSGDSLARGYL  YKTGDI    GRLDDQIKIRGYRVELGEIE   LPHFMIP    NGKVDK
   12       GELCVSGAGLARGYL  YRTGDL    GRIDEQVKIRGYRIELGEIE   LPEYMIP    NGKIDK
    3       GELCIGGEGVALGYL  YRSGDL    GRLDDQVKIRGHRIELGEIE   LPEYMIP    NGKVNK
    7       GELCIGGVGIAPGYW  YKTGDL    GRIDDQVKIRGHRIELGEIE   LPDYMIP    SGKVNK
   10       GELCVGGEGVARGYL  YKTGDL    GRMDGQVKIRGFRIELGEIE   LPDYMIP    NGKIDK
   11       GELCIAGAGLSRGYL  YKTGDV    GRMDDQVKVRGNRVELGEVT   LPEFMIP    NGKVNK
    1       GELYVSGKGVARGYL  YRTGDL    GRIDHQVKIRGYRIELGEIE   LPSYMIP    NGKIDK
CONSENSUS   GELCVGGEGLARGYL  YRTGDL    GRMDEQVKIRGHRIELGEIE   LPEYMIP    NGKVDK
```

FIGURE 4B. ALIGNMENT OF THIOLATION (T-) DOMAINS OF THE BT NRPS

```
MODULE
    6       DMFFELGGHSL
    8       DNFFELGGHSL
    4       DTFFELGGHSL
    5       DTFFELGGHSL
    2       DSFYELGGHSL
   12       DHFFELGGHSL
   10       DNFFELGGHSI
    3       DNFFELGGDSI
    7       DNFFELGGDSI
    9       DNFFKLGGDSI
   11       DNFFERGGDSI
    1       DNYFALGGDSI
   13       DNLFELGGHSL
CONSENSUS   DNFFELGGHSL
```

FIGURE 4C. ALIGNMENT OF CONDENSATION (C-) DOMAINS OF THE BT NRPS
(WITH THE * SYMBOLS STANDING FOR START C DOMAINS)

| MODULE | C1 | C2 | C3 | C4 | C5 |
|---|---|---|---|---|---|
| 7 | SSAQRRMYVV | RHESLRTSF | MHHIISDGVS | YKDYAVW | IVGMFVNTLAIR |
| 9 | SSAQRRMYVV | RHESLRTSF | MHHIISDGVS | YKDYAVW | IVGMFVNTLAFR |
| 6 | SNAQRRMYVV | RHESLRTSF | MHHIISDGVS | YKDFAVW | IVGMFVNTLAIR |
| 5 | SFAQRRMFVV | RHESMRTSF | THHIISDGVS | YKDFAVW | IVGMFVNTLAIR |
| 13 | SFAQRRMYVV | RHESLRTSF | MHHIISDGVS | YKDYAVW | MIGMFVNTLAIR |
| 3 | TAAQKRMYIA | RHESLRTSF | MHHIISDGFS | YKDYAVW | VFGMFVNTLAIR |
| 11 | SSAQKRMYVI | RHESLRTSF | VHHIVGDGVS | YKDYAVW | TVGMFVNTLAVR |
| 4* | SPMQKGILFH | KHDILRTVF | NHHIIMDGWC | YSKHIQW | MVGLFINTIPVR |
| 12* | SPMQRGMLFH | KYDVLRTIF | SHHIIDGWC | YSRYIRW | IVGIFINTIPVR |
| 8* | SPLQKGMLFH | KYDMFRSVF | HHHILMDGWC | YSEYIRW | MVGLFSNTIPIR |
| 10* | SPLQKGMLFQ | KYDVLRTVF | FHHILMDGWC | YSEYIRW | MVGLFINTVPIR |
| 2* | SDIQLGMVYH | KHDILKTSF | FHHAILDGWS | YKDYVID | VLGCFLNSVPFR |
| CONSENSUS | SSAQRRMYVV | RHESLRTSF | MHHIISDGVS | YKDYAVW | IVGMFVNTLAIR |

| MODULE | C6 | C7 |
|---|---|---|
| 7 | NAEYPFE | RDMSRHPL |
| 9 | NAEYPFE | RDLSRHPL |
| 6 | NADYPFE | RDMSRHPL |
| 5 | NAEYPFE | RDLSRQPL |
| 13 | NAEYPFE | RDMSRHPL |
| 3 | NPDYPFE | RDVSRNPL |
| 11 | HQEYPFE | RDTSRHPL |
| 4* | YDYLSLA | ------DF |
| 12* | YNYLTLA | -----HAL |
| 8* | YGYLSLA | -----HQL |
| 10* | YEFVSLA | -----GQL |
| 2* | YGRLSFA | TGSERNPV |
| CONSENSUS | NAEYPFE | RDMSRHPL |

FIGURE 4D. ALIGNMENT OF EPIMERIZATIONS (E-) DOMAINS OF THE BT NRPS

| MODULE | E1 | E2 | E3 | E4 | E5 |
|---|---|---|---|---|---|
| 9 | PIQEWF | HHLVVDAVS | DLLLTALA | EGHGRE | RTVGWFTSMYPVV |
| 11 | PIQSWF | HHLLIDGVS | DLLLAALV | EGHGRE | RTIGWFTIYPVL |
| 3 | PIQHWF | HHLVVDGVS | DLLLTALA | EGHGRE | RTVGWFTSEYPVA |
| 7 | PIQKAF | HHLVIDGVS | DLLLAALG | EGHGRE | RTVGWFTSLFPFV |
| CONSENSUS | PIQEWF | HHLVVDGVS | DLLLTALA | EGHGRE | RTVGWFTSMYPVV |

| MODULE | E6 | E7 |
|---|---|---|
| 9 | PNKGIGYG | FNYLGQ |
| 11 | PNNGIGFG | FNYLGQ |
| 3 | PNKGFGYG | FNYLGQ |
| 7 | PNKGMGYG | FNYLGV |
| CONSENSUS | PNKGIGYG | FNYLGQ |

FIGURE 4E. ALIGNMENT OF REDUCTASE (R-) DOMAINS FROM BT NRPS AND OTHER PROTEINS

```
                    10         20         30         40         50         60
                    |          |          |          |          |          |
LYS2_REDUCTASE    NVFVTGVTGFLGSYILADLLGRSPKNYSFKVFAHVRAKDEEAAFARLQKAGITYGTWNEK
MXCG_REDUCTASE    QVLLTGATGFVGAHLLDQLLRQT----QAKVVCLVRARDEAHAMERLREAMTSQRLSTAS
BTF_REDUCTASE     HVLLLGSTGFLGIHLLHELLQKT----EATILCVIRAENDEAAMQRLRKKIDFYFTSQYS
CONSENSUS            VLLTG TGFLG HLL  LL  T        KV C VRA DEEAAM RLRKA   Y TS  S 70         80         90         100        110        120
                    |          |          |          |          |          |
LYS2_REDUCTASE    FA------SNIKVVLGDLSKSQFGLSDEKWMDLANTVDIIIHNGALVHWVYPYAKLRDPN
MXCG_REDUCTASE    LS------ERVLALPADLGQPWLGLSSARFHGLAAECDMILHNAAVVSVVREYGSLQATN
BTF_REDUCTASE     SSQIDEWFTRIQIIHGDITQANFGLEAKHYESLGAIVDTVIHTAALVKHYGHMEEFERAN
CONSENSUS           S       RI   GDL Q  FGLS     LAA VD IIHNAALV V Y  L    N 130        140        150        160        170        180
                    |          |          |          |          |          |
LYS2_REDUCTASE    VISTINVMSLAAVGKPKFFDFVSSTSTLDTEYYFNLSDKLVSEGKPGILESDDLMNSASG
MXCG_REDUCTASE    VRGTRELLRLAASVRPKPLHYVS---TLAVAPQANLSPEVP----------EAFVPAHPG
BTF_REDUCTASE     VHGTQQVVTFCLN-NKLPMHYVS---TLSVSGTTVEEATELVEFT-----EKDFYVGQNY
CONSENSUS         V GT  V   LAA   PKP HYVS   TL V    NLS   E              DF     G 190        200        210        220        230        240
                    |          |          |          |          |          |
LYS2_REDUCTASE    LTGGYGQSKWAAEYIIRRAGERGLRGCIVRPGYVTGASANGSSNT---DDFLLRFLKGSV
MXCG_REDUCTASE    LRDGYQQSKWAAERLVEQASERGLPVTVYRLGRVSGALDSGIVNP---QDLVWRILLAGI
BTF_REDUCTASE     ESNVYLRSKFEAEAVLVGGMENGLDARIYRVGNLTGRFQDCWFQENINENMFYLLSKAFL
CONSENSUS          L  GY QSKWAAE    A  ERGL    IYR G  VTGA    G  N       D  R LKA 250        260
                    |          |
LYS2_REDUCTASE    QLG--KIPDIENSVNMVPVDHVARVVV
MXCG_REDUCTASE    PAG--ALPQLDVGEVWTPVDYVARALV
BTF_REDUCTASE     ELGGFDQEIMQGMVDLTPIDICAQAII
CONSENSUS          LG   P       V TPVD VARA V
```

FIGURE 5.
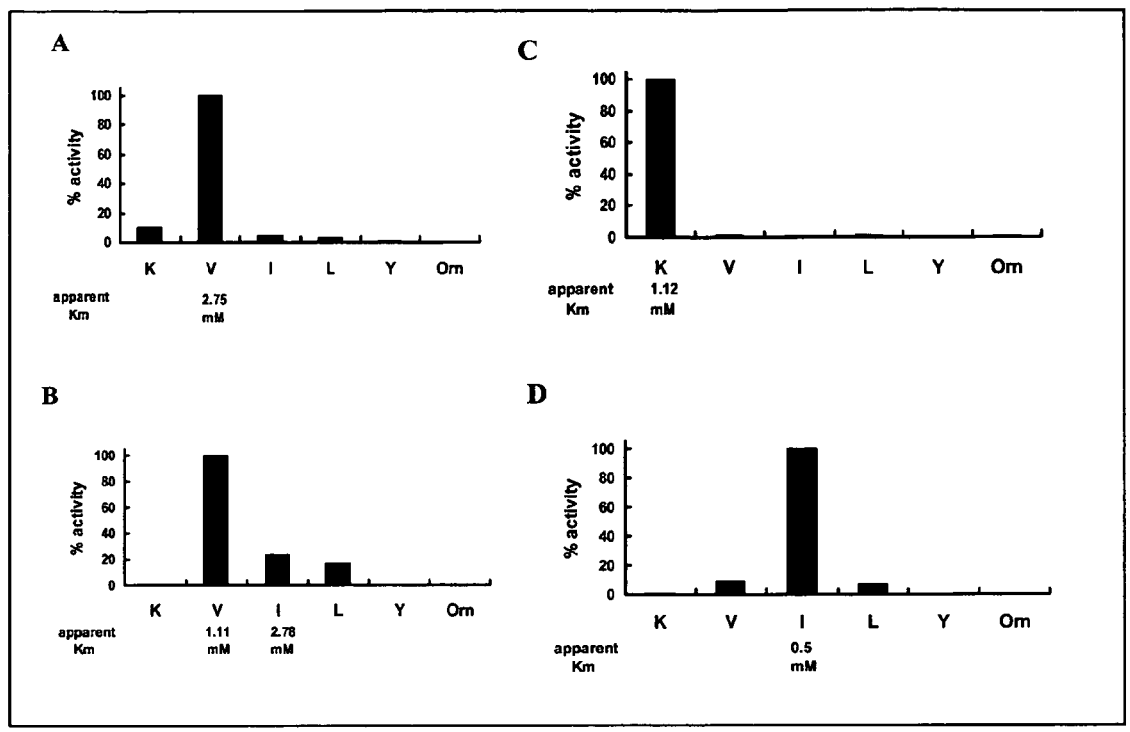
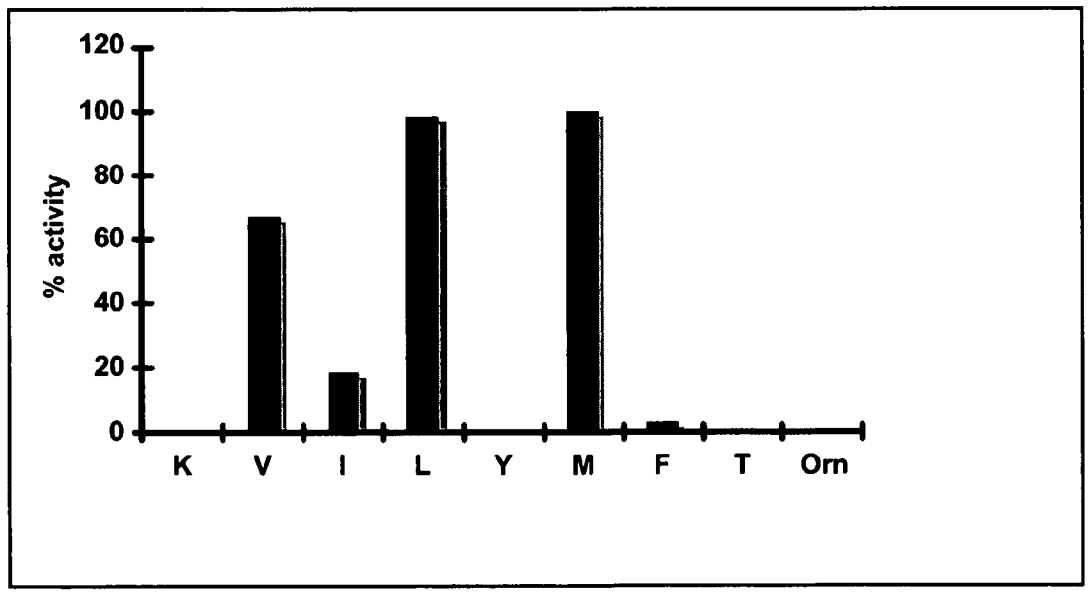
FIGURE 5E

FIGURE 6.

A
BT1583: (CH$_3$)$_2$-Bnt-L-dO-I- V-V-dK-V-dL-K-dY-L-V-CH$_2$OH
P81: CH$_3$(CH$_2$)$_6$CO-T-L-dO-I- V-V-dK-V-dL-K-dY-L-V-CH$_2$OH
P59: CH$_3$(CH$_2$)$_6$CO-T-L-dO-I- V-V-dK-V-dL-K-dY-L-V-NH$_2$
P58: T-L-dO-I- V-V-dK-V-dL-K-dY-L-V-NH$_2$
P80: CH$_3$(CH$_2$)$_6$CO-T-L-dO-I-dV-V-dK-V-dL-K-dY-L-V-NH$_2$

B

| | Antibiotic activity | Pronase Resistance |
|---|---|---|
| BT1583 | +++ | + |
| P81 | +++ | + |
| P59 | +++ | - |
| P58 | + | n.d. |
| P80 | - | n.d. |

COMPOSITIONS, METHODS AND USES FOR A NOVEL FAMILY OF PEPTIDES

This application claims benefit of U.S. Provisional application 60/540,569 filed Jan. 30, 2004.

TECHNICAL FIELD OF THE INVENTION

The present invention relates in general to the field of novel isolated and purified peptides, and more particularly, to the identification, characterization and use of a novel group of peptides from the newly discovered organism *Brevibacillus texasporus*.

BACKGROUND OF THE INVENTION

This application claims priority to U.S. Provisional Patent Application Ser. No. 60/540,569, filed Jan. 30, 2004, relevant portions incorporated herein by reference. Without limiting the scope of the invention, its background is described in connection with antibiotics and feed additives.

Antibiotic overuse has led to widespread bacterial drug resistance. Novel antibiotics are needed to combat infections caused by bacterial resistant to conventional antibiotics. It is well known that microbes produce a huge variety of antibiotics to wage chemical warfare against competing microbes.

Many peptide antibiotics of microbial origin are synthesized by non-ribosomal peptide synthases (NRPS) and they contain unusual amino acids. NRPS enzymes usually have a co-linear modular architecture (Mootz, et al., 2002). The N-terminal to C-terminal order and specificities of the individual modules correspond to the sequential order and identities of the amino acid residues in the peptide product. Each NRPS module recognizes a specific amino acid and catalyzes stepwise condensation to form a growing peptide chain. The identity of the amino acid recognized by a particular module can be predicted by comparisons to other modules of known specificities (Challis, et al., 2000). Such strict correlation made it possible to identify genes encoding the NRPS enzymes for a number of microbial non-ribosomal peptides with known structures, as demonstrated by the identification of the mycobactin biosynthesis operon in the genome of Mycobacterium tuberculosis (Quadri, et al., 1998). Nevertheless, the art recognizes the continuing need to isolate, identify and characterize novel antimicrobial agents.

Examples of feed additives are widely known in the art. For example, U.S. Pat. No. 6,682,762 issued to Register, discloses one such Poultry and livestock feed additive. Briefly, this patent teaches a poultry and livestock feed additive composition containing 36 wt. % electrolytes, roughage and mineral oil to increase their dietary electrolyte balance. Addition of the electrolyte additive composition improves breeder hen performance as to egg production, body weight, and reduced mortality from heat stress. Broiler chickens on this diet result in increased processing yield, feed conversion and body weight. A method of preparing this dietary electrolyte feed for poultry and livestock is also described.

Yet another example of a feed additive is a taught by Nagai, et al., in U.S. Pat. No. 6,503,544, which teaches an animal feed additive that includes at least two components selected from the group consisting of the following three components (a), (b) and (c): (a) at least one herb selected from Pine Needle, Hawthorn Fruit, Bighead Atractylodes Rhizome, Milkvetch Root, Skullcap Root, Tangerine Fruit and Mint Siftings; (b) a live bacteria mixture composed of a yeast cell wall and a live bacteria preparation containing *Lactobacillus acidophilus* and/or *Enterococcus faecium*; and (c) an organic acid.

Feed additives may also include the byproducts of fermentation and other precesses, such as those taught by U.S. Pat. No. 5,863,574 issued to Julien for a feed additive for ruminant animals containing fungal and/or bacterial fermentation byproducts. The feed additive for ruminants, includes dried fungal and/or bacterial fermentation by products which provide glutamic acid fermentation solubles, dried corn fermentation solubles, or a mixture of dried glutamic acid fermentation solubles and dried corn fermentation solubles, wherein the dried solubles have been dried to a total moisture content of less than 30% by weight at a temperature not less than about 80° F. and not more than about 900° F.

SUMMARY OF THE INVENTION

In one embodiment, the present invention is a feed additive that includes an isolated and purified, heat stable, amino terminus-methylated, carboxy-terminus reduced peptide comprising two or more D-amino acids isolated from *Brevibacillus* sp. The carboxy-terminus —COOH group of the C-terminal Valine of the peptide may be reduced to —CH$_2$OH, and may confer protease resistance to the peptide. The peptide feed additive may be stable at a pH of 1.0, at a pH 13.0, resistant to proteases or combinations thereof. Examples of the peptide may be selected from one or more of SEQ ID NOS: 1 to 20 (collectively called the BT peptides). It has been found that the peptide kills, gram positive bacteria, gram negative bacteria, fungi, protozoa or combinations thereof. The peptide may be isolated from *Brevibacillus texasporus* (ATCC PTA-5854) and may be added to feed at between about 0.5 and about 100 ppm. In one use, the peptide was added at between about 6 and about 12 ppm and demonstrated statistically significant growth stimulation.

The additive peptide may be added to a feed adapted for use by one or more of poultry, livestock, farm-raised fish, crabs, shrimp and fresh-water turtles. For example, the peptide may be included in a cereal-based animal feed, e.g., at least one cereal selected from barley, soya, wheat, triticale, rye and maize; and an isolated and purified, heat stable, amino terminus-methylated, carboxy-terminus reduced peptide comprising two or more D-amino acids isolated from *Brevibacillus* sp. The peptide-based feed additive may be include at between about 1 and 1000 ppm of an isolated and purified, heat stable, amino terminus-methylated, carboxy-terminus reduced peptide having two or more D-amino acids isolated from *Brevibacillus* sp. In fact, the present invention may be used with any of a large variety of feeds.

The present invention also includes an antimicrobial peptide that has two or more D-amino acids, carboxy-terminus reduced pH and heat stable isolated from *Brevibacillus* sp. For example, the present invention includes a biologically pure culture of microorganism *Brevibacillus texasporus* deposit No. ATCC PTA-5854) that produces an antimicrobial peptide that is carboxy-terminus reduced heat stable, amino terminus-methylated peptide and may include two or more D-amino acids. The feed additive may even be an isolated and purified microorganism of ATCC PTA-5854. The additive may be mixed with a feed for livestock selected from the group consisting of a milk replacer, a grower feed, a finisher feed, a pre-starter feed and a starter feed.

The present invention also includes a method for increasing body weight gain efficiency and feed efficiency in animals, by providing one or more of the BT peptides in an effective amount sufficient to increase growth in an animal feed. The animal feed is adapted for feeding livestock selected from the group consisting of, e.g., cattle, swine, chicken, horse, turkey, sheep, goat, farm-raised fish, crab, shrimp and turtle. Examples of feeds also include those for feeding birds selected from the group consisting of, e.g., chicken, turkey, duck, quail, Cornish hens, and pigeon. As such, the feed may be selected from the group consisting of, e.g., a cereal, soybean meal, isolated soybean protein, isolated soybean oil, isolated soybean fat, skimmed milk, fish meal, meat meal, bone meal, blood meal, blood plasma protein, whey, rice bran, wheat bran, a sweetener, a mineral, a vitamin, salt, and grass. Daily dose of the peptide ranges from about 0.01 to about 10 grams per kg body weight of the animal.

In yet another embodiment, the present invention is a broad spectrum antimicrobial compound for topical use comprising a peptide having two or more D-amino acids, carboxy-terminus reduced, pH and heat stable isolated from *Brevibacillus* sp. (*Brevibacillus texasporus*) For example, the peptide may have the sequence Me₂Bmt-L-dO-I-V-V-dK-V-dL-K-dY-L-Vol (SEQ ID NO.: 1), wherein Vol is Valine alcohol, or any one of SED ID NOS.: 1-20.

Yet another embodiment is an isolated and purified nucleic acid having the sequence of BT operon (SEQ ID NO.: 21) that produces a heat stable, amino terminus-methylated, carboxy-terminus reduced peptide comprising two or more D-amino acids. The isolated and purified nucleic acid that encode one or more polypeptide sequences for BT operon proteins (SEQ ID NOS.: 22 to 28) that include one or more enzymes used to make a heat stable, amino terminus-methylated, carboxy-terminus reduced peptide comprising two or more D-amino acids. The invention also includes those isolated nucleic acids having at least 75% homology to SEQ ID NO.: 21. More specifically, the nucleic acid may encodes one or more polypeptide sequences for peptide synthesis operon proteins (SEQ ID NOS.: 22 to 28) that are enzymes used to make a heat stable, amino terminus-methylated, carboxy-terminus reduced peptide comprising two or more D-amino acids. One or more BT operon polypeptides are expressed from SEQ ID NO.:21 and comprise one or more enzymes used to make a heat stable, amino terminus-methylated, carboxy-terminus reduced peptide comprising two or more D-amino acids.

An isolated bacterial sample for use with the present invention may include an isolated bacterial strain of *Brevibacillus texasporus* E58. Another embodiment is an isolated and purified, heat stable, amino terminus-methylated, carboxy-terminus reduced peptide having two or more D-amino acids isolated from *Brevibacillus* sp that inhibits the growth of at least one bacterium selected from the group consisting of: *Staphylococcus, Enterococcus, Pneumococcus, Bacilli, Methanococcus, Haemophilus, Archaeoglobus, Borrelia, Synedrocyptis, Mycobacteria, Pseudomonas* and *E. coli*. A bacteria may be transformed with an isolated and purified nucleic acid having the sequence of BT operon (SEQ ID NO.: 21) that produces a heat stable, amino terminus-methylated, carboxy-terminus reduced peptide comprising two or more D-amino acids. The protein expressed from the nucleic acid may include one or more BT operon proteins, or those related thereto. A vector may be modified or isolated that includes an isolated and purified nucleic acid having the sequence of BT operon (SEQ ID NO.: 21) that produces a heat stable, amino terminus-methylated, carboxy-terminus reduced peptide comprising two or more D-amino acids. One or more proteins may be expressed from the nucleic acid that encodes one or more BT operon proteins. The feed additive may also include an isolated and purified, heat stable, amino terminus-methylated carboxy-terminus reduced peptide that has greater than 75% sequence homology to SEQ ID NOS.: 1-20.

The present invention also relates to peptides, and non-ribosomal peptide synthases that synthesize these peptides containing unusual amino acids and other types of modifications. The invention also includes methods of producing and using the peptides alone or synergistically with conventional antibiotics in the treatment and prevention of various microbial infections and protozoal infections and disorders related to such infections; tumor cell proliferation, growth and spread; or as an immune modulating agents.

BRIEF DESCRIPTION OF THE DRAWINGS

For a more complete understanding of the features and advantages of the present invention, reference is now made to the detailed description of the invention along with the accompanying figures and in which:

FIG. 1A is a gel that shows the purification of peptide BT. Tricine gel separation of BT and the associated antibiotic activity. Chloroform extracted peptides were separated on a precast 16.5% Tricine gel (purchase from BioRad). One gel was stained with coomassie blue (left) to show peptide bands. Another gel (right) was overlaid with agar embedded with *Bacillus cereus*. Clear zones in the bacterial lawn correspond to the species that collapses into a single band with a molecular weight of ~1500. Molecular weight markers are as follows: triosephosphate isomerase 26.6 kD, myoglobin 17.0 kD, alpha-lactalbumin 14.4 kD, aprotinin 6.5 kD, insulin b chain, oxidized 3.5 kD, and bacitracin 1.4 kD.

FIG. 1B is a graph of mass spectrometry of chloroform-extracted BT Chloroform-extracted BT was ionized by addition of sodium chloride and then subjected to mass spectrometry analysis. Five ionized BT isomer groups (BT1555, BT1571, BT1583, BT1599 and BT1613) were detected and labeled.

FIG. 1C is a graph of mass spectrometry of purified BT1583. Fraction 33 of the C18 reverse phase HPLC was subjected to mass spectrometry analysis. Only protonated, sodium and potassium ionized BT1583 were detected;

FIG. 2A is a graph of BT1583 tandem mass spectrometry data. FIG. 2B is a partial BT1583 sequence structure deduced from amino acid composition and MS/MS experiments (Tables 1 and 2)(for complete motif and sequences see Tables 5 and 6, respectively);

FIGS. 3A to 3D are maps of the BT NRPS operon. FIG. 3A is a map of the construction of a supercontig from two contigs linked by a mate pair. Contig1 and contig 2 share a mate pair from a clone. The contigs are ordered and arranged to form a supercontig, which contains the sequences of contig 1 and contig 2, separated by an unsequenced gap region;

FIG. 3B is a map of the region sequenced in this work and the location of 9 ORFs found in the region. Six ORFs btA through btF encode the BT NRPS subunits (BtA, BtB, BtC, BtD, BtE and BtF);

FIG. 3C is a map of the domain organization of the BT NRPS subunits. The predicted amino acid substrate specificity of each module is marked in each A-domain;

FIG. 3D is a Phylogenetic tree of a multiple sequence alignment of all 13 binding pocket constituents as described in Table 3. The putative specificity was assigned using the partial BT1583 sequence. It is shown that those binding pockets of A-domains that supposedly activate the same or similar substrate cluster together;

FIGS. 3E-1 to 3E-12 are the nucleic acid sequence of the BT operon (SEQ ID NO.:21), the entire sequence is subdivided into 12 figures;

FIG. 3F is the amino acid sequence of BtA (SEQ ID NO.: 22);

FIG. 3G is the amino acid sequence of BtB (SEQ ID NO.:23);

FIGS. 3H-1 and 3H-2 are the amino acid sequence of BtC (SEQ ID NO.:24), the entire sequence is divided into 2 figures;

FIG. 3I is the amino acid sequence of BtD (SEQ ID NO.:25);

FIG. 3J is the amino acid sequence of BtE (SEQ ID NO.:26);

FIG. 3K is the amino acid sequence of BtF (SEQ ID NO.:27);

FIG. 3L is the amino acid sequence of BtG (SEQ ID NO.:28);

FIGS. 4A to 4E are sequence alignment of conserved motifs and alignments of the adenylation, consensation, thilation, epimerization and reductase domains from the BT NRPS modules, respectively. Conserved motifs were identified according to (Marahiel, 1997). Consensus sequences were placed under each alignment. Residues agree with consensus were black shaded. All 12 C-domains were aligned together, with the * symbols indicate the start C domains that are known to be less conserved;

FIGS. 5A to 5E are ATP-PPi exchange assays for the relative substrate specificities of the purified A-domains of Modules 8, 5, 7, 4 and 2, respectively, obtained from the ATP-PPi exchange assays were listed A) to D), respectively. The highest activity was defined as 100%. All 20 proteinogenic amino acids and L-Orn were tested in each assay, and background was usually below 1%. Apparent Km of the A-domains toward specific amino acids were listed underneath; and FIG. 6A is a summary of synthetic BT variants and FIG. 6B is a correlation between the BT variants and their properties for antibiotic activity and Pronase resistance as previously described.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used herein, the term "domestic animal" describes, e.g., swine, cattle, horse, goat, sheep, deer, dog, cat and any of a number of useful rodents. The term "poultry" as used herein includes, e.g., chicken, hen, quail, turkey, guinea fowl and so forth. The term "nursery fishes" used here includes, e.g., carp, catfish, rainbow trout, ayu (sweet fish), eel, tilapia, conger, salmon, trout, red seabream, yellow tail, flounder, globefish, and so forth. A number of other animals are contemplated to also be useful, e.g., shrimp and prawn.

As used herein, the terms "additive" and "feed additive" are used to describe compositions from bacteria that may be used in conjunction with animal feed as feed additive resulting in an improvement of the health of livestock, poultry and fish, and a reduction of economic loss due to reduced or low weight and/or increasing the rate of growth (e.g., weight) of existing health animals. For example, the feed additive of the present invention may be used from bacterial isolates, partially or wholly degraded bacteria, isolated, isolated and purified from bacteria and/or synthesized synthetically in whole or in part. The additive or feed additive for the domestic animals, poultry and fishes may be of powder, grain or liquid form and will be used in accordance with the feeding condition and installations of the farm and the target animal.

Suitable animal feedstuffs include, e.g., green feed, silages, dried green feed, roots, tubers, fleshy fruits, grains and seeds, brewer's grains, pomace, brewer's yeast, distiller's spent grains, milling byproducts, byproducts of the production of sugar, starch and oil recovery and various food wastes. The feed additive of the present invention may be used alone or in conjunction with other well-known feed additives such as antioxidants or mixtures of various substances (mineral mixtures, vitamin mixtures) that can be added to such feeds for enhancement. Specific feeds may also adapted for certain animal species depending on age and stages of development.

Base feeds suitable for use in conjunction with the peptides of the present invention may be prepared as is well-known to the artisan skilled in the art of preparing feeds, e.g., they may use those as described in Kirk-Othmer, Encyclopedia of Chemical Technology, 4th Ed., vol. 10, pp. 288-300, Wiley, N.Y., 1993, relevant portions incorporated herein by reference. For example, the base feed may include one or more of the following ingredients: corn, sorghum, barley, wheat, soybean, peanut, canola, fish meal, milk products, fats and oils, vitamins and minerals.

The present inventor recognized that an NRPS operon may be a source of information that allows one to learn certain structural details of the peptide product. The identification of the BT NRPS operon results in critical refinements of the BT1583 peptide structure. Soil microorganisms were screened for strains that produce novel antibiotics. A *Bacillus* spp. E58 (ATCC PTA-5854) was isolated for its ability to produce an antibiotic BT against *Staphylococcal aureus* that cause life-threatening hospital-acquired infections in immunity-compromised patients The strain was named *Brevibacillus texasporus* based on its relatedness to *Brevibacillus laterosporus*.

The modules of an NRPS are composed of smaller units or "domains" that each carries out a specific role in the recognition, activation, modification or joining of amino acid precursors to form the peptide product. One type of domain, the adenylation (A-) domain, is responsible for selectively recognizing and activating the amino acid that is to be incorporated by a particular module of the NRPS. Through analysis of the substrate-binding pocket of the A-domain of the PheA subunit of the Gramicidin S NRPS in combination with sequence comparison with other A-domains, it was possible to define ten residues that are the main determinants of the substrate specificity for an A-domain (Conti, et al., 1997; Stachelhaus, et al., 1999). The ten residues are considered an NRPS 'codon'. The NRPS codon collection is still growing as new NRPS codons continue to be discovered. The present invention includes the isolated and purified nucleic acids and the proteins encoded thereby for a group of novel NRPS codons for Valine, Lysine, Ornithine and Tyrosine.

The amino acid activation step is ATP-dependent and involves the transient formation of an amino-acyl-adenylate. The activated amino acid is covalently attached to the peptide synthase through another type of domain, the thiolation (T-) domain that is generally located adjacent to the A-domain. The T-domain is post-translationally modified by the covalent attachment of a phosphopantetheinyl prosthetic arm to a conserved serine residue. The activated amino acid substrates are tethered onto the NRPS via a thioester bond to the phosphopantetheinyl prosthetic arm of the respective T-domains. Amino acids joined to successive units of the NRPS are subsequently covalently linked together by the formation of amide bonds catalyzed by another type of domain, the condensation (C-) domain. NRPS modules can also occasionally contain additional functional domains that carry out auxiliary reactions, the most common being epimerization of an amino acid substrate from the L- to the D-form. This reaction is catalyzed by a domain referred to as an epimerization (E-) domain that is generally located adjacent to the T-domain of a given NRPS module. Thus, a typical NRPS module has the following domain organization: C-A-T-(E).

Figure 1:
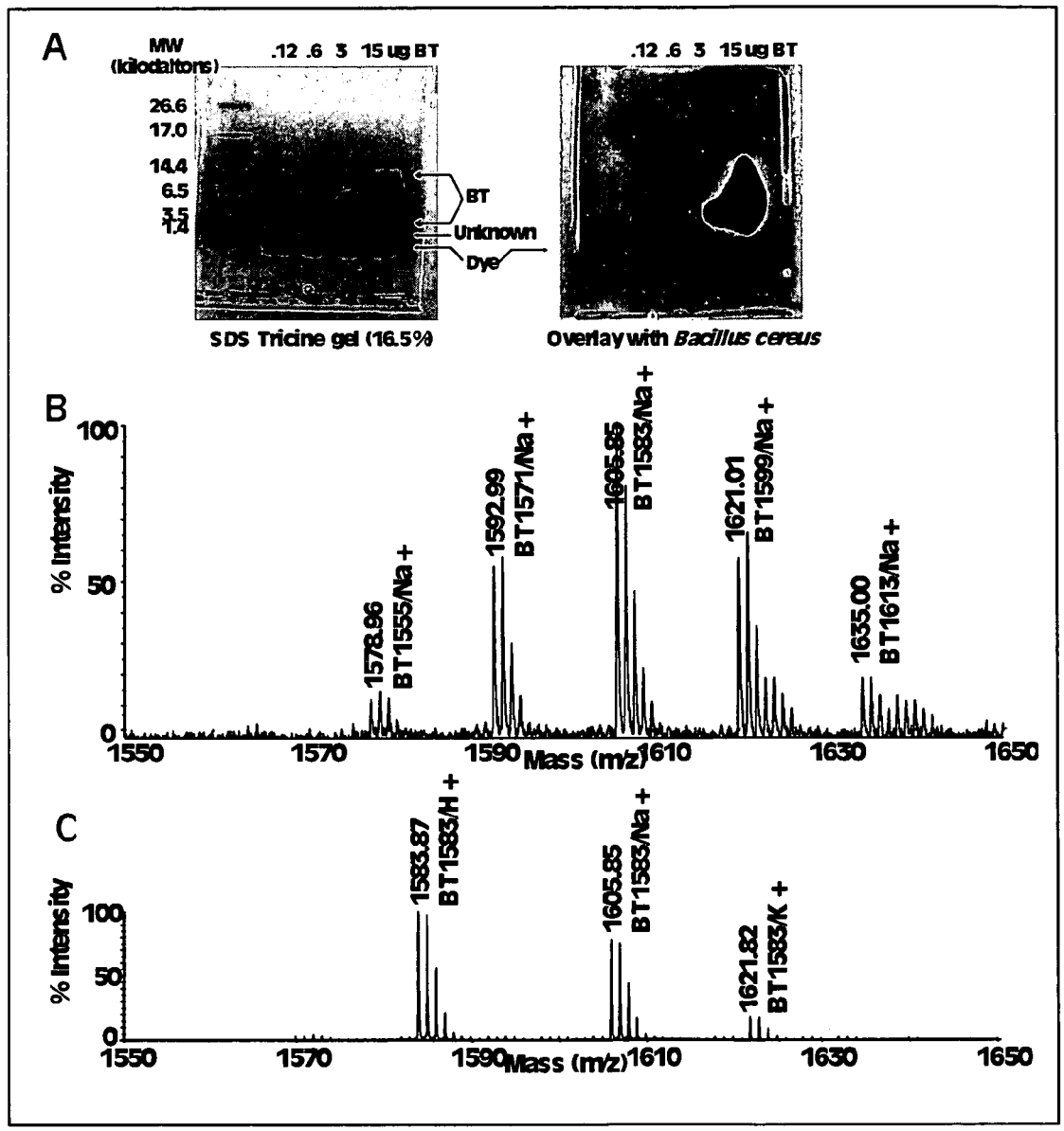

Product assembly by NRPS involves three distinct phases, namely chain initiation, chain elongation, and chain termination (Keating & Walsh, 1999). Peptide chain initiation is carried out by specialized modules termed a "starter module" that comprises an A-domain and a T-domain. Elongation modules have, in addition, a C-domain that is located upstream of the A-domain. It has been experimentally demonstrated that such elongation domains cannot initiate peptide bond formation due to interference by the C-domain (Linne & Marahiel, 2000). All the growing peptide intermediates are covalently tethered to the NRPS during translocations as an elongating series of acyl-S-enzyme intermediates. To release the mature peptide product from the NRPS, the terminal acyl-S-enzyme bond must be broken. This process is the chain termination step and is usually catalyzed by a C-terminal thioesterase (TE) domain. Thioesterase-mediated release of the mature peptide from the NRPS enzyme involves the transient formation of an acyl-O-TE intermediate that is then hydrolyzed or hydrolyzed and concomitantly cyclized to release the mature peptide (Keating, et al., 2001). An alternative termination scheme involves reduction of the tethered C-terminal residue by a reductase (R-) domain that resides in the last NRPS module, resulting in release of a peptide with an alcoholic C-terminal residue (Gaitatzis, et al., 2001; Kessler, et al., 2004). Such reductase-mediated termination/C-terminal modification occurs in BT biosynthesis and contributes to super protease resistance of the BT peptides.

Identification and isolation of the NRPS operon was useful to the studies of a peptide antibiotic, however, identification of a specific NRPS operon remains a challenging task. Identification of an NRPS operon traditionally starts with identification of clones in a genomic BAC or cosmid library by hybridization with DNA probes from known NRPS genes or by gene fragments amplified by PCR of genomic DNA using degenerate primers. Because the amino acid sequences of NRPS domains are usually quite similar, such approaches can be successful, however, because probes or primers are often imperfect, some NRPS operons can be missed. Moreover, microbes often contain multiple NRPS operons, so that the probes or primers may reveal some NRPS operons but not the one sought. This often results in ill-fated efforts devoted towards an incorrect gene (Hopwood, 1997). A novel in silica approach was used as described herein to allow rapid and accurate identification of an NRPS operon.

Materials and Methods. Partial purification of BT. E58 *B. texasporus* cells were grown in one liter of LB in a 37° C. air shaker for three days. The culture was spun in a clinical centrifuge at 3000 rpm for 15 minutes. The supernatant was collected and 500 grams of ammonium sulfate was added and dissolved. The sample was spun in the clinical centrifuge at 3000 rpm for 15 minutes. The pellets were dissolved in 200 ml of distilled water. The solution was then boiled for 15 minutes and then cooled on ice. The sample was filtered with a 0.2 micron filter (Nalgen). The filtrate was mixed with 0.2 liter of chloroform at room temperature for 20 minutes with a stir bar. The mixture was separated into two phases through centrifugation in the clinical centrifuge at 3000 rpm for 15 minutes. The organic phase was collected and dried in a vacuum evaporator.

C18 reverse phase HPLC. The dried chloroform extract was dissolved in 2 ml of sterile distilled water. The solution was fractionated on a C18 reverse phase HPLC column in a gradient from 30% B to 55% Solution B (Solution B is 0.075% TFA in acetonitrile, Solution A is 0.1% TFA in water). Resultant fractions were dried and dissolved in sterile distilled water and analyzed for anti-*S. aureus* activity in a plate clear zone assay The peak fraction (Fraction 33) was subjected to amino acid composition, mass spectrometry, tandem mass spectrometry and chirality analyses.

Amino acid composition. Amino acid analysis was performed by the Protein Chemistry Laboratory at Texas A&M University in College Station, Tex. Samples were mixed with internal standards, dried in glass tubes in a vacuum concentrator and subjected to vapor phase hydrolysis by 6N HCl at 110° C. for 24 hours under argon atmosphere in the presence of phenol. The samples were subsequently reconstituted in borate buffer and transferred to a Hewlett Packard AminoQuant II system for automated derivatization and loading. The AminoQuant analyzes peptides and proteins by pre-column derivatization of hydrolyzed samples with o-phthalaldehyde (OPA) and 9-fluoromethyl-chloroformate (FMOC). The derivatized amino acids are separated by reverse phase HPLC and detected by UV absorbance with a diode array detector or by fluorescence using an in-line fluorescence detector.

Mass spectrometry and tandem mass spectrometry. Detection of D-form amino acid residues. The chiral analysis of amino acid residues in BT was performed by Commonwealth Biotechnologies, Inc. of Richmond, Va. BT was subjected to hydrolysis in 6N HCl in vacuum for 18 hours at 110° C. The amino acids were derivatized to FMOC amino acids and separated by HPLC chromatography. The elution profile of each amino acid was then determined on a chiral column. For both types of chromatography columns, peaks were identified by comparisons with appropriate standards.

Genomic DNA preparation. Log-phase E58 cells were harvested from an LB culture and lysed with Lysis Buffer [10 mM Tris (pH 8.0), 100 mM EDTA, 0.5% SDS]. RNase A was added to digest contaminating RNA. Genomic DNA was extracted with phenol/choloroform and then precipitated with ethanol. Dried DNA was resuspended in TE and an aliquot was run in 0.5% agarose gel for quality control.

Library construction and genome sequencing. The E58 genomic library construction, shot-gun sequencing and the assembly were performed by Agencourt Biosciences Corporation (Beverly, Mass.). Briefly, the whole genome library was constructed with an average insert length around 5 kb. 10,000 such clones were subject to automated DNA sequencing from both ends of the insert. 16,901 successfully sequenced reads were collected and assembled.

Nucleotide sequences and data analysis. All BLAST analyses against E58 genome were performed by use of WU BLAST software package (version 2.0) installed on a local computer (Gish, W. 1996-2003. http://blast.wustl.edu). Amino acid sequence homology searches were performed by use of the BLAST server at the National Center for Biotechnology Information (Bethesda, Md.) and nonredundant protein sequence database with default parameter values (Altschul, et al., 1990). Amino acid sequence alignments were performed by use of the CLUSTALW program (Thompson, et al., 1994) running at NPS@ web server at Institute of Biology and Chemistry of Proteins (Lyon, France).

The BT NRPS operon. The BT NRPS operon (Supercontig 3) contained 11 contigs, spanning a region of at least 46 kb. There were unsequenced regions, regions that were just sequenced once, and regions with bad sequencing quality. Also, carboxyl region of the thirteenth module was not covered by Supercontig 3. Three rounds of primer extension sequencing and one round of genome walking were performed to achieve the finishing of the NRPS operon. All original sequencing reads in Superontig 3 were extracted and reassembled using the SeqMan (Lasergene, DNASTAR Inc.). The default parameters were used for the reassembly. A higher stringency adopted by SeqMan caused the reassembled Supercotig 3 to break into 17 contigs with 16 unsequenced gaps. All contigs were further examined manually for single coverage and bad quality regions. Primers were designed to sequence into a gap as well as to obtain additional reads in the single coverage and low quality regions. New sequencing reads were joined with the original reads to create a new supercotig. The new supercotig was checked again for gaps, single coverage and low quality regions. After three rounds of such primer extension and reassembly, the putative BT NRPS operon was assembled into a single contig of 48,997 bp in length. To verify the assembled sequence, an EcoRI plus HindIII double digestion was performed with 20 clones that collectively spanned the whole region. Resultant digestion patterns were in perfect agreement with the restriction map predicted by the contig (data not shown). To sequence the downstream region of the contig, genome walking was successfully performed with E58 genomic DNA using GenomeWalker kit from Clontech. The effort resulted in a DNA sequence of 50,674 bp covering the putative BT NRPS operon.

Cloning, overexpression, and purification of His10-tagged BT A-domain proteins. DNA fragments encoding the A-domains of the BT NRPS Modules 8, 5, 7, 4 and 2 (Bt8A, Bt5A, Bt7A, Bt4A and Bt2A) were PCR-amplified and the PCR products were inserted into the His10-tag recombinant protein expression vector pET16b (Novagen). The A-domain borders were determined as defined by (Konz, et al., 1999). The expression constructs were transformed into the *E.coli* BL21 -AI strain (Invitrogen). Transformants were grown in L-broth at 37° C. to an A600 of 0.6 and then induced with 1 mM IPTG (isopropyl-β-D-thiogalactopyranoside) plus 0.2% L-arabinose. The cells were allowed to grow for two additional hours at 30° C. before being harvested. Purification of the His10-tag recombinant proteins was achieved using the TALON metal affinity resins (BD Biosciences) under conditions recommended in the manual with modifications. Briefly, the *E. coli* cells were broken by sonication. Cell lysates were cleared by centrifugation at 25,000× g for one hour. His-tagged recombinant proteins were then incubated with the TALON resin, washed, and eluted with 500 mM imidazole. Eluted proteins were dialyzed against a buffer (50 mM HEPES, pH 8.0, 100 mM sodium chloride, 10 mM magnesium chloride, and 1 mM EDTA) and then analyzed with SDS PAGE plus Coomassie Blue staining. The recombinant proteins displayed apparent molecular weights compatible with calculated ones, and they appeared to be purified to homogeneity. Concentrations of the purified proteins were determined by using the calculated molar extinction coefficient for the $A_{280}$.

ATP-PPi exchange assay. ATP-PPi exchange assays were performed to determine the substrate specificity of an A-domain. ATP-PPi exchanges were assayed as previously described (Stachelhaus, et al., 1998) with minor modifications. The assay mixture contained 50 mM HEPES (pH 8.0), 100 mM NaCl, 10 mM MgCl2, 2 mM ATP, 0.5 mM amino acid, 0.05 mM PPi, 0.15 μCi tetrasodium [$^{32}$P]pyrophosphate. Exchange was initiated by addition of purified recombinant A-domain proteins to a total volume of 0.1 ml. The protein concentrations were 0.2 μM for Module 4 and Module 5 A-domains while 2 μM for Module 7 and Module 8 A-domains. After incubation at 37° C. for 15 min, the reaction was stopped by addition of 0.5 ml of Termination Mix (100 mM tetrasodium pyrophosphate, 3.5% HClO4, and 1.6% [w/v] activated charcoal). The charcoal was pelleted by centrifugation, washed first with 40 mM pyrophosphate plus 1.4% perchloric acid and then with water, and was re-suspended in 0.5 ml of water. The charcoal/water suspension was added to a scintillation vial containing 5.0 ml of scintillation fluid, and the bound radioactivity was determined by liquid scintillation counting. The apparent Km values were determined with substrate concentrations ranging from 0.1 to 10 mM.

MIC determination assays. *Staphylococcal aureus* was grown to mid-log phase in LB at 37° C., and diluted by 500-fold with fresh LB and dispensed into 96-well micro-titer plates. Different concentrations of peptides were added, and the micro-titer plates were incubated at 37° C. with shaking. A minimal inhibition concentration (MIC) was determined as the lowest peptide concentration that produced a clear well. All experiments were performed in triplicates, and highly consistent MICs were obtained.

Identification of the BT peptides. The bacterial strain E58 was isolated from soil in an effort to identify soil microorganisms that produce novel antibiotics against Staphylococcus aureus. E58 was found to be closely related to *Brevibacillus laterosporus* based on the 16S rDNA sequence homology (98.5% identity). E58 was named *Brevibacillus texasporus* and deposited to ATCC (catalog number PTA-5854). The antibiotic produced by E58 was named BT and its activity could be detected in the supernatant of a liquid E58 LB culture. Cell-free culture supernatant was, therefore, the starting material for BT purification. The antibiotic activity was precipitated by ammonium sulfate, which suggested that the antibiotic be a protein or peptide (data not shown). The activity was further extracted into chloroform, indicating that BT is made of small molecules. The antibiotic chloroform extract was evaporated in a vacuum evaporator, dissolved in water and then run on a SDS tricine gel. The two halves of a gel with identical lanes in each half were either stained for proteins/peptides or overlaid with agar embedded with BT-sensitive bacteria *Bacillus cereus* to test for antibiotic activity (FIG. 1A). Three species were visible after staining: the Bromophenol Blue dye originated from the gel loading buffer, an unknown peptide with a mass<1.4 kD and a third species with an antibiotic activity. This third species ran as a ~1.5 kD band at low concentrations (clearly visible on the original gel) and were later shown made up of a group of related peptides (see below). Their apparent masses increased with concentration suggesting that the peptides aggregate at higher concentrations. An antibiotic activity was seen associated with the peptides at higher concentrations, and we therefore concluded that the peptides likely conferred the BT antibiotic activity. The peptides were referred as the BT peptides. The BT peptides apparently were not toxic to *B. cereus* at the lower concentrations in this assay. Since the smallest detectable BT band ran at ~1.5 kD, therefore the BT peptides contained approximately 13 residues.

The chloroform-extracted BT was subject to a mass spectrometry assay. A group of peptides were detected in a range between 1550 and 1650 Daltons (FIG. 1B). The main species showed a molecular weight of 1583, and it was named BT1583. The other peptides were later shown to be isomers of BT1583 (Tables 5 and 6).

Partial BT Sequence Determination. The chloroform-extracted BT was purified further by C18 reverse phase HPLC (see Materials and Methods for details). BT1583 was purified to homogeneity in Fraction 33 of the C18 HPLC (FIG. 1C). An amino acid composition analysis of BT1583 (Fraction 33) showed BT1583 contained residues of Tyr, Lys, Leu, Ile, Val and Orn. BT1583 was refractory to N-terminal sequencing and resistant to degradation by aminopeptidase M, suggesting that a non-standard N-terminal residue. BT1583 was also resistant to cleavage by carboxypeptidase Y, suggesting a non-standard C-terminal amino acid. Carboxyl-terminal sequencing was, therefore, not attempted.

Figure 2:
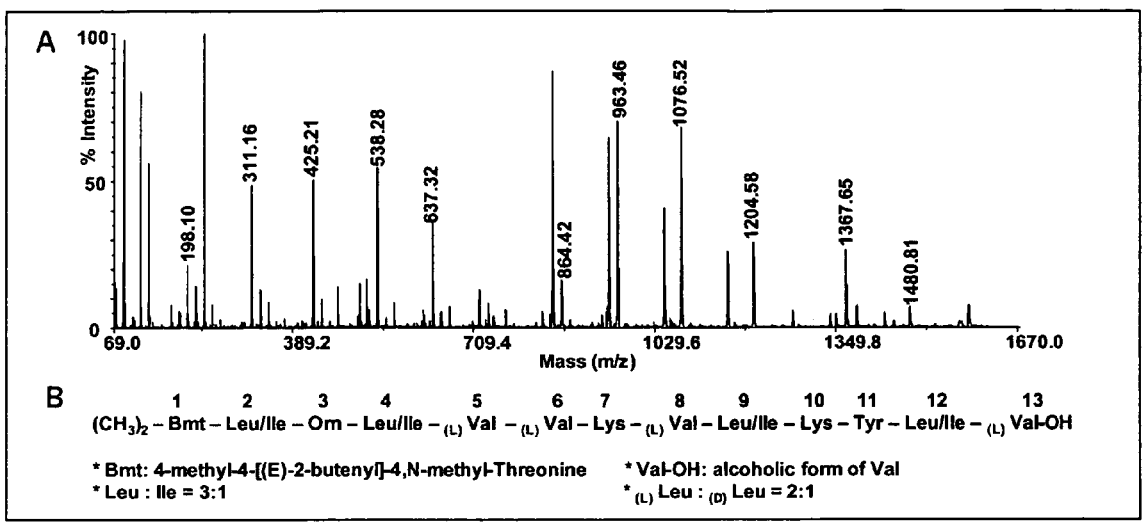

Tandem mass spectrometry (MS/MS) was then chosen to sequence the BT1583 peptide. MS/MS data were obtained for BT1583 and they are shown in FIG. 2A and Table 2. The MS/MS data indicated that BT1583 contained 13 amino acid residues that correlated well with the amino acid composition. As expected, the masses of Residues 1 and 13 did not correspond to any standard amino acids. The last residue showed a mass of 103 daltons, which appeared to be compatible with a Valine having its C-terminus reduced from a carboxylic acid to an alcohol. The presence of a C-terminal alcoholic Valine was further confirmed by the presence of a reductase domain in the 13th Valine-specific module of the BT NRPS (see below). The identity of the N-terminal residue was more difficult to determine. Nonetheless, an N-terminal residue with a mass of 198 seemed to be compatible with the N,N-methylated form of Bmt {4-methyl-4-[(E)-2-butenyl]-4,N-methyl-Threonine} (Offenzeller, et al., 1996; Offenzeller, et al., 1993)

The presence of Ornithine in BT1583 indicated that BT1583 could not be synthesized by ribosomes. The presence of D-amino acids would strengthen this idea. We chose to assess the chiral properties of two of the most abundant residues in BT1583, Val and Leu. Chiral analyses revealed uniform L-Val residues but both L- and D-Leu residues at a ratio of 2:1.

The above biochemical and structural analyses were able to provide us with a partial BT1583 peptide sequence (Table 2 and FIG. 2B). The structures of the N- and C-terminal residues were not fully determined. Isoleucine and Leucine could not be distinguished. The position of the D-form Leu was not specified. Chiral properties of other residues in the peptide were not determined.

Shot-gun sequencing of the E58 genome. To better understand the structure and biosynthesis of the BT1583 peptide, we decided to identify the gene or operon that is responsible for the BT biosynthesis. The presence of non-proteinogenic Ornithine and D-form amino acids in the peptide led us to believe that BT1583 was synthesized by the NRPS in vivo (Marahiel, 1997). Most of the NRPS genes are co-linear reflecting a strict correlation between NRPS modules and the amino acid residues in the peptide product. If the BT NRPS operon is co-linear, it should encode 13 modules corresponding to the 13 amino acid residues in the BT1583 peptide. Assuming that on average, each module is encoded by an average 3.5 kb DNA fragment, a DNA fragment of 46 kb long would be necessary to accommodate the BT NRPS operon. As mentioned before, the traditional method to identify an NRPS operon involves probing a cosmid library with a generic probe. Since an imperfect generic probe may miss the target gene and there are usually multiple NRPS operons in a bacterial genome, such method frequently causes researchers to chase the wrong NRPS operon. To avoid such pitfall, we developed a genomic approach that provides an unbiased in silica overview of all NRPS operons in a genome to allow direct comparisons of the NRPS operons and therefore rational candidate operon selection. This novel approach resulted in rapid and accurate identification of the BT NRPS operon.

The E58 genome was estimated to be 5 Mb. An E58 genomic library was constructed with an average insert size of 5 kb. The whole genome was sequenced for a two-fold coverage. After sequence assembly, the E58 genome was represented by 1919 contigs with sizes ranging from 700 bp to 22.6 kb and 932 singlets. Such coverage would allow 99.995% of the genome to be represented by clones. Also, the average length of the gap between two neighboring contigs would be as small as 250 bp so that supercontigs could be constructed (see below). Moreover, supercontigs at such resolution would contain sufficient information to allow accurate in silica NRPS operon identification.

In silica identification of the BT NRPS operon. A three-step procedure was used to select the candidate BT NRPS operon. First, all contigs and singlets were searched for sequences encoding NRPS modules. Since E58 is related to *B. subtilis*, the putative peptide synthetase PPS1 from *B. subtilis* was chosen as the query sequence for BLAST analysis against a database containing all assembled E58 contigs. 128 contigs showed translated amino acid sequence similarities to PPS1, with P-values arranging from 0 to 1.

Second, supercontigs were constructed from the 128 contigs. Two sequencing reads from the ends of the same insert form a mate pair. A supercontig is a collection of contigs joined mate pairs that reside in different contigs. Identification of mate pairs allowed neighboring contigs to be ordered and orientated to form a supercontig (FIG. 3A). 31 supercontigs were successfully constructed to represent the whole E58 NRPS operon portfolio.

The candidate BT NRPS operon was selected from the E58 NRPS operon portfolio. The 31 supercontigs were examined for the possibility of harboring the BT NRPS operon, and Supercontig 3 (whose genetic features based on finished sequence are shown in FIG. 3B and 3C) was chosen as the candidate based on the following analyses.

Supercontig 3 potentially contained DNA sequence encoding 13 NRPS modules. Available information regarding the A-domian substrate specificities of Supercontig 3 showed compatibility with the partial BT1583 sequence. Complete sets of substrate specificity-conferring amino acid residues could be identified for eleven modules (except Modules 2 and 13 due to incomplete DNA sequence). Although not all specificity predictions could be made, good correlations were established between predicted NRPS amino acid substrates and the partial BT1583 sequence. Specifically, Module 4 was predicted to incorporate Ile, and Modules 9 and 12 were predicted to incorporate Leu (Table 3, see below for details). The partial BT1583 sequence had Leu or Ile at Positions 4, 9 and 12. Phylogenetic analysis of the substrate conferring amino acids of the eleven modules showed that modules expected to incorporate the same or highly similar amino acid did group together (FIG. 3D). For example, Modules 5, 6 and 8 that were all predicted to incorporate Val formed a cluster. Modules 7, 10 and 3 that were predicted to incorporate similar cationic amino acids (Lys and Orn respectively) formed another cluster.

The E-domain positions in the NRPS encoded by Supercontig 3 showed compatibility with the partial BT1583 peptide structure. Four E-domains were found in Modules 3, 7, 9 and 11 (FIG. 3C). Their positions were consistent with the aforementioned BT1583 chiral properties of all L-form Val residues and a 2:1 L- to D-form Leu residue ratio.

Supercontig 3 was therefore identified as the candidate locus for the BT NRPS operon. Primer extensions and genome walking were performed to obtain high quality sequence of the locus. The efforts resulted in a contig of 51,821 bp covering the putative BT NRPS operon (Genbank accession #), see FIG. 3F.

Figure 3:
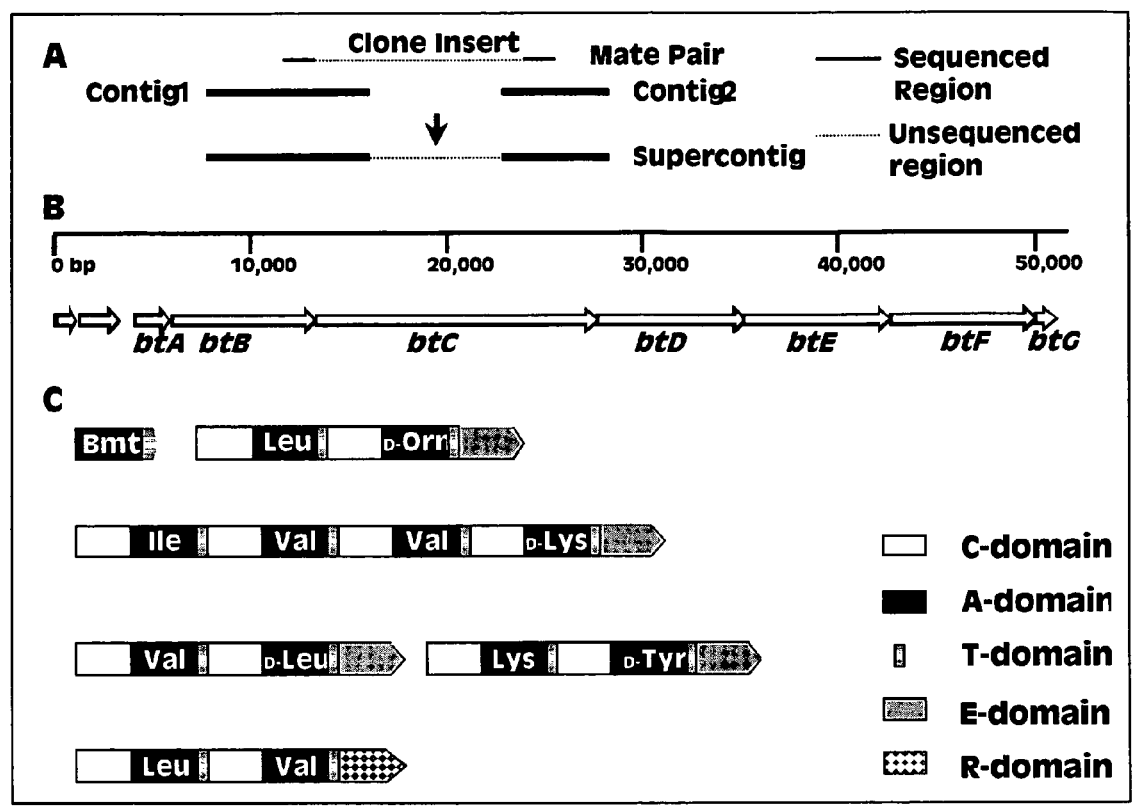
Figure 3D:
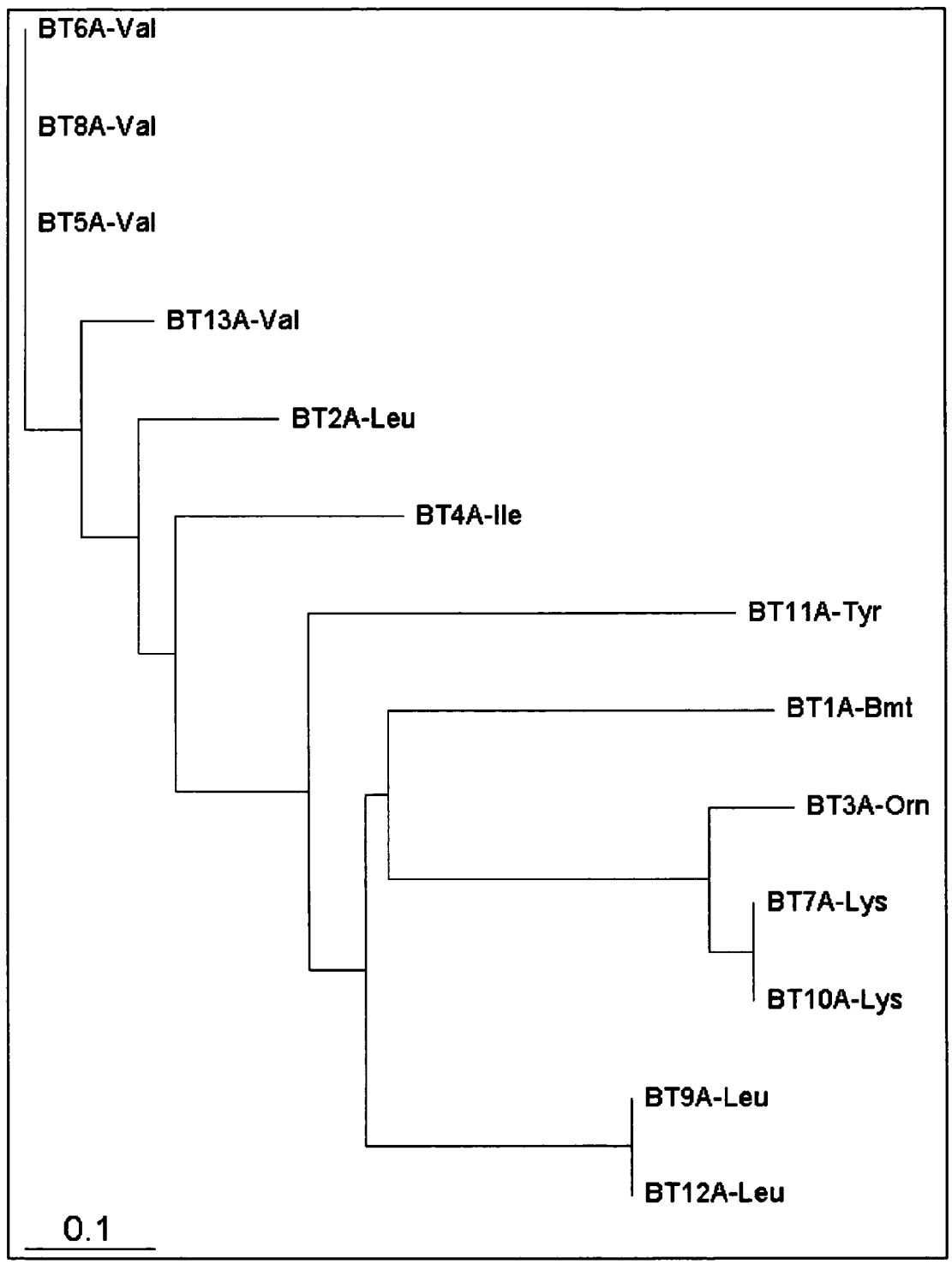

Putative BT NRPS subunits. Ten open reading frames (ORFs) were identified in the sequenced region through translation analysis and blast searches (Altschul, et al., 1997) (FIG. 3B). The middle six ORFs (named btA through btF) were predicted to encode six subunits of the BT NRPS (BtA through BtF), and their coordinates are listed in Table 4. Sequence analysis of the putative subunits confirmed the modular structure of a typical co-linear NRPS (FIG. 3C). The modules, each containing an A-domain and a T-domain, are linked by a C-domain. The loading module BtA has an A-domain followed by a T-domain. There are two noticeable overall features for the putative BT NRPS subunits. First, four out of six subunits exhibit a two-module structure. Second, all auxiliary E-domains are present at the end rather than in the middle of the putative NRPS subunits. Sequence alignments of conserved domains are shown in FIG. 4.

A reductase domain in Module 13. A domain of about 500 amino acids was identified at the C-terminus of BtF or Module 13. BLAST analysis showed that it has high similarity with several NADPH-dependent reductases from other NRPSs and polyketide synthetases. Its alignment with the reductase domains from MxcG of *S. aurantiaca* and Lys2 of *S. cereviciae* is shown in FIG. 4E. A similar reductase domain has also been identified in the Gramicidin A NRPS (Kessler, et al., 2004). All three reductases have been experimentally demonstrated to reduce their substrates to corresponding aldehydes in an NADPH-dependent reaction (Gaitatzis, et al., 2001; Kessler, et al., 2004; Sagisaka & Shimura, 1959). For myxochelin A and gramicidin A, the aldehydes are further reduced to alcohols. The exact mechanism for the second reduction step has not been identified. Either those reductase themselves or another proteins carry out the second reduction step, or the second reduction step is spontaneous. The MS/MS experiment suggested that the C-terminal residue of BT1583 might be the alcoholic form of Valine (FIG. 2B). The A-domain specificity prediction of the last putative BT NRPS module and the presence of a reductase domain in the module confirmed this proposal.

btG encodes an ABC transporter. btG is an ORF that is immediately downstream of btF, and it is transcribed in the same direction as are other bt ORFs. The initiation codon ATG is located 61 bp downstream of the btF stop codon. Translated amino acid sequence showed high similarity to members of the ATP-binding cassette (ABC) transporter super-family (data not shown). ABC transporter ORFs are found in typical NRPS operons. Their roles have been proposed to provide host with resistance to the peptide antibiotic product by pumping the peptide out of the cells. The exact role of the putative BtG ABC transporter needs to be established.

BT1583 peptide sequence refinement. The substrate specificity-conferring residues (Stachelhaus, et al., 1999) were extracted from all 13 A-domains and were compared to the collection of the amino acid-binding pocket constituents in the public NRPS codon database (raynam.chm.jhu.edu/~nrps/index.html) (Challis, et al., 2000). Substrate specificity predictions were made based on the sequence alignments and they are listed in Table 3. The amino acid-binding pocket constituents of the first module showed a perfect match with an NRPS codon for Threonine/Dehydrothreonine, and it was predicted that Module 1 incorporates a Threonine derivative. N,N-methylated Bmt was proposed to be the N-terminal amino acid residue according to the MS/MS data (FIG. 2B and Table 2). Although the two proposals do not agree with each other 100%, both call for a Threonine derivative as the N-terminal amino acid residue.

As mentioned before three unambiguous specificity assignments could be made for Module 4 (Ile), Module 9 (Leu) and Module 12 (Leu) according to the NRPS codon database. These assignments were compatible with the partial BT1583 sequence and accordingly Positions 4, 9 and 12 of the BT1583 peptide were refined to Ile, Leu and Leu respectively. Since the only Ile of the BT1583 peptide had been assigned to Position 4, the remainder Leu was assigned to Position 2 of the BT1583 peptide. The A-domain specificity of Module 2 was therefore deduced to be Leu. These assignments in conjunction with the E-domain positional information allowed us to refine the BT1583 peptide sequence to $(CH_3)_2$-Bmt-Leu-dOrn-Ile-Val-Val-dLys-Val-dLeu-Lys-dTyr-Leu-Val-ol, wherein Val-ol is Valine alcohol.

Novel NRPS codons in BT biosynthesis. The amino acid-binding pocket constituents of Modules 5, 6 and 8 are identical. They differ with those of Module 13 by only one residue. No good matches were found for these sets of amino acid-binding pocket constituents in the NRPS codon database. However, they showed similarities to certain Ile, Leu or Val NRPS codons in the database. Since the partial BT1583 peptide sequence had Val residues at Positions 5, 6, 8 and 13, Modules 5, 6, 8 and 13 were deduced to incorporate Val. The amino acid-binding pocket constituents of Modules 5, 6, 8 and 13 represent potential novel NRPS codons for Val.

The amino acid-binding pocket constituents of Modules 7 and 10 are identical and they differ with those of Module 3 by only one residue. No match was found for these sets of amino acid-binding pocket constituents in the NRPS codon database. Since the partial BT1583 peptide sequence had Lys residues at Positions 7 and 10, the specificities of these modules were deduced to be Lys. Likewise the partial BT1583 peptide sequence had an Orn residue (which is highly similar to Lys in structure) at Position 3, and the specificity of Module 3 was therefore deduced to be Orn. The amino acid-binding pocket constituents of Modules 7 and 10 represent potentially the first NRPS codon for Lys, while those of Module 3 represent a potential novel NRPS codon for Orn.

The specificity prediction for Module 11 was quite ambiguous according the NRPS codon database. No good match was found for this set of amino acid-binding pocket constituents in the NRPS codon database. However, it showed similarities to certain Phe, Trp or Tyr NRPS codons in the database (data not shown). Since the partial BT1583 peptide sequence had Tyr residues at Position 11, the A-domain specificity of Module 11 was therefore deduced to be Tyr. The amino acid-binding pocket constituents of Module 11 represent a potential novel NRPS codon for Tyr.

Identity verification of the BT NRPS operon. Since the BT biosynthesis involves novel NRPS codons, experimental establishment of the novel codons (especially the novel Valine and Lysine codons) is critical to verifying the identity of the BT NRPS operon. In addition, since the placement of Ile at position 4 in BT1583 affects the placement of three Leu residues, the Module 4 codon also needed to be tested.

Since a purified recombinant A-domain of an NRPS module can selectively and efficiently activate the cognate amino acid substrate of the NRPS module in an ATP-PPi exchange assay (Konz, et al., 1999; Mootz & Marahiel, 1997), ATP-PPi exchange assays have been used to experimentally establish NRPS module specificities and novel NRPS codons. Recombinant A-domains of Modules 8, 5, 7, 4 and 2 of the BT NRPS were produced and purified as described in Methods and Materials. Almost completely soluble recombinant A-domain proteins were obtained. A-domain specificities were determined in ATP-PPi exchange and aa Km assays (see Methods and Materials), and the results are shown in FIG. 5. All 20 proteinogenic amino acids and L-Orn were tested for each A-domain protein, and background noise in the experiments was usually below 1%.

The Module 8 A-domain protein was shown to activate L-Val (100%), with minor activation of L-Lys (10%) and L-Ile (4%). The apparent $K_m$ was determined to be 2.75 mM for L-Val. These results confirmed the novel Valine NRPS codon. Similarly, the Module 5 A-domain protein was found to activate L-Val (100%), L-Ile (23%), and L-Leu (17%). The apparent $K_m$ was determined to be 1.11 mM for L-Val and 2.78 mM for L-Ile, clearly showing that L-Val is the preferred substrate for Module 5.

L-Lys was the only amino acid that activated by the Module 7 A-domain protein. The apparent $K_m$ value was determined to be 1.12 mM. These results established the first Lys NRPS codon.

The Module 4 A-domain protein was shown to selectively activate L-Ile (100%), with minor activation of L-Val (9%) and L-Leu (7%). The apparent $K_m$ value for L-Ile was measured at 0.5 mM.

The Module 2 A-domain protein was found to be quite ambiguous. It activated L-Leu (98%) and L-Met (100%) with nearly equal efficiency, with significant activation of L-Val (67%) and minor activation of L-Ile (19%) and L-Phe (3.5%).

In general, all purified A-domain proteins were found to selectively activate predicted amino acid substrates in the ATP-PPi exchange assays. These results experimentally confirmed the identity of the BT NRPS operon.

Synthetic peptides. To further verify the BT peptide sequence as well as the identity of the BT NRPS operon, a synthetic peptide P81 (FIG. 6) was made (by Biomer Technology, Concord, Calif.) and tested for its properties. Since Bmt is not commercially available, we were not able to synthesize a peptide according to the refined BT1583 sequence and we used octanic acid-modified Threonine to synthesize the lipopeptide P81 to mimic BT1583. P81 showed full antibiotic activity and Pronase resistance as BT1583. These results lend support to the refined BT1583 peptide sequence and the identity of the BT NRPS operon.

To investigate the significance of the C-terminal alcoholic modification, an amide form of P81 (P59) was synthesized. P59 displayed antibiotic activity but no Pronase resistance. These results indicated that the C-terminal alcoholic modification plays a key role in conferring protease resistance to P81 and likely BT1583 as well.

Since the codon for the first BT NRPS module matches perfectly with known Thr NRPS codons, the possibility of an active BT isomer with an unmodified Thr at Position 1 needed to be investigated. An amide form of P81 (P58) was therefore synthesized, and P58 displayed poor antibiotic activity. This result confirmed that a Thr derivative (rather than unmodified) Thr needs to be at Position 1 to confer antibiotic activity.

The L- and D-form residues alternate in the middle of BT1583 with the exception of Position 5 (Val). Since the alternating chirality is a key structural feature for the peptide antibiotic Gramicidine A, we decided to investigate whether we missed the coding sequence of an E-domain for Module 5. A D/L alternating version of P59 (P80) was synthesized. P80 displayed no antibiotic activity. The above results confirmed not only the BT1583 peptide structure (with the exception of the N-terminal residue) but also the identity of the BT NRPS operon.

The BT1583 peptide structure, the BT NRPS operon and the BT NRPS allow us to propose a degenerate formula for isomers of BT1583 (Table 5). Based on the relative substrate selectivty of each module, the BT isomers likely to be produced by E58 in significant amounts were predicted and listed in Table 6. Most of the predicted BT isomers were experimentally verified by MS/MS (data not shown).

The structure and biosynthesis of the BT peptide was determined using an integrated approach of biochemistry, biophysics and genomics. Amino acid composition and tandem mass spectrometry experiments with purified BT1583 (the main BT isomer) produced a partial peptide structure. The presence of Ornithine and D-form residues in the partial structure indicated that the peptide was synthesized by a non-ribosomal peptide synthase in vivo. The BT NRPS operon was rapidly and accurately identified via a novel in silica gene hunting scheme. Sequence analysis of the BT NRPS operon revealed that it encodes a co-linear modular NRPS. The co-linear nature of the BT NRPS enabled us to use the BT operon genomic information and refine the BT1583 peptide sequence to $Me_2$Bmt-L-dO-I-V-V-dK-V-dL-K-dY-L-Vol (SEQ ID NO.: 1), wherein Vol stands for Valine alcohol. Moreover, new NRPS codons for Valine, Lysine, Ornithine and Tyrosine were discovered and are reported here.

In silica NRPS operon identification. Traditional NRPS gene identification involves probing a genomic cosmid library with a generic probe. Such approach has the inherited shortcoming of causing researchers to chase the wrong gene in a genome with multiple NRPS operons. As shown herein, NRPS gene identification is improved for all NRPS operons in the genome when compared at the same time to find a best fit. Such comparison requires a draft genome. Fortunately, sequencing cost has decreased significantly to allow routine sequencing of microbial genomes. A two-fold coverage was sufficient for accurate NRPS operon identification. In actual BT NRPS operon selection, the following two sets of information are generated and compared to find the best candidate: the NRPS module clustering pattern of according to similarities of the substrate-binding pocket constituents; and positional information such as the positions of D-form residues. The module clustering technique is especially powerful in establishing the candidacy of an operon that involves novel NRPS codons (i.e., in the case of Modules 5, 6 and 8 of the BT NRPS operon). The in silica strategy is particularly useful for NRPS operon identification in strains (such as E58) that have a large number of NRPS operons in the genome.

TABLE 1

Amino acid composition of purified BT1583 peptide

| Amino Acid | nmoles | Molar ratios normalized to Tyr | Molar ratios normalized to Ile | Residues per peptide |
|---|---|---|---|---|
| Tyrosine | 1.75 | 1.00 | 1.16 | 1 |
| Valine | 4.58 | 2.62 | 3.05 | 3 |
| Isoleucine | 1.50 | 0.86 | 1.00 | 1 |
| Leucine | 5.32 | 3.04 | 3.54 | 3 |
| Lysine | 3.57 | 2.04 | 2.38 | 2 |
| Ornithine | 1.2 | 0.69 | 0.80 | 1 |
| Total # of derivatizable residues | | 10.25 | 11.93 | 11 |

TABLE 2

Tandem mass spectrometry of BT1583

| M/H+ b-series | ΔM | Possible amino acid residue | M/H+ y-series | ΔM | Possible amino acid residue | Compiled (N to C) |
|---|---|---|---|---|---|---|
| 198.1 | | (CH3)$_2$-Bmt(?) | | | | (CH3)$_2$-Bmt(?) |
| 311.16 | 113.06 | L/I | 1386.73 | 113.12 | L/I | L/I |
| 425.21 | 114.05 | O | 1273.61 | 114.04 | O | O |
| 538.28 | 113.07 | L/I | 1159.57 | 113.05 | L/I | L/I |
| 637.32 | 99.04 | V | 1046.52 | 198.08 | V + V | V |
| | | | | | | V |
| 864.42 | 227.10 | V + K | 848.44 | 128.07 | K | K |
| 963.46 | 99.04 | V | 720.37 | 99.04 | V | V |
| 1076.52 | 113.06 | L/I | 621.33 | | | L/I |
| 1204.58 | 128.06 | K | | | | K |
| 1367.65 | 163.07 | Y | | | | Y |
| 1480.81 | 113.16 | L/I | | | | L/I |
| 1583.87 | 103.06 | Valine alcohol | | | | Valine alcohol |

TABLE 3

Predicted BT NRPS module substrate specificities and refinement of the BT1583 peptide structure. The residues were numbered according to the corresponding residues of PheA (Conti, et al., 1997).

| | PheA Numbering | | | | | | | | | | Predicted Substrate Specificity | Partial BT1583 Seq. | Refined BT1583 Seq. |
|---|---|---|---|---|---|---|---|---|---|---|---|---|---|
| Module | 235 | 236 | 239 | 278 | 299 | 301 | 322 | 330 | 331 | 517 | | | |
| 1 | D | F | W | N | I | G | M | V | H | K | Thr/Dht | (CH$_3$)$_2$-Bmt* | (CH$_3$)$_2$-Bmt |
| 2 | D | G | F | L | L | G | G | V | F | K | Ile/Leu | Leu/Ile | Leu** |
| 3 | D | S | G | P | S | G | A | V | D | K | | Orn* | Orn |
| 4 | D | G | F | F | L | G | V | V | Y | K | Ile* | Leu/Ile | Ile |
| 5 | D | G | F | F | V | G | G | V | F | K | Ile/Leu/Val | Val* | Val |
| 6 | D | G | F | F | V | G | G | V | F | K | Ile/Leu/Val | Val* | Val |
| 7 | D | A | G | P | S | G | A | V | D | K | | Lys* | Lys |
| 8 | D | G | F | F | V | G | G | V | F | K | Ile/Leu/Val | Val* | Val |
| 9 | D | A | W | F | L | G | N | V | V | K | Leu* | Leu/Ile | Leu |
| 10 | D | A | G | P | S | G | A | V | G | K | | Lys* | Lys |
| 11 | D | A | A | A | V | V | G | V | A | K | Phe/Trp/Tyr | Tyr* | Tyr |
| 12 | D | A | W | F | L | G | N | V | W | K | Leu* | Leu/Ile | Leu |
| 13 | D | G | F | F | A | G | G | V | F | K | Ile/Leu/Val | Valine alcohol* | Valine alcohol |

*The information was used for the BT1583 peptide sequence refinement.
**The Leu at this position was deduced from the fact that the only Ile had been assigned to Position 4.

TABLE 4

The BT NRPS operon (see FIGS. 3G–3L).

| | ORF | | | Gene product | | | |
|---|---|---|---|---|---|---|---|
| | Start (nt) | End (nt) | Length (bp) | SEQ ID NO.: | length (amino acid) | MW (kD) | Homology to |
| btA | 2,889 | 4,814 | 1,926 | 22 | 641 | 72.87 | NRPS |
| btB | 4,817 | 12,409 | 7,593 | 23 | 2,530 | 288.99 | NRPS |
| btC | 12,438 | 26,291 | 13,854 | 24 | 4,617 | 526.68 | NRPS |
| btD | 26,321 | 33,946 | 7,626 | 25 | 2,541 | 289.31 | NRPS |
| btE | 33,976 | 41,556 | 7,581 | 26 | 2,526 | 288.45 | NRPS |
| btF | 41,584 | 49,059 | 7,476 | 27 | 2,491 | 284.46 | NRPS |
| btG | 49,120 | 49,842 | 723 | 28 | 240 | 26.95 | ABC transporter |

TABLE 5

A degenerate formula for the BT isomers

| 1 | 2 | 3 | 4 | 5 | 6 | 7 | 8 | 9 | 10 | 11 | 12 | 13 |
|---|---|---|---|---|---|---|---|---|----|----|----|----|
| Me$_2$Bmt | L | dO | I | V | V | dK | V | dL | K | dY | L | Valine alcohol |
|  | M |  |  | V |  |  |  |  |  |  |  |  |
|  | V |  |  | I |  |  |  |  |  |  |  |  |
|  | I |  |  | L |  |  |  |  |  |  |  |  |
|  | F |  |  |  |  |  |  |  |  |  |  |  |

Numbers indicate the amino acid residue positions.

TABLE 6

Summary of BT isomers

| Name | Peptide sequences of the predicted products by the BT NRPS | MW | SEQ ID NO.: |
|---|---|---|---|
| BT1583 | Me$_2$Bmt-L-dO-I-V-V-dK-V-dL-K-dY-L-Vol | 1583 | 1 |
| BT1601 | Me$_2$Bmt-M-dO-I-V-V-dK-V-dL-K-dY-L-Vol | 1601 | 2 |
| BT1569V2 | Me$_2$Bmt-V-dO-I-V-V-dK-V-dL-K-dY-L-Vol | 1569 | 3 |
| BT1583I2 | Me$_2$Bmt-I-dO-I-V-V-dK-V-dL-K-dY-L-Vol | 1583 | 4 |
| BT1617 | Me$_2$Bmt-F-dO-I-V-V-dK-V-dL-K-dY-L-Vol | 1617 | 5 |
| BT1597I5 | Me$_2$Bmt-L-dO-I-I-V-dK-V-dL-K-dY-L-Vol | 1597 | 6 |
| BT1597L5 | Me$_2$Bmt-L-dO-I-L-V-dK-V-dL-K-dY-L-Vol | 1597 | 7 |
| BT1615I5 | Me$_2$Bmt-M-dO-I-I-V-dK-V-dL-K-dY-L-Vol | 1615 | 8 |
| BT1615L5 | Me$_2$Bmt-M-dO-I-L-V-dK-V-dL-K-dY-L-Vol | 1615 | 9 |
| BT1583V2I5 | Me$_2$Bmt-V-dO-I-I-V-dK-V-dL-K-dY-L-Vol | 1583 | 10 |
| BT1583V2L5 | Me$_2$Bmt-V-dO-I-L-V-dK-V-dL-K-dY-L-Vol | 1583 | 11 |
| BT1597I2I5 | Me$_2$Bmt-I-dO-I-I-V-dK-V-dL-K-dY-L-Vol | 1597 | 12 |
| BT1597I2L5 | Me$_2$Bmt-I-dO-I-L-V-dK-V-dL-K-dY-L-Vol | 1597 | 13 |
| BT1631I5 | Me$_2$Bmt-F-dO-I-I-V-dK-V-dL-K-dY-L-Vol | 1631 | 14 |
| BT1631L5 | Me$_2$Bmt-F-dO-I-L-V-dK-V-dL-K-dY-L-Vol | 1631 | 15 |
| BT1569V4 | Me$_2$Bmt-L-dO-V-V-V-dK-V-dL-K-dY-L-Vol | 1569 | 16 |
| BT1587M2V4 | Me$_2$Bmt-M-dO-V-V-V-dK-V-dL-K-dY-L-Vol | 1587 | 17 |
| BT1555 | Me$_2$Bmt-V-dO-V-V-V-dK-V-dL-K-dY-L-Vol | 1555 | 18 |
| BT1569I2V4 | Me$_2$Bmt-I-dO-V-V-V-dK-V-dL-K-dY-L-Vol | 1569 | 19 |
| BT1603 | Me$_2$Bmt-F-dO-V-V-V-dK-V-dL-K-dY-L-Vol | 1603 | 20 |

BT as a Feed Additive. (Semi-purified BT peptides rather than BT1583 were used in chicken growth promotion experiments.)

Based on the structure of the BT peptides and its biological and biochemical properties the present investigator produced sufficient material to test its use as a feed additive. In summary, the properties of the peptide used were as follows, 13 amino acid residues with numerous potential natural variants or isomers (>8) and derivatives (>30). Biologically, it was found that the BT peptides were a natural product produced by a Gram(+) bacterium. The BT peptide family is synthesized by a non-ribosome peptide synthase (NRPS), the cloning and characterization is disclosed herein. One such peptide, BT1583: Me$_2$Bmt-L-dO-I-V-V-dK-V-dL-K-dY-L-Vol. (SEQ ID NO.: 1) (Vol stands for Valine alcohol) was selected for further studies because it is cationic and likely amphipathic, It contains unusual amino acid residues and/or includes multiple modifications.

BT1583 was also selected due to its high level of stability. The high stability observed for this peptide included one or more of the following characteristics: (1) no known enzymes can digest it; (2) it is not digested in the mouse or chicken GI track; (3) it can be autoclaved; (4) it survived the feed pelleting process; (5) it can stand extreme pHs (pH 1.0 and pH 13.0); and (6) the only known in vitro method to inactivate it is pH 1.0 plus 100° C. overnight.

In addition to the remarkable stability of BT1583, it demonstrated, in vitro, antibacterial against Gram-positive bacteria, e.g., for most Gram (+): MIC=1 microgram/ml. For Gram (−) the following were the antimicrobial activities observed: *E. coli*: MIC>20 microgram/ml; *Pseudomonas* and *Salmonella*: MIC>100 microgram/ml. BT1583 also shows antifungal, e.g., *S. cerevisiae*: MIC=50 microgram/ml. Anti-protozoal activity was also observed for BT1583 against, *Tetrahymena*: MIC=25 microgram/ml.

The E58 strain for producing BT1583 was selected because it was a fast growing and high peptide producer strain. Furthermore, in addition to fast peptide biosynthesis the strain is also grows in cheap media, e.g., with medium cost as low as 0.4 cents/L and a yield of, e.g., 0.5 g/L. Growth is generally carried out in an air shaker but may also be fermented. Furthermore, the peptide and the strain may be used without extensive adaptation of well-known procedures to an easy, one-step purification process.

The following tables and examples show the growth promotion capabilities and characteristics of the BT1583 peptide in Broiler Chicken, e.g., in a 21-day battery study.

TABLE 7

Summary of Growth Promoting Studies.

| Study | BT1583 concentration | Feed conversion improvement (point) | Additional weight gain (%) |
|---|---|---|---|
| 1-1 | 10 ppm | 7 | 17 |
| 1-2 | 30 ppm | 8 | 17 |
| 2-1 | 6 ppm | 9 | 6.7 |
| 2-2 | 12 ppm | 10 | 11 |
| 3-1 | 12 ppm | 9 | 16 |
| 3-2 | 12 ppm with Coban | 9 (vs Coban alone) | 5.4 |
| 4-1 | 24 ppm with direct coccidial challenge | 13 | 7.1 |
| 4-2 | 48 ppm with direct coccidial challenge | 17 | 9.3 |

Briefly, the peptide was used in a semi-purified form to study the growth and feed conversion of 20-day old straight run broilers in batteries (Studies 2-1 and 2-2). Two amounts were tested against a feed control, peptide at 6 ppm and peptide at 12 ppm, 12 repetitions were carried out per treatment with 4 birds per pen. The diet used in the study was as follows.

TABLE 8

Basic Feed for Studies 2-1 and 2-2

| | PERCENT |
|---|---|
| INGREDIENTS (Mash Feed) | |
| TAMU Corn | 62.91 |
| TAMU Dehulled Soybean Meal | 30.67 |
| DL Methionine | 0.07 |
| Blended A-V Fat | 2.68 |
| Limestone | 1.45 |
| Mono-Dicalcium Phosphate | 1.58 |
| Salt | 0.33 |
| TAMU Trace Minerals | 0.05 |
| TAMU Vitamins | 0.25 |
| NUTRIENT CONTENT (Calculated) | |
| Metabolizable Energy (kcal/kg) | 3100 |
| Protein (%) | 20.0 |
| Lysine (%) | 1.05 |
| Methionine + Cystine (%) | 0.72 |
| Threonine (%) | 0.75 |

BT1583 added in 200 grams of corn meal carrier

Table 9 shows the Statistics for a Dependent Variable: 20-day cumulative weight gain.

| Treatment | Mean | Std. Deviation | Number |
|---|---|---|---|
| Control | 554.8236 | 38.13395 | 12 |
| BT1583 @ 12 ppm | 618.9340 | 46.79301 | 12 |
| BT1583 @ 6 ppm | 591.9750 | 47.93018 | 12 |
| Total | 588.5775 | 50.77136 | 36 |

Table 10 shows the Tests of Between-Subjects Effects

Dependent Variable: 20-day cumulative weight gain

| Source | Type III Sum of Squares | df | Mean Square | F | Sig. |
|---|---|---|---|---|---|
| Corrected Model | 24868.642(a) | 2 | 12434.321 | 6.279 | .005 |
| Intercept | 12471247.008 | 1 | 12471247.008 | 6297.459 | .000 |
| TRE | 24868.642 | 2 | 12434.321 | | .005 |
| Error | 65351.939 | 33 | 1980.362 | 6.279 | |
| Total | 12561467.588 | 36 | | | |
| Corrected Total | 90220.580 | 35 | | | |

(a)R Squared = .276 (Adjusted R Squared = .232)

Table 11 shows the estimated marginal means for the study.

Dependent Variable: 20-day cumulative weight gain

| | | | 95% Confidence Interval | |
|---|---|---|---|---|
| Treatment | Mean | Std. Error | Lower Bound | Upper Bound |
| Control | 554.824 | 12.846 | 528.687 | 580.960 |
| BT1583 @ 12 ppm | 618.934 | 12.846 | 592.798 | 645.070 |
| BT1583 @ 6 ppm | 591.975 | 12.846 | 565.839 | 618.111 |

Table 12 shows the Post Hoc Tests for Homogeneous Subsets

Dependent Variable: 20-day cumulative weight gain Duncan

| | | Subset | |
|---|---|---|---|
| Treatment | N | 1 | 2 |
| Control | 12 | 554.8236 | |
| BT1583 @ 6 ppm | 12 | | 591.9750 |
| BT1583 @ 12 ppm | 12 | | 618.9340 |
| Sig. | | 1.000 | .147 |

Means for groups in homogeneous subsets are displayed.
Based on Type III Sum of Squares
The error term is Mean Square(Error) = 1980.362.
a Uses Harmonic Mean Sample Size = 12.000.
b Alpha = .05.

Table 13 shows the Descriptive Statistics

Dependent Variable: 20-day cumulative feed conversion rate

| Treatment | Mean | Std. Deviation | N |
|---|---|---|---|
| Control | 1.5922 | .13721 | 12 |
| BT1583 @ 12 ppm | 1.4959 | .10089 | 12 |
| BT1583 @ 6 ppm | 1.5065 | .04795 | 12 |
| Total | 1.5315 | .10841 | 36 |

Table 14 shows the Tests of Between-Subject Effects
Dependent Variable: 20-day cumulative feed conversion rate

| Source | Type III Sum of Squares | df | Mean Square | F | Sig. |
|---|---|---|---|---|---|
| Corrected Model | 6.702E−02(a) | 2 | 3.351E−02 | 3.212 | .005 |
| Intercept | 84.440 | 1 | 84.440 | 8092.585 | .000 |
| TRE | 6.702E−02 | 2 | 3.351E−02 | 3.212 | .053 |
| Error | .344 | 33 | 1.043E−02 | 6.279 | |
| Total | 84.851 | 36 | | | |
| Corrected Total | .411 | 35 | | | |

(a)R Squared = .163 (Adjusted R Squared = .112)

Table 15 shows the Estimated Marginal Means
Dependent Variable: 20-day cumulative feed conversion rate

| | | | 95% Confidence Interval | |
|---|---|---|---|---|
| Treatment | Mean | Std. Error | Lower Bound | Upper Bound |
| Control | 1.592 | .029 | 1.532 | 1.652 |
| BT1583 @ 12 ppm | 1.496 | .029 | 1.436 | 1.556 |
| BT1583 @ 6 ppm | 1.506 | .029 | 1.446 | 1.566 |

Table 16 shows the Post Hoc Tests for Homogeneous Subsets
Dependent Variable: 20-day cumulative feed conversion rate-Duncan

| | | Subset | |
|---|---|---|---|
| Treatment | N | 1 | 2 |
| BT1583 @ 12 ppm | 12 | 1.4959 | |
| BT1583 @ 6 ppm | 12 | 1.5065 | |
| Control | 12 | | 1.5922 |
| Sig. | | .801 | 1.000 |

Means for groups in homogeneous subsets are displayed.
Based on Type III Sum of Squares
The error term is Mean Square (Error) = 1.043E−02.
a Uses Harmonic Mean Sample Size = 12.000.
b Alpha = .05.

To evaluate TAMUS BT1583 on growth and feed conversion of 3-wk old straight run broilers fed an industry type pelleted starter feed (in batteries, Studies 3-1 and 3-2). Briefly, the following six treatment regimens were examined: Control, Monensin at 90 ppm, BMD 50 at 50 ppm, BT1583 at 12 ppm, Monensin+BMD 50, Monensin+and BT1583 at 12 ppm. Eight (8) study repetitions per treatment were used, again with 4 birds per pen.

TABLE 17

Basic Feed for Studies 3-1 and 3-2.

| | PERCENT |
|---|---|
| INGREDIENTS (Pelleted Feed) | |
| TAMU Corn | 56.11 |
| TAMU Dehulled Soybean Meal | 35.90 |

TABLE 17-continued

Basic Feed for Studies 3-1 and 3-2.

| | PERCENT |
|---|---|
| DL Methionine | 0.22 |
| Blended A-V Fat | 4.02 |
| Limestone | 1.43 |
| Mono-Dicalcium Phosphate | 1.55 |
| Salt | 0.46 |
| TAMU Trace Minerals | 0.05 |
| TAMU Vitamins | 0.25 |
| NUTRIENT CONTENT (Calculated) | |
| Metabolizable Energy (kcal/kg) | 3100 |
| Protein (%) | 22.31 |
| Lysine (%) | 1.21 |
| Methionine + Cystine (%) | 0.92 |
| Threonine (%) | 0.84 |

BT1583 added via 200 grams of corn meal

Table 18 shows the Descriptive Statistics
Dependent Variable: 20-day cumulative weight gain

| Treatment | Mean | Std. Deviation | Number |
|---|---|---|---|
| BT1583 @ 12 ppm | 831.7396 | 40.47789 | 8 |
| BMD @ 50 ppm | 832.9688 | 30.12576 | 8 |
| COB @ 90 ppm | 792.8438 | 67.05913 | 8 |
| COB + BT1583 | 835.7604 | 62.00447 | 8 |
| COB + BMD | 810.2188 | 74.64333 | 8 |
| Control | 719.7813 | 71.97.115 | 8 |
| Total | 803.8854 | 70.02414 | 48 |

Table 19 shows the Tests of Between-Subjects Effects
Dependent Variable: 20-day cumulative weight gain

| Source | Type III Sum of Squares | df | Mean Square | F | Sig. |
|---|---|---|---|---|---|
| Corrected Model | 78986.007(a) | 5 | 15797.201 | 4.380 | .003 |
| Intercept | 31019124.630 | 1 | 31019124.630 | 8600.903 | .000 |
| TRE | 78986.007 | 5 | 15797.201 | 4.380 | .003 |
| Error | 151472.835 | 42 | 3606.496 | | |
| Total | 31249583.472 | 48 | | | |
| Corrected Total | 230458.842 | 47 | | | |

(a)R Squared = .343 (Adjusted R Squared = .264)

Table 20 shows the Estimated Marginal Means
Dependent Variable: 21-day cumulative weight gain

| | | | 95% Confidence Interval | |
|---|---|---|---|---|
| Treatment | Mean | Std. Error | Lower Bound | Upper Bound |
| BT1583 | 831.740 | 21.232 | 788.891 | 874.588 |
| BMD | 832.969 | 21.232 | 790.120 | 875.817 |
| COB | 792.844 | 21.232 | 749.995 | 835.692 |
| COB + BT1583 | 835.760 | 21.232 | 792.912 | 878.609 |
| COB + BMD | 810.219 | 21.232 | 767.370 | 853.067 |
| Control | 719.781 | 21.232 | 676.933 | 762.630 |

Table 21 shows the Post Hoc Tests for Homogeneous Subsets
Dependent Variable: 21-day cumulative weight gain-Duncan

|  |  | Subset | |
| --- | --- | --- | --- |
| Treatment | N | 1 | 2 |
| Control | 8 | 719.7813 |  |
| COB | 8 |  | 792.8438 |
| COB + BMD | 8 |  | 810.2188 |
| BT1583 | 8 |  | 831.7396 |
| BMD | 8 |  | 832.9688 |
| COB + BT1583 | 8 |  | 835.7604 |
| Sig. |  | 1.000 | .211 |

Means for groups in homogeneous subsets are displayed.
Based on Type III Sum of Squares
The error term is Mean Square(Error) = 3606.496.
a Uses Harmonic Mean Sample Size = 8.000.
b Alpha = .05.

Table 22 shows the Descriptive Statistics
Dependent Variable: 20-day cumulative feed conversion rate

| Treatment | Mean | Std. Deviation | N |
| --- | --- | --- | --- |
| BT1583 | 1.3308 | .03340 | 8 |
| BMD | 1.3397 | .03132 | 8 |
| COB | 1.3712 | .03023 | 8 |
| COB + BT1583 | 1.2816 | .02680 | 8 |
| COB + BMD | 1.3435 | .02477 | 8 |
| Control | 1.4154 | .03299 | 8 |
| Total | 1.3470 | .04989 | 48 |

Table 23 shows the Tests of Between-Subjects Effects
Dependent Variable: 21-day cumulative feed conversion rate

| Source | Type III Sum of Squares | df | Mean Square | F | Sig. |
| --- | --- | --- | --- | --- | --- |
| Corrected Model | 7.894E−02(a) | 5 | 1.579E−02 | 17.442 | .000 |
| Intercept | 87.096 | 1 | 87.096 | 96218.356 | .000 |
| TRE | 7.894E−02 | 5 | 1.579E−02 | 17.442 | .000 |
| Error | 3.802E−02 | 42 | 9.052E−04 |  |  |
| Total | 87.213 | 48 |  |  |  |
| Corrected Total | .117 | 47 |  |  |  |

(a)R Squared = .675 (Adjusted R Squared = .636)

Table 24 shows the Estimated Marginal Means
Dependent Variable: 21-day cumulative feed conversion rate

|  |  |  | 95% Confidence Interval | |
| --- | --- | --- | --- | --- |
| Treatment | Mean | Std. Error | Lower Bound | Upper Bound |
| BT1583 | 1.331 | .011 | 1.309 | 1.352 |
| BMD | 1.340 | .011 | 1.318 | 1.361 |
| COB | 1.371 | .011 | 1.350 | 1.393 |
| COB + BT1583 | 1.282 | .011 | 1.260 | 1.303 |
| COB + BMD | 1.344 | .011 | 1.322 | 1.365 |
| Control | 1.415 | .011 | 1.394 | 1.437 |

Table 25 shows the Dependent Variable:
20-day cumulative feed conversion rate-Duncan

|  |  | Subset | | | |
| --- | --- | --- | --- | --- | --- |
| Treatment | N | 1 | 2 | 3 | 4 |
| COB + BT1583 | 8 | 1.2816 |  |  |  |
| BT1583 | 8 |  | 1.3308 |  |  |
| BMD | 8 |  | 1.3397 | 1.3397 |  |
| COB + BMD | 8 |  | 1.3435 | 1.3435 |  |
| COB | 8 |  |  | 1.3712 |  |
| Control | 8 |  |  |  | 1.4154 |
| Sig. |  | 1.000 | .432 | .053 | 1.000 |

Means for groups in homogeneous subsets are displayed.
Based on Type III Sum of Squares
The error term is Mean Square(Error) = 9.052E−04.
a Uses Harmonic Mean Sample Size = 8.000.
b Alpha = .05.

A more complete study to evaluate TAMUS BT1583 on growth and feed conversion of 42 day old straight run broilers in floor pens may be as follows: Treatments of six (6) groups, Control, Monensin at 90 ppm, BT1583 at 12 ppm, Monensin+BMD at 50 ppm, Monensin+BT1583 at 12 ppm and BMD at 50 ppm. 10 study repetitions per treatment were used to evaluate the effect of using the BT1583 peptide as a feed additive, this time with 40 birds per pen.

When used to promote growth in food-producing animals it was found that the BT1583 peptide provided about 10 points in feed conversion plus extra weight gains. One distinct advantage of the present invention is that no or very little absorption by the chicken GI track, thereby making it useful for widespread use. Furthermore, unlike conventional antibiotics, the present invention may target the bacterial membrane, and there is currently not a drug target that can be altered with one or two mutations to allow development of drug resistance. Furthermore, it was found that growth promotion via possible host immunity modulation is intrinsic to chicken and independent of drug resistance. Alternatively, but in no way limiting the present invention, the present invention may be used as an animal-use only antibiotic for bacterial infections. Also, to date, there has been no observed decrease in the growth promoting activity of the peptide.

A broiler floor pen trial to compare the performance of a new anti-microbial designated for this project as BT1583 alone and in combination with the widely used coccidiostat monensin (MON) to MON fed alone, MON in combination with the also widely used antimicrobial Bacitracin MD (BMD) and BMD alone.

The following levels of each treatment were evaluated:
1: Non-supplemented
2: Monensin (MON) 99 ppm
3: BT1583 12 ppm
4: BT1583 12 ppm+MON 99 ppm
5: MON 99 ppm+BMD 55 ppm
6: BMD 55 ppm The study design included 10 pens per treatment and 40 birds per pen housed on day of hatch. Two basal corn-soy based diets of decreasing protein (approximately 23 to 20%) and increasing metabolizable energy (approximately 1400 to 1455 kcal/lb) were used from Day 0 to 21 (starter feed) and Days 22 to 42 (grower feed), respectively. Treatment premixes were measured and blended into diets at required levels. Between days 0 and 21 mortality was less than 1% with all birds growing optimally and of high health across all groups.

Beginning on study day 22, the study director modulated house temperature and air flow to mimic industry conditions conducive to outbreaks of colibacillosis within naive broiler flocks. This was done to stimulate a natural challenge for this study. Mortality climbed to a house average of approximately 10% by Day 42. A majority of these deaths occurred in groups not receiving BT1583 or MON. Lesions were consistent with those of colibacillosis (air sac, pneumonia, peri-hepatitis, peri-carditis and extreme morbidity). All mortality was documented (weight at death and post-mortem observations). All birds and feeds were weighed at 42 days. All remaining birds were euthanized on Day 42 by asphyxiation with the carcasses submitted for rendering.

All data were analyzed as described below and are displayed in Tables 26 through 30. The following variables were tested: Response Variables: Gain Per Bird, Feed Per Gain, Mortality (%), Adjusted Feed Per Gain. F test from One Way ANOVA with one blocking factor=location, at Day 42 using 0.05 level of significance.

All Response Variables: LSD T-test procedure for pairwise comparisons with Type 1 error of means when ANOVA F ratio is significant, overall significance level of 0.05 used. Lines below means (see Table 30, below) indicate groups with insignificant differences in means.

TABLE 26

Weight gains (in lb) per bird

| Treatment | Day 42 Gain/Bird |
| --- | --- |
| Non-supplemented | $3.900^d$ |
| Monensin (MON) 99 ppm | $4.111^{bcd}$ |
| BT1583 12 ppm | $4.333^{ab}$ |
| MON 99 ppm + BT1583 12 ppm | $4.385^a$ |
| MON 99 ppm + BMD 55 ppm | $4.127^c$ |
| BMD 55 ppm | $3.971^{cd}$ |

Weight gains were heaviest for the 2 groups of broilers receiving BT1583 measured at 42 days with the MON+BT1583 significantly heavier (p<0.05) than that provided by the MON+BMD and MON groups.

Feed/Gain: Table 27 shows that MON+BT1583 fed broilers had the feed/gain values which were lower (p<0.05) than all other groups with the exception of the group receiving BT1583 alone.

TABLE 27

Feed/Gain

| Treatment | Day 42 Feed/Gain |
| --- | --- |
| Non-supplemented | $2.189^c$ |
| Monensin (MON) 99 ppm | $1.854^b$ |
| BT1583 12 ppm | $1.722^{ab}$ |
| MON 99 ppm + BT1583 12 ppm | $1.689^a$ |
| MON 99 ppm + BMD 55 ppm | $1.885^{bc}$ |
| BMD 55 ppm | $2.147^c$ |

Adjusted Feed/Gain: The total weight of mortality in each pen was added to the final live weight, that value reduced by subtracting the initial weight and then dividing that value into the Total feed consumed to calculate the Adjusted Feed/Gain.

Table 28 demonstrates the effects of the natural challenge on feed/gain values. Even with the adjustments for mortality, MON+BT1583 fed broilers had an adjusted feed/gain value which again was significantly lower (p<0.05) than all other groups with the exception of the group receiving BT1 583 alone.

TABLE 28

Feed/Gain Adjusted

| Treatment | Day 42 Adjusted Feed/Gain |
| --- | --- |
| Non-supplemented | $1.928^c$ |
| Monensin (MON) 99 ppm | $1.761^b$ |
| BT1583 12 ppm | $1.704^{ab}$ |
| MON 99 ppm + BT1583 12 ppm | $1.654^a$ |
| MON 99 ppm + BMD 55 ppm | $1.725^b$ |
| BMD 55 ppm | $1.838^{bc}$ |

Mortality: The majority of the deaths were caused by acute and chronic colibacillosis. Broilers receiving BT1583 or Monensin alone or in combination had lower mortality rates than the non-supplemented controls.

TABLE 29

Mortality by acute and chronic colibacillosis.

| Treatment | Day 42 Mortality (%) |
| --- | --- |
| Non-supplemented | $17.50^c$ |
| Monensin (MON) 99 ppm | $8.00^a$ |
| BT1583 | $2.75^a$ |
| MON 99 ppm + BT1583 12 ppm | $3.50^a$ |
| MON 99 ppm + BMD 55 ppm | $7.75^{abc}$ |
| BMD 55 ppm | $18.25^{bc}$ |

Monensin is a polyether antibiotic that is approved and used as an anti-protozoal agent in the poultry industry. Slight efficacy by monensin and other polyether antibiotics against gram negative bacteria has been documented by many researchers and poultry industry personnel. BT1583 has also been stated to have efficacy against gram negative bacteria. *Escherichia coli* has been a major problem in the food industries both health wise and financially. Most products highly effective against this pathogen are too costly to use in broiler older than 21 days or have been pulled off the market due to similarities to human health products raising public health concerns. This study demonstrated that BT1583 is highly effective against colibacillosis in 3 to 4 week old naive broiler chickens raised under simulated commercial broiler conditions. The 20+ point weight gain advantages and 10+ point feed/gain advantages held by BT1583 over monensin and BMD fed alone and in combination observed on this trial is a strong indicator that this product may be an invaluable tool for the future of the poultry industry.

TABLE 30

P-Values Comparisons

| | Day 42 Wt/Gain WtGn (lb) | Day 42 Indiv. Bird Wt (lb) | Day 42 Gain/Bird (lb) | Day 42 Feed/Gain (FdWt/WTGn) | Day 42 Adjusted Feed/Gain (Adj Feed/Gn) | Day 42 Mortality (%) |
| --- | --- | --- | --- | --- | --- | --- |
| Controls vs. MON | | 0.216456 | 0.153695 | 0.001923 | 0.023562 | 0.013284 |
| Controls vs. BT1583 | | 0.000028 | 0.000023 | 0.000134 | 0.002449 | 0.001433 |

TABLE 30-continued

P-Values Comparisons

| Day 42 Wt/Gain WtGn (lb) | Day 42 Indiv. Bird Wt (lb) | Day 42 Gain/Bird (lb) | Day 42 Feed/Gain (FdWt/WTGn) | Day 42 Adjusted Feed/Gain (Adj Feed/Gn) | Day 42 Mortality (%) |
|---|---|---|---|---|---|
| Controls vs. MON + BT1583 | 0.000421 | 0.000333 | 0.000115 | 0.000147 | 0.006250 |
| Controls vs. MON + BMD | 0.004270 | 0.002816 | 0.096440 | 0.003283 | 0.179121 |
| Controls vs. BMD | 0.523702 | 0.546456 | 0.754966 | 0.231502 | 0.845776 |
| MON vs. BT1583 | 0.177311 | 0.192494 | 0.159703 | 0.425156 | 0.172685 |
| MON vs. MON + BT1583 | 0.018776 | 0.022738 | 0.041045 | 0.033717 | 0.234506 |
| MON vs. MON + BMD | 0.805698 | 0.905725 | 0.840264 | 0.275135 | 0.967501 |
| MON vs. BMD | 0.521589 | 0.443090 | 0.123047 | 0.453955 | 0.031824 |
| BT1583 vs. MON + BT1583 | 0.645444 | 0.638704 | 0.472007 | 0.338775 | 0.663743 |
| BT1583 vs. MON + BMD | 0.014212 | 0.011862 | 0.254035 | 0.712535 | 0.336982 |
| BT1583 vs. BMD | 0.005943 | 0.005142 | 0.017789 | 0.091063 | 0.006670 |
| MON + BT1583 vs. MON + BMD | 0.006085 | 0.004962 | 0.145588 | 0.037877 | 0.386550 |
| MON + BT1583 vs. BMD | 0.006044 | 0.005385 | 0.013376 | 0.034621 | 0.003991 |
| MON + BMD vs BMD | 0.244875 | 0.214655 | 0.181891 | 0.205577 | 0.134645 |

(Note: Bold type and underlining indicate comparisons where p-value is less than 0.05)

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Altschul, S. F., Gish, W., Miller, W., Myers, E. W. & Lipman, D. J. (1990). Basic local alignment search tool. J Mol Biol 215(3), 403-10.

Altschul, S. F., Madden, T. L., Schaffer, A. A., Zhang, J., Zhang, Z., Miller, W. & Lipman, D. J. (1997). Gapped BLAST and PSI-BLAST: a new generation of protein database search programs. Nucleic Acids Res 25(17), 3389-402.

Challis, G. L., Ravel, J. & Townsend, C. A. (2000). Predictive, structure-based model of amino acid recognition by non-ribosomal peptide synthetase adenylation domains. Chem Biol 7(3), 211-24.

Conti, E., Stachelhaus, T., Marahiel, M. A. & Brick, P. (1997). Structural basis for the activation of phenylalanine in the non-ribosomal biosynthesis of gramicidin S. Embo J 16(14), 4174-83.

Gaitatzis, N., Kunze, B. & Muller, R. (2001). In vitro reconstitution of the myxochelin biosynthetic machinery of Stigmatella aurantiaca Sg a15: Biochemical characterization of a reductive release mechanism from nonribosomal peptide synthetases. Proc Natl Acad Sci USA 98(20), 11136-41. Epub Sep. 18, 2001.

Gonzalez-Pastor, J. E., Hobbs, E. C. & Losick, R. (2003). Cannibalism by sporulating bacteria. Science 301(5632), 510-3. Epub Jun. 19, 2003.

Hopwood, D. A. (1997). Genetic Contributions to Understanding Polyketide Synthases. Chem Rev 97(7), 2465-2498.

Keating, T. A., Ehmann, D. E., Kohli, R. M., Marshall, C. G., Trauger, J. W. & Walsh, C. T. (2001). Chain termination steps in nonribosomal peptide synthetase assembly lines: directed acyl-S-enzyme breakdown in antibiotic and siderophore biosynthesis. Chembiochem 2(2), 99-107.

Keating, T. A. & Walsh, C. T. (1999). Initiation, elongation, and termination strategies in polyketide and polypeptide antibiotic biosynthesis. Curr Opin Chem Biol 3(5), 598-606.

Kessler, N., Schuhmann, H., Morneweg, S., Linne, U. & Marahiel, M. A. (2004). The linear pentadecapeptide gramicidin is assembled by four multimodular nonribosomal peptide synthetases that comprise 16 modules with 56 catalytic domains. J Biol Chem 279(9), 7413-9.

Konz, D., Doekel, S. & Marahiel, M. A. (1999). Molecular and biochemical characterization of the protein template controlling biosynthesis of the lipopeptide lichenysin. J Bacteriol 181(1), 133-40.

Linne, U. & Marahiel, M. A. (2000). Control of directionality in nonribosomal peptide synthesis: role of the condensation domain in preventing misinitiation and timing of epimerization. Biochemistry 39(34), 10439-47.

Marahiel, M. A. (1997). Protein templates for the biosynthesis of peptide antibiotics. Chem Biol 4(8), 561-7.

Mootz, H. D. & Marahiel, M. A. (1997). The tyrocidine biosynthesis operon of *Bacillus brevis:* complete nucleotide sequence and biochemical characterization of functional internal adenylation domains. J Bacteriol 179(21), 6843-50.

Mootz, H. D., Schwarzer, D. & Marahiel, M. A. (2002). Ways of assembling complex natural products on modular nonribosomal peptide synthetases. Chembiochem 3(6), 490-504.

Offenzeller, M., Santer, G., Totschnig, K., Su, Z., Moser, H., Traber, R. & Schneider-Scherzer, E. (1996). Biosynthesis of the unusual amino acid (4R)-4-[(E)-2-butenyl]-4-methyl-L-threonine of cyclosporin A: enzymatic analysis of the reaction sequence including identification of the methylation precursor in a polyketide pathway. Biochemistry 35(25), 8401-12.

Offenzeller, M., Su, Z., Santer, G., Moser, H., Traber, R., Memmert, K. & Schneider-Scherzer, E. (1993). Biosynthesis of the unusual amino acid (4R)-4-[(E)-2-butenyl]-4-methyl-L-threonine of cyclosporin A. Identification of 3(R)-hydroxy-4(R)-methyl-6(E)-octenoic acid as a key intermediate by enzymatic in vitro synthesis and by in vivo labeling techniques. J Biol Chem 268(35), 26127-34.

Quadri, L. E., Sello, J., Keating, T. A., Weinreb, P. H. & Walsh, C. T. (1998). Identification of a *Mycobacterium tuberculosis* gene cluster encoding the biosynthetic enzymes for assembly of the virulence-conferring siderophore mycobactin. Chem Biol 5(11), 631-45.

Sagisaka, S. & Shimura, K. (1959). Enzymic reduction of alpha-amino-adipic acid by yeast enzyme. Nature 184 (Suppl 22), 1709-10.

Sanglier, J. J., Traber, R., Buck, R. H., Hofmann, H. & Kobel, H. (1990). Isolation of (4R)-4-[(E)-2-butenyl]-4-methyl-L-threonine, the characteristic structural element of cyclosporins, from a blocked mutant of *Tolypocladium inflatum*. J Antibiot (Tokyo) 43(6), 707-14.

Stachelhaus, T., Mootz, H. D., Bergendahl, V. & Marahiel, M. A. (1998). Peptide bond formation in nonribosomal peptide biosynthesis. Catalytic role of the condensation domain. J Biol Chem 273(35), 22773-81.

Stachelhaus, T., Mootz, H. D. & Marahiel, M. A. (1999). The specificity-conferring code of adenylation domains in nonribosomal peptide synthetases. Chem Biol 6(8), 493-505.

Thompson, J. D., Higgins, D. G. & Gibson, T. J. (1994). CLUSTAL W: improving the sensitivity of progressive multiple sequence alignment through sequence weighting, position-specific gap penalties and weight matrix choice. Nucleic Acids Res 22(22), 4673-80.

What is claimed is:

1. A feed additive comprising: an isolated and purified, heat stable, amino terminus-methylated, carboxy-terminus reduced peptide with two or more D-amino acids isolated from *Brevibacillus texasporus*, comprising Me$_2$Bmt-L-dO-I-V-V-dK-V-dL-K-dY-L-Vol (SEQ ID NO: 1), SEQ ID NO: 2-4 or SEQ ID NO: 5.

2. The additive of claim 1, wherein the Vol is valine alcohol produced by reducing —COOH group of the C-terminal Valine to —CH$_2$OH.

3. The additive of claim 1, wherein the carboxy-terminus —COOH group of the C-terminal Valine is reduced to —CH$_2$OH and confers protease resistance to the peptide.

4. The additive of claim 1, wherein the peptide is stable at a pH of 1.0, at a pH 13.0, resistant to proteases or combinations thereof.

5. The additive of claim 1, wherein the peptide is Me$_2$Bmt-L-dO-I-V-V-dK-V-dL-K-dY-L-Vol (SEQ ID NO: 1).

6. The additive of claim 1, wherein the peptide kills, gram positive bacteria, gram negative bacteria, fungi, protozoa or combinations thereof.

7. The additive of claim 1, wherein the peptide is added at between about 0.5 and about 100 ppm.

8. The additive of claim 1, wherein the peptide is added at between about 6 and about 12 ppm.

9. The additive of claim 1, wherein the peptide is added to a feed adapted for use by one or more of poultry, livestock, farm-raised fish, crabs, shrimp and fresh-water turtles.

10. A cereal-based animal feed comprising: at least one cereal selected from barley, soya, wheat, triticale, rye and maize; and an isolated and purified, heat stable, amino terminus-methylated, carboxy-terminus reduced peptide comprising two or more D-amino acids isolated from *Brevibacillus texasporus*, wherein the peptide comprises the sequence Me$_2$Bmt-L-dO-I-V-V-dK-V-dL-K-dY-L-Vol (SEQ ID NO: 1).

11. A peptide-based feed additive comprising: between about 1 and 1000 ppm of an isolated and purified, heat stable, amino terminus-methylated, carboxy-terminus reduced peptide comprising two or more D-amino acids isolated from *Brevibacillus texasporus*, wherein the peptide comprises the sequence Me$_2$Bmt-L-dO-I-V-V-dK-V-dL-K-dY-L-Vol (SEQ ID NO: 1).

12. An antimicrobial peptide comprising two or more D-amino acids, carboxy-terminus reduced pH and heat stable isolated from *Brevibacillus texasporus*, wherein the peptide comprises the sequence Me$_2$Bmt-L-dO-I-V-V-dK-V-dL-K-dY-L-Vol (SEQ ID NO: 1).

13. A broad spectrum antimicrobial compound for topical use comprising a peptide comprising two or more D-amino acids, carboxy-terminus reduced, pH and heat stable isolated from *Brevibacillus texasporus*, wherein the peptide comprises the sequence Me$_2$Bmt-L-dO-I-V-V-dK-V-dL-K-dY-L-Vol (SEQ ID NO: 1).

14. An isolated and purified, heat stable, amino terminus-methylated, carboxy-terminus reduced peptide comprising two or more D-amino acids isolated from *Brevibacillus texasporus* that inhibits the growth of at least one bacterium selected from the group consisting of: *Staphylococcus, Enterococcus, Pneumococcus, Bacilli, Methanococcus, Haemophilus, Archaeoglobus, Borrelia, Synedrocyptis, Mycobacteria, Pseudomonas* and *E. coli.*, wherein the peptide comprises the sequence Me$_2$Bmt-L-dO-I-V-V-dK-V-dL-K-dY-L-Vol (SEQ ID NO: 1).

* * * * *

SEQUENCE LISTING

```
<160> NUMBER OF SEQ ID NOS: 28

<210> SEQ ID NO 1
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Orn
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-Form of leucine
<220> FEATURE:
<221> NAME/KEY: MOD_RES
<222> LOCATION: (11)..(11)
<223> OTHER INFORMATION: D-Form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 1

Xaa Leu Xaa Ile Val Val Xaa Val Xaa Lys Xaa Leu Xaa
1               5                   10

<210> SEQ ID NO 2
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
```

-continued

```
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-Form of leucine
<220> FEATURE:
<221> NAME/KEY: MOD_RES
<222> LOCATION: (11)..(11)
<223> OTHER INFORMATION: D-Form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 2

Xaa Met Xaa Ile Val Val Xaa Val Xaa Lys Xaa Leu Xaa
1               5                   10

<210> SEQ ID NO 3
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of  tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 3

Xaa Val Xaa Ile Val Val Xaa Val Xaa Lys Xaa Leu Xaa
1               5                   10

<210> SEQ ID NO 4
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
```

```
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 4

Xaa Ile Xaa Ile Val Val Xaa Val Xaa Lys Xaa Leu Xaa
1               5                   10

<210> SEQ ID NO 5
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 5

Xaa Phe Xaa Ile Val Val Xaa Val Xaa Lys Xaa Leu Xaa
1               5                   10

<210> SEQ ID NO 6
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
```

```
<221> NAME/KEY: MOD_RES
<222> LOCATION: (13)..(13)
<223> OTHER INFORMATION: C-terminal Alcoholic Valine

<400> SEQUENCE: 6

Xaa Leu Xaa Ile Ile Val Xaa Val Xaa Lys Xaa Leu Xaa
1               5                   10

<210> SEQ ID NO 7
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 7

Xaa Leu Xaa Ile Leu Val Xaa Val Xaa Lys Xaa Leu Xaa
1               5                   10

<210> SEQ ID NO 8
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 8

Xaa Met Xaa Ile Ile Val Xaa Val Xaa Lys Xaa Leu Xaa
1               5                   10
```

<210> SEQ ID NO 9
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of Ornithine lysine leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 9

Xaa Met Xaa Ile Leu Val Xaa Val Xaa Lys Xaa Leu Xaa
1               5                   10

<210> SEQ ID NO 10
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 10

Xaa Val Xaa Ile Ile Val Xaa Val Xaa Lys Xaa Leu Xaa
1               5                   10

<210> SEQ ID NO 11
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine

```
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 11

Xaa Val Xaa Ile Leu Val Xaa Val Xaa Lys Xaa Leu Xaa
 1               5                  10

<210> SEQ ID NO 12
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 12

Xaa Ile Xaa Ile Ile Val Xaa Val Xaa Lys Xaa Leu Xaa
 1               5                  10

<210> SEQ ID NO 13
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
```

<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 13

Xaa Ile Xaa Ile Leu Val Xaa Val Xaa Lys Xaa Leu Xaa
1               5                   10

<210> SEQ ID NO 14
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 14

Xaa Phe Xaa Ile Ile Val Xaa Val Xaa Lys Xaa Leu Xaa
1               5                   10

<210> SEQ ID NO 15
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES

```
<222> LOCATION: (13)..(13)
<223> OTHER INFORMATION: C-terminal Alcoholic Valine

<400> SEQUENCE: 15

Xaa Phe Xaa Ile Leu Val Xaa Val Xaa Lys Xaa Leu Xaa
1               5                   10

<210> SEQ ID NO 16
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form ofleucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 16

Xaa Leu Xaa Val Val Val Xaa Val Xaa Lys Xaa Leu Xaa
1               5                   10

<210> SEQ ID NO 17
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of Ornithine lysine leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 17

Xaa Met Xaa Val Val Val Xaa Val Xaa Lys Xaa Leu Xaa
1               5                   10
```

```
<210> SEQ ID NO 18
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 18

Xaa Val Xaa Val Val Val Xaa Val Xaa Lys Xaa Leu Xaa
1               5                   10

<210> SEQ ID NO 19
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of  tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 19

Xaa Ile Xaa Val Val Val Xaa Val Xaa Lys Xaa Leu Xaa
1               5                   10

<210> SEQ ID NO 20
<211> LENGTH: 13
<212> TYPE: PRT
<213> ORGANISM: Brevibacillus texasporus
<220> FEATURE:
<221> NAME/KEY: MOD_RES
<222> LOCATION: (1)..(1)
<223> OTHER INFORMATION: 4-methyl-4-[(E)-2-butenyl]-4,N-methyl-Threonine
<220> FEATURE:
```

```
<221> NAME/KEY: MOD_RES
<222> LOCATION: (3)..(3)
<223> OTHER INFORMATION: D-form of Ornithine
<220> FEATURE:
<221> NAME/KEY: MOD_RES
<222> LOCATION: (7)..(7)
<223> OTHER INFORMATION: D-form of lysine
<220> FEATURE:
<221> NAME/KEY: MOD_RES
<222> LOCATION: (9)..(9)
<223> OTHER INFORMATION: D-form of leucine
<220> FEATURE:
<221> NAME/KEY: MOD_RES
<222> LOCATION: (11)..(11)
<223> OTHER INFORMATION: D-form of tyrosine
<220> FEATURE:
<221> NAME/KEY: MOD_RES
<222> LOCATION: (13)..(13)
<223> OTHER INFORMATION: C-terminal Alcoholic Valine

<400> SEQUENCE: 20

Xaa Phe Xaa Val Val Val Xaa Val Xaa Lys Xaa Leu Xaa
 1               5                  10

<210> SEQ ID NO 21
<211> LENGTH: 50674
<212> TYPE: DNA
<213> ORGANISM: Brevibacillus texasporus

<400> SEQUENCE: 21
attcgttgga tccagtgtgg tggaattcaa accctcagtg ggtaaagata ttgccagagt      60
cttgaaatgt accaaacagg gaaatgggta ccttgaaggc gacaaatatg tagtaacctg     120
ggcatttggc catctggtta cgctggctga tcctgaagcc tatggagaga catataaagc     180
ttggaagctg gaggatttac cactgttgcc gtctcgcctg caattaactg tcatcagaca     240
gagctccaag caatatcaga ttgtaaaaaa attattagcg cgtcaggata tttcagaagt     300
gattattgct actgatgctg gtcgtgaagg tgagctggtg gcgcgatgga ttttagaaaa     360
ggcacatgtg aaaaagccta ttaaacgact atggatttcc tctgtgactg ataaagcaat     420
cagtgatggc ttcagaaaagc tgcgagatgg caaggaatac gagaatctct atgcttctgc     480
tgtagctcgc gctgaagctg actggtttgt cgggatcaat gccactcgtg ctcttacaac     540
gaagcataat gcccagctct cctgcgggcg tgtacaaact cctacagtgg caatgattgc     600
caaacgtgag gaggagattc aaaggttcgt tcctcgcccc tattatggtg ttcaagcgat     660
cacaggtaat ggattaaagc ttacgtggca ggatcagcaa accaaagata tgaagacgtt     720
taccaaggag aaggctgaga aaattgtcga aagcagtaaa aacaagcaag ctgaaattat     780
tgacatcaag aaggctgaca agaaaagctt cgcccccagct ttatatgatc taactgagct     840
acaacgtgat gcgaataagc gttttggttt ttcggcaaag gaaaccctct ccattatgca     900
agggctatac gaaacacata aggtactcac atacccgcgg acagattctc gctatttgac     960
atcagatatt gtcgaaacat acctgatcg attgagagcg atatctgtta agccatacac    1020
tccgtttgca gctaagctgt taagcaacc gattcgagct ggtaaacatg tagtggataa    1080
tagcaaggta tctgatcacc atgcgattat tccaactgag caatctgtgc tgttaaataa    1140
gcttagcgat aaggaacgta aaatttatga ccttgtggtt aaacgctttc tggctgtgct    1200
atatccgcct tttgaatatg aacaaattag tattcgtgcc cgaattggca acgaggaatt    1260
tctagcaaaa gggaagacga taacgcatca gggctggaag gaaatttatg ataatcactt    1320
tgatgaagag gatcaaggag atggattaaa agaacagctt ttaccaacgc ttgtacaagg    1380
```

```
tgagcaacta tctgtacaaa ccgtttcttt tacaaaaggg gaaacaaaac ctccagagcc    1440
atttacggag gctacactcc tttcagctat ggagaatcct gtccgttata tgggacaggt    1500
tgataagcag ctagccaaaa cattaggtga gacaggtgga ttaggaactg ttgctactcg    1560
cgccgatatt attgaaaaat tgtttaatag cttcctcatt gaaaagcgca gcaagcatat    1620
tcatattact tctaaaggaa agcaattact tgagcttgta ccagaaggac ttcgctcacc    1680
ggctcttact gctgaatggg aagtgaagct tggagcgatc tcgaaggaa gcctggctaa    1740 aaacagcttc atacaggaaa tgaagaagta tgcagagcaa atcgttcaac agatcaaatt    1800
tagtgagcaa aagtttcgtc atgacaatct gactcgctcc aaatgcccgg attgtggaaa    1860
gctgatgctt gaggtaaatg ggaaaaaagg aaaaatgtta gtttgtcagg atcgtgagtg    1920
tggtcaccgt aaggccgtat ccaaggttac aaatgccaga tgcccacaat gtcgaaagaa    1980
gatggagatg cgtggggaag agaaggaaa gatattcgta tgcaaatgcg gacatcgtga    2040
aaaactgtcg acgtttaacg acagacgtag caaggagaaa cagacaaatg tttcgaaacg    2100
agatgtagcc cagtatatga aaatcagca acgagatcaa gaaagcttag gtaatccagc    2160
cttgatggag gcattaaaga attttaagct agatcagtaa gtcatttat atagaaaaga    2220 taggctcgaa aataaggcgc ccgctctctt tattagctaa gagaaagggc gtctatttta    2280
gcttctcttt tctatatgga aaaaaggaat taacaaaatc tgaagaaaat ttcagaattt    2340 attatttta tgttaagaga ttttgaaaga agtgcatcta tttactttat ccataaatga    2400
aagcaaaaat gagattgtta tattccataa aatgtaaatg ttttatatc ttggaaaaca    2460 tagagtcgag aacgctgttc actatacaag aagactatag atacgagctt ttacggctat    2520
ttttacgatt tgataacgcc ttcttttttt agtctaataa aaaacagtaa cgaatcgaaa    2580
aaataacaat aatttgattg gtaaataaca ttgttactaa ttcacagaaa acaaaatcat    2640
tatttttaca taataaaaac ataataataa aatgtgatag aaaaatattg aagaaaatgt    2700
ccattattgg tagtattgaa aaataaacct gtaattttat gtattataat gcaattattt    2760
gtcgcatatt tactagcata aatgttagcg atgatgtgag caaatcgtta cctgttagaa    2820
ggaagatcag ctacatatga ttcaaaattt ttcgtttttt tattttaaaa gacaaagagg    2880
tggtcctgat ggatttatct acattaaatt ttttgggtga aacagaaaag cataagttat    2940
tgaatcaatt caatgatacg gacgctaatt ttcctcagga gatgaccatt catgggctgt    3000
ttgaaaagca agtccaagaa agaccgaatc aaactgcggt aattttaat gaacaaagta    3060 tgacgtataa agaaatgaat gaacgagcca atcaagtagc acatagctta cggaagcatg    3120
gagctgctcc agatgagatc gttggaattc tagcagatcg caacatggac atgcttattt    3180
ccattctcgg cgtattaaag gctggagctg cttatatgcc tattgatcct acataccta    3240 cagaacgtat tctttatatg atccatgata gccagaccaa aattgtctta gctgaacata    3300
gagagatggt tccggaaggc tgtaatgcag agctgatcct cttgcacgat agctcccttt    3360
taaacgaaga gacatctgat ctagagcatg taaataagcc tgaagatttg gcctatatta    3420
tctatacatc aggttctact ggtaaaccaa aaggggttat gattgaacat cgaaatgtca    3480
ttcgcttgct atttaatgac agaaacctat ttgatttta tagtgatgat gtctggaccg    3540
ttttccattc gttctgtttt gacttctctg tttgggagat gtatgggct ttactgtatg    3600 gaggaaaaat cgttctcgtc tcttttgaga tagctagaga tcctcaggcc ttccgagatt    3660
tacttcagga gcaaaaggtt acgatttaa atcaaaccc tacagctttt tatcagctct    3720
cgtctcaaga gatgcagcac tcagacagca atctatcgat tcgtaaaatc attttggtg    3780
```

```
gagaagcgtt gacgccatca cagttgaaag catggaaaca aaaatatcca aatacagcct    3840
tgattaatat gtacggtatt acagaaacaa ctgttcatgt gacttataag gagtttcaat    3900
tacatgatat ggacagcaca gttagcaata tcggaaagcc tatcccaacg cttagaacct    3960
atgttttaga ttccaagaga aacctagctc caattggagt gaaaggtgaa ctgtatgtga    4020
gcggcaaggg agtagcccgc ggttatttaa acaaacctga attgacggaa gaacggttta    4080
tggataaccc gtttgttgct ggagaaagaa tgtatcgcac aggagaccta gctagatggc    4140
tacctgaagg agagctagaa tatctaggca ggattgacca tcaggtaaaa atcgagaggct    4200 atcgcattga actcggagaa atagaagccg agctattgaa gcaaaaggg attaaagaag    4260 cagtagtttt agttacaaat gataaagatg cacaaccaca attacatgcc tatttaacat    4320
ctaaggaaga tttggcagca gcagatcttc gtaatcaact tactacaaca ttaccctctt    4380
acatgattcc ggctcatttc atttttgtgt cgcaaatgcc tgttacgcca aatggaaaaa    4440
ttgataaaga atcacttcgt aaaatagaac catcacttca agaaagccct acagaagctt    4500
atgtagctcc acaaacacct acagaaaagc aattagtcca catatgggaa gaaaatattg    4560
gaatgcaacc gatcagcata gacgataatt attttgctct aggtggtgat tccatcaaag    4620
cgattaagct attgcatgct ataaataaag agttttcagat tagtttccaa attggagatt    4680
tgtataagca tggaaccatt agagaaatgg gacagcaaat cggtgaaaag ggcaagcaat    4740
ctagcaatca aaaactgttg aaacttcagg aattggaccg tttaaaagag aaaattttgg    4800
gaagtgagaa atagtcatgt cggataagct aagcaacgct aaagacctat ttccaatgag    4860
cgatatacag ctagggatgg tctaccattc gttaaaacat gtacacgaag ctgtatacca    4920
tgatcaattt gtttatcaag tagatgatga ttcatttgat gttcatgtgc tagagcaagc    4980
gatgagaatg atggttgata agcacgacat cttaaaaacc agctttcata ttgaggaatt    5040
ttccactcca gttcaagtag tgcaccagga ggtttctgtt cgaattgatg agacagacat    5100
tacgcatctg ggagaaaaac aaaaagagta tatccatcag tatttggcac aggatcgtca    5160 atccccttt gatgtaacaa ccgctcctct atggagaatg agcgttttta aactgaatgc    5220
aagccaagtt gctttagtct ggatctttca tcatgctatt ttggatggat ggagtgttgc    5280
atcttttatt acggaattaa ttgatgtttta tttcaaatta agcacaaaaa cttgcactttt    5340 ggagcatttg aacacgacct ataaggatta tgtgattgat cagatgctat tatctgagca    5400
aaatgagctc cgtgaatatt ggaaagaaga attaaaagat tacaaacggc tacagctccc    5460
agtaaaagtg gatgaaaatg gcggtgttca cgttaccgtt gttgagaagc tagaccctga    5520
cattataaat aaatgcagag aaattgcaca agctcatcac attccattaa agaccgtatg    5580
cctaacagcc tttctttcta tgatgcatat gatttcttat gagagagacc tgactgtggg    5640
attgattgag aacaaccgac caattataga agatgctgaa aaggtgttgg gatgttttct    5700
taactcagtt ccattccgcg ccattataaa gaaagatatg agctacagag agctattaga    5760
gcagacacag caaaagcttg ttgagattaa acatatggga agactttcct ttgctaagat    5820
tattgaagta attggcgata cgggaagcga gcgtaatcca gttttttgact gtctttttaa    5880 ctttgtcgac ttccatgtat ttaaagggat aaaggatcat aaagtaaagt tttggttaga    5940
tggatatgaa aaaacaaaca ccatgtttga ctttttctgtt tcgaccacaa tggatgacta    6000
ttttgttcgg gttgtatctg cactgccaga agaagatacg ataaaactaa ttaactatta    6060
tcaacgaatt ttagaaaaga ttgctcttca catagatgaa aaaatagata aacaagccaa    6120
```

```
tcttgatgaa aaggaaagcc acttgctgct agaggaatgg aatcaaacgt cagttgatta   6180
tccagacaag caaacattgc ataaacggtt tgaggagcaa gtagccaaaa atgaagatca   6240
ggtagcgctg gaatatgagg ataagcagct tacctatagg gaattgaacg ctaaagccaa   6300
tcaattggca cgtgttttac agaagcataa tacgctgcca actcaggtag ttggtctaat   6360
ggcagagcgt tcactagaga tgataatagg cattcttggg atattaaaag ccggcggagc   6420
ttatatgcct attgacccta cgtatcctgc ggagcgtatc caatatatgc tcgaagatag   6480
tcgatcctat ctcttacttg tacaaaaagc agaaatgatt ccagccaatt atcaggggga   6540
agtacttatc ctcacagagg aactttgggc agatgagaat acagagaacc tggaactagt   6600
caatcagccg caggatgttg ccaatatcat gtatacatct gggactacag gaaagccaaa   6660
aggtatcctg atcactcatc gaaacattat gactaccata atcaacaatg ctatctcga    6720
tattttttca acagatcgaa tattgcaaat atctaactat gcttttgatg gttctacctt   6780
tgatatatac agtgctttgc taaacggagc tactctcgtg ctagttccca agcaaacact   6840
catgaatacg accgatctgt tagcaatcat caaagatagc aatatcacgg tagctttaat   6900
gacaacctct ctattcaata cgttggttga tcttgatgta accagcttcc aacatacacg   6960
taaggtttta tttggcgggg aaaaggcttc atgtaagcat gtagaaaaag cattggatta   7020
tttgggtgaa gggcgcctag taaatggata tggtccgaca gaaacaacgg tgttcgctac   7080
tacctataca gtcgataaca cgattaaaaa gctgggaagt atcccgatcg gacgtccttt   7140
gagcaacact tcggtatata tttttggatt agatgatcaa ttacaaccac ttggagtacc   7200
aggggagtta tgtgtagcag gagaatgcat ttcgcctgga tatctgaatc gtcccgactt   7260
aacggcagac aaatttattg ataatccact taaaccaggt gagagaatgt accgtacagg   7320
tgacctagtt cgttggctgc ctgaaggtgt catggaatac atggggcgga ttgatgaaca   7380
agtcaagatt cgtggacatc gtatcgagct aggggagatt gaggcaaagc tgcttgagca   7440
tccttcgatt cgagaaacag tgctggtggc taaacaggat gcaaatggcc attctttttt   7500
aggtgcgtat cttgttacag acaacttctg ccctgtaacg gaattacgga attatctgat   7560
ggaaaccttg ccagaatata tggttccttc ttattttatc gagctggata gcctaccgct   7620
tacttcaaat ggaaaagtag ataagcgagc attgcccgaa ccggaatctc aggctttaca   7680
cgcatatacc atgccggaga atgagacgga agaaaaattg gttcagctat tccaggaagt   7740
gatggatgta gagcgtgttg gtactcaaga tagcttttat gaattaggcg gtcattcctt   7800
aaaagcaatg cttttggttt cacgaattca taaggatttt ggaataaaga taccgttgaa   7860
ggaagtattc agtcgtccga ccgtgaagga attggctgcc tatctgactg ggtcagaaga   7920
agcaaactat attgaaattg aagcagcaga agagaaacca tactatccag ttactgccgc   7980
ccaaaaacgg atgtatatcg cccagcaatg ggaggatggg aagccacta gcagttatca   8040
catgccgttt atgatggaaa tcacagggcc tcttcaagta gaaaagctac aacaaacagt   8100
aaagagtctt gtcgcaaggc acgagtcgtt gcggacatca tttcacatga tcaatgaagt   8160
attgatgcaa aagatacatg cagatgtatt gtgggattta gacattgatc tagagtcagt   8220
tgtcgcttca gagcaagaaa ttgatgaaaa aatgttccaa ttcctccgca aatttgattt   8280
gagtcaagct cctctctttta gagctaagct gattcgtgtc aatgctagtc ggcatgtatt   8340
gttattagat atgcaccata ttatttcgga tggattttca taccagatat ttttgatga    8400
gcttaccaag ctgtatcagg gcgatgaact gccatctctc aaaatacaat ataaggatta   8460
tgccgtttgg cagcattcgg aagaacaaca gaagcgtttg caacagcaag aggattattg   8520
```

```
gttaggtcaa ttccaagggg aaattcctgt tctggaattg cctacggatt accagcgccc    8580
ggttgataaa cagtttgctg gagcattatt cacacacggg ttatctgctg gtctaacaga    8640
gaagctgaga aaattagcga ttaaggaaaa aacgacgtta tacaccgtac tgctgacggt    8700
ctataacatt ctattgagca aatatacaag tcaagaggac ctcattgtag gtacaccgat    8760
tgctggacgt ccacatgctg atttagacag agtatttggg atgtttgtaa acacgctggc    8820
catcagaaca gctccaaaag tagagcattc cttcttaacg tatctatctg aggtcaaaga    8880
aacagtgcta ggtgcttatc aaaatccaga ctatccattt gaggagctgg ttgaaaaaac    8940
gctagttcag cgcgatgtaa gccgtaatcc tttattcgat gtaatgttct ccgtagagaa    9000
attaccatct gctgtacagt tcgatgattt acgtttctgc ccacgcttat ttgattggaa    9060
gaaggcaaaa tttgacttgg attggacagt ggtggaaggt gaatcattgg aggttttggt    9120
tgaatatagc acgagcttgt tcgatcgggc gaccattgag cgcatggcta agcattttga    9180
gcatattttg gagcaaatcc ttgatcagcc agacctgtct atttctgaga ttgaactgct    9240
gaccgaggca gaaaaacaac aaattttgat tgagtttaat caatcggata aatcctttga    9300
cagcgaaaaa acaattcagg agcaatttga agaatgggca gaaaaagccc cgcacagcat    9360
tgccttagtc tttaaagaca agcaaatgac ctatcaggaa ttaaatcaac gtgctaacca    9420
agttgcgcat ttattacgtg gcaatgggat ttccgcaaat gattttatcg gtttaatggt    9480
ggatcgatcg tttgagatga tcattagtat gctaggtatt ttgaaggcgg gtggagccta    9540
cctacctatt gatcctgatt atcctgagga ccgtatcgat tatatgttat ctgacagcaa    9600
agcgaagatt ctcttaaagc aaagtgacca aactgcacca gcttcctttg aaggtaaagt    9660
catcgctatt gatactccag aattgctaga gatggatata gaaaatattc ctaaggtgaa    9720
taactcatcc gacttggctt atatcattta tacatctgga tcaaccggaa aaccaaaagg    9780
agtattgatt aatcatcgat gcgtgatcaa tatgcagctt acagctgaaa cctttggtat    9840
ctatccttcg agtcgtattc tacagtttgc atcctttagt tttgattcat ctgtgggcga    9900
gatttttttat acattattaa acggagcatg cctgtatttg gtagaaaagg atttgctttt    9960
atccggtaat gaattcgtgg catggctaaa gaaaaatcgg attagctcga ttccatttat   10020
ttcaccgtcg gctctgcgga tgcttcctta tgaggattta cctgatctcg catatataag   10080
tacgggtggg gagacattgc cggctgacct tgttaaagcg tggggagaaa atcgtgtctt   10140
cctaaatgca tatggcccga cggaaacaac tgtagatgcc actgtcggtg tatgtacacc   10200
agaagggaaa ccgcatatcg gtagacccgt tacgaataaa aaggtgtacg tagtaaatag   10260
taacaatcaa ttacagccga ttggtgttcc tggcgagctt tgcattggcg gggaaggggt   10320
tgcacttggc tatctaaaca gacctgatct aacccaagaa aaattcgttt ccaatccgtt   10380
tgccccgggt gaaagaatgt accgctccgg agacttagtc agatggctac ctgatggaac   10440
aattgagtac ttcggaagat tagacgatca agtaaaaatt agaggtcacc gtattgaact   10500
aggagagatt gaaacaaggc tactagcaga tccatccatt aaagaagcca ttgtcattcc   10560
acgttctgat gagtcagagg ctacatattt atgcagctat ttgattgcag aaggatcatg   10620
gaatgcggct gacttacgta agtatttgaa ggcttcttta ccggaatata tgataccttc   10680
gtattttgtg gagctgcacg agctaccgct aacacctaat ggaaaagtta ataaaaaagc   10740
attaccaaaa ccagaaaagc aaatgcagag agggaaggat tatgtagccc ctactaaccc   10800
tatccaatcc attttatctc agatttggac tgatgtgctt ggtgttgaaa atataggaat   10860
```

```
tcacgacaat ttctttgaat taggtggaga ttcaattaaa gccatccaaa tttcagctcg   10920
acttaataag cataatctca aggttaaaat gcgggaattg tttaagaacc caacgattgc   10980
tgagctaagt ctgcttgtac aacagatcgt tcaggagatc gatcaaggag tagtagaagg   11040
aaatattccg cttacaccga tccagcattg gttctttacc caatcattcc cgcaggtcaa   11100
ccattacaat caatcggttc ttcttttaa tgcggagggc tgggatgagc agaaagtaga   11160
caaagctttt gagatgctaa cccagcacca tgatgcactg cgaatcgtat atagcctcga   11220
cgagcaaggg gttgtacagc gtaaccgggg attggaaggc tcgaactatc atttcgaaat   11280
cattgatgca agacaagatg gagaagatca gtcgaactgg aaagcagcgg cgaatcggat   11340
gcaggcaagt atggatatcg tagaaggacc tttagtgcag atcggattgt ccgtgctaa    11400 tgaaggagct tatttgttaa ttgccattca tcacttagtg gtagatgggg tgtcttggcg   11460
tatcctacta gaagacttct atcatttata taacggaaac gactctttgc cattaaaaac   11520
gacctcgttc caagcatggt ctcaaaagct ccaagagtac gcccaaagca aggagctaga   11580
acatgagctt tcctattggc gccatttaga tgaagctatc acggactata ccttacacaa   11640
agatatagaa gccgcaacct caaataagac aacctatgag gaattttaa ctgtatcgat    11700 gtctttatca actgaggaaa cccaacagct agtaacagag gctcataaag cgtaccaaac   11760
ggaaataaat gatctgctac tcacggcact ggctttagct ttgaaggaat ggacgaataa   11820
agagcagttg ctagttagta tggagggca tggacgtgaa gaaattctag ataacgtaga    11880
tatctcccgt acagttgggt ggtttacatc agagtatccg gttgctattc atctgacgaa   11940
aacagacatt tcgtttgcca ttaaacaagt aaaggaaacg ttgcgtcgtg tacctaacaa   12000
agggtttggc tatgggattc ttaaatattt ggcaaaagag acgttcaagc ttaagccaga   12060
aatcagtttt aactatctag gccaatttac agataaggaa gagggaaact cctctttaat   12120
gggtgatctg attagcccgg caaataccag tgagctgtcc ctagatatca atggaagtat   12180
agaagctgac agactgcaaa tgcactttag ttataactct cgtgcgtact atccagagac   12240
aatcgcaacc cttgttcaaa acttcaaatc ctacttgctt gagattatca atcattgccg   12300
ggcgaaagaa ggagtagagc atacaccaag cgactttgat atcaatgatc tcaccatgga   12360
agaactagat gatattttg atgacctgga agaagaggta tacaaataac taggcaaaaa    12420
tatggagtga tttagatatg tttagcagaa gtaatgtgca aaatttgtat cgcttatctc   12480
ctatgcaaaa agggatctta tttcattcct taaaagataa agaaaatcat gcctattttg   12540
atcaactgat cttcactttg gaaggtaagg tagagcttga atatttggaa gaagccttta   12600
cccaattaat caaaaagcat gatattttac gaactgtttt tcgttacaaa aaagtaaaag   12660
aacctgtaca aatggtatta aaggaaagaa gctccactat ttatttgaa gatatttctc    12720 atctggagcc agaagaaaaa gtgaattaca ttaagcagtt taaaatgagg atcgggaga    12780 aggggtttga cctctcccgg gacctcctca tccgaatgtc attatttaag cttgatcagg   12840
agcagtatca gttaataatg agtaatcacc atatcattat ggatggttgg tgccttggca   12900
ttatccttac tgatttctta cgtatgtata aaggaatcgt gaatcatacc cctgttccat   12960
acgagcatgt gacaccttac agtaagcata ttcaatggct agaaaaacag gatcatcagg   13020
aagcaaagga tttttatcaa cagctattag agggatacga caaagtaaca ggtgttccac   13080
agcaattagt acgggcgaat cacgaagaat atactcacgg acaatgcatc gtgaaattaa   13140
atcaagaaac tgccgaccga ttgattgcca tagccaaagc ctaccaggtt acagtcaata   13200
ccgtcttcca aacgatttgg gggatattat tacaaaaata taataatacg gatgacatag   13260
```

```
tatttggatc agttgtctcg gggagaccgg cagagattcc tgatgttgaa aaaatggttg   13320
ggctatttat caatacaatt cctgtgcgaa tcaaagctga tcaacaagag cgatttgaca   13380
cgctagtagc caaagtacag gaaatggcct tggcttcaga atcatatgat tatctttcgt   13440
tggcagatat tcatccagaa gctggcgatt ttatcaatca tattattgcg tttgaaaatt   13500
tttatatcga tatggacagc tttaatcagc tagcagataa aaaagagctt ggattctcgc   13560
tcgcattcgc cacagatcat cacgagcaaa ccaattatga tctaagtgtg caggcgcaga   13620
ttggtgatga atcttccatt aaaatttat ataattccaa gctttataca tcggaataca   13680
tagcaaatgt aattgatcat tttgttactg tggctgacat agtggctgct aatcctagca   13740
tccctgtaaa ggaaatcgat attttaacaa aagataaaaa agatcagatt ctctatggtt   13800
ttaacaatac ctatgcagat tatccaagag agaagaccat ccatcagcta tttgaagaac   13860
aagtagataa aaatccgaat cagatcgcac ttgtgtttaa agaagagaag ctgacttacg   13920
gtgaggtaaa tgcgaaagca aatcagttgg catacgtgtt aagaaagcaa ggtgtacagc   13980
ctaatgatgt aatcggcatc atcaccgaac gctccccaga aatgatcata ggcattttgg   14040 cgattttaa agcaggcgga gcttatatgc caattgatcc ttcttatccg gctgaacgca   14100
ttcaatatat gctacaggat aatcaaacga agctattatt agtgcaaaaa caagaaatga   14160
taccagccaa ttatcaggga gaggtattgt tcttaaccca agagagttgg atgcatgagg   14220
aaacatctaa tccggctcat attactcaag cacaggcttt agcatatgtg atgtatacct   14280
ctggttctac aggagagcct aagggcattt tgacaacaca tcaaaatatt atgaagaccg   14340
tcattcataa cggttatgtt gagattacgc caggagattg cttgtcgcag ctctccaatt   14400
atgcctttga cggctctacc tttgaaatct atggggcatt attgcatgga gctacattac   14460
ttttagtaac aaaagaggct gtactcaata tgaatgagct ggcacgtctt attaagaagg   14520
agcaagtgac ggtttccttc atgacgactg ctctgtttaa tacactggtg gatttggata   14580
taacgtgctt tcaatcgata cgaaaggtgt tgttcggagg agagcttgct tcggttaagc   14640
atgtcctgaa agcccttgat tatttaggcg agcaccgggt tatcaatgtg tatggaccaa   14700
cggaaactac cgtgtatgct acctattact ctgtagatca ctccatgctg acgagggcat   14760
ctgttcctat cggaagaccg attaataaca cgaaagctta cattgtaaat acagatggac   14820
agcctcagcc aataggagta gtcggtgagc tatgcattgg cggtgagggg gtagcatgtg   14880
gttatcttaa ccgtcagag ctgacaaaga aacatttcgt ggataatccg tttgtcttgg   14940
gtgaacgaat gtattgtacc ggagatttag cccgcttttt accagacggc aacatcgaat   15000
acatcgggcg gatggatgaa caggtaaaga ttcgtggtca ccggattgag ctgggcgaaa   15060
tcgaaaaggt tcttttacag cacccagcta tcagcgagac agtgcttta gcaaaacgag   15120 atgagcaagg ccattcctat ctgtgtgcgt atatagtagg tcaggtattt tggactgtta   15180
cagagctgcg tcaacacttg atggaatcct tgccagaata catggtgcct tcctacttta   15240
tcgagattga gaaactaccg cttacggcaa acgggaaggt agataagcga gcgttgcctg   15300
aaccagacag aaaaatgggc agtgcttacg ttgctccaga gaacgaaaca gaggagaagc   15360
tggttcaatt tttccaagag atttt gggtg ttgagcgagt tggcacgcag gatacatttt   15420
tcgagcttgg tggtcactcc cttaaggcaa tgatgctcgt tttacagatt cataaagaaa   15480
tgggcattga agtcccgtta aaggagatat ttacacgtcc taccatcaaa gaattagcgg   15540
cgtatattca taagatggat cgctctgcct acagcatgat tgagccaact gccaaacaag   15600
```

```
agtattatcc agtctccttt gcccaaagac gaatgtttgt agtgcagcaa attagagata   15660
cgaatacaac cagctacaat atgccgattt tgctagaaat agaagggggct cttgataggg   15720
aaaatgtgag acaaactctg aagaaattga tagagcgtca tgaatcaatg agaacgtcat   15780
tccatatgat tgacgagacc ttgctacaaa aggtgcatga tgatgtgaca tgggaaatgg   15840
aggagatgga agcgtctgag gaagaagttt atgctttgac aaaatccttc attcgtcctt   15900
ttgatctcgg tcaagctcca ttgtttagag caggattaat tcgtgttaat tctgagcgtc   15960
atttgctgct gctagatacg catcacatta tctcagatgg cgtatctact aacatactct   16020
ttcaagattt tacgcaatta tatcgtggac gagagctgcc tgccctgcga attcaataca   16080
aggatttcgc cgtctggcaa caaggagagg ctcagcttgc tcgtttgcaa gaacaagaag   16140
aatactggct gaaacaattt tcagagagtg tgcctgtact agagcttcct actgattttc   16200
cacgtccagc gatgcagcag tttgatggtg acgtattgga ctttgcatta aatcagcaag   16260
tatggcagga attacaacag ctcattgtta aagagggctg tacggcttac atgatattgc   16320
tggcggctta tcatgtcttg cttctccaagt attcgtcgca aaacgatatt gtgataggtt   16380
ccccgatagc aggccgaaca aatgctgatt tgcaatcgat tgtcgggatg tttgttaaca   16440
cgctggctat ccgcaccaaa tcagagggaa ctcagacatt ccgcgagttt ctctctacga   16500
ttaaacaact ggttcttcaa gctcaatcca atgcagagta tccatttgaa gagctggttg   16560
ataaggtaaa tccaagtcgc gatctaagtc gccagccttt atttgacaca atctttgtca   16620
tgcaaaacat ggatattacc gaggttgcga tacaaggtct ttcaatcgta acgaaggaca   16680
tggaatggaa gcattcaaaa tttgatctta catgggcggc tgtagagaaa gaatccttgc   16740
attttttcagt tgaatatagt acccgcttat ttaagaaaga acaatcgag cggatggcga   16800
agcattttgc ccatttgcta aatcaagtgg cggaaaatcc tgacttgagc ctttcagata   16860
tggaattggc aacggatgaa gaagtgtacc agcttttgga ggagtttaat aatacagaag   16920
ctgattatcc gagtgataaa acgattcacc agcagtttga gcagaaggta gaggaaaacc   16980
ctgatcagat agcgttgtta tttaaagata aggaaattac ttacggacag ttgaatgcaa   17040
aagcaaatca atttgctcgc gtattaagaa agcatggggt acagccggat caagtggttg   17100
gattaatcac tgatcgttcc attgaaatga tgataggaat tttggcaatc ttaaaagctg   17160
gcggagccta tttgccaatt gatccttctt atccattaga acggattacc tacatgctag   17220
aggatagtca ggcacagctt ttgattgtgc aggaagctgc tatgattcca gaggggtatc   17280
agggcaaagt attgcttcta gcagaagagt gttggatgca ggaggaagcg tccaacttag   17340
agttgattaa tgatgcccag gatttggcgt atgtgatgta tacctcaggg tctactggta   17400
agccaaaggg caatctgacg actcaccaaa acattttgag aaccatcatc aacaatggat   17460
ttatcgagat tgtaccagca gaccgtctat tacagctatc gaactacgcc tttgatggct   17520
ctaccttcga tatctacagc gcgctattaa atggagccac tcttgtactg gtgccaaaag   17580
aggtcatgct aaatccaatg gagctggcga ggatcgtccg cgagcaggat attacggttt   17640
cgtttatgac cacgtccctg ttccatacgc tagtggagct tgacgtgact agtatgaaat   17700
ccatacgcaa ggttgtattt ggtggggaaa aggcttcata caagcatgta gaaaaggctc   17760
tggattatct cggagaaggc cgtttagtaa atggatacgg ccctacagaa caaccgtttt   17820
ttgctaccac atacacggtg gattctagta tcaaggaaac gggaattgta ccgattggcc   17880
gtccgttaaa caatacgagt gtctatattt tgaatgagaa taatcaacca cagccgattg   17940
gagtaccagg ggaattgtgc gttggcggag caggaattgc acgtggatat ttaaaccgtc   18000
```

```
cagagctgac agcagagcgc tttgtggata atccgtttct tgtaggagat agaatgtatc   18060
ggacgggaga tatggctaga ttcttaccag atggcaacat tgagtacatc ggacgaatgg   18120
atgaacaagt gaagattcgc ggacatcgaa ttgaactggg cgaaattgaa aaagtctcc   18180 tggagtaccc tgctatcagt gaagcagtac ttgtcgcaaa acgtgatgaa caaggtcatt   18240
cctatctgtg cgcttatgtt gtaagcacgg atcaatggac ggtggctaag gtacgtcaac   18300
acatactgga ggctctgcca gagtacatgg taccatccta tttcgttgag cttgaaaagc   18360
tacctcttac ttctaatggc aaggtagaca agcgtgcatt gcctgaacca gatcgagtga   18420
ttaccaatga gtatgtggcg gcagtcaatg agacagagga gaagctagtt cagttttttcc   18480 aagagatctt agctgtagac cgagtcggaa cgcaggatac attctttgaa ttgggtggtc   18540
attccctaaa agcaatgatg ctggtttcaa gaatacacaa ggaattagaa atagaggttc   18600
cgttaaaaga agtattcgcc agacaaaccg ttaaagaatt agcagcctat atcagacagg   18660
ctgaacagtc ggattacagc gaaatccaac cggccatgga gcaagaatac tacccggtat   18720
ctaatgcaca gcgacggatg tatgtggttc agcaaatgag agatgtagaa acaacaggct   18780
acaatatgcc gttctatta gaaatggagg gtgctcttga ggtagaaaag ctatctctag   18840
ctttgaaaca actaattgag cgtcatgagt cattgcgaac ctccttccat atggttgaag   18900
atgaactgat gcaaaaggta catgcagaag tcgcatggga gatggaaatg attcatgccg   18960
tagaggaaga agttcaacag ctgaccgatt cctttatgcg tccttcgat cttgctaagg   19020 cgccattatt ccgagcgaga ctcattcaaa tcaatccgaa gcgacattta ttgatgctgg   19080
atatgcatca tatcatctca gatggggtat cgatgaatgt attgttccag gatataacgc   19140
agttgtatca agggatagag ctgagtcctc tcaagattca atacaaggat tttgcggtgt   19200
ggcaacaagg catcgctcag gttgtccgtt tcaggagca ggaaaggtat tggttaaacc   19260
aattctctgg tgacctacca attttggaaa tggtaactga ttatccacga ccagccatac   19320
agcagttcga cggagattcc tggtcatttg aaattgatgc caaagtattg gacagcataa   19380
agcaattgtc agctaagcaa ggcactacgt tgtatatgac tctattggcg atttatcaaa   19440
tcctgttagc caagtatacc cgtcaagatg acatcattgt cggaactccg atcgcaggaa   19500
gacctcatgc agacacagag agcattgtgg ggatgtttgt caatacacta gccctacgtg   19560
gtcaaccaaa agaagagcaa tctttcatct cttacttatc agaagtgaaa gaaaacgtac   19620
tacaagccta tgccaacgct gattatccat ttgaagagtt ggtagagaag ctgcatttgc   19680
aaagagatat gagtcgtcat ccattgtttg atacgatgtt tgttttacaa aacatggata   19740
tgtccgatat aaatatttct ggtctaaagc ttcattcgcg tgatttaaac tggaaaaatg   19800
caaaatttga tatgacctgg atgatagccg aacaaaataa tctattgatt tcggttgagt   19860
acagtaccaa cctgttttaaa catgaaacca ttcaaaggct agaaaagcat ttcacttatt   19920
tagtagaaca agtggctaag catccggatt gcttactcag agatttagaa ctcacaacag   19980
acgaagaaaa acagcaaata ctgacggtat ttaacgatac tgctactgat gatttacagg   20040
atttatccat ttgccatcta ttcgaacaac aagtgcagcg ttttttcagat cggccggcac   20100 ttgtgtttaa agaaaagcag ctcacataca gtgagttcca tgcaaaagta aatcaattag   20160
cccgggtact cagaaagaaa ggtgtgcagc cggatcaagc ggttggatta atcaccgatc   20220
gttccattga gatgatgata gggattttcg ccatcctaaa agcaggcgga gcttatatgc   20280
caattgatcc ttccctatcca atcgatcgga tcgagcacat gctagaggac agccggacta   20340
```

```
agttgttatt cgtgcaaaaa acagaaatga tccctgctag ctatcagggg gaggtattac   20400
tcctagcgga agagtgctgg atgcatgaag attcatcgaa tttggagctg atcaataaaa   20460
cacaggattt ggcatatgtc atgtataccc caggttctac tggtaaacca aagggcaacc   20520
tgacaacgca ccaaaacatt ttgaccacca tcatcaacaa tggctatatc gagatcgcgc   20580
caacagaccg tctattacag ctatctaact atgcttttga tggctctacc ttcgatatct   20640
acagtgcgct attaaatgga gccactcttg tactggtgcc aaaagaggtc atgttaaatc   20700
caatggagct ggcgaagatc gtccgcgagc aggatattac ggtttcgttt atgaccacgt   20760
ccctgttcca tacgctagtg gagcttgacg tgactagtat gaaatccatg cgcaaggttg   20820
tatttggcgg ggaaaaggct tcatacaagc atgtagaaaa ggctctggat tatctcggag   20880
aaggccgttt agtaaatgga tacgccccta cagaaacaac cgttttcgct accacataca   20940
ccgtggattc tagcatcaag gaaacgggaa tcgtaccgat tggacgtccg ttaaacaata   21000
cgagtgtcta tgtcttaaat gagaataatc agcttcagcc gattggagta ccaggggaat   21060
tgtgcgttgg cggagcagga attgcacggg ctatttaaa tcgtccagag ctaacagcag   21120
agcgctttgt ggaaaatcct ttcgtgtcag gagatagaat gtatcgtacc ggtgatttag   21180
cacgttggtt gccggatgga agcatggagt atttaggacg gatggatgag caggttaagg   21240
tacgcggtta ccgaattgag ctgggagaaa tagagacaag attattggag catccttcta   21300
taagcgcagc ggttttacta gcaaagcaag atgagcaagg gcattcgtac ctatgtgctt   21360
acatcgttgc aaatggggta tggacggttg cggaactacg taagcatcta agcgaggctt   21420
tgccagaata catggtgcct acttattttg ttgaactaga gcagatacca ttcacttcta   21480
atggaaaggt gaacaaacgc gctttaccag agccagaagg acaaatgacc agtgtatatg   21540
tggccccaga aacggagaca gaagcaaaag tagcagcgtt attccaagag attttgggtg   21600
tcgagagagt tggtacacag gacatgttct ttgagctggg tggtcattcg ctaaaagcga   21660
tgatgctcgt tttacgaatg aataaagaac tgggcatcga ggtgcctttg aaagaggtat   21720
tcgcccatcc tactgtcaag gaattggcag caacgatcga ccttcttgat cgatcaggcc   21780
actcagagat tgagcctgcc ccaaggcagg aattctatcc ggtatcttcc gcgcagagac   21840
ggatgtacgt ggtgcagcat ttaggaaatg tccaaacaac cagctacaat atgccgcttt   21900
tccttgaagt ggagggagct ttagaaattg ataagcttca tctagcactt gagaaattgg   21960
tcgaaagaca cgagtcgcta cgaacctcct ttcatatggt tgacgaagag ctgatgcagc   22020
aggtgcatga agaggtggcc tgggatttag agatcatgga tggaacggaa ggagaccttg   22080
caagcatcac agcaggattt atacgtccgt ttgatctcag ccaagctcca ttgttccgtg   22140
caggcatcgt gcggattagc cctgagagat tccttttcat gctagatatg caccatatca   22200
tctcagacgg agtttctacc aatgtattgt tcaaggatat aacgcagctc tatcaaggaa   22260
aggacctgcc ccctcttccg atacagtaca aggactacgc tgtgtggcaa caagctgatg   22320
ctcaagtgac tcgcttacaa gatcaggaaa gctattggtt acatcaattt gctggagaag   22380
cttctgtctt ggaaatgccg acagatttcc cgcgtcctgc agtccagcag ttcgaaggag   22440
atgtatggac ctttgagatt gatgctgaca ttctcagcca gttgaaaaaa ttatcagtga   22500
gtcagggttc tactctatat atgactttat tggcggttta tcaggtgttg ctggctaagt   22560
ataccggtca agatgatatt attgtcggtt caccaattgc cggacgccct catgcggatg   22620
tagagagcat cgtcggtatg ttcgtcaaca cgctagcttt acgtggacag cctgtaggag   22680
agcagacgtt tattacctat ctggcacaag ttaaggaaca ggttttacaa gcttatgcca   22740
```

```
atgcagagta tccatttgag aaattggtag agaagctcga tttacaacga gatatgagtc  22800
gccatccact cttcgatacg atgtttactt tgcaaaacat ggagatgact gatattgatt  22860
tggcaggctt gaccttcaag ccatttgatt ttgaatggaa aaatgccaag tttgacatgg  22920
attggacaat gcttgaggaa gaaacactca aggtagctat tgaatacagt acaagcctgt  22980
atacaaaaga aaccattagc agaatggctc aacatttcac ctatgtttta caacaaatta  23040
ttgagcatcc agccattcgt ttggctgaaa tcaaaattgc tactctacca gaaattgaac  23100
agattttaac gcaatttaat gatactaggg ccaattaccc tgataaccaa accattcata  23160
gtctattcga gcaacaagtg gagcgtacac cagaacagat agctgttgtc tatcaggatc  23220
aatccatcac gtatcgtgag cttaatgaac gtgcaaatag attggcacgt tgcttgatcg  23280
acaagggat acagagaaat caatttgttg caatcatggc ggatcgttcc atagaaaccg  23340
ttattggaat gatgggaatt ctcaaagcag gaggagctta tgttccaatt gatcctgatt  23400
accctctaga tcgaaagctg tatattcttg aagacagcca tgcatcacta ttattgttcc  23460
agcaaaagca tgaggtcccc tcagaattca caggtgatcg gatattaatt gagcagatgc  23520
agtggtacca agcggctgat acgaatgtgg ggatcgtcaa tacagctcaa gatttggcgt  23580
atatgatcta tacctcaggt tctacaggtc aaccaaaagg ggtaatgatt gatcatcaag  23640
cagtatgtaa cctatgctta atggcccaaa cctatggaat ctttgcgaat agtcgcgttc  23700
tacagtttgc ctcctttagc tttgacgctt ccgtaggaga ggttttccat acccttacaa  23760
atggagccac tctctatctg atggatcgca atttgctcat ggctggcgtt gagtttgttg  23820
aatggttacg agtaaatgaa ataacttcta ttccgtttat ctcgccttct gcattgcgtg  23880
cattgccgta tgaggattta ccagcattga aatatatcag tacaggtggg gaagcattac  23940
ctgtagattt agtcagacta tggggaactg agcgaatctt cttaaatgca tatggcccga  24000
ctgaaacaac agtagatgca acgattggct tatgtacgcc agaggataag ccacatattg  24060
gtaagcctgt gttgaataaa aaagcctaca ttattaatcc aaattatcaa cttcagccaa  24120
ttggggtacc gggtgagtta tgcatcggtg gagtagggat tgctcctgga tattggaacc  24180
gccctgaact aactagagag aaatttgtgg ataatccatt tgcccaaggc gaaagaatgt  24240
ataagacggg ggacttagta cgttggcttc cagatggaaa tattgagttt ttaggacgta  24300
ttgatgatca ggtgaaaatt cgtggacacc gaattgaatt gggtgaaatt gagacgcggc  24360
ttcttgagca tgagcaggta atagaggcgg ttgtgctggc gcgtgaagat gaacaaggtc  24420
aagcttatct gtgtgcttat ctggtagcag cagatgaatg gacggtagca gaactgcgca  24480
aacatctagg aaaaacactg cccgattata tgattcctgc ttattttatc gagcttgagg  24540
agtttccttt gacaccaagc gggaaggtga ataaaaaagc tttaccagag cctgatggac  24600
aaatacaaac gggagtggag tacgtagagg ctactaccga aagccaaaaa atccttgttg  24660
agctttggca agaggtgtta cgtgtcgagc ggatcggtat ttacgataac ttcttttgagc  24720
tgggcggtga ctccatcaaa gcaattcaaa tcacagcaag attgcgtcgc caccaccgca  24780
agctggaaat cagccatctg tttaagcacc caacgattgc agagcttgct ccatggatgc  24840
aaaccagtca ggcattactt gaacaaggaa ctgttgaagg cgaagttatg ctcacgccaa  24900
ttcaaaaagc attctttgaa gaaaatcagg aacagccgca gcattttaat caggattcgt  24960
tactgtacag ctcgaatggc tggaaccaag atgcgatcga gcaggtattt gaaaaaataa  25020
cggagcatca cgatgccctg cgaatggtgt atccgcatac cgagggcaag gtgactcaga  25080
```

```
tcaacagggg acttgaggac aaggcgttca cattgcaggt gttcgatttt acccaagaac    25140
caactgatac gcaggcaacg aaaattgagc aaatcgctac tcaattgcaa gcgagctttg    25200
atttaaaaaa gggacctctg gtacgacttg gcttatttac caccaaggct ggggattatt    25260
tactgatcgt gatccatcac ctagtgattg acggcgtctc ttggcgtata ttgcttgagg    25320
attttcataa tgcttatcag caagtcattc aaggtcaagc aattgtactt cctgaaaaaa    25380
cgacctcctt taaaacatgg agtgagcgct tgaatgaata tgcaaatagt catgctcttt    25440
tacacgagat tccatattgg aagcagatgg aagaaatatc gatcgcccct cttcctaaaa    25500
aaggaaacaa tgacggtaga tattatgtga aggacagcga atatgccacg atgagtctaa    25560
cagaagaaga aacccaaaat cttcttactc gtgtacatcg agcttatcga acggagatta    25620
atgatctgtt gcttgctgca ttaggattag caagtaagga atggacaaaa gagaatcgag    25680
tggctatcca cttagagggt catggtcgtg aggaaatagg tgaaggggta gatgtcaacc    25740
gcactgttgg atggtttacc tccctgttcc cattcgtgat tgatttagaa aatgacgaat    25800
tgcctctcat cattaaatcg gtaaaagaaa ccttgcgccg agttcctaat aaaggcatgg    25860
gctacggcat actcaagcat ctgacaagcg atgcgaacaa acaggagata accttctcgc    25920
ttcgcccaga gatcagcttt aactatctgg gggtatttga tcaacaagag gaggaaagcg    25980
aatctgctgg gattcctact ggtcagccga tcagcccgca atattatgac acgcacctgc    26040
tggagtttaa tggagcggtc tcgaataacc agttgcatgt aaattgccga tttgctcctg    26100
cagccgttga tcgagcgatt gttgaaattt tgatggagcg cttcaagcac catttacttc    26160
taattagtaa gcattgcttg gaaaaggata ccgtagaatt tacacctact gattttacag    26220
aaaaggaatt aagccaagaa cagcttgacg atctattaga tgatttgttt gaagacatag    26280
atgatctgta atcgcaatga gataggtggt gccacacatc gtgcaaaaaa aagacaagat    26340
caaagatatc tattcacttt ctccgttgca aagggtatg ctatttcatt ccatgaaaga    26400
cccgcagagc gatgcctatt tcgagcaggt taccctttg ctggaggggg ttgtaaaccc    26460
aacctatttg gctgaaagta ttcagggact cgtacaaaaa tacgacatgt tccgaagtgt    26520
gttccgctat aaaaaagtag accctgttca ggttgtgctt agtgaacgaa aaatagattt    26580
acagattgag gaccttactc aaatcaatga agaagagcaa cggaaattca ttgaggaata    26640
tagaaaaaag gaccgggaaa gaggcttcga cctttcccgg gatatcctgc tacgttttac    26700
attgtttcaa acagccgcca atcggtatga attactgtgg agtcatcatc atatcctgat    26760
ggatggctgg tgtacgggta tcgttttca ggatttattt caaatgtacc aacgtcgctt    26820
gtcaggacag gccttacttc cagaggtggc ccctcaatat agcgaatata tacgctggtt    26880
aaagaaacaa gatgaccaac aagcattggc attttggaag gagtatctac aggggtttga    26940
aaaccttacg ggaatcccgc gtctaaggtc aggcaatcat ccctacaagc aagaggaatt    27000 catttctctcc ttgggagagg aagctacaca aaaactaacg caaacggctc aaaagtatca    27060
ggtgacctta aatactgttg tgcaaacaat ttggggagcg ttattgcaaa aatacaataa    27120
cacgaatgac gcgcctacg gtgtggttgt ctccggacga cccgccgagg tgccaaatgt    27180
tgaacaaatg gtgggttat ttagtaatac cattcctatt cgtattaaaa agaagcagg    27240 aaaaacgttt ggggaagtgc tgaaaaacgt acagcaaaca gcgctggagg cagaaaaata    27300
cggatatctt tctttagccg atattcaggc gagcgcagct tatacgcatc aattgcttga    27360
tcatatttta gcgtttgaaa atttcccgat ggatcaagaa acatttaatc aagaaaacgt    27420
tctcggattt gccgtgaagg atgcccacac gtttgagcag acgcactatg atctgaccgt    27480
```

```
gctagtcatt cctggcaagg aattaatctt taagtttatg tataacgaaa gtgttcattc    27540
aaaagagtac ctcaatcttt tagagctgaa tatgaaaaag ctggtctctt tggttattga    27600
gcagcaggat atctttgacc cagctaccga gtttgtatct gatttggaaa aggataagct    27660
tttaaccatt tttaatcgta cggatgcaaa gtacccaaga gaaaaacga ttcatgagct     27720 gtttcaagag caggttgaca agaaccctga tcaagtggca ctcgtatttg gcaggctca    27780 actaacatac cgcgagctga acgaaaaggc gaatcaaatg gcccgcggtt tgcgcaaaca    27840
aggggtttta cctgatcagg tgatagggtt acttacggat cgttccttag agatgatcat    27900
agccattcta gcgatcttta aagctggtgg cgcttatatg cctatcgacc catcttatcc    27960
gagtgaacgc attaataca tgctagcaga tagtcgtacc catttgctat tggtgcaaaa     28020
agctgaaatg atcccagcta attatcaggg tgaggtacta ctgttaacag aagatagctg    28080
gatggacgag aatacagata atttagattt ggtcaaccaa gcacaagacc ttgcttatgt    28140
catgtatacc tcaggttcaa caggtaaacc aaagggaaat ctgacaaccc atcaaaatat    28200
cgtcaagacc atcatgaaca atggttacat ggagattacg ccaaatgatc gtcttctcca    28260
gttgtccaat tacgcgtttg atggatcaac ctttgatata tacagcgcat tgttaaacgg    28320
agcttctctt attttagtac caacgcatgt actgatgaat ccgactgatt tggcatcggt    28380
cattcaagac cagcatatta ccgtgtcctt tatgacaaca tctctattta acactctggt    28440
tgagctggat gtgactagtc tcaaacacat gcgtaaggtg gtgtttggag agaaaaggc    28500 ttcgatcaag cacgtagaaa aagcgctgga ttatttggga gctggacgtt tggtcaatgg    28560
gtatggacca acagaaacta ctgttttttgc cactacctat acggtggacc atacgatcaa    28620
ggagacgggg attatgccga taggtcgccc gttgaacaat acgaaggtgt ttatttttagg    28680 agcagacaat caactacagc cgataggtgc attaggcgag ctatgtgtga gcggggaagg    28740
gcttgcccgc gggtatctca atcttccaga gctgactgct gatcgtttcg ttgaaaatcc    28800
ttttatgcgg ggagagagaa tgtatcgcac aggggattta gcgcgttggt taccggatgg    28860
aagcattgag tacgtaggta gaatagatga acaagttaag attcggggac atcggatcga    28920
attaggtgaa attgaagcta gattactaga gcatcctgct attagcgaga ccgttttgct    28980
ggcgaagcag gatgagcagg gcattccttt cctatgtgcc tatctagtga caaatggtgc    29040
ctggtcagtc gcagagcttc gcaagcatat caaggaaaca ttgccggatt ctatggtgcc    29100
atcttatttt atcgagatag ataaaatgcc gctcacttca aatggcaagg cagacaagcg    29160
tgcattgcca gagccagatg ttcaacaagt aagctcttat attgctcctg agaccgaaac    29220
agaggaaaag ctggttcaat tatttcaaga atcctaagt gttgaacaag tcggtacgca     29280
ggataatttc ttcgagctgg gcggacattc gttaaaagcg atgatgctgg tttcaagaat    29340
gcacaaggaa ttagatatag aagtaccgct caaggacgtg tttgctcgac cttcagtaaa    29400
agaattggcc gcatttctta caaacacaga agtgtcggat tatatagcga ttgaaccggc    29460
ggcaaaacag gaattttatc cggtttcttc tgcacagcgc cgaatgtatg tagtagagca    29520
aatcggtagc agtaatacaa ccagctacaa tatgcctttt ttgcttgaaa taggaggagc    29580
cctcgatgta gtaggggttac aaaaagcatt aaagaaactg gtcataagac atgaatcgtt    29640
gagaacgtcc tttcacatgg ttgatgaggt attaatgcag aagatccatc ctgacgtgga    29700
atgggattta atggtcatgg aagcaaaaga cgaggacctt ccgcaaatca ttgatggttt    29760
tatccagccg tttgatttaa gtgacgcttc tttatttaga gcgggactcg tacgaatgga    29820
```

```
agctgatcga catctactga tgcttgatat gcaccatatt atttcagatg gggtatcaac   29880
caatgtatta ttccaagacc tgatgcaaat ctatcagggc aaggagctcc cttctcttag   29940
aattcaatac aaggattatg ctgtttggca gcaggcagaa gcccaggtta atcgtttacg   30000
agaacaggag cagtattggc ttaaccaatt ttcgggagag ttacctgtac tggaaatgcc   30060
taccgattac actcgtccat ctattccagca gtcagaaggg gatatatggt catttgaaat   30120
tagtgccgag atcataaaca aagtaaagaa actgtcctcc tcgcagggta caaccttgta   30180
tatgacattg ctggccgcct accaagtatt attgtcaaaa tatacggggc aagaggacgt   30240
tattgtgggt tctcctattg ctggccgacc tcatgcggat gtagaaaaga ttgttggtat   30300
gttcgtgaac acgttagcct tcagagggca gccaaaatca actcaaacct ttagtacata   30360
tctgtccgag gttaaggagc aggtattgca cgcctatgac aatgcagaat atccgtttga   30420
ggaattactt gaaaagcttg atttagaaag agatctaagt cgtcatccac tgtttgatac   30480
catgtttgct ttgcagaata tggaaatggc tgaaatcaat atcatggatc tctcctttca   30540
gccgcgggat ttaacatgga aaatgcaaa attcgacctg acatggatga tggcggaagc   30600
ggaaaatttg tatgtcacca ttgagtatag tacctcgctc tttaagccag aaacaattga   30660
gcgattaggt aaacgattca cccatttact aaaacagatc ggggatgctc ctgaacgttt   30720
gattgctgac ttagaagtag cgacggagga tgaaaaacat cagattttat cggtatttaa   30780
tttgactcaa tcggattatc cagtaaataa aaccgttcat cagctctttg aggagcaagt   30840
gcaaaatatg cctgatcaaa aggcgatagt atttggtgaa gagcaagtaa catacaaaga   30900
attaaacgcc aaagccaacc atctggctac cctcttaaaa caaaaggca taacaaacga   30960
gcaacttgtg gctgttatga ttgagccttc catcgagttt tttgtaggca ttctagctgt   31020
tctaaaagca ggagggcctt atctaccaat tgacccaact tatccgacgg aacgaattgc   31080
ctatattttg gaggatagtc aatcaaaggt tctgttagtg agaggtcatg aacaggtaca   31140
gacacaattt gctggggaaa tcttggaaat tgatagcaag aagttgtcta ccgaagagct   31200
gaaagacgta cctatgaata caaagtaac cgatctagcc tatgtcattt atacatcggg   31260
ttccactggg caaccaaaag gtgtcatggt ggagcataga tcgttgatga atctttcagc   31320
ttggcacgtt cagtattttg gcatcacaaa ggatgatcga agcaccaaat acgcaggggt   31380
tggatttgat gcatctgtat gggaggtctt cccttactta atagctggtg caacgattta   31440
cgtcatcgat caagagacaa gatacgatgt agaaaaactg aatcagtacg taacagatca   31500
agggattacg atcagctttt tacctacgca atttgctgaa cagtttatgc tgacagatca   31560
tacggatcat actgccctac gctggttgct tatcggcggt gataaagccc agcaagccgt   31620
tcagcagaag cagtatcaga ttgtaaataa ctatgggcct actgagaaca cggttgtaac   31680
aaccagctat atagtgagtc ctgaggataa aaaaatcccg ataggcgtc caattgctaa   31740
taatcaggta tttatcctga ataaagagaa tcaattacag ccagtaggga ttccaggtga   31800
actatgcgtt agcggcgaca gcctagcacg cggctatctg catcgtccag agttaacgag   31860
tgagcgtttt gtagctaatc cgtttgtccc tggcgaacgc atgtataaaa ccggagatat   31920
tgcccgctgg ttaccagatg gaaatattga gtatctaggt agattggatg atcaaattaa   31980
gatcagagga taccggggttg aattaggtga gatagaatcc gctattttgg agcatgaagc   32040
aattcatgag acagtagtgc tcgcaagaca agacgatcag aatcagacat atctatgtgc   32100
ttatgttgta ccgaaaaaat cttttgatgt agccgagctt cgtcaatatc taggcagaaa   32160
gctacctcac tttatgattc cggccttttt tacggaaatg acagagttcc caattacatc   32220
```

```
gaatgggaaa gtagataaaa aagcactccc actaccggat tgtccaagc aatcagagat    32280 cgattacgtt gccccaacca ccacgttaga agaaacgctg gcggaactat ggacagaagt    32340
gctaggagtt tcccaagtgg gaatccatga taacttcttt aaactgggtg gggattcgat    32400
caaggctatt cagattgcag caagattaaa tacgaagcaa ttaaaattgg aagttaagga    32460
tttattccag gcacaaacga ttgctcaggt tattccatac atcaaaacca aggaaagtaa    32520
agctgagcaa ggaattgttc aaggaaaggt agagctaacc cctatacagg aatggttttt    32580
ccagcaatcc ttcgatattc cacatcattg gaatcagtcc atgatgtttt atcgaaagga    32640
agggtgggat cagcacgttg tacaaagggt gttccaaaaa attgcagaac accatgatgc    32700
cttgcgaatg gcttatcagc aggaaaatgg caaaacgatt cagatcaatc gcggagtgga    32760
aggcaagttg tttgagctaa gcattttga ctttaaacaa caggcgaatg tgccagagct    32820
gatcgagcaa gcagctaatc gtctacaatc cgcaatgaac ttgcaggacg gtccattggt    32880
tcaactggga ctcttttcaga catctgaggg ggatcatctt ttgatagcaa ttcatcactt    32940
agtggtcgat gccgtttcat ggcgaatcat tacggaggat ttcatgaatg gctatcaaca    33000
agatttgcag ggagagccga ttgcatttac gagcaaaaca gactcctacc aaaaatgggc    33060
caagagcctg ctagagtacg ctactagtga agaaattcaa tcagagctga atactggca    33120 aagcatgatt gcaaaagggt tacctgcatt gccaagagat tcaaaagtag gtgccccgta    33180
tctactcaag gatatacaag aggtcgctat ccaattgaca aaagagcaaa cgaataaact    33240
attaacggat gcccataacg cctacaacac acagattaac gatcttttgt tgacagcatt    33300
agctctaact attcaggaat gggcacaaac caattcaatc gcaattacac tagaaggaca    33360
tggacgcgag gatattgggg tggacattga cattaaccgt acagttggtt ggtttacgtc    33420
catgtatcca gtggtatttg atttgcagaa gcaagggatt gcaaatacgg ttaagcaagt    33480
aaaagaagag ctgcgacaaa taccgaataa agggattggc tatggggttg ttagatacct    33540
atcgaatcaa ggaagtacag agctggatct aagctcccat gcgataaatc cagagattag    33600
cttcaattac cttgggcaaa tggatcaatc tggacaggaa gaggagtatc aattgtcccc    33660
attgtcttcc ggtcaacaga ttagtcagat gaatcaaggc ttgttcccga taaatgtgag    33720
tggaattgta gtgaaaatc agttgtccat tcaaatatct tatgatagcc aagcttatca    33780
tgattctact atggaaaagc tgattcaacg ttatcaatat cacttgttgg agattattaa    33840
tcattgtgtt cagcagacag aaacagaatt aaccccgagt gatttttcca ccaaagagct    33900
ttcgatggag gatttagaat cagtatttga gttactagat gaataaactt tggttatgtc    33960
attaggaggc tttatatgtt aagtaaagca aatattaaag acatctatac attatctccg    34020 ctacaaaag gcatgttatt tcagcattta aagaagaaa gcacggctta ttttgagcaa    34080
ttacacttta cgattaaggg acaactatat gtagatagct ttgaagcaag ctttcagcat    34140
ctcataaaca aatatgatgt gctacgaacc gttttttctgt ataaaatat gacccagccc    34200 atgcaaatgg ttttaaaaga aagaaaaaca agtgtgcatt ttgaagatat ctcccaccta    34260
gattctaaag ccgtgagtga atatgttgaa gagtttaaaa atcaggatcg ggagaaggga    34320
tttgaactct cgaaggacat tctcatgcgt tttgctattt tgaaggctgg tgctgagtcc    34380 tatcattaa tttggagctt ccatcatatt ttaatggacg gctggtgcat gggcattgtg    34440
ttacaggatt tgttcagaat gtatcagcag catcgtcaaa atataccgat taccgttgag    34500
agcgttcctg cctatagcga gtatatccgt tggcttgaga agcagaatgt aacaaaggcg    34560
```

```
agggattact ggaaaaatta cttagagggc tatgaggaat taacaggtat cattcgtctc    34620
gatacgaagc atacgagtca caacaacgag gtacaggaat gcgcctttac actggataag   34680
gacataacgg aaggacttac tcagcttgct cgtcattatt cagtgacagt aaatacgctt   34740
tttcaaacaa tttggggcat gctgttgcaa aagtataaca ataaggatga tgttgtgttt   34800
ggtgcggtcg tatctggccg cccctctgaa atccatggcg tagaaaacat ggttggcttg   34860
tttatcaaca ctgtccctat tcgtattcaa aaacaaatga atgatacctt tagccattta   34920
ttaaaaagag ttcacgaatc tacgctattg tctaaacagt atgagtttgt atccttggca   34980
gatattcaaa ccgatgcagg attttctggt caattgctag atcacatctt agtttttgaa   35040
aactatccga taagtgaagg ttcttttgag gaagaagaat ttacgatgga tagtataaaa   35100
acctatgaga aaacaagcta tgacctaaac gtgatgattc ggcctaatga ggatcagctt   35160
gatattgcct tccaattcaa cgatgacgtg tactcaagcg aaaatgtaaa aagactgttc   35220
cagcatatga agcaactggc tctagctgta atcaagaatc cggatgtgcg cttggaagaa   35280
atagcaatga tcacagaaga ggaacgctat caaatcttgc acgatttcca aggggagata   35340
gttgattttg taacagaaaa aacgcttcct gaactgtttg aagaccaggt gaaacgaact   35400
ccagaagcaa ttgcacttcg atttgaagat caacaattga cctatcagga gctaaatcag   35460
cgagtaaatc aattagcttg gacactaaga atgaagggct tgcagcaaga agaactcgtt   35520
ggaattatgg tgcagcgctc attagaaatg atcgttggtg tgctagccgt tataaaagca   35580
ggcggcgcat acgtaccaat tgatccggaa tatccgcttg accgaatcca atatatgctg   35640
gaagacagtg gaaccaattg gctgttaacc acgaaacaga gcgaaattcc ttccatctat   35700
ctagggcatg tcctgtatct tgaggaagat acggtgtatc acgagcggtc ttcagatgta   35760
gagattgtaa atcaatccag cgacttagct tatattatct acacgtccgg ttctactggt   35820
cagcctaagg gtgtcatgat tgatcatcgt gctgttcata atttgcattt gtcagcagga   35880
atctatggaa tcgcacaggg aagccaggtt ttgcagtttg cctctcttaag ctttgatgct   35940 tcggtgggtg atatcttcca cagcctatta acgggagcta ccttgcatct tgtaaaaaaa   36000
gagcaattgc tatccggaca cgcctttatg gagtggttag acgaagctgg cattacgact   36060
attccgttta ttccaccaag cgtcctaaaa gaattaccat atgcaaaact gcctaagctc   36120
aaaacaatca gtactggcgg ggaagaatta ccggctgatt tagtaaggat ttggggagca   36180
aaccgcacat tttaaaatgc atatggtccg acagaaacga cggttgatgc ttcgattggt   36240
aattgtgtag agatgacgga taagccttcg attggtacgc caaccgttaa taagcgagcg   36300
tatattttgg atcaatacgg tcatattcag ccaatcggtg ttcccgggga attatgcgta   36360
ggtggagaag gcgtagctcg tggatattta catagacctg agcttacaga tgaaaagttc   36420
gtgaacgatc cttatgtacc aaacgggaga atgtataaaa cgggagactt agctagatgg   36480
ttgccggatg gaacaatcga ttttttaggc cgtatggatg ccaagtaaa aattcgtgga   36540 tttaggattg agcttggaga aattgaagct cggctaaacc aagcccccatc tgtaaagcaa   36600 gctgtggttc tagctcgttc aggagaacaa aagcaggtat acctatgcgc atatttggtg   36660
acggacaacg atttaaaggt ttctgcccta cgtaaggaat taagtcaaac gttaccagac   36720
tatatgattc catcgttttt tataaaagtc gaaaagattc cagtcacagt aaacggcaag   36780
atagacaaga aagccttgcc agaaccagaa aaagaagtag agctgcaaac cgaatatgta   36840
gctccaacga acccaacaga ggagattctt gtacagattt ggcaaaaggt gctgggaatg   36900
gagcgagtag ggatagagga taacttcttt gagctaggtg gtcactctat caaggcaatg   36960
```

```
atgcttgctt ccaatattta taaggaatta aagattgatc tgcctttgcg tgagattttt   37020
aagcatacga cagtaaaaga aatggcgcgt tttatcgacg gtcgggatga ggaagaatac   37080
gtcggaattc aacccgcagc caaacaagaa tactaccctg tctcttctgc acaaaaaagg   37140
atgtatgtca ttcaatcatt ggaagataag gctcaaggca cgagctataa tatgccgtct   37200
ttctataaaa tgaagggctc ggtagatgca gagaaattag agaaggtatt ccaaacatta   37260
ttggatcggc acgaatcatt acgaacctcc tttcatatga tcgaggagca gctagttcaa   37320
aaggttcacg aacaggtttc atggaaaatg gacatgaaaa ccgtcagcgc caatgatgtt   37380
tcaagattaa aggattcgtt tgtccaaccg tttgacatca gtacagctcc tttgttccga   37440
gccagtcttc ttacgattca taaagatgag cacattctta tgatggatgt acaccatatt   37500
gtaggagacg gtgtttcgac cacgatcttg ttccaggagc ttatccagtt gtatcaaggg   37560
caagcgctac ctgaagtgaa ggtacactat aaagattacg ctgtgtggca attgtcccag   37620
caggatcgtt tgaaagaaag tgaaaatttc tggttgcagc aattttctgg agagttgccg   37680
gtgttggagc tacctactga ttattctcgt cccccaattc gccgattgga aggagaatat   37740
gtaagccaaa gcctacgtgg tgatctccat gaaagcgtaa aagccttcat gaaaaatcac   37800
gaagtaacgc tatatatggt actgcttgcg acatataacg ttcttctgca caaatacacg   37860
aatcagcacg acattattgt tggtacgcct gtttcggacc gaccgcatcc agatgtcatg   37920
tccactgtcg gtatgtttgt aaatacgctg gcagtccgaa atcagttgga gtctgagcaa   37980
accttcgaaa agttttttagc aaatgtgaaa aataaaatgc tagaggtcta tggtcatcag   38040
gagtatccgt ttgaagatgt aattgaaaaa gtaaaggttc aaagggatac aagcagacat   38100
ccgctatttg acacaatgtt tggtgtacaa aatctggaga tatcccacgt ggagctaccc   38160
gattggggta tagaagcatt ggatattgac tggactaact ccaagtttga tatgagctgg   38220
atggtatttg aagcagacgg tctagaaatt ggcgtggagt atagcacaag cctatttgag   38280
cgcaatacga ttcagcgaat gatcggacac tttgaacata tcatcgagca gattatggaa   38340
aatcctcaaa ttcgtttagc tgatattcag ttgacgacag aagatgagag aatccaaatc   38400
ttagaggaat tcaatcatca accaacaaaa ataacctacg atcaggcaat ccaaaacaga   38460
tttgaagaac aggctatgaa gacacctgat gcagtggcac ttgtatataa aggtcaggag   38520
ttaacctatc gtgagcttaa ccaaagatca aatcagatgg ctcgtacatt aagagagcat   38580
ggggtcgggc gtgatcaaat aattgcggtc atgattaatc gttcacatga gctgatcatt   38640
agtatcctag ccgtattaaa ggcaggagga gcatacctgc caattgatcc aacgtacccg   38700
cttgatcgga ttgaacacat gctagaggat agccagactg caatgctgtt aactcaaaaa   38760
gaaatccaaa tacctacagg atattcaggg gaagttctct tcgttgatca agctgatatt   38820
tatcatgagg atgctacgga tttatctagt atgaatcagc ctgcggattt ggcctatatt   38880
atttacacat caggctctac tggaaagtcc aagggagtaa tgatcgagca tcgttcatta   38940
cataatctga ttcatatttc tcaccccctat aaaaatggga caggaagcag agtccttcaa   39000
tttgcctcta gcagctttga tgcctcggta gcagagatct ttccagctct tttaactgga   39060
tcaactttat atatagaaga gaaagaggag ctattaacca atttagttcc ctacttactt   39120
gagaatcaaa taacaacagt agcattgccg ccatctttat taagatccgt tccttatagg   39180
gaactgccag ctttagagtg catagttagt gtcggagaag cttgcacatt tgacattgta   39240
caaacttggg ggcaaaaccg caccttttata aacggatacg gccctacaga atcaactgtt   39300
```

```
tgcagtgcct tggtgtggt tacagcagag gacaagcgta tcacgattgg taaaccgttc   39360
cctaatcaaa aggtctatat catcaatgaa atcaacagc tacaaccaat cggggttcca   39420
ggtgagcttt gcatagcagg ggctggatta agccgtgggt acttgaatcg tccagagctg   39480
acacaggaaa aatttgtaaa caacccctt gcacctggtg agcgtatgta taaaacagga   39540
gacgtagctc gctggttgcc tgatggcaat atcgaatatg ccggtcgtat ggatgatcag   39600
gttaaagtac gcggaaatcg ggtcgagctt ggggaggtta ccagccaatt acttacgcat   39660
ccttcgatta cagaagctgt tgttgtacca atagtcgata cacatggagc aacgacacta   39720
tgcgcctatt tcatcgagga taaagaagtg aaggtcaacg atttgcgcca tcatttggct   39780
aaagctctac ctgagtttat gattcctact tactttatta agtagatca tattccattg   39840 acaggaaacg gaaggtaaa taaacaagca ttacctgacc cttccgaatt catttcagca   39900
caaacaggcc atgaaatcgt tgccccttct tctcaggacg aggaaatact ggttcaggta   39960
tgggaagaag tcctgcagtt caaaccgatt ggggtagagg acaacttctt tgaacgaggc   40020
ggagactcca ttaaggcatt gcaaatcgta gctagactta gtaaatataa tcggaaattg   40080
gatagtagac atatttttaa aaatccaacg atttccatgc tggctcctta ccttgaacaa   40140
agaggtgctt tgattgaaca agattcaatt gaaggcgaag tgccgcttac accgattcaa   40200
tcctggttct tgaacaacc ctttgtgtat ccacaccact ttaatcaatc tatgcttcta   40260
ccaaatgaac aaggctggga tcgtcaacga atagaacaag catttacaac cattgttaga   40320
caccatgatg ccttaagaat gaagtaccag tttagagaga agatcattca agaaaatcag   40380
ggtatcgagg gagagttttt taccctgcat gaggtggatg taaccaagga aagagactgg   40440
caaatgcgca tcgaacaaga agcgaatcaa ctccaagcaa gctttgattt gacaacaggc   40500
cctcttgtaa agcttggctt ataccatacg gcatatggcg attatcttct gattgttgta   40560
catcatctct taattgatgg tgtctcatgg cgcatcctgc tggaggattt ccagacgctt   40620
tatgagcaaa agggtgagtt gccagcgaaa accacttcct ttaaggcgtg ggctgtacaa   40680
ctggaggggt atgctcgcag caaaaagcta caagacgagg caagctactg gaaagggttg   40740
ttgaataaat cgataagaga gctgcctgcg gataaggaat caagcgatac attcctcttt   40800
ggagatacaa aagaagtaca gcttaccttt gatataaatg aaacccaaga cctgcttacg   40860
gatgcccacc atgcttataa gacaaaagcg gatgattat tgctggcagc gttggttctt   40920
agcataaatg agtggacgaa gcaaagcgat atcatagtga atttggaagg tcatggccgt   40980
gagacgatcg gcgaaggcat tgatttgagc cgtacaattg gctggtttac tacaatttat   41040
ccagttctgt ttgaagtaga gaaccatcaa ctttccagcg tgattaaaca tgtaaaagaa   41100
acgctgcgca atgtaccgaa taatggtatt ggttttggga tcttacaaca catgtctcat   41160
tctgatgtaa gccagagcca attaagttct catcacataa gcttcaacta cctaggtcag   41220
atgggagaag attccgctag tcagtctgag acgataatg gagtccttat caatacagga   41280
gaccagataa gcccaatgaa cgcaaatccg ggctcgctta atatgacttg ccttgtaatg   41340
aataatacgt tgcttgttac ttttgattat aatccgcaac gttacgaaca ggagacaatt   41400
caacgtctgg cagatcgtta taagagcaat ttaaaagcag tcctcgatca ttgtgttcaa   41460
cgagagcaga cagagcgaac acctagtgat tttagtacga agaagctttc tttagaggac   41520
ttagacgacg tgtttgcaac acttaaaaat ctataaaggt atcctgagga ggagaagatt   41580
aacttgatta atacctcaga cgtcaaagac atttatagtt tatccccgat gcaacgagga   41640
atgttatttc atacattaaa agacaaagaa aaccttgcct attttgatca gacaactttt   41700
```

```
caaatagaag gtgacatatg tgtcgaatcc cttgagaaaa gttttaacga gctgattcgc   41760
aagtatgatg ttctgcgtac gatcttttta tatcagaaat taaaagagcc gatgcaggtt   41820
gtgttaaagg agagaacagc aaacattcat tatgaggatt tctctatgaa gagcgagtcg   41880
gataaagcaa aggctcttcg tgtagcaaaa cagagggacc gggacgaggg ctttgacctc   41940
tcccgggaca tcctcatgcg gttatcttta ttaaaagtcg cccctaacca atacgaatta   42000
gtgatcagta gccaccatat tatcattgat ggatggtgta caggaatttt gtatcaggag   42060 ctgtttatt tttatcaatg cttcgtagca aatcaaccta tccctgctga gaaatcgatt   42120
ccgtatagca gatatattcg ttggcttgaa gaacaggatg aagaggaagg aaaagcctat   42180
tggggtgaat atctacaaga tttcgagggg gcatctgtta tccctaagca aaacgctaag   42240
ggagagaagg aagtatgctc cattgataag gtaaccttcc actttgataa aaagctgacg   42300
gaggaactgg tgcaggtagc aaaaacttgc caagtaacaa taagtacctt gtttcaaaca   42360
atgtggggca tcctgctcca aaagtataat aactcgcagg aagctatatt tggatcggtt   42420
atttcaggaa gatcaccaga gattcctgat gtggaaaaaa tagttggaat ttttattaat   42480
accattcctg ttcgcattcg tacattggac aagcaaacct tcaaggaatt gctgatccag   42540
gttcaggagg catctgtcaa ctctgaaaaa tataattatc taacattggc tgatattcaa   42600
gcggttaccg gatcgaatca tgcacttatc catcatattg tggcatttga aaatttcccg   42660
attgcctcgg acagcttcgt agattcgagc gattccgatt cagaagaatt gaaagttgtg   42720
aacgtcatag acgatcatga aaagaccaac tttgatttta gtgtgcaagt tcagcttgat   42780
acagagttac tagtaaaaat ctcttataat caacatcttt atcatagaag ctttattgaa   42840
aatatctttc atcacctgca acagattgcc gggtctatca ctcataaccc agatattcaa   42900
ataaatgaga tagctattgt ttctaaggaa gagaagaagc aactattacg ctattccact   42960
ccagccaagt cagattttcc aatggataaa accattcatc agctatttga ggagcaggta   43020
tcacggacac cagagcagat cgcggtcgtt tttaaggggg agtccttcac ctatcgcgag   43080
ttaaatgaaa aggcaaatca attggcatgg gtgctaagaa aacgggaggt aagacctaac   43140
gagatcgttg cgatcatggc agagcactct ctagagatgc tggttggggt gattgggact   43200
ttaaaggcag gtgcggccta tcttcctatt gacccatcct acccagaaaa aagaatcgct   43260
catatgctac aagatagcaa agcggagcaa ctacttatcc agcctcattt gaatatgcca   43320
caggacttta agggaagtgt cttatggtta acagaagaga gctgggcgaa ggagagtacg   43380
accgatctgc cgcttgcaac gagtgcaaat gatctagcat acatgattta tacctcaggc   43440
tcaacaggac tgccgaaggg agttatggtt gagcatcaag ccttggttaa tttagttatg   43500
tggcataacg aggcatttgg cgtaaccatg actgatcaat gcacgaaatt ggcgggattt   43560
ggattcgatg cgtcggtgtg ggagaccttc cctccgctta cagggagc gacgcttcat   43620 gtgttagagg aatcgagacg tggagatatt tatgctctgc atgaatactt tgaaaagaat   43680
gcgatcacca ttagcttctt gcctactcaa ttagccgaac aatttatgga gcttacaagc   43740
agtacattac gtgtgttact cattggcggt gaccgagccc aaaaggttaa agagacatcg   43800
tatcaaatca taaacaacta cggtccaacc gaaaatacag tagtcacgac gagcggtcaa   43860
ctgcatcctg agcaggatgt cttccctatt ggaaagccga tcaccaatca cagcgtttat   43920
attttagatc agaacagaca tctacagccg atcggaatac ctggcgagct gtgcgtcagt   43980
ggtgcagggc ttgctagagg ctaccttaat cagcctgaac tcaccgtaga acgctttgtt   44040
```

-continued

```
gataatccct ttgtacctgg agagagaatg tatcgcacag gggacttagt tcgttggaga   44100
atcgatggta gcatcgaata tctgggaagg attgacgagc aagtcaagat tcgaggatac   44160
agaattgagt taggtgagat cgaaacaaag cttcttgagc atccttccat tagtgaggcg   44220
ctcgtcgtgg ctcgaaatga cgagcaaggt tatacctatc tatgcgctta tgtggtagca   44280
actggggcct ggagcgtatc ttcattacgt gagcatttaa tcgaaacatt gcccgaatat   44340
atgattccag cttacatgat ggaagtggaa aaaatgccgc ttactgcaaa cggaaagata   44400
gataagcgag cgttaccagt gcctgatagg caaagaatga acgaatatgt ggcacctgca   44460
acagagacag aggaaaagct agttctactg ttccaagaga ttttaggact tgagcgtatt   44520
ggtactaaag atcacttctt tgaattaggg ggacattcgc tgaaggcgat gatgcttgtg   44580
tctcgtatgc acaaggagct aggtgtggat gtgcagttaa atgagatgtt tgctcgtcca   44640
acggttaaag atctatctgc ttacatagat cagatgaacg gctctgctta cacagcaatt   44700
caaccagtgg aggaacagcc ttattatcct gtttctttg cccaaagaag aatgtatgtt   44760
gtacagcaaa tgagagatag tgaaacgacg agctataaca tgccgtttac gtttgagcta   44820
aaaggaaagc tacatctgga caagctgcga gaagcgttac agattctggt tctacgacat   44880
gaaagtctgc gtacatcctt tcatatgatt gatgaaaatc ttgttcaaaa agtgaataaa   44940
gatatttcat gggatttaga agtaataaa gctcaggagt cagagataga agtaaaactg   45000
gaggaattta tcagaccgtt ccatttaagt gaggctccgc ttttcagagc tcgtttaatt   45060
tgcttgaatc cacagcatca tcttttgagc ttagacatgc atcatattat ttcagatgga   45120
gtatctatga acctgttcct acaggaattc atgacactct atcagggaga agcattgcca   45180
gcgctctcta ttcaatacaa ggattacgcc gtatggcaac aatcagacaa gcagcgagct   45240
agattaaaag agcaggaaaa atattggtta catcattttt ctggagagct gcctacctta   45300
gaattgccaa cagattttcc acgccctgca atacagcaat ttgatggaga tgaatgggcg   45360
tttgaaatga atgctgatct tttagcgaag gtcaaacaga tctgctctag ccaaggcacg   45420
acgttatata tgacgcttct cgctgcttat caggtgttct tagccagata taccgggcag   45480
gaggatatca ttgtaggttc tccaattgct ggacgttctc atgctgattt ggaaaacatg   45540
ataggtatgt ttgtcaatac attagctttg cgcggtaagc caaaggcaga tcaatccttc   45600
ctctcctatt taaaacaggt aaaagagacc gtattccaag catacgcgaa cgcagaatat   45660
ccatttgaag agttgattga gaaactcgat ttagaacgag atatgagccg tcatccgcta   45720
tttgatacct tgttctcttt gcaaaatatg gaaatatctg agttccaaat gaataatcta   45780 gagattttc cttatgaaac gggacaaaag aatgcaaaat tcgctcttag ctggttaata   45840
gcagaaggag agtcccttta tgtaacaatc gaatacagca ccaaatgctt taagcgagaa   45900
accattaaac gcatggcaag tcattttgaa caactgctag cccaaattgt tgagcaaccg   45960
gaagcgcgca ttggccaact ggagttagta gcagatgccg aaagaaaaat gttactggaa   46020
gactttaatc tgacaaaagt cgactatcca cgggaaaaaa caattcaaga attatttgaa   46080
gagcaggtgg acaaaaaccc tgatcaaatc gcgcttatat gtggagagca acagtttacc   46140
tacgaacaat taaatgtgaa atttaaccaa ttagctcacg tattaagaag agaaggcgtt   46200
caacccaatc aggtaatagg gctaattacg gatcgatcgc tgtcgatgat tgtaggtatt   46260
tttggaatta taaaagcagg tggggggctat ctgccaatcg atccgaccta tcctaccgaa   46320
agaattgaat acatgcttga agatagtcaa actcacctat tgttggtaca acacagagac   46380
atggttccag caggttatca gggagaggtt ttgataatag aggatgagat aagtcgagat   46440
```

```
gaacaagtag ctaacataga attgatcaat cagccgcaag acttggctta tgtcatgtac    46500
acatctggct ctacaggtaa accaaagggg aacctgacta ctcatcgaaa cattatcaaa    46560
acggtatgca ataacggata tattgagata acgactgagg atcgtctttt gcagttatct    46620
aattatgctt ttgacggctc tacctttgat atattcagct cgttattaca cggagcaacg    46680
ctggtactgg taccaaaaga agtgatcttg aatccaacag acttgattac attgatacgc    46740
gaacagcaga tcactgtatc gtttatgact acctcattgt ttaatgcatt agtggaactg    46800
gatgtaagca gttccaaaa catgcgcaag atcgcatttg gaggagaaaa ggcttccttt    46860
aagcatgtgg aaaaggcatt ggatttcctc ggaaatggac gattggtgaa tggatatggt    46920
cccacagaaa caaccgtttt tgctacaacc tacactgtgg atgagcgcat aaaggaatgg    46980
gggattatac cgattggtcg accgctacat aatactacgg tccacatttt aagcgctgat    47040
gacaagctac agccaattgg agtcattgga gaactgtgcg taagcggtga aggattggca    47100
cgcggttacc ttaatctacc agagttgacg atggagcgat tgttgaaaa tccatttaga    47160 cctggtgaaa gaatgtaccg cacaggggac ttggctcgtt ggttaccgga tggggttctt    47220
gaatatgtag gacgcaagga tgaacaagtg aaaattgcg gacatcgcat tgagcttagt    47280
gaaattgaaa caaggatatt ggagcatcct gcgatcagtg aaacggttct gctagccaag    47340
cgaaatgagc aaggcagctc atacctgtgc gcttatattg ttgcccatgg ccaatggaat    47400
atccaagaat tgcgcaaaca tgtaagagat gttttgccag aacacatggt gccttcttat    47460
tttattggct tagacaaact tccacttacc tccaatggta aagtcgacaa acgagcattg    47520
ccagaaccag agggcagcct gcaactgact agagaaattg ttgctccacg caatgaatct    47580
gaaaaacagt tagttgaaat tgttgctgag gttctgggac tagaagctag tgaaataagt    47640
attaccgata atctttttga gctaggtgga cattccctaa cgattctgag aatccttgct    47700
aaggttcata catgtaactg gaagcttgaa atgaaagact tctataattg caagaacctt    47760
gaggaaatag caagcaaggc aactgatatg caggaaaatc aaaatctgtc tggcagtggc    47820 tcagtctttta aaagggtgg gaagaaatca atcccgtag tacccgtcca cgatagacaa    47880
aaagaaatgg agcatgtttt attgctcggc tccactggtt tcttaggtat tcatttgcta    47940
catgagctgc tacagaaaac agaagcgaca attctttgcg tcattcgtgc agaaaatgat    48000
gaggctgcta tgcaacgact acgcaaaaaa attgattttt actttacctc acagtacagt    48060
agctctcaaa ttgatgagtg gtttacccgc atccaaatca ttcacggtga tattacgcaa    48120
gccaactttg gattagaggc aaaacattac gagtcgctag gagctatcgt tgacactgtc    48180
attcatacgg ctgcattggt gaagcactac gggcactatg aagagttga aagagcaaat    48240 gtacatggaa ctcagcaagt agttacctt tgcttgaaca ataaattacc aatgcactat    48300
gtttcaaccc tgagcgtttc gggaaccacc gttgaagaag caacagagct tgtagaattt    48360
accgagaagg acttttatgt tggtcaaaac tatgagtcaa atgtatatct gagaagtaaa    48420
tttgaagccg aagccgtact tgttggcgga atggaaaacg gactcgatgc acgtatctac    48480
cgggttggca atttaacagg acgctttcag gatggatggt tccaggaaaa tatcaatgaa    48540
aatatgtttt atctcctatc gaaagccttc cttgagcttg gaggttttga tcaggaaatt    48600
atgcagggta tggttgattt aaccccctatt gatatatgtg cacaagctat tatacacatc    48660
atcaacagca aaggaattga ggaaagagtc ttccatttac agaatccgca cttggtaaca    48720
tacgatgata tgtatcgtgt atttgaaggg cttggctttt ctagacgggt acaaagtcga    48780
```

```
gaagatgtta cacgtgaact agatgtaatg atgtctcagg gtaatgaaaa gctattttg    48840
gctgggattc tgaccacgat gttggatgat gtagagcgtg ctgaacaatt taatgttgca   48900
gtcgattcaa gtaggacaat gcagctatta gaggatacct cgtttaccta tcctgttcct   48960
gatgatgagt atttgcgcaa gctggctatg catatgatca aagttgggtt tgttactcct   49020
aatcatactg ttgctgaaaa gataggaact agtcgttagc gctatgctag cgactggttc   49080
ccaacctaaa tgaatagcta aggaaggag agggaaccca tggcagtcat tgaactaaaa    49140
aaccttacga aaaagtataa tgaggtctat gctgttgatc atctaaatat agaagtacct   49200
caaggacata tttatgcgtt tttaggtagc aatgggcgg gaaagacaac cacaattaaa    49260
atgatgacgg gccaattgaa cccttcagag ggagaggttc tatttctagg gcgcaatatt   49320
tggcaggatc gtgaggcaag aagaattgcg ggctatgctc cagacgttcc acttcttcat   49380
gaaggattga cagtcagaga aatggtacgc tttgtggggg ctctttatgg tagtgacgaa   49440
gatctgaata aacgtgttga cacgttgtta gaacattttg agctggcaga taaagcagac   49500
cagcttatta aagaatactc attaggaatg aaacgaaagg tttcgattgc ttgcgcattg   49560
attcatcgcc ccaaaatctt gctattagac gaagttacga atgggttgga cccaaaggcg   49620
acccgtgaag tgaaaaatta tattcgacat tttgccaaag aagagggtgg tactgttttt   49680
attacgaccc atattttgga cattgttgaa gaattagccg ataccatttc catcctgcat   49740
aaaggaaaaa tcaaagtgac gggaagcatg gaagaattgc gtcatgtggc aggcaatgaa   49800
gaaggtcgat tggaagatat cttttttatcc gctatcgagt agtaggaggt gacagaattg   49860
tatgtgggca caaacgaaat ggattagttt cttttacaca agacccttct ttaatcgctt   49920
tttatccat agtccttcta aatggatcat ttatgtgggc ttgggaacca ttgctattgc    49980
catgtacttt tcggagaatt ttgggcagct tctcttacat gccagtctca gtgctagatt   50040
gatgcttctc ataggggaat gtattttttgt cggtttgctt cgtggcatga atacgttgac   50100
acaacaaatg tacgctgatc gattactgac attgttttat gtatcgggag tttctccgtt   50160
tcggatgatc cttgggcaat ctacttcaag tctacctctg tacacgtggt catccattat   50220
gattgctatt ccattaacga ttggctattc cgccatggaa agagttctgt atgttttgtt   50280
attcctagtc gtttctctat tgatgatttg gttaacagac atcttaagcc gatttttaat   50340
ggttctgacc atgcggtttt tccctattat tgtcaaaaca ttcgtaggta tctcctcgct   50400
tgcctatgtt gctttaattg gcctattggt ttgggcattg attgaggttg aaacaatttc   50460
tccagaagct tggcagagct tagagcgttt tatggtatat gttttgtgca ttttcgcggt   50520
cggtcttgga gcgttgtttc tattctctga acaaattgga gggttttatt acgaaagctg   50580
gctgaaccat gcggagtcgc aagataggac cagaccagaa acacaggaaa atctatcgaa   50640
tttggtcaaa aacgctcatg atgccatcgt tttt                              50674
```

<210> SEQ ID NO 22
<211> LENGTH: 641
<212> TYPE: PRT
<213> ORGANISM: Brevibacillus texasporus

<400> SEQUENCE: 22

Met Asp Leu Ser Thr Leu Asn Phe Leu Gly Glu Thr Glu Lys His Lys
1               5                   10                  15

Leu Leu Asn Gln Phe Asn Asp Thr Asp Ala Asn Phe Pro Gln Glu Met
            20                  25                  30

Thr Ile His Gly Leu Phe Glu Lys Gln Val Gln Glu Arg Pro Asn Gln

-continued

```
                35                  40                  45
Thr Ala Val Ile Phe Asn Glu Gln Ser Met Thr Tyr Lys Glu Met Asn
 50                  55                  60

Glu Arg Ala Asn Gln Val Ala His Ser Leu Arg Lys His Gly Ala Ala
 65                  70                  75                  80

Pro Asp Glu Ile Val Gly Ile Leu Ala Asp Arg Asn Met Asp Met Leu
                 85                  90                  95

Ile Ser Ile Leu Gly Val Leu Lys Ala Gly Ala Ala Tyr Met Pro Ile
                100                 105                 110

Asp Pro Thr Tyr Pro Thr Glu Arg Ile Leu Tyr Met Ile His Asp Ser
                115                 120                 125

Gln Thr Lys Ile Val Leu Ala Glu His Arg Glu Met Val Pro Glu Gly
130                 135                 140

Cys Asn Ala Glu Leu Ile Leu Leu His Asp Ser Ser Leu Leu Asn Glu
145                 150                 155                 160

Glu Thr Ser Asp Leu Glu His Val Asn Lys Pro Glu Asp Leu Ala Tyr
                165                 170                 175

Ile Ile Tyr Thr Ser Gly Ser Thr Gly Lys Pro Lys Gly Val Met Ile
                180                 185                 190

Glu His Arg Asn Val Ile Arg Leu Leu Phe Asn Asp Arg Asn Leu Phe
                195                 200                 205

Asp Phe Thr Ser Asp Asp Val Trp Thr Val Phe His Ser Phe Cys Phe
210                 215                 220

Asp Phe Ser Val Trp Glu Met Tyr Gly Ala Leu Leu Tyr Gly Gly Lys
225                 230                 235                 240

Ile Val Leu Val Ser Phe Glu Ile Ala Arg Asp Pro Gln Ala Phe Arg
                245                 250                 255

Asp Leu Leu Gln Glu Gln Lys Val Thr Ile Leu Asn Gln Thr Pro Thr
                260                 265                 270

Ala Phe Tyr Gln Leu Ser Ser Gln Glu Met Gln His Ser Asp Ser Asn
                275                 280                 285

Leu Ser Ile Arg Lys Ile Ile Phe Gly Gly Glu Ala Leu Thr Pro Ser
290                 295                 300

Gln Leu Lys Ala Trp Lys Gln Lys Tyr Pro Asn Thr Ala Leu Ile Asn
305                 310                 315                 320

Met Tyr Gly Ile Thr Glu Thr Thr Val His Val Thr Tyr Lys Glu Phe
                325                 330                 335

Gln Leu His Asp Met Asp Ser Thr Val Ser Asn Ile Gly Lys Pro Ile
                340                 345                 350

Pro Thr Leu Arg Thr Tyr Val Leu Asp Ser Lys Arg Asn Leu Ala Pro
                355                 360                 365

Ile Gly Val Lys Gly Glu Leu Tyr Val Ser Gly Lys Gly Val Ala Arg
                370                 375                 380

Gly Tyr Leu Asn Lys Pro Glu Leu Thr Glu Glu Arg Phe Met Asp Asn
385                 390                 395                 400

Pro Phe Val Ala Gly Glu Arg Met Tyr Arg Thr Gly Asp Leu Ala Arg
                405                 410                 415

Trp Leu Pro Glu Gly Glu Leu Glu Tyr Leu Gly Arg Ile Asp His Gln
                420                 425                 430

Val Lys Ile Arg Gly Tyr Arg Ile Glu Leu Gly Glu Ile Glu Ala Glu
                435                 440                 445

Leu Leu Lys Gln Lys Gly Ile Lys Glu Ala Val Val Leu Val Thr Asn
450                 455                 460
```

```
Asp Lys Asp Ala Gln Pro Gln Leu His Ala Tyr Leu Thr Ser Lys Glu
465                 470                 475                 480

Asp Leu Ala Ala Ala Asp Leu Arg Asn Gln Leu Thr Thr Thr Leu Pro
                485                 490                 495

Ser Tyr Met Ile Pro Ala His Phe Ile Phe Val Ser Gln Met Pro Val
            500                 505                 510

Thr Pro Asn Gly Lys Ile Asp Lys Glu Ser Leu Arg Lys Ile Glu Pro
        515                 520                 525

Ser Leu Gln Glu Ser Pro Thr Glu Ala Tyr Val Ala Pro Gln Thr Pro
    530                 535                 540

Thr Glu Lys Gln Leu Val His Ile Trp Glu Glu Asn Ile Gly Met Gln
545                 550                 555                 560

Pro Ile Ser Ile Asp Asp Asn Tyr Phe Ala Leu Gly Gly Asp Ser Ile
                565                 570                 575

Lys Ala Ile Lys Leu Leu His Ala Ile Asn Lys Glu Phe Gln Ile Ser
                580                 585                 590

Phe Gln Ile Gly Asp Leu Tyr Lys His Gly Thr Ile Arg Glu Met Gly
            595                 600                 605

Gln Gln Ile Gly Glu Lys Gly Lys Gln Ser Ser Asn Gln Lys Leu Leu
        610                 615                 620

Lys Leu Gln Glu Leu Asp Arg Leu Lys Lys Ile Leu Gly Ser Glu
625                 630                 635                 640

Lys

<210> SEQ ID NO 23
<211> LENGTH: 2530
<212> TYPE: PRT
<213> ORGANISM: Brevibacillus texasporus

<400> SEQUENCE: 23

Met Ser Asp Lys Leu Ser Asn Ala Lys Asp Leu Phe Pro Met Ser Asp
1               5                   10                  15

Ile Gln Leu Gly Met Val Tyr His Ser Leu Lys His Val His Glu Ala
            20                  25                  30

Val Tyr His Asp Gln Phe Val Tyr Gln Val Asp Asp Ser Phe Asp
            35                  40                  45

Val His Val Leu Glu Gln Ala Met Arg Met Val Asp Lys His Asp
    50                  55                  60

Ile Leu Lys Thr Ser Phe His Ile Glu Glu Phe Ser Thr Pro Val Gln
65              70                  75                  80

Val Val His Gln Glu Val Ser Val Arg Ile Asp Glu Thr Asp Ile Thr
                85                  90                  95

His Leu Gly Glu Lys Gln Lys Glu Tyr Ile His Gln Tyr Leu Ala Gln
            100                 105                 110

Asp Arg Gln Ser Pro Phe Asp Val Thr Thr Ala Pro Leu Trp Arg Met
        115                 120                 125

Ser Val Phe Lys Leu Asn Ala Ser Gln Val Ala Leu Val Trp Ile Phe
    130                 135                 140

His His Ala Ile Leu Asp Gly Trp Ser Val Ala Ser Phe Ile Thr Glu
145                 150                 155                 160

Leu Ile Asp Val Tyr Phe Lys Leu Lys His Lys Thr Cys Thr Leu Glu
                165                 170                 175

His Leu Asn Thr Thr Tyr Lys Asp Tyr Val Ile Asp Gln Met Leu Leu
            180                 185                 190
```

-continued

```
Ser Glu Gln Asn Glu Leu Arg Glu Tyr Trp Lys Glu Leu Lys Asp
        195                 200                 205

Tyr Lys Arg Leu Gln Leu Pro Val Lys Val Asp Glu Asn Gly Gly Val
    210                 215                 220

His Val Thr Val Val Glu Lys Leu Asp Pro Asp Ile Ile Asn Lys Cys
225                 230                 235                 240

Arg Glu Ile Ala Gln Ala His His Ile Pro Leu Lys Thr Val Cys Leu
            245                 250                 255

Thr Ala Phe Leu Ser Met Met His Met Ile Ser Tyr Glu Arg Asp Leu
        260                 265                 270

Thr Val Gly Leu Ile Glu Asn Asn Arg Pro Ile Ile Glu Asp Ala Glu
    275                 280                 285

Lys Val Leu Gly Cys Phe Leu Asn Ser Val Pro Phe Arg Ala Ile Ile
290                 295                 300

Lys Lys Asp Met Ser Tyr Arg Glu Leu Leu Glu Gln Thr Gln Gln Lys
305                 310                 315                 320

Leu Val Glu Ile Lys Thr Tyr Gly Arg Leu Ser Phe Ala Lys Ile Ile
            325                 330                 335

Glu Val Ile Gly Asp Thr Gly Ser Glu Arg Asn Pro Val Phe Asp Cys
        340                 345                 350

Leu Phe Asn Phe Val Asp Phe His Val Phe Lys Gly Ile Lys Asp His
    355                 360                 365

Lys Val Lys Phe Trp Leu Asp Gly Tyr Glu Lys Thr Asn Thr Met Phe
370                 375                 380

Asp Phe Ser Val Ser Thr Thr Met Asp Asp Tyr Phe Val Arg Val Val
385                 390                 395                 400

Ser Ala Leu Pro Glu Glu Asp Thr Ile Lys Leu Ile Asn Tyr Tyr Gln
            405                 410                 415

Arg Ile Leu Glu Lys Ile Ala Leu His Ile Asp Glu Lys Ile Asp Lys
        420                 425                 430

Gln Ala Asn Leu Asp Glu Lys Glu Ser His Leu Leu Glu Glu Trp
    435                 440                 445

Asn Gln Thr Ser Val Asp Tyr Pro Asp Lys Gln Thr Leu His Lys Arg
450                 455                 460

Phe Glu Glu Gln Val Ala Lys Asn Glu Asp Gln Val Ala Leu Glu Tyr
465                 470                 475                 480

Glu Asp Lys Gln Leu Thr Tyr Arg Glu Leu Asn Ala Lys Ala Asn Gln
            485                 490                 495

Leu Ala Arg Val Leu Gln Lys His Asn Thr Leu Pro Thr Gln Val Val
        500                 505                 510

Gly Leu Met Ala Glu Arg Ser Leu Glu Met Ile Ile Gly Ile Leu Gly
    515                 520                 525

Ile Leu Lys Ala Gly Gly Ala Tyr Met Pro Ile Asp Pro Thr Tyr Pro
530                 535                 540

Ala Glu Arg Ile Gln Tyr Met Leu Glu Asp Ser Arg Ser Tyr Leu Leu
545                 550                 555                 560

Leu Val Gln Lys Ala Glu Met Ile Pro Ala Asn Tyr Gln Gly Glu Val
            565                 570                 575

Leu Ile Leu Thr Glu Glu Leu Trp Ala Asp Glu Asn Thr Glu Asn Leu
        580                 585                 590

Glu Leu Val Asn Gln Pro Gln Asp Val Ala Asn Ile Met Tyr Thr Ser
    595                 600                 605
```

```
Gly Thr Thr Gly Lys Pro Lys Gly Ile Leu Ile Thr His Arg Asn Ile
    610                 615                 620

Met Thr Thr Ile Ile Asn Asn Gly Tyr Leu Asp Ile Phe Ser Thr Asp
625                 630                 635                 640

Arg Ile Leu Gln Ile Ser Asn Tyr Ala Phe Asp Gly Ser Thr Phe Asp
                645                 650                 655

Ile Tyr Ser Ala Leu Leu Asn Gly Ala Thr Leu Val Leu Val Pro Lys
            660                 665                 670

Gln Thr Leu Met Asn Thr Thr Asp Leu Leu Ala Ile Ile Lys Asp Ser
        675                 680                 685

Asn Ile Thr Val Ala Leu Met Thr Thr Ser Leu Phe Asn Thr Leu Val
    690                 695                 700

Asp Leu Asp Val Thr Ser Phe Gln His Thr Arg Lys Val Leu Phe Gly
705                 710                 715                 720

Gly Glu Lys Ala Ser Cys Lys His Val Glu Lys Ala Leu Asp Tyr Leu
                725                 730                 735

Gly Glu Gly Arg Leu Val Asn Gly Tyr Gly Pro Thr Glu Thr Thr Val
            740                 745                 750

Phe Ala Thr Thr Tyr Thr Val Asp Asn Thr Ile Lys Lys Leu Gly Ser
        755                 760                 765

Ile Pro Ile Gly Arg Pro Leu Ser Asn Thr Ser Val Tyr Ile Phe Gly
    770                 775                 780

Leu Asp Asp Gln Leu Gln Pro Leu Gly Val Pro Gly Glu Leu Cys Val
785                 790                 795                 800

Ala Gly Glu Cys Ile Ser Pro Gly Tyr Leu Asn Arg Pro Asp Leu Thr
                805                 810                 815

Ala Asp Lys Phe Ile Asp Asn Pro Leu Lys Pro Gly Glu Arg Met Tyr
            820                 825                 830

Arg Thr Gly Asp Leu Val Arg Trp Leu Pro Glu Gly Val Met Glu Tyr
        835                 840                 845

Met Gly Arg Ile Asp Glu Gln Val Lys Ile Arg Gly His Arg Ile Glu
850                 855                 860

Leu Gly Glu Ile Glu Ala Lys Leu Leu Glu His Pro Ser Ile Arg Glu
865                 870                 875                 880

Thr Val Leu Val Ala Lys Gln Asp Ala Asn Gly His Ser Phe Leu Gly
                885                 890                 895

Ala Tyr Leu Val Thr Asp Asn Phe Cys Pro Val Thr Glu Leu Arg Asn
            900                 905                 910

Tyr Leu Met Glu Thr Leu Pro Glu Tyr Met Val Pro Ser Tyr Phe Ile
        915                 920                 925

Glu Leu Asp Ser Leu Pro Leu Thr Ser Asn Gly Lys Val Asp Lys Arg
    930                 935                 940

Ala Leu Pro Glu Pro Glu Ser Gln Ala Leu His Ala Tyr Thr Met Pro
945                 950                 955                 960

Glu Asn Glu Thr Glu Glu Lys Leu Val Gln Leu Phe Gln Glu Val Met
                965                 970                 975

Asp Val Glu Arg Val Gly Thr Gln Asp Ser Phe Tyr Glu Leu Gly Gly
            980                 985                 990

His Ser Leu Lys Ala Met Leu Leu  Val Ser Arg Ile His  Lys Asp Phe
        995                 1000                 1005

Gly Ile  Lys Ile Pro Leu Lys  Glu Val Phe Ser Arg  Pro Thr Val
    1010                 1015                 1020

Lys Glu  Leu Ala Ala Tyr Leu  Thr Gly Ser Glu Glu  Ala Asn Tyr
```

-continued

```
            1025                1030                1035
Ile Glu Ile Glu Ala Ala Glu Lys Pro Tyr Tyr Pro Val Thr
    1040                1045                1050

Ala Ala Gln Lys Arg Met Tyr Ile Ala Gln Gln Trp Glu Asp Gly
    1055                1060                1065

Glu Ala Thr Ser Ser Tyr His Met Pro Phe Met Met Glu Ile Thr
    1070                1075                1080

Gly Pro Leu Gln Val Glu Lys Leu Gln Gln Thr Val Lys Ser Leu
    1085                1090                1095

Val Ala Arg His Glu Ser Leu Arg Thr Ser Phe His Met Ile Asn
    1100                1105                1110

Glu Val Leu Met Gln Lys Ile His Ala Asp Val Leu Trp Asp Leu
    1115                1120                1125

Asp Ile Asp Leu Glu Ser Val Val Ala Ser Glu Gln Glu Ile Asp
    1130                1135                1140

Glu Lys Met Phe Gln Phe Leu Arg Lys Phe Asp Leu Ser Gln Ala
    1145                1150                1155

Pro Leu Phe Arg Ala Lys Leu Ile Arg Val Asn Ala Ser Arg His
    1160                1165                1170

Val Leu Leu Leu Asp Met His His Ile Ile Ser Asp Gly Phe Ser
    1175                1180                1185

Tyr Gln Ile Phe Phe Asp Glu Leu Thr Lys Leu Tyr Gln Gly Asp
    1190                1195                1200

Glu Leu Pro Ser Leu Lys Ile Gln Tyr Lys Asp Tyr Ala Val Trp
    1205                1210                1215

Gln His Ser Glu Glu Gln Gln Lys Arg Leu Gln Gln Gln Glu Asp
    1220                1225                1230

Tyr Trp Leu Gly Gln Phe Gln Gly Glu Ile Pro Val Leu Glu Leu
    1235                1240                1245

Pro Thr Asp Tyr Gln Arg Pro Val Asp Lys Gln Phe Ala Gly Ala
    1250                1255                1260

Leu Phe Thr His Gly Leu Ser Ala Gly Leu Thr Glu Lys Leu Arg
    1265                1270                1275

Lys Leu Ala Ile Lys Glu Lys Thr Thr Leu Tyr Thr Val Leu Leu
    1280                1285                1290

Thr Val Tyr Asn Ile Leu Leu Ser Lys Tyr Thr Ser Gln Glu Asp
    1295                1300                1305

Leu Ile Val Gly Thr Pro Ile Ala Gly Arg Pro His Ala Asp Leu
    1310                1315                1320

Asp Arg Val Phe Gly Met Phe Val Asn Thr Leu Ala Ile Arg Thr
    1325                1330                1335

Ala Pro Lys Val Glu His Ser Phe Leu Thr Tyr Leu Ser Glu Val
    1340                1345                1350

Lys Glu Thr Val Leu Gly Ala Tyr Gln Asn Pro Asp Tyr Pro Phe
    1355                1360                1365

Glu Glu Leu Val Glu Lys Thr Leu Val Gln Arg Asp Val Ser Arg
    1370                1375                1380

Asn Pro Leu Phe Asp Val Met Phe Ser Val Glu Lys Leu Pro Ser
    1385                1390                1395

Ala Val Gln Phe Asp Asp Leu Arg Phe Cys Pro Arg Leu Phe Asp
    1400                1405                1410

Trp Lys Lys Ala Lys Phe Asp Leu Asp Trp Thr Val Val Glu Gly
    1415                1420                1425
```

-continued

```
Glu Ser Leu Glu Val Leu Val Glu Tyr Ser Thr Ser Leu Phe Asp
    1430                1435                1440

Arg Ala Thr Ile Glu Arg Met Ala Lys His Phe Glu His Ile Leu
    1445                1450                1455

Glu Gln Ile Leu Asp Gln Pro Asp Leu Ser Ile Ser Glu Ile Glu
    1460                1465                1470

Leu Leu Thr Glu Ala Glu Lys Gln Gln Ile Leu Ile Glu Phe Asn
    1475                1480                1485

Gln Ser Asp Lys Ser Phe Asp Ser Glu Lys Thr Ile Gln Glu Gln
    1490                1495                1500

Phe Glu Glu Trp Ala Glu Lys Ala Pro His Ser Ile Ala Leu Val
    1505                1510                1515

Phe Lys Asp Lys Gln Met Thr Tyr Gln Glu Leu Asn Gln Arg Ala
    1520                1525                1530

Asn Gln Val Ala His Leu Leu Arg Gly Asn Gly Ile Ser Ala Asn
    1535                1540                1545

Asp Phe Ile Gly Leu Met Val Asp Arg Ser Phe Glu Met Ile Ile
    1550                1555                1560

Ser Met Leu Gly Ile Leu Lys Ala Gly Gly Ala Tyr Leu Pro Ile
    1565                1570                1575

Asp Pro Asp Tyr Pro Glu Asp Arg Ile Asp Tyr Met Leu Ser Asp
    1580                1585                1590

Ser Lys Ala Lys Ile Leu Leu Lys Gln Ser Asp Gln Thr Ala Pro
    1595                1600                1605

Ala Ser Phe Glu Gly Lys Val Ile Ala Ile Asp Thr Pro Glu Leu
    1610                1615                1620

Leu Glu Met Asp Ile Glu Asn Ile Pro Lys Val Asn Asn Ser Ser
    1625                1630                1635

Asp Leu Ala Tyr Ile Ile Tyr Thr Ser Gly Ser Thr Gly Lys Pro
    1640                1645                1650

Lys Gly Val Leu Ile Asn His Arg Cys Val Ile Asn Met Gln Leu
    1655                1660                1665

Thr Ala Glu Thr Phe Gly Ile Tyr Pro Ser Ser Arg Ile Leu Gln
    1670                1675                1680

Phe Ala Ser Phe Ser Phe Asp Ser Ser Val Gly Glu Ile Phe Tyr
    1685                1690                1695

Thr Leu Leu Asn Gly Ala Cys Leu Tyr Leu Val Glu Lys Asp Leu
    1700                1705                1710

Leu Leu Ser Gly Asn Glu Phe Val Ala Trp Leu Lys Lys Asn Arg
    1715                1720                1725

Ile Ser Ser Ile Pro Phe Ile Ser Pro Ser Ala Leu Arg Met Leu
    1730                1735                1740

Pro Tyr Glu Asp Leu Pro Asp Leu Ala Tyr Ile Ser Thr Gly Gly
    1745                1750                1755

Glu Thr Leu Pro Ala Asp Leu Val Lys Ala Trp Gly Glu Asn Arg
    1760                1765                1770

Val Phe Leu Asn Ala Tyr Gly Pro Thr Glu Thr Thr Val Asp Ala
    1775                1780                1785

Thr Val Gly Val Cys Thr Pro Glu Gly Lys Pro His Ile Gly Arg
    1790                1795                1800

Pro Val Thr Asn Lys Lys Val Tyr Val Val Asn Ser Asn Asn Gln
    1805                1810                1815
```

-continued

```
Leu Gln Pro Ile Gly Val Pro Gly Glu Leu Cys Ile Gly Gly Glu
    1820            1825                1830

Gly Val Ala Leu Gly Tyr Leu Asn Arg Pro Asp Leu Thr Gln Glu
    1835            1840                1845

Lys Phe Val Ser Asn Pro Phe Ala Pro Gly Glu Arg Met Tyr Arg
    1850            1855                1860

Ser Gly Asp Leu Val Arg Trp Leu Pro Asp Gly Thr Ile Glu Tyr
    1865            1870                1875

Phe Gly Arg Leu Asp Asp Gln Val Lys Ile Arg Gly His Arg Ile
    1880            1885                1890

Glu Leu Gly Glu Ile Glu Thr Arg Leu Leu Glu His Pro Ser Ile
    1895            1900                1905

Lys Glu Ala Ile Val Ile Pro Arg Ser Asp Glu Ser Glu Ala Thr
    1910            1915                1920

Tyr Leu Cys Ser Tyr Leu Ile Ala Glu Gly Ser Trp Asn Ala Ala
    1925            1930                1935

Asp Leu Arg Lys Tyr Leu Lys Ala Ser Leu Pro Glu Tyr Met Ile
    1940            1945                1950

Pro Ser Tyr Phe Val Glu Leu His Glu Leu Pro Leu Thr Pro Asn
    1955            1960                1965

Gly Lys Val Asn Lys Lys Ala Leu Pro Lys Pro Glu Lys Gln Met
    1970            1975                1980

Gln Arg Gly Lys Asp Tyr Val Ala Pro Thr Asn Pro Ile Gln Ser
    1985            1990                1995

Ile Leu Ser Gln Ile Trp Thr Asp Val Leu Gly Val Glu Asn Ile
    2000            2005                2010

Gly Ile His Asp Asn Phe Phe Glu Leu Gly Gly Asp Ser Ile Lys
    2015            2020                2025

Ala Ile Gln Ile Ser Ala Arg Leu Asn Lys His Asn Leu Lys Val
    2030            2035                2040

Lys Met Arg Glu Leu Phe Lys Asn Pro Thr Ile Ala Glu Leu Ser
    2045            2050                2055

Leu Leu Val Gln Gln Ile Val Gln Glu Ile Asp Gln Gly Val Val
    2060            2065                2070

Glu Gly Asn Ile Pro Leu Thr Pro Ile Gln His Trp Phe Phe Thr
    2075            2080                2085

Gln Ser Phe Pro Gln Val Asn His Tyr Asn Gln Ser Val Leu Leu
    2090            2095                2100

Phe Asn Ala Glu Gly Trp Asp Glu Gln Lys Val Asp Lys Ala Phe
    2105            2110                2115

Glu Met Leu Thr Gln His His Asp Ala Leu Arg Ile Val Tyr Ser
    2120            2125                2130

Leu Asp Glu Gln Gly Val Val Gln Arg Asn Arg Gly Leu Glu Gly
    2135            2140                2145

Ser Asn Tyr His Phe Glu Ile Ile Asp Ala Arg Gln Asp Gly Glu
    2150            2155                2160

Asp Gln Ser Asn Trp Lys Ala Ala Ala Asn Arg Met Gln Ala Ser
    2165            2170                2175

Met Asp Ile Val Glu Gly Pro Leu Val Gln Ile Gly Leu Phe Arg
    2180            2185                2190

Ala Asn Glu Gly Ala Tyr Leu Leu Ile Ala Ile His His Leu Val
    2195            2200                2205

Val Asp Gly Val Ser Trp Arg Ile Leu Leu Glu Asp Phe Tyr His
```

```
               2210                2215                2220

Leu Tyr Asn Gly Asn Asp Ser Leu Pro Leu Lys Thr Thr Ser Phe
        2225                2230                2235

Gln Ala Trp Ser Gln Lys Leu Gln Glu Tyr Ala Gln Ser Lys Glu
        2240                2245                2250

Leu Glu His Glu Leu Ser Tyr Trp Arg His Leu Asp Glu Ala Ile
        2255                2260                2265

Thr Asp Tyr Thr Leu His Lys Asp Ile Glu Ala Ala Thr Ser Asn
        2270                2275                2280

Lys Thr Thr Tyr Glu Glu Phe Leu Thr Val Ser Met Ser Leu Ser
        2285                2290                2295

Thr Glu Glu Thr Gln Gln Leu Val Thr Glu Ala His Lys Ala Tyr
        2300                2305                2310

Gln Thr Glu Ile Asn Asp Leu Leu Leu Thr Ala Leu Ala Leu Ala
        2315                2320                2325

Leu Lys Glu Trp Thr Asn Lys Glu Gln Leu Leu Val Ser Met Glu
        2330                2335                2340

Gly His Gly Arg Glu Glu Ile Leu Asp Asn Val Asp Ile Ser Arg
        2345                2350                2355

Thr Val Gly Trp Phe Thr Ser Glu Tyr Pro Val Ala Ile His Leu
        2360                2365                2370

Thr Lys Thr Asp Ile Ser Phe Ala Ile Lys Gln Val Lys Glu Thr
        2375                2380                2385

Leu Arg Arg Val Pro Asn Lys Gly Phe Gly Tyr Gly Ile Leu Lys
        2390                2395                2400

Tyr Leu Ala Lys Glu Thr Phe Lys Leu Lys Pro Glu Ile Ser Phe
        2405                2410                2415

Asn Tyr Leu Gly Gln Phe Thr Asp Lys Glu Gly Asn Ser Ser
        2420                2425                2430

Leu Met Gly Asp Leu Ile Ser Pro Ala Asn Thr Ser Glu Leu Ser
        2435                2440                2445

Leu Asp Ile Asn Gly Ser Ile Glu Ala Asp Arg Leu Gln Met His
        2450                2455                2460

Phe Ser Tyr Asn Ser Arg Ala Tyr Tyr Pro Glu Thr Ile Ala Thr
        2465                2470                2475

Leu Val Gln Asn Phe Lys Ser Tyr Leu Leu Glu Ile Ile Asn His
        2480                2485                2490

Cys Arg Ala Lys Glu Gly Val Glu His Thr Pro Ser Asp Phe Asp
        2495                2500                2505

Ile Asn Asp Leu Thr Met Glu Glu Leu Asp Asp Ile Phe Asp Asp
        2510                2515                2520

Leu Glu Glu Glu Val Tyr Lys
        2525                2530

<210> SEQ ID NO 24
<211> LENGTH: 4617
<212> TYPE: PRT
<213> ORGANISM: Brevibacillus texasporus

<400> SEQUENCE: 24

Met Phe Ser Arg Ser Asn Val Gln Asn Leu Tyr Arg Leu Ser Pro Met
1               5                   10                  15

Gln Lys Gly Ile Leu Phe His Ser Leu Lys Asp Lys Glu Asn His Ala
            20                  25                  30
```

-continued

```
Tyr Phe Asp Gln Leu Ile Phe Thr Leu Glu Gly Lys Val Glu Leu Glu
             35                  40                  45
Tyr Leu Glu Glu Ala Phe Thr Gln Leu Ile Lys Lys His Asp Ile Leu
 50                  55                  60
Arg Thr Val Phe Arg Tyr Lys Lys Val Lys Glu Pro Val Gln Met Val
 65                  70                  75                  80
Leu Lys Glu Arg Ser Ser Thr Ile Tyr Phe Glu Asp Ile Ser His Leu
                     85                  90                  95
Glu Pro Glu Glu Lys Val Asn Tyr Ile Lys Gln Phe Lys Met Arg Asp
             100                 105                 110
Arg Glu Lys Gly Phe Asp Leu Ser Arg Asp Leu Leu Ile Arg Met Ser
             115                 120                 125
Leu Phe Lys Leu Asp Gln Glu Gln Tyr Gln Leu Ile Met Ser Asn His
 130                 135                 140
His Ile Ile Met Asp Gly Trp Cys Leu Gly Ile Ile Leu Thr Asp Phe
145                  150                 155                 160
Leu Arg Met Tyr Lys Gly Ile Val Asn His Thr Pro Val Pro Tyr Glu
                 165                 170                 175
His Val Thr Pro Tyr Ser Lys His Ile Gln Trp Leu Glu Lys Gln Asp
                 180                 185                 190
His Gln Glu Ala Lys Asp Phe Tyr Gln Gln Leu Leu Glu Gly Tyr Asp
             195                 200                 205
Lys Val Thr Gly Val Pro Gln Gln Leu Val Arg Ala Asn His Glu Glu
             210                 215                 220
Tyr Thr His Gly Gln Cys Ile Val Lys Leu Asn Gln Glu Thr Ala Asp
225                 230                 235                 240
Arg Leu Ile Ala Ile Ala Lys Ala Tyr Gln Val Thr Val Asn Thr Val
                 245                 250                 255
Phe Gln Thr Ile Trp Gly Ile Leu Leu Gln Lys Tyr Asn Asn Thr Asp
                 260                 265                 270
Asp Ile Val Phe Gly Ser Val Ser Gly Arg Pro Ala Glu Ile Pro
             275                 280                 285
Asp Val Glu Lys Met Val Gly Leu Phe Ile Asn Thr Ile Pro Val Arg
             290                 295                 300
Ile Lys Ala Asp Gln Gln Glu Arg Phe Asp Thr Leu Val Ala Lys Val
305                 310                 315                 320
Gln Glu Met Ala Leu Ala Ser Glu Ser Tyr Asp Tyr Leu Ser Leu Ala
                 325                 330                 335
Asp Ile His Pro Glu Ala Gly Asp Phe Ile Asn His Ile Ile Ala Phe
             340                 345                 350
Glu Asn Phe Tyr Ile Asp Met Asp Ser Phe Asn Gln Leu Ala Asp Lys
             355                 360                 365
Lys Glu Leu Gly Phe Ser Leu Ala Phe Ala Thr Asp His His Glu Gln
 370                 375                 380
Thr Asn Tyr Asp Leu Ser Val Gln Ala Gln Ile Gly Asp Glu Ser Ser
385                 390                 395                 400
Ile Lys Ile Leu Tyr Asn Ser Lys Leu Tyr Thr Ser Glu Tyr Ile Ala
                 405                 410                 415
Asn Val Ile Asp His Phe Val Thr Val Ala Asp Ile Val Ala Ala Asn
                 420                 425                 430
Pro Ser Ile Pro Val Lys Glu Ile Asp Ile Leu Thr Lys Asp Lys Lys
             435                 440                 445
Asp Gln Ile Leu Tyr Gly Phe Asn Asn Thr Tyr Ala Asp Tyr Pro Arg
```

-continued

```
            450                 455                 460
Glu Lys Thr Ile His Gln Leu Phe Glu Glu Val Asp Lys Asn Pro
465                 470                 475                 480

Asn Gln Ile Ala Leu Val Phe Lys Glu Glu Lys Leu Thr Tyr Gly Glu
                485                 490                 495

Val Asn Ala Lys Ala Asn Gln Leu Ala Tyr Val Leu Arg Lys Gln Gly
                500                 505                 510

Val Gln Pro Asn Asp Val Ile Gly Ile Thr Glu Arg Ser Pro Glu
                515                 520                 525

Met Ile Ile Gly Ile Leu Ala Ile Phe Lys Ala Gly Ala Tyr Met
                530                 535                 540

Pro Ile Asp Pro Ser Tyr Pro Ala Glu Arg Ile Gln Tyr Met Leu Gln
545                 550                 555                 560

Asp Asn Gln Thr Lys Leu Leu Leu Val Gln Lys Gln Glu Met Ile Pro
                565                 570                 575

Ala Asn Tyr Gln Gly Glu Val Leu Phe Leu Thr Gln Glu Ser Trp Met
                580                 585                 590

His Glu Glu Thr Ser Asn Pro Ala His Ile Thr Gln Ala Gln Ala Leu
                595                 600                 605

Ala Tyr Val Met Tyr Thr Ser Gly Ser Thr Gly Glu Pro Lys Gly Ile
                610                 615                 620

Leu Thr Thr His Gln Asn Ile Met Lys Thr Val Ile His Asn Gly Tyr
625                 630                 635                 640

Val Glu Ile Thr Pro Gly Asp Cys Leu Ser Gln Leu Ser Asn Tyr Ala
                645                 650                 655

Phe Asp Gly Ser Thr Phe Glu Ile Tyr Gly Ala Leu Leu His Gly Ala
                660                 665                 670

Thr Leu Leu Leu Val Thr Lys Glu Ala Val Leu Asn Met Asn Glu Leu
                675                 680                 685

Ala Arg Leu Ile Lys Lys Glu Gln Val Thr Val Ser Phe Met Thr Thr
690                 695                 700

Ala Leu Phe Asn Thr Leu Val Asp Leu Asp Ile Thr Cys Phe Gln Ser
705                 710                 715                 720

Ile Arg Lys Val Leu Phe Gly Gly Glu Leu Ala Ser Val Lys His Val
                725                 730                 735

Leu Lys Ala Leu Asp Tyr Leu Gly Glu His Arg Val Ile Asn Val Tyr
                740                 745                 750

Gly Pro Thr Glu Thr Thr Val Tyr Ala Thr Tyr Tyr Ser Val Asp His
                755                 760                 765

Ser Met Leu Thr Arg Ala Ser Val Pro Ile Gly Arg Pro Ile Asn Asn
770                 775                 780

Thr Lys Ala Tyr Ile Val Asn Thr Asp Gly Gln Pro Gln Pro Ile Gly
785                 790                 795                 800

Val Val Gly Glu Leu Cys Ile Gly Gly Val Ala Cys Gly Tyr
                805                 810                 815

Leu Asn Arg Pro Glu Leu Thr Lys Lys His Phe Val Asp Asn Pro Phe
                820                 825                 830

Val Leu Gly Glu Arg Met Tyr Cys Thr Gly Asp Leu Ala Arg Phe Leu
                835                 840                 845

Pro Asp Gly Asn Ile Glu Tyr Ile Gly Arg Met Asp Glu Gln Val Lys
                850                 855                 860

Ile Arg Gly His Arg Ile Glu Leu Gly Glu Ile Glu Lys Val Leu Leu
865                 870                 875                 880
```

-continued

```
Gln His Pro Ala Ile Ser Glu Thr Val Leu Leu Ala Lys Arg Asp Glu
                885                 890                 895
Gln Gly His Ser Tyr Leu Cys Ala Tyr Ile Val Gly Gln Val Phe Trp
            900                 905                 910
Thr Val Thr Glu Leu Arg Gln His Leu Met Glu Ser Leu Pro Glu Tyr
        915                 920                 925
Met Val Pro Ser Tyr Phe Ile Glu Ile Glu Lys Leu Pro Leu Thr Ala
    930                 935                 940
Asn Gly Lys Val Asp Lys Arg Ala Leu Pro Glu Pro Asp Arg Lys Met
945                 950                 955                 960
Gly Ser Ala Tyr Val Ala Pro Glu Asn Glu Thr Glu Lys Leu Val
                965                 970                 975
Gln Phe Phe Gln Glu Ile Leu Gly Val Glu Arg Val Gly Thr Gln Asp
            980                 985                 990
Thr Phe Phe Glu Leu Gly Gly His Ser Leu Lys Ala Met Met Leu Val
        995                 1000                1005
Leu Gln Ile His Lys Glu Met Gly Ile Glu Val Pro Leu Lys Glu
    1010                1015                1020
Ile Phe Thr Arg Pro Thr Ile Lys Glu Leu Ala Ala Tyr Ile His
    1025                1030                1035
Lys Met Asp Arg Ser Ala Tyr Ser Met Ile Glu Pro Thr Ala Lys
    1040                1045                1050
Gln Glu Tyr Tyr Pro Val Ser Phe Ala Gln Arg Arg Met Phe Val
    1055                1060                1065
Val Gln Gln Ile Arg Asp Thr Asn Thr Thr Ser Tyr Asn Met Pro
    1070                1075                1080
Ile Leu Leu Glu Ile Glu Gly Ala Leu Asp Arg Glu Asn Val Arg
    1085                1090                1095
Gln Thr Leu Lys Lys Leu Ile Glu Arg His Glu Ser Met Arg Thr
    1100                1105                1110
Ser Phe His Met Ile Asp Glu Thr Leu Leu Gln Lys Val His Asp
    1115                1120                1125
Asp Val Thr Trp Glu Met Glu Glu Met Glu Ala Ser Glu Glu Glu
    1130                1135                1140
Val Tyr Ala Leu Thr Lys Ser Phe Ile Arg Pro Phe Asp Leu Gly
    1145                1150                1155
Gln Ala Pro Leu Phe Arg Ala Gly Leu Ile Arg Val Asn Ser Glu
    1160                1165                1170
Arg His Leu Leu Leu Leu Asp Thr His His Ile Ile Ser Asp Gly
    1175                1180                1185
Val Ser Thr Asn Ile Leu Phe Gln Asp Phe Thr Gln Leu Tyr Arg
    1190                1195                1200
Gly Arg Glu Leu Pro Ala Leu Arg Ile Gln Tyr Lys Asp Phe Ala
    1205                1210                1215
Val Trp Gln Gln Gly Glu Ala Gln Leu Ala Arg Leu Gln Glu Gln
    1220                1225                1230
Glu Glu Tyr Trp Leu Lys Gln Phe Ser Glu Ser Val Pro Val Leu
    1235                1240                1245
Glu Leu Pro Thr Asp Phe Pro Arg Pro Ala Met Gln Gln Phe Asp
    1250                1255                1260
Gly Asp Val Leu Asp Phe Ala Leu Asn Gln Gln Val Trp Gln Glu
    1265                1270                1275
```

-continued

| | | | | | | | | | | | |
|---|---|---|---|---|---|---|---|---|---|---|---|
| Leu | Gln | Gln | Leu | Ile | Val | Lys | Glu | Gly | Cys | Thr | Ala | Tyr | Met | Ile |
| 1280 | | | | | 1285 | | | | | 1290 | | | | |
| Leu | Leu | Ala | Ala | Tyr | His | Val | Leu | Leu | Ser | Lys | Tyr | Ser | Ser | Gln |
| 1295 | | | | | 1300 | | | | | 1305 | | | | |
| Asn | Asp | Ile | Val | Ile | Gly | Ser | Pro | Ile | Ala | Gly | Arg | Thr | Asn | Ala |
| 1310 | | | | | 1315 | | | | | 1320 | | | | |
| Asp | Leu | Gln | Ser | Ile | Val | Gly | Met | Phe | Val | Asn | Thr | Leu | Ala | Ile |
| 1325 | | | | | 1330 | | | | | 1335 | | | | |
| Arg | Thr | Lys | Ser | Glu | Gly | Thr | Gln | Thr | Phe | Arg | Glu | Phe | Leu | Ser |
| 1340 | | | | | 1345 | | | | | 1350 | | | | |
| Thr | Ile | Lys | Gln | Leu | Val | Leu | Gln | Ala | Gln | Ser | Asn | Ala | Glu | Tyr |
| 1355 | | | | | 1360 | | | | | 1365 | | | | |
| Pro | Phe | Glu | Glu | Leu | Val | Asp | Lys | Val | Asn | Pro | Ser | Arg | Asp | Leu |
| 1370 | | | | | 1375 | | | | | 1380 | | | | |
| Ser | Arg | Gln | Pro | Leu | Phe | Asp | Thr | Ile | Phe | Val | Met | Gln | Asn | Met |
| 1385 | | | | | 1390 | | | | | 1395 | | | | |
| Asp | Ile | Thr | Glu | Val | Ala | Ile | Gln | Gly | Leu | Ser | Ile | Val | Thr | Lys |
| 1400 | | | | | 1405 | | | | | 1410 | | | | |
| Asp | Met | Glu | Trp | Lys | His | Ser | Lys | Phe | Asp | Leu | Thr | Trp | Ala | Ala |
| 1415 | | | | | 1420 | | | | | 1425 | | | | |
| Val | Glu | Lys | Glu | Ser | Leu | His | Phe | Ser | Val | Glu | Tyr | Ser | Thr | Arg |
| 1430 | | | | | 1435 | | | | | 1440 | | | | |
| Leu | Phe | Lys | Lys | Glu | Thr | Ile | Glu | Arg | Met | Ala | Lys | His | Phe | Ala |
| 1445 | | | | | 1450 | | | | | 1455 | | | | |
| His | Leu | Leu | Asn | Gln | Val | Ala | Glu | Asn | Pro | Asp | Leu | Ser | Leu | Ser |
| 1460 | | | | | 1465 | | | | | 1470 | | | | |
| Asp | Met | Glu | Leu | Ala | Thr | Asp | Glu | Glu | Val | Tyr | Gln | Leu | Leu | Glu |
| 1475 | | | | | 1480 | | | | | 1485 | | | | |
| Glu | Phe | Asn | Asn | Thr | Glu | Ala | Asp | Tyr | Pro | Ser | Asp | Lys | Thr | Ile |
| 1490 | | | | | 1495 | | | | | 1500 | | | | |
| His | Gln | Gln | Phe | Glu | Gln | Lys | Val | Glu | Glu | Asn | Pro | Asp | Gln | Ile |
| 1505 | | | | | 1510 | | | | | 1515 | | | | |
| Ala | Leu | Leu | Phe | Lys | Asp | Lys | Glu | Ile | Thr | Tyr | Gly | Gln | Leu | Asn |
| 1520 | | | | | 1525 | | | | | 1530 | | | | |
| Ala | Lys | Ala | Asn | Gln | Phe | Ala | Arg | Val | Leu | Arg | Lys | His | Gly | Val |
| 1535 | | | | | 1540 | | | | | 1545 | | | | |
| Gln | Pro | Asp | Gln | Val | Val | Gly | Leu | Ile | Thr | Asp | Arg | Ser | Ile | Glu |
| 1550 | | | | | 1555 | | | | | 1560 | | | | |
| Met | Met | Ile | Gly | Ile | Leu | Ala | Ile | Leu | Lys | Ala | Gly | Gly | Ala | Tyr |
| 1565 | | | | | 1570 | | | | | 1575 | | | | |
| Leu | Pro | Ile | Asp | Pro | Ser | Tyr | Pro | Leu | Glu | Arg | Ile | Thr | Tyr | Met |
| 1580 | | | | | 1585 | | | | | 1590 | | | | |
| Leu | Glu | Asp | Ser | Gln | Ala | Gln | Leu | Leu | Ile | Val | Gln | Glu | Ala | Ala |
| 1595 | | | | | 1600 | | | | | 1605 | | | | |
| Met | Ile | Pro | Glu | Gly | Tyr | Gln | Gly | Lys | Val | Leu | Leu | Leu | Ala | Glu |
| 1610 | | | | | 1615 | | | | | 1620 | | | | |
| Glu | Cys | Trp | Met | Gln | Glu | Ala | Ser | Asn | Leu | Glu | Leu | Ile | Asn |
| 1625 | | | | | 1630 | | | | | 1635 | | | | |
| Asp | Ala | Gln | Asp | Leu | Ala | Tyr | Val | Met | Tyr | Thr | Ser | Gly | Ser | Thr |
| 1640 | | | | | 1645 | | | | | 1650 | | | | |
| Gly | Lys | Pro | Lys | Gly | Asn | Leu | Thr | Thr | His | Gln | Asn | Ile | Leu | Arg |
| 1655 | | | | | 1660 | | | | | 1665 | | | | |
| Thr | Ile | Ile | Asn | Asn | Gly | Phe | Ile | Glu | Ile | Val | Pro | Ala | Asp | Arg |

-continued

```
            1670                1675                1680
Leu Leu Gln Leu Ser Asn Tyr Ala Phe Asp Gly Ser Thr Phe Asp
        1685                1690                1695
Ile Tyr Ser Ala Leu Leu Asn Gly Ala Thr Leu Val Leu Val Pro
        1700                1705                1710
Lys Glu Val Met Leu Asn Pro Met Glu Leu Ala Arg Ile Val Arg
        1715                1720                1725
Glu Gln Asp Ile Thr Val Ser Phe Met Thr Thr Ser Leu Phe His
        1730                1735                1740
Thr Leu Val Glu Leu Asp Val Thr Ser Met Lys Ser Ile Arg Lys
        1745                1750                1755
Val Val Phe Gly Gly Glu Lys Ala Ser Tyr Lys His Val Glu Lys
        1760                1765                1770
Ala Leu Asp Tyr Leu Gly Glu Gly Arg Leu Val Asn Gly Tyr Gly
        1775                1780                1785
Pro Thr Glu Thr Thr Val Phe Ala Thr Thr Tyr Thr Val Asp Ser
        1790                1795                1800
Ser Ile Lys Glu Thr Gly Ile Val Pro Ile Gly Arg Pro Leu Asn
        1805                1810                1815
Asn Thr Ser Val Tyr Ile Leu Asn Glu Asn Asn Gln Pro Gln Pro
        1820                1825                1830
Ile Gly Val Pro Gly Glu Leu Cys Val Gly Gly Ala Gly Ile Ala
        1835                1840                1845
Arg Gly Tyr Leu Asn Arg Pro Glu Leu Thr Ala Glu Arg Phe Val
        1850                1855                1860
Asp Asn Pro Phe Leu Val Gly Asp Arg Met Tyr Arg Thr Gly Asp
        1865                1870                1875
Met Ala Arg Phe Leu Pro Asp Gly Asn Ile Glu Tyr Ile Gly Arg
        1880                1885                1890
Met Asp Glu Gln Val Lys Ile Arg Gly His Arg Ile Glu Leu Gly
        1895                1900                1905
Glu Ile Glu Lys Ser Leu Leu Glu Tyr Pro Ala Ile Ser Glu Ala
        1910                1915                1920
Val Leu Val Ala Lys Arg Asp Glu Gln Gly His Ser Tyr Leu Cys
        1925                1930                1935
Ala Tyr Val Val Ser Thr Asp Gln Trp Thr Val Ala Lys Val Arg
        1940                1945                1950
Gln His Ile Leu Glu Ala Leu Pro Glu Tyr Met Val Pro Ser Tyr
        1955                1960                1965
Phe Val Glu Leu Glu Lys Leu Pro Leu Thr Ser Asn Gly Lys Val
        1970                1975                1980
Asp Lys Arg Ala Leu Pro Glu Pro Asp Arg Val Ile Thr Asn Glu
        1985                1990                1995
Tyr Val Ala Ala Val Asn Glu Thr Glu Glu Lys Leu Val Gln Phe
        2000                2005                2010
Phe Gln Glu Ile Leu Ala Val Asp Arg Val Gly Thr Gln Asp Thr
        2015                2020                2025
Phe Phe Glu Leu Gly Gly His Ser Leu Lys Ala Met Met Leu Val
        2030                2035                2040
Ser Arg Ile His Lys Glu Leu Glu Ile Glu Val Pro Leu Lys Glu
        2045                2050                2055
Val Phe Ala Arg Gln Thr Val Lys Glu Leu Ala Ala Tyr Ile Arg
        2060                2065                2070
```

```
Gln Ala Glu Gln Ser Asp Tyr Ser Glu Ile Gln Pro Ala Met Glu
    2075                2080                2085

Gln Glu Tyr Tyr Pro Val Ser Asn Ala Gln Arg Arg Met Tyr Val
    2090                2095                2100

Val Gln Gln Met Arg Asp Val Glu Thr Thr Gly Tyr Asn Met Pro
    2105                2110                2115

Phe Tyr Leu Glu Met Glu Gly Ala Leu Glu Val Glu Lys Leu Ser
    2120                2125                2130

Leu Ala Leu Lys Gln Leu Ile Glu Arg His Glu Ser Leu Arg Thr
    2135                2140                2145

Ser Phe His Met Val Glu Asp Glu Leu Met Gln Lys Val His Ala
    2150                2155                2160

Glu Val Ala Trp Glu Met Glu Met Ile His Ala Val Glu Glu Glu
    2165                2170                2175

Val Gln Gln Leu Thr Asp Ser Phe Met Arg Pro Phe Asp Leu Ala
    2180                2185                2190

Lys Ala Pro Leu Phe Arg Ala Arg Leu Ile Gln Ile Asn Pro Lys
    2195                2200                2205

Arg His Leu Leu Met Leu Asp Met His His Ile Ile Ser Asp Gly
    2210                2215                2220

Val Ser Met Asn Val Leu Phe Gln Asp Ile Thr Gln Leu Tyr Gln
    2225                2230                2235

Gly Ile Glu Leu Ser Pro Leu Lys Ile Gln Tyr Lys Asp Phe Ala
    2240                2245                2250

Val Trp Gln Gln Gly Ile Ala Gln Val Val Arg Phe Gln Glu Gln
    2255                2260                2265

Glu Arg Tyr Trp Leu Asn Gln Phe Ser Gly Asp Leu Pro Ile Leu
    2270                2275                2280

Glu Met Val Thr Asp Tyr Pro Arg Pro Ala Ile Gln Gln Phe Asp
    2285                2290                2295

Gly Asp Ser Trp Ser Phe Glu Ile Asp Ala Lys Val Leu Asp Ser
    2300                2305                2310

Ile Lys Gln Leu Ser Ala Lys Gln Gly Thr Thr Leu Tyr Met Thr
    2315                2320                2325

Leu Leu Ala Ile Tyr Gln Ile Leu Leu Ala Lys Tyr Thr Arg Gln
    2330                2335                2340

Asp Asp Ile Ile Val Gly Thr Pro Ile Ala Gly Arg Pro His Ala
    2345                2350                2355

Asp Thr Glu Ser Ile Val Gly Met Phe Val Asn Thr Leu Ala Leu
    2360                2365                2370

Arg Gly Gln Pro Lys Glu Glu Gln Ser Phe Ile Ser Tyr Leu Ser
    2375                2380                2385

Glu Val Lys Glu Asn Val Leu Gln Ala Tyr Ala Asn Ala Asp Tyr
    2390                2395                2400

Pro Phe Glu Glu Leu Val Glu Lys Leu His Leu Gln Arg Asp Met
    2405                2410                2415

Ser Arg His Pro Leu Phe Asp Thr Met Phe Val Leu Gln Asn Met
    2420                2425                2430

Asp Met Ser Asp Ile Asn Ile Ser Gly Leu Lys Leu His Ser Arg
    2435                2440                2445

Asp Leu Asn Trp Lys Asn Ala Lys Phe Asp Met Thr Trp Met Ile
    2450                2455                2460
```

-continued

Ala Glu Gln Asn Asn Leu Leu Ile Ser Val Glu Tyr Ser Thr Asn
2465                2470                2475

Leu Phe Lys His Glu Thr Ile Gln Arg Leu Glu Lys His Phe Thr
2480                2485                2490

Tyr Leu Val Glu Gln Val Ala Lys His Pro Asp Cys Leu Leu Arg
2495                2500                2505

Asp Leu Glu Leu Thr Thr Asp Glu Glu Lys Gln Gln Ile Leu Thr
2510                2515                2520

Val Phe Asn Asp Thr Ala Thr Asp Asp Leu Gln Asp Leu Ser Ile
2525                2530                2535

Cys His Leu Phe Glu Gln Gln Val Gln Arg Phe Ser Asp Arg Pro
2540                2545                2550

Ala Leu Val Phe Lys Glu Lys Gln Leu Thr Tyr Ser Glu Phe His
2555                2560                2565

Ala Lys Val Asn Gln Leu Ala Arg Val Leu Arg Lys Lys Gly Val
2570                2575                2580

Gln Pro Asp Gln Ala Val Gly Leu Ile Thr Asp Arg Ser Ile Glu
2585                2590                2595

Met Met Ile Gly Ile Phe Ala Ile Leu Lys Ala Gly Gly Ala Tyr
2600                2605                2610

Met Pro Ile Asp Pro Ser Tyr Pro Ile Asp Arg Ile Glu His Met
2615                2620                2625

Leu Glu Asp Ser Arg Thr Lys Leu Leu Phe Val Gln Lys Thr Glu
2630                2635                2640

Met Ile Pro Ala Ser Tyr Gln Gly Glu Val Leu Leu Leu Ala Glu
2645                2650                2655

Glu Cys Trp Met His Glu Asp Ser Ser Asn Leu Glu Leu Ile Asn
2660                2665                2670

Lys Thr Gln Asp Leu Ala Tyr Val Met Tyr Thr Ser Gly Ser Thr
2675                2680                2685

Gly Lys Pro Lys Gly Asn Leu Thr Thr His Gln Asn Ile Leu Thr
2690                2695                2700

Thr Ile Ile Asn Asn Gly Tyr Ile Glu Ile Ala Pro Thr Asp Arg
2705                2710                2715

Leu Leu Gln Leu Ser Asn Tyr Ala Phe Asp Gly Ser Thr Phe Asp
2720                2725                2730

Ile Tyr Ser Ala Leu Leu Asn Gly Ala Thr Leu Val Leu Val Pro
2735                2740                2745

Lys Glu Val Met Leu Asn Pro Met Glu Leu Ala Lys Ile Val Arg
2750                2755                2760

Glu Gln Asp Ile Thr Val Ser Phe Met Thr Thr Ser Leu Phe His
2765                2770                2775

Thr Leu Val Glu Leu Asp Val Thr Ser Met Lys Ser Met Arg Lys
2780                2785                2790

Val Val Phe Gly Gly Glu Lys Ala Ser Tyr Lys His Val Glu Lys
2795                2800                2805

Ala Leu Asp Tyr Leu Gly Gly Arg Leu Val Asn Gly Tyr Gly
2810                2815                2820

Pro Thr Glu Thr Thr Val Phe Ala Thr Thr Tyr Thr Val Asp Ser
2825                2830                2835

Ser Ile Lys Glu Thr Gly Ile Val Pro Ile Gly Arg Pro Leu Asn
2840                2845                2850

Asn Thr Ser Val Tyr Val Leu Asn Glu Asn Asn Gln Leu Gln Pro

-continued

```
            2855                2860                2865
Ile Gly Val Pro Gly Glu Leu Cys Val Gly Gly Ala Gly Ile Ala
    2870                2875                2880
Arg Gly Tyr Leu Asn Arg Pro Glu Leu Thr Ala Glu Arg Phe Val
    2885                2890                2895
Glu Asn Pro Phe Val Ser Gly Asp Arg Met Tyr Arg Thr Gly Asp
    2900                2905                2910
Leu Ala Arg Trp Leu Pro Asp Gly Ser Met Glu Tyr Leu Gly Arg
    2915                2920                2925
Met Asp Glu Gln Val Lys Val Arg Gly Tyr Arg Ile Glu Leu Gly
    2930                2935                2940
Glu Ile Glu Thr Arg Leu Leu Glu His Pro Ser Ile Ser Ala Ala
    2945                2950                2955
Val Leu Leu Ala Lys Gln Asp Glu Gln Gly His Ser Tyr Leu Cys
    2960                2965                2970
Ala Tyr Ile Val Ala Asn Gly Val Trp Thr Val Ala Glu Leu Arg
    2975                2980                2985
Lys His Leu Ser Glu Ala Leu Pro Glu Tyr Met Val Pro Thr Tyr
    2990                2995                3000
Phe Val Glu Leu Glu Gln Ile Pro Phe Thr Ser Asn Gly Lys Val
    3005                3010                3015
Asn Lys Arg Ala Leu Pro Glu Pro Glu Gly Gln Met Thr Ser Val
    3020                3025                3030
Tyr Val Ala Pro Glu Thr Glu Thr Glu Ala Lys Val Ala Ala Leu
    3035                3040                3045
Phe Gln Glu Ile Leu Gly Val Glu Arg Val Gly Thr Gln Asp Met
    3050                3055                3060
Phe Phe Glu Leu Gly Gly His Ser Leu Lys Ala Met Met Leu Val
    3065                3070                3075
Leu Arg Met Asn Lys Glu Leu Gly Ile Glu Val Pro Leu Lys Glu
    3080                3085                3090
Val Phe Ala His Pro Thr Val Lys Glu Leu Ala Ala Thr Ile Asp
    3095                3100                3105
Leu Leu Asp Arg Ser Gly His Ser Glu Ile Glu Pro Ala Pro Arg
    3110                3115                3120
Gln Glu Phe Tyr Pro Val Ser Ser Ala Gln Arg Arg Met Tyr Val
    3125                3130                3135
Val Gln His Leu Gly Asn Val Gln Thr Thr Ser Tyr Asn Met Pro
    3140                3145                3150
Leu Phe Leu Glu Val Glu Gly Ala Leu Glu Ile Asp Lys Leu His
    3155                3160                3165
Leu Ala Leu Glu Lys Leu Val Glu Arg His Glu Ser Leu Arg Thr
    3170                3175                3180
Ser Phe His Met Val Asp Glu Glu Leu Met Gln Gln Val His Glu
    3185                3190                3195
Glu Val Ala Trp Asp Leu Glu Ile Met Asp Gly Thr Glu Gly Asp
    3200                3205                3210
Leu Ala Ser Ile Thr Ala Gly Phe Ile Arg Pro Phe Asp Leu Ser
    3215                3220                3225
Gln Ala Pro Leu Phe Arg Ala Gly Ile Val Arg Ile Ser Pro Glu
    3230                3235                3240
Arg Phe Leu Phe Met Leu Asp Met His His Ile Ile Ser Asp Gly
    3245                3250                3255
```

-continued

```
Val Ser Thr Asn Val Leu Phe Lys Asp Ile Thr Gln Leu Tyr Gln
3260                3265                3270

Gly Lys Asp Leu Pro Pro Leu Pro Ile Gln Tyr Lys Asp Tyr Ala
    3275                3280                3285

Val Trp Gln Gln Ala Asp Ala Gln Val Thr Arg Leu Gln Asp Gln
3290                3295                3300

Glu Ser Tyr Trp Leu His Gln Phe Ala Gly Glu Ala Ser Val Leu
3305                3310                3315

Glu Met Pro Thr Asp Phe Pro Arg Pro Ala Val Gln Gln Phe Glu
3320                3325                3330

Gly Asp Val Trp Thr Phe Glu Ile Asp Ala Asp Ile Leu Ser Gln
3335                3340                3345

Leu Lys Lys Leu Ser Val Ser Gln Gly Ser Thr Leu Tyr Met Thr
3350                3355                3360

Leu Leu Ala Val Tyr Gln Val Leu Leu Ala Lys Tyr Thr Gly Gln
3365                3370                3375

Asp Asp Ile Ile Val Gly Ser Pro Ile Ala Gly Arg Pro His Ala
3380                3385                3390

Asp Val Glu Ser Ile Val Gly Met Phe Val Asn Thr Leu Ala Leu
3395                3400                3405

Arg Gly Gln Pro Val Gly Glu Gln Thr Phe Ile Thr Tyr Leu Ala
3410                3415                3420

Gln Val Lys Glu Gln Val Leu Gln Ala Tyr Ala Asn Ala Glu Tyr
3425                3430                3435

Pro Phe Glu Lys Leu Val Glu Lys Leu Asp Leu Gln Arg Asp Met
3440                3445                3450

Ser Arg His Pro Leu Phe Asp Thr Met Phe Thr Leu Gln Asn Met
3455                3460                3465

Glu Met Thr Asp Ile Asp Leu Ala Gly Leu Thr Phe Lys Pro Phe
3470                3475                3480

Asp Phe Glu Trp Lys Asn Ala Lys Phe Asp Met Asp Trp Thr Met
3485                3490                3495

Leu Glu Glu Glu Thr Leu Lys Val Ala Ile Glu Tyr Ser Thr Ser
3500                3505                3510

Leu Tyr Thr Lys Glu Thr Ile Ser Arg Met Ala Gln His Phe Thr
3515                3520                3525

Tyr Val Leu Gln Gln Ile Ile Glu His Pro Ala Ile Arg Leu Ala
3530                3535                3540

Glu Ile Lys Ile Ala Thr Leu Pro Glu Ile Glu Gln Ile Leu Thr
3545                3550                3555

Gln Phe Asn Asp Thr Arg Ala Asn Tyr Pro Asp Asn Gln Thr Ile
3560                3565                3570

His Ser Leu Phe Glu Gln Gln Val Glu Arg Thr Pro Glu Gln Ile
3575                3580                3585

Ala Val Val Tyr Gln Asp Gln Ser Ile Thr Tyr Arg Glu Leu Asn
3590                3595                3600

Glu Arg Ala Asn Arg Leu Ala Arg Cys Leu Ile Asp Lys Gly Ile
3605                3610                3615

Gln Arg Asn Gln Phe Val Ala Ile Met Ala Asp Arg Ser Ile Glu
3620                3625                3630

Thr Val Ile Gly Met Met Gly Ile Leu Lys Ala Gly Gly Ala Tyr
3635                3640                3645
```

-continued

```
Val Pro Ile Asp Pro Asp Tyr Pro Leu Asp Arg Lys Leu Tyr Ile
3650                3655                3660

Leu Glu Asp Ser His Ala Ser Leu Leu Leu Phe Gln Gln Lys His
3665                3670                3675

Glu Val Pro Ser Glu Phe Thr Gly Asp Arg Ile Leu Ile Glu Gln
3680                3685                3690

Met Gln Trp Tyr Gln Ala Ala Asp Thr Asn Val Gly Ile Val Asn
3695                3700                3705

Thr Ala Gln Asp Leu Ala Tyr Met Ile Tyr Thr Ser Gly Ser Thr
3710                3715                3720

Gly Gln Pro Lys Gly Val Met Ile Asp His Gln Ala Val Cys Asn
3725                3730                3735

Leu Cys Leu Met Ala Gln Thr Tyr Gly Ile Phe Ala Asn Ser Arg
3740                3745                3750

Val Leu Gln Phe Ala Ser Phe Ser Phe Asp Ala Ser Val Gly Glu
3755                3760                3765

Val Phe His Thr Leu Thr Asn Gly Ala Thr Leu Tyr Leu Met Asp
3770                3775                3780

Arg Asn Leu Leu Met Ala Gly Val Glu Phe Val Glu Trp Leu Arg
3785                3790                3795

Val Asn Glu Ile Thr Ser Ile Pro Phe Ile Ser Pro Ser Ala Leu
3800                3805                3810

Arg Ala Leu Pro Tyr Glu Asp Leu Pro Ala Leu Lys Tyr Ile Ser
3815                3820                3825

Thr Gly Gly Glu Ala Leu Pro Val Asp Leu Val Arg Leu Trp Gly
3830                3835                3840

Thr Glu Arg Ile Phe Leu Asn Ala Tyr Gly Pro Thr Glu Thr Thr
3845                3850                3855

Val Asp Ala Thr Ile Gly Leu Cys Thr Pro Glu Asp Lys Pro His
3860                3865                3870

Ile Gly Lys Pro Val Leu Asn Lys Lys Ala Tyr Ile Ile Asn Pro
3875                3880                3885

Asn Tyr Gln Leu Gln Pro Ile Gly Val Pro Gly Glu Leu Cys Ile
3890                3895                3900

Gly Gly Val Gly Ile Ala Pro Gly Tyr Trp Asn Arg Pro Glu Leu
3905                3910                3915

Thr Arg Glu Lys Phe Val Asp Asn Pro Phe Ala Gln Gly Glu Arg
3920                3925                3930

Met Tyr Lys Thr Gly Asp Leu Val Arg Trp Leu Pro Asp Gly Asn
3935                3940                3945

Ile Glu Phe Leu Gly Arg Ile Asp Asp Gln Val Lys Ile Arg Gly
3950                3955                3960

His Arg Ile Glu Leu Gly Glu Ile Glu Thr Arg Leu Leu Glu His
3965                3970                3975

Glu Gln Val Ile Glu Ala Val Val Leu Ala Arg Glu Asp Glu Gln
3980                3985                3990

Gly Gln Ala Tyr Leu Cys Ala Tyr Leu Val Ala Ala Asp Glu Trp
3995                4000                4005

Thr Val Ala Glu Leu Arg Lys His Leu Gly Lys Thr Leu Pro Asp
4010                4015                4020

Tyr Met Ile Pro Ala Tyr Phe Ile Glu Leu Glu Glu Phe Pro Leu
4025                4030                4035

Thr Pro Ser Gly Lys Val Asn Lys Lys Ala Leu Pro Glu Pro Asp
```

-continued

```
           4040              4045              4050
Gly Gln Ile Gln Thr Gly Val Glu Tyr Val Glu Ala Thr Thr Glu
           4055              4060              4065
Ser Gln Lys Ile Leu Val Glu Leu Trp Gln Glu Val Leu Arg Val
           4070              4075              4080
Glu Arg Ile Gly Ile Tyr Asp Asn Phe Phe Glu Leu Gly Gly Asp
           4085              4090              4095
Ser Ile Lys Ala Ile Gln Ile Thr Ala Arg Leu Arg Arg His His
           4100              4105              4110
Arg Lys Leu Glu Ile Ser His Leu Phe Lys His Pro Thr Ile Ala
           4115              4120              4125
Glu Leu Ala Pro Trp Met Gln Thr Ser Gln Ala Leu Leu Glu Gln
           4130              4135              4140
Gly Thr Val Glu Gly Glu Val Met Leu Thr Pro Ile Gln Lys Ala
           4145              4150              4155
Phe Phe Glu Glu Asn Gln Glu Gln Pro Gln His Phe Asn Gln Asp
           4160              4165              4170
Ser Leu Leu Tyr Ser Ser Asn Gly Trp Asn Gln Asp Ala Ile Glu
           4175              4180              4185
Gln Val Phe Glu Lys Ile Thr Glu His His Asp Ala Leu Arg Met
           4190              4195              4200
Val Tyr Pro His Thr Glu Gly Lys Val Thr Gln Ile Asn Arg Gly
           4205              4210              4215
Leu Glu Asp Lys Ala Phe Thr Leu Gln Val Phe Asp Phe Thr Gln
           4220              4225              4230
Glu Pro Thr Asp Thr Gln Ala Thr Lys Ile Glu Gln Ile Ala Thr
           4235              4240              4245
Gln Leu Gln Ala Ser Phe Asp Leu Lys Lys Gly Pro Leu Val Arg
           4250              4255              4260
Leu Gly Leu Phe Thr Thr Lys Ala Gly Asp Tyr Leu Leu Ile Val
           4265              4270              4275
Ile His His Leu Val Ile Asp Gly Val Ser Trp Arg Ile Leu Leu
           4280              4285              4290
Glu Asp Phe His Asn Ala Tyr Gln Gln Val Ile Gln Gly Gln Ala
           4295              4300              4305
Ile Val Leu Pro Glu Lys Thr Thr Ser Phe Lys Thr Trp Ser Glu
           4310              4315              4320
Arg Leu Asn Glu Tyr Ala Asn Ser His Ala Leu Leu His Glu Ile
           4325              4330              4335
Pro Tyr Trp Lys Gln Met Glu Glu Ile Ser Ile Ala Pro Leu Pro
           4340              4345              4350
Lys Lys Gly Asn Asn Asp Gly Arg Tyr Tyr Val Lys Asp Ser Glu
           4355              4360              4365
Tyr Ala Thr Met Ser Leu Thr Glu Glu Thr Gln Asn Leu Leu
           4370              4375              4380
Thr Arg Val His Arg Ala Tyr Arg Thr Glu Ile Asn Asp Leu Leu
           4385              4390              4395
Leu Ala Ala Leu Gly Leu Ala Ser Lys Glu Trp Thr Lys Glu Asn
           4400              4405              4410
Arg Val Ala Ile His Leu Glu Gly His Gly Arg Glu Glu Ile Gly
           4415              4420              4425
Glu Gly Val Asp Val Asn Arg Thr Val Gly Trp Phe Thr Ser Leu
           4430              4435              4440
```

-continued

```
Phe Pro  Phe Val Ile Asp Leu  Glu Asn Asp Glu Leu  Pro Leu Ile
    4445                 4450                 4455

Ile Lys  Ser Val Lys Glu Thr  Leu Arg Arg Val Pro  Asn Lys Gly
    4460                 4465                 4470

Met Gly  Tyr Gly Ile Leu Lys  His Leu Thr Ser Asp  Ala Asn Lys
    4475                 4480                 4485

Gln Glu  Ile Thr Phe Ser Leu  Arg Pro Glu Ile Ser  Phe Asn Tyr
    4490                 4495                 4500

Leu Gly  Val Phe Asp Gln Gln  Glu Glu Glu Ser Glu  Ser Ala Gly
    4505                 4510                 4515

Ile Pro  Thr Gly Gln Pro Ile  Ser Pro Gln Tyr Tyr  Asp Thr His
    4520                 4525                 4530

Leu Leu  Glu Phe Asn Gly Ala  Val Ser Asn Asn Gln  Leu His Val
    4535                 4540                 4545

Asn Cys  Arg Phe Ala Pro Ala  Ala Val Asp Arg Ala  Ile Val Glu
    4550                 4555                 4560

Ile Leu  Met Glu Arg Phe Lys  His His Leu Leu Leu  Ile Ser Lys
    4565                 4570                 4575

His Cys  Leu Glu Lys Asp Thr  Val Glu Phe Thr Pro  Thr Asp Phe
    4580                 4585                 4590

Thr Glu  Lys Glu Leu Ser Gln  Glu Gln Leu Asp Asp  Leu Leu Asp
    4595                 4600                 4605

Asp Leu  Phe Glu Asp Ile Asp  Asp Leu
    4610                 4615

<210> SEQ ID NO 25
<211> LENGTH: 2541
<212> TYPE: PRT
<213> ORGANISM: Brevibacillus texasporus

<400> SEQUENCE: 25

Met Gln Lys Lys Asp Lys Ile Lys Asp Ile Tyr Ser Leu Ser Pro Leu
1               5                   10                  15

Gln Lys Gly Met Leu Phe His Ser Met Lys Asp Pro Gln Ser Asp Ala
            20                  25                  30

Tyr Phe Glu Gln Val Thr Leu Leu Leu Glu Gly Val Val Asn Pro Thr
        35                  40                  45

Tyr Leu Ala Glu Ser Ile Gln Gly Leu Val Gln Lys Tyr Asp Met Phe
    50                  55                  60

Arg Ser Val Phe Arg Tyr Lys Lys Val Asp Pro Val Gln Val Val Leu
65                  70                  75                  80

Ser Glu Arg Lys Ile Asp Leu Gln Ile Glu Asp Leu Thr Gln Ile Asn
                85                  90                  95

Glu Glu Glu Gln Arg Lys Phe Ile Glu Glu Tyr Arg Lys Lys Asp Arg
            100                 105                 110

Glu Arg Gly Phe Asp Leu Ser Arg Asp Ile Leu Leu Arg Phe Thr Leu
        115                 120                 125

Phe Gln Thr Ala Ala Asn Arg Tyr Glu Leu Leu Trp Ser His His His
    130                 135                 140

Ile Leu Met Asp Gly Trp Cys Thr Gly Ile Val Phe Gln Asp Leu Phe
145                 150                 155                 160

Gln Met Tyr Gln Arg Arg Leu Ser Gly Gln Ala Leu Leu Pro Glu Val
                165                 170                 175

Ala Pro Gln Tyr Ser Glu Tyr Ile Arg Trp Leu Lys Lys Gln Asp Asp
```

-continued

```
               180                 185                 190
Gln Gln Ala Leu Ala Phe Trp Lys Glu Tyr Leu Gln Gly Phe Glu Asn
            195                 200                 205
Leu Thr Gly Ile Pro Arg Leu Arg Ser Gly Asn His Pro Tyr Lys Gln
        210                 215                 220
Glu Glu Phe Ile Phe Ser Leu Gly Glu Ala Thr Gln Lys Leu Thr
225                 230                 235                 240
Gln Thr Ala Gln Lys Tyr Gln Val Thr Leu Asn Thr Val Val Gln Thr
                245                 250                 255
Ile Trp Gly Ala Leu Leu Gln Lys Tyr Asn Asn Thr Asn Asp Ala Ala
            260                 265                 270
Tyr Gly Val Val Val Ser Gly Arg Pro Ala Glu Val Pro Asn Val Glu
        275                 280                 285
Gln Met Val Gly Leu Phe Ser Asn Thr Ile Pro Ile Arg Ile Lys Lys
    290                 295                 300
Glu Ala Gly Lys Thr Phe Gly Glu Val Leu Lys Asn Val Gln Gln Thr
305                 310                 315                 320
Ala Leu Glu Ala Glu Lys Tyr Gly Tyr Leu Ser Leu Ala Asp Ile Gln
                325                 330                 335
Ala Ser Ala Ala Tyr Thr His Gln Leu Leu Asp His Ile Leu Ala Phe
            340                 345                 350
Glu Asn Phe Pro Met Asp Gln Glu Thr Phe Asn Gln Glu Asn Val Leu
        355                 360                 365
Gly Phe Ala Val Lys Asp Ala His Thr Phe Glu Gln Thr His Tyr Asp
    370                 375                 380
Leu Thr Val Leu Val Ile Pro Gly Lys Glu Leu Ile Phe Lys Phe Met
385                 390                 395                 400
Tyr Asn Glu Ser Val His Ser Lys Glu Tyr Leu Asn Leu Leu Glu Leu
                405                 410                 415
Asn Met Lys Lys Leu Val Ser Leu Val Ile Glu Gln Gln Asp Ile Phe
            420                 425                 430
Asp Pro Ala Thr Glu Phe Val Ser Asp Leu Glu Lys Asp Lys Leu Leu
        435                 440                 445
Thr Ile Phe Asn Arg Thr Asp Ala Lys Tyr Pro Arg Glu Lys Thr Ile
    450                 455                 460
His Glu Leu Phe Gln Glu Gln Val Asp Lys Asn Pro Asp Gln Val Ala
465                 470                 475                 480
Leu Val Phe Gly Glu Ala Gln Leu Thr Tyr Arg Glu Leu Asn Glu Lys
                485                 490                 495
Ala Asn Gln Met Ala Arg Gly Leu Arg Lys Gln Gly Val Leu Pro Asp
            500                 505                 510
Gln Val Ile Gly Leu Leu Thr Asp Arg Ser Leu Glu Met Ile Ile Ala
        515                 520                 525
Ile Leu Ala Ile Phe Lys Ala Gly Gly Ala Tyr Met Pro Ile Asp Pro
    530                 535                 540
Ser Tyr Pro Ser Glu Arg Ile Gln Tyr Met Leu Ala Asp Ser Arg Thr
545                 550                 555                 560
His Leu Leu Leu Val Gln Lys Ala Glu Met Ile Pro Ala Asn Tyr Gln
                565                 570                 575
Gly Glu Val Leu Leu Leu Thr Glu Asp Ser Trp Met Asp Glu Asn Thr
            580                 585                 590
Asp Asn Leu Asp Leu Val Asn Gln Ala Gln Asp Leu Ala Tyr Val Met
        595                 600                 605
```

-continued

Tyr Thr Ser Gly Ser Thr Gly Lys Pro Lys Gly Asn Leu Thr Thr His
    610             615             620

Gln Asn Ile Val Lys Thr Ile Met Asn Asn Gly Tyr Met Glu Ile Thr
625             630             635             640

Pro Asn Asp Arg Leu Leu Gln Leu Ser Asn Tyr Ala Phe Asp Gly Ser
            645             650             655

Thr Phe Asp Ile Tyr Ser Ala Leu Leu Asn Gly Ala Ser Leu Ile Leu
        660             665             670

Val Pro Thr His Val Leu Met Asn Pro Thr Asp Leu Ala Ser Val Ile
        675             680             685

Gln Asp Gln His Ile Thr Val Ser Phe Met Thr Thr Ser Leu Phe Asn
690             695             700

Thr Leu Val Glu Leu Asp Val Thr Ser Leu Lys His Met Arg Lys Val
705             710             715             720

Val Phe Gly Gly Glu Lys Ala Ser Ile Lys His Val Glu Lys Ala Leu
            725             730             735

Asp Tyr Leu Gly Ala Gly Arg Leu Val Asn Gly Tyr Gly Pro Thr Glu
        740             745             750

Thr Thr Val Phe Ala Thr Thr Tyr Thr Val Asp His Thr Ile Lys Glu
        755             760             765

Thr Gly Ile Met Pro Ile Gly Arg Pro Leu Asn Asn Thr Lys Val Phe
770             775             780

Ile Leu Gly Ala Asp Asn Gln Leu Gln Pro Ile Gly Ala Leu Gly Glu
785             790             795             800

Leu Cys Val Ser Gly Glu Gly Leu Ala Arg Gly Tyr Leu Asn Leu Pro
            805             810             815

Glu Leu Thr Ala Asp Arg Phe Val Glu Asn Pro Phe Met Arg Gly Glu
        820             825             830

Arg Met Tyr Arg Thr Gly Asp Leu Ala Arg Trp Leu Pro Asp Gly Ser
        835             840             845

Ile Glu Tyr Val Gly Arg Ile Asp Glu Gln Val Lys Ile Arg Gly His
850             855             860

Arg Ile Glu Leu Gly Glu Ile Glu Ala Arg Leu Leu Glu His Pro Ala
865             870             875             880

Ile Ser Glu Thr Val Leu Leu Ala Lys Gln Asp Glu Gln Gly His Ser
            885             890             895

Phe Leu Cys Ala Tyr Leu Val Thr Asn Gly Ala Trp Ser Val Ala Glu
        900             905             910

Leu Arg Lys His Ile Lys Glu Thr Leu Pro Asp Ser Met Val Pro Ser
        915             920             925

Tyr Phe Ile Glu Ile Asp Lys Met Pro Leu Thr Ser Asn Gly Lys Ala
        930             935             940

Asp Lys Arg Ala Leu Pro Glu Pro Asp Val Gln Gln Val Ser Ser Tyr
945             950             955             960

Ile Ala Pro Glu Thr Glu Thr Glu Lys Leu Val Gln Leu Phe Gln
            965             970             975

Glu Ile Leu Ser Val Glu Gln Val Gly Thr Gln Asp Asn Phe Phe Glu
        980             985             990

Leu Gly Gly His Ser Leu Lys Ala  Met Met Leu Val Ser  Arg Met His
        995              1000            1005

Lys Glu  Leu Asp Ile Glu Val  Pro Leu Lys Asp Val  Phe Ala Arg
   1010            1015            1020

-continued

Pro Ser Val Lys Glu Leu Ala Ala Phe Leu Thr Asn Thr Glu Val
1025                1030                1035

Ser Asp Tyr Ile Ala Ile Glu Pro Ala Lys Gln Glu Phe Tyr
1040                1045                1050

Pro Val Ser Ser Ala Gln Arg Arg Met Tyr Val Val Glu Gln Ile
1055                1060                1065

Gly Ser Ser Asn Thr Thr Ser Tyr Asn Met Pro Phe Leu Leu Glu
1070                1075                1080

Ile Gly Gly Ala Leu Asp Val Val Gly Leu Gln Lys Ala Leu Lys
1085                1090                1095

Lys Leu Val Ile Arg His Glu Ser Leu Arg Thr Ser Phe His Met
1100                1105                1110

Val Asp Glu Val Leu Met Gln Lys Ile His Pro Asp Val Glu Trp
1115                1120                1125

Asp Leu Met Val Met Glu Ala Lys Asp Glu Asp Leu Pro Gln Ile
1130                1135                1140

Ile Asp Gly Phe Ile Gln Pro Phe Asp Leu Ser Asp Ala Ser Leu
1145                1150                1155

Phe Arg Ala Gly Leu Val Arg Met Glu Ala Asp Arg His Leu Leu
1160                1165                1170

Met Leu Asp Met His His Ile Ile Ser Asp Gly Val Ser Thr Asn
1175                1180                1185

Val Leu Phe Gln Asp Leu Met Gln Ile Tyr Gln Gly Lys Glu Leu
1190                1195                1200

Pro Ser Leu Arg Ile Gln Tyr Lys Asp Tyr Ala Val Trp Gln Gln
1205                1210                1215

Ala Glu Ala Gln Val Asn Arg Leu Arg Glu Gln Glu Gln Tyr Trp
1220                1225                1230

Leu Asn Gln Phe Ser Gly Glu Leu Pro Val Leu Glu Met Pro Thr
1235                1240                1245

Asp Tyr Thr Arg Pro Ser Ile Gln Gln Ser Glu Gly Asp Ile Trp
1250                1255                1260

Ser Phe Glu Ile Ser Ala Glu Ile Ile Asn Lys Val Lys Lys Leu
1265                1270                1275

Ser Ser Ser Gln Gly Thr Thr Leu Tyr Met Thr Leu Leu Ala Ala
1280                1285                1290

Tyr Gln Val Leu Leu Ser Lys Tyr Thr Gly Gln Glu Asp Val Ile
1295                1300                1305

Val Gly Ser Pro Ile Ala Gly Arg Pro His Ala Asp Val Glu Lys
1310                1315                1320

Ile Val Gly Met Phe Val Asn Thr Leu Ala Phe Arg Gly Gln Pro
1325                1330                1335

Lys Ser Thr Gln Thr Phe Ser Thr Tyr Leu Ser Glu Val Lys Glu
1340                1345                1350

Gln Val Leu His Ala Tyr Asp Asn Ala Glu Tyr Pro Phe Glu Glu
1355                1360                1365

Leu Leu Glu Lys Leu Asp Leu Glu Arg Asp Leu Ser Arg His Pro
1370                1375                1380

Leu Phe Asp Thr Met Phe Ala Leu Gln Asn Met Glu Met Ala Glu
1385                1390                1395

Ile Asn Ile Met Asp Leu Ser Phe Gln Pro Arg Asp Leu Thr Trp
1400                1405                1410

Lys Asn Ala Lys Phe Asp Leu Thr Trp Met Met Ala Glu Ala Glu

-continued

```
                1415                1420                1425

Asn Leu Tyr Val Thr Ile Glu Tyr Ser Thr Ser Leu Phe Lys Pro
        1430                1435                1440

Glu Thr Ile Glu Arg Leu Gly Lys Arg Phe Thr His Leu Leu Lys
        1445                1450                1455

Gln Ile Gly Asp Ala Pro Glu Arg Leu Ile Ala Asp Leu Glu Val
        1460                1465                1470

Ala Thr Glu Asp Glu Lys His Gln Ile Leu Ser Val Phe Asn Leu
        1475                1480                1485

Thr Gln Ser Asp Tyr Pro Val Asn Lys Thr Val His Gln Leu Phe
        1490                1495                1500

Glu Glu Gln Val Gln Asn Met Pro Asp Gln Lys Ala Ile Val Phe
        1505                1510                1515

Gly Glu Glu Gln Val Thr Tyr Lys Glu Leu Asn Ala Lys Ala Asn
        1520                1525                1530

His Leu Ala Thr Leu Leu Lys Gln Lys Gly Ile Thr Asn Glu Gln
        1535                1540                1545

Leu Val Ala Val Met Ile Glu Pro Ser Ile Glu Phe Phe Val Gly
        1550                1555                1560

Ile Leu Ala Val Leu Lys Ala Gly Gly Ala Tyr Leu Pro Ile Asp
        1565                1570                1575

Pro Thr Tyr Pro Thr Glu Arg Ile Ala Tyr Ile Leu Glu Asp Ser
        1580                1585                1590

Gln Ser Lys Val Leu Leu Val Arg Gly His Glu Gln Val Gln Thr
        1595                1600                1605

Gln Phe Ala Gly Glu Ile Leu Glu Ile Asp Ser Lys Lys Leu Ser
        1610                1615                1620

Thr Glu Glu Leu Lys Asp Val Pro Met Asn Asn Lys Val Thr Asp
        1625                1630                1635

Leu Ala Tyr Val Ile Tyr Thr Ser Gly Ser Thr Gly Gln Pro Lys
        1640                1645                1650

Gly Val Met Val Glu His Arg Ser Leu Met Asn Leu Ser Ala Trp
        1655                1660                1665

His Val Gln Tyr Phe Gly Ile Thr Lys Asp Asp Arg Ser Thr Lys
        1670                1675                1680

Tyr Ala Gly Val Gly Phe Asp Ala Ser Val Trp Glu Val Phe Pro
        1685                1690                1695

Tyr Leu Ile Ala Gly Ala Thr Ile Tyr Val Ile Asp Gln Glu Thr
        1700                1705                1710

Arg Tyr Asp Val Glu Lys Leu Asn Gln Tyr Val Thr Asp Gln Gly
        1715                1720                1725

Ile Thr Ile Ser Phe Leu Pro Thr Gln Phe Ala Glu Gln Phe Met
        1730                1735                1740

Leu Thr Asp His Thr Asp His Thr Ala Leu Arg Trp Leu Leu Ile
        1745                1750                1755

Gly Gly Asp Lys Ala Gln Gln Ala Val Gln Gln Lys Gln Tyr Gln
        1760                1765                1770

Ile Val Asn Asn Tyr Gly Pro Thr Glu Asn Thr Val Val Thr Thr
        1775                1780                1785

Ser Tyr Ile Val Ser Pro Glu Asp Lys Lys Ile Pro Ile Gly Arg
        1790                1795                1800

Pro Ile Ala Asn Asn Gln Val Phe Ile Leu Asn Lys Glu Asn Gln
        1805                1810                1815
```

-continued

```
Leu Gln Pro Val Gly Ile Pro Gly Glu Leu Cys Val Ser Gly Asp
    1820            1825                1830
Ser Leu Ala Arg Gly Tyr Leu His Arg Pro Glu Leu Thr Ser Glu
    1835            1840                1845
Arg Phe Val Ala Asn Pro Phe Val Pro Gly Glu Arg Met Tyr Lys
    1850            1855                1860
Thr Gly Asp Ile Ala Arg Trp Leu Pro Asp Gly Asn Ile Glu Tyr
    1865            1870                1875
Leu Gly Arg Leu Asp Asp Gln Ile Lys Ile Arg Gly Tyr Arg Val
    1880            1885                1890
Glu Leu Gly Glu Ile Glu Ser Ala Ile Leu Glu His Glu Ala Ile
    1895            1900                1905
His Glu Thr Val Val Leu Ala Arg Gln Asp Asp Gln Asn Gln Thr
    1910            1915                1920
Tyr Leu Cys Ala Tyr Val Val Pro Lys Lys Ser Phe Asp Val Ala
    1925            1930                1935
Glu Leu Arg Gln Tyr Leu Gly Arg Lys Leu Pro His Phe Met Ile
    1940            1945                1950
Pro Ala Phe Phe Thr Glu Met Thr Glu Phe Pro Ile Thr Ser Asn
    1955            1960                1965
Gly Lys Val Asp Lys Lys Ala Leu Pro Leu Pro Asp Leu Ser Lys
    1970            1975                1980
Gln Ser Glu Ile Asp Tyr Val Ala Pro Thr Thr Thr Leu Glu Glu
    1985            1990                1995
Thr Leu Ala Glu Leu Trp Thr Glu Val Leu Gly Val Ser Gln Val
    2000            2005                2010
Gly Ile His Asp Asn Phe Phe Lys Leu Gly Gly Asp Ser Ile Lys
    2015            2020                2025
Ala Ile Gln Ile Ala Ala Arg Leu Asn Thr Lys Gln Leu Lys Leu
    2030            2035                2040
Glu Val Lys Asp Leu Phe Gln Ala Gln Thr Ile Ala Gln Val Ile
    2045            2050                2055
Pro Tyr Ile Lys Thr Lys Glu Ser Lys Ala Glu Gln Gly Ile Val
    2060            2065                2070
Gln Gly Lys Val Glu Leu Thr Pro Ile Gln Glu Trp Phe Phe Gln
    2075            2080                2085
Gln Ser Phe Asp Ile Pro His His Trp Asn Gln Ser Met Met Phe
    2090            2095                2100
Tyr Arg Lys Glu Gly Trp Asp Gln His Val Val Gln Arg Val Phe
    2105            2110                2115
Gln Lys Ile Ala Glu His His Asp Ala Leu Arg Met Ala Tyr Gln
    2120            2125                2130
Gln Glu Asn Gly Lys Thr Ile Gln Ile Asn Arg Gly Val Glu Gly
    2135            2140                2145
Lys Leu Phe Glu Leu Ser Ile Phe Asp Phe Lys Gln Gln Ala Asn
    2150            2155                2160
Val Pro Glu Leu Ile Glu Gln Ala Ala Asn Arg Leu Gln Ser Ala
    2165            2170                2175
Met Asn Leu Gln Asp Gly Pro Leu Val Gln Leu Gly Leu Phe Gln
    2180            2185                2190
Thr Ser Glu Gly Asp His Leu Leu Ile Ala Ile His His Leu Val
    2195            2200                2205
```

-continued

```
Val Asp  Ala Val Ser Trp Arg  Ile Ile Thr Glu Asp  Phe Met Asn
    2210                 2215                 2220

Gly Tyr  Gln Gln Asp Leu Gln  Gly Glu Pro Ile Ala  Phe Thr Ser
    2225                 2230                 2235

Lys Thr  Asp Ser Tyr Gln Lys  Trp Ala Lys Ser Leu  Leu Glu Tyr
    2240                 2245                 2250

Ala Thr  Ser Glu Glu Ile Gln  Ser Glu Leu Lys Tyr  Trp Gln Ser
    2255                 2260                 2265

Met Ile  Ala Lys Gly Leu Pro  Ala Leu Pro Arg Asp  Ser Lys Val
    2270                 2275                 2280

Gly Ala  Pro Tyr Leu Leu Lys  Asp Ile Gln Glu Val  Ala Ile Gln
    2285                 2290                 2295

Leu Thr  Lys Glu Gln Thr Asn  Lys Leu Leu Thr Asp  Ala His Asn
    2300                 2305                 2310

Ala Tyr  Asn Thr Gln Ile Asn  Asp Leu Leu Leu Thr  Ala Leu Ala
    2315                 2320                 2325

Leu Thr  Ile Gln Glu Trp Ala  Gln Thr Asn Ser Ile  Ala Ile Thr
    2330                 2335                 2340

Leu Glu  Gly His Gly Arg Glu  Asp Ile Gly Val Asp  Ile Asp Ile
    2345                 2350                 2355

Asn Arg  Thr Val Gly Trp Phe  Thr Ser Met Tyr Pro  Val Val Phe
    2360                 2365                 2370

Asp Leu  Gln Lys Gln Gly Ile  Ala Asn Thr Val Lys  Gln Val Lys
    2375                 2380                 2385

Glu Glu  Leu Arg Gln Ile Pro  Asn Lys Gly Ile Gly  Tyr Gly Val
    2390                 2395                 2400

Val Arg  Tyr Leu Ser Asn Gln  Gly Ser Thr Glu Leu  Asp Leu Ser
    2405                 2410                 2415

Ser His  Ala Ile Asn Pro Glu  Ile Ser Phe Asn Tyr  Leu Gly Gln
    2420                 2425                 2430

Met Asp  Gln Ser Gly Gln Glu  Glu Glu Tyr Gln Leu  Ser Pro Leu
    2435                 2440                 2445

Ser Ser  Gly Gln Gln Ile Ser  Gln Met Asn Gln Gly  Leu Phe Pro
    2450                 2455                 2460

Ile Asn  Val Ser Gly Ile Val  Val Glu Asn Gln Leu  Ser Ile Gln
    2465                 2470                 2475

Ile Ser  Tyr Asp Ser Gln Ala  Tyr His Asp Ser Thr  Met Glu Lys
    2480                 2485                 2490

Leu Ile  Gln Arg Tyr Gln Tyr  His Leu Leu Glu Ile  Ile Asn His
    2495                 2500                 2505

Cys Val  Gln Gln Thr Glu Thr  Glu Leu Thr Pro Ser  Asp Phe Ser
    2510                 2515                 2520

Thr Lys  Glu Leu Ser Met Glu  Asp Leu Glu Ser Val  Phe Glu Leu
    2525                 2530                 2535

Leu Asp  Glu
    2540

<210> SEQ ID NO 26
<211> LENGTH: 2526
<212> TYPE: PRT
<213> ORGANISM: Brevibacillus texasporus

<400> SEQUENCE: 26

Met Leu Ser Lys Ala Asn Ile Lys Asp Ile Tyr Thr Leu Ser Pro Leu
1               5                   10                  15
```

-continued

```
Gln Lys Gly Met Leu Phe Gln His Leu Lys Glu Glu Ser Thr Ala Tyr
             20                  25                  30
Phe Glu Gln Leu His Phe Thr Ile Lys Gly Gln Leu Tyr Val Asp Ser
         35                  40                  45
Phe Glu Ala Ser Phe Gln His Leu Ile Asn Lys Tyr Asp Val Leu Arg
     50                  55                  60
Thr Val Phe Leu Tyr Lys Asn Met Thr Gln Pro Met Gln Met Val Leu
 65                  70                  75                  80
Lys Glu Arg Lys Thr Ser Val His Phe Glu Asp Ile Ser His Leu Asp
                 85                  90                  95
Ser Lys Ala Val Ser Glu Tyr Val Glu Glu Phe Lys Asn Gln Asp Arg
            100                 105                 110
Glu Lys Gly Phe Glu Leu Ser Lys Asp Ile Leu Met Arg Phe Ala Ile
        115                 120                 125
Leu Lys Ala Gly Ala Glu Ser Tyr His Leu Ile Trp Ser Phe His His
    130                 135                 140
Ile Leu Met Asp Gly Trp Cys Met Gly Ile Val Leu Gln Asp Leu Phe
145                 150                 155                 160
Arg Met Tyr Gln Gln His Arg Gln Asn Ile Pro Ile Thr Val Glu Ser
                165                 170                 175
Val Pro Ala Tyr Ser Glu Tyr Ile Arg Trp Leu Glu Lys Gln Asn Val
            180                 185                 190
Thr Lys Ala Arg Asp Tyr Trp Lys Asn Tyr Leu Glu Gly Tyr Glu Glu
        195                 200                 205
Leu Thr Gly Ile Ile Arg Leu Asp Thr Lys His Thr Ser His Asn Asn
    210                 215                 220
Glu Val Gln Glu Cys Ala Phe Thr Leu Asp Lys Asp Ile Thr Glu Gly
225                 230                 235                 240
Leu Thr Gln Leu Ala Arg His Tyr Ser Val Thr Val Asn Thr Leu Phe
                245                 250                 255
Gln Thr Ile Trp Gly Met Leu Leu Gln Lys Tyr Asn Asn Lys Asp Asp
            260                 265                 270
Val Val Phe Gly Ala Val Val Ser Gly Arg Pro Ser Glu Ile His Gly
        275                 280                 285
Val Glu Asn Met Val Gly Leu Phe Ile Asn Thr Val Pro Ile Arg Ile
    290                 295                 300
Gln Lys Gln Met Asn Asp Thr Phe Ser His Leu Leu Lys Arg Val His
305                 310                 315                 320
Glu Ser Thr Leu Leu Ser Lys Gln Tyr Glu Phe Val Ser Leu Ala Asp
                325                 330                 335
Ile Gln Thr Asp Ala Gly Phe Ser Gly Gln Leu Leu Asp His Ile Leu
            340                 345                 350
Val Phe Glu Asn Tyr Pro Ile Ser Glu Gly Ser Phe Glu Glu Glu Glu
        355                 360                 365
Phe Thr Met Asp Ser Ile Lys Thr Tyr Glu Lys Thr Ser Tyr Asp Leu
    370                 375                 380
Asn Val Met Ile Arg Pro Asn Glu Asp Gln Leu Asp Ile Ala Phe Gln
385                 390                 395                 400
Phe Asn Asp Asp Val Tyr Ser Ser Glu Asn Val Lys Arg Leu Phe Gln
                405                 410                 415
His Met Lys Gln Leu Ala Leu Ala Val Ile Lys Asn Pro Asp Val Arg
            420                 425                 430
```

-continued

Leu Glu Glu Ile Ala Met Ile Thr Glu Glu Arg Tyr Gln Ile Leu
        435                 440                 445

His Asp Phe Gln Gly Glu Ile Val Asp Phe Val Thr Glu Lys Thr Leu
        450                 455                 460

Pro Glu Leu Phe Glu Asp Gln Val Lys Arg Thr Pro Glu Ala Ile Ala
465                 470                 475                 480

Leu Arg Phe Glu Asp Gln Gln Leu Thr Tyr Gln Glu Leu Asn Gln Arg
                485                 490                 495

Val Asn Gln Leu Ala Trp Thr Leu Arg Met Lys Gly Leu Gln Gln Glu
            500                 505                 510

Glu Leu Val Gly Ile Met Val Gln Arg Ser Leu Glu Met Ile Val Gly
        515                 520                 525

Val Leu Ala Val Ile Lys Ala Gly Gly Ala Tyr Val Pro Ile Asp Pro
    530                 535                 540

Glu Tyr Pro Leu Asp Arg Ile Gln Tyr Met Leu Glu Asp Ser Gly Thr
545                 550                 555                 560

Asn Trp Leu Leu Thr Thr Lys Gln Ser Glu Ile Pro Ser Ile Tyr Leu
                565                 570                 575

Gly His Val Leu Tyr Leu Glu Glu Asp Thr Val Tyr His Glu Arg Ser
            580                 585                 590

Ser Asp Val Glu Ile Val Asn Gln Ser Ser Asp Leu Ala Tyr Ile Ile
        595                 600                 605

Tyr Thr Ser Gly Ser Thr Gly Gln Pro Lys Gly Val Met Ile Asp His
    610                 615                 620

Arg Ala Val His Asn Leu His Leu Ser Ala Gly Ile Tyr Gly Ile Ala
625                 630                 635                 640

Gln Gly Ser Gln Val Leu Gln Phe Ala Ser Leu Ser Phe Asp Ala Ser
                645                 650                 655

Val Gly Asp Ile Phe His Ser Leu Leu Thr Gly Ala Thr Leu His Leu
            660                 665                 670

Val Lys Lys Glu Gln Leu Leu Ser Gly His Ala Phe Met Glu Trp Leu
        675                 680                 685

Asp Glu Ala Gly Ile Thr Thr Ile Pro Phe Ile Pro Pro Ser Val Leu
    690                 695                 700

Lys Glu Leu Pro Tyr Ala Lys Leu Pro Lys Leu Lys Thr Ile Ser Thr
705                 710                 715                 720

Gly Gly Glu Glu Leu Pro Ala Asp Leu Val Arg Ile Trp Gly Ala Asn
                725                 730                 735

Arg Thr Phe Leu Asn Ala Tyr Gly Pro Thr Glu Thr Thr Val Asp Ala
                740                 745                 750

Ser Ile Gly Asn Cys Val Glu Met Thr Asp Lys Pro Ser Ile Gly Thr
        755                 760                 765

Pro Thr Val Asn Lys Arg Ala Tyr Ile Leu Asp Gln Tyr Gly His Ile
    770                 775                 780

Gln Pro Ile Gly Val Pro Gly Glu Leu Cys Val Gly Gly Glu Gly Val
785                 790                 795                 800

Ala Arg Gly Tyr Leu His Arg Pro Glu Leu Thr Asp Glu Lys Phe Val
                805                 810                 815

Asn Asp Pro Tyr Val Pro Asn Gly Arg Met Tyr Lys Thr Gly Asp Leu
            820                 825                 830

Ala Arg Trp Leu Pro Asp Gly Thr Ile Glu Phe Leu Gly Arg Met Asp
        835                 840                 845

Gly Gln Val Lys Ile Arg Gly Phe Arg Ile Glu Leu Gly Glu Ile Glu

```
                    850                855                860
Ala Arg Leu Asn Gln Ala Pro Ser Val Lys Gln Ala Val Val Leu Ala
865                 870                875                880

Arg Ser Gly Glu Gln Lys Gln Val Tyr Leu Cys Ala Tyr Leu Val Thr
                    885                890                895

Asp Asn Asp Leu Lys Val Ser Ala Leu Arg Lys Glu Leu Ser Gln Thr
                    900                905                910

Leu Pro Asp Tyr Met Ile Pro Ser Phe Phe Ile Lys Val Glu Lys Ile
                    915                920                925

Pro Val Thr Val Asn Gly Lys Ile Asp Lys Lys Ala Leu Pro Glu Pro
                    930                935                940

Glu Lys Glu Val Glu Leu Gln Thr Glu Tyr Val Ala Pro Thr Asn Pro
945                 950                955                960

Thr Glu Glu Ile Leu Val Gln Ile Trp Gln Lys Val Leu Gly Met Glu
                    965                970                975

Arg Val Gly Ile Glu Asp Asn Phe Phe Glu Leu Gly Gly His Ser Ile
                    980                985                990

Lys Ala Met Met Leu Ala Ser Asn Ile Tyr Lys Glu Leu Lys Ile Asp
                    995                1000               1005

Leu Pro Leu Arg Glu Ile Phe Lys His Thr Thr Val Lys Glu Met
     1010                1015               1020

Ala Arg Phe Ile Asp Gly Arg Asp Glu Glu Glu Tyr Val Gly Ile
     1025                1030               1035

Gln Pro Ala Ala Lys Gln Glu Tyr Tyr Pro Val Ser Ser Ala Gln
     1040                1045               1050

Lys Arg Met Tyr Val Ile Gln Ser Leu Glu Asp Lys Ala Gln Gly
     1055                1060               1065

Thr Ser Tyr Asn Met Pro Ser Phe Tyr Lys Met Lys Gly Ser Val
     1070                1075               1080

Asp Ala Glu Lys Leu Glu Lys Val Phe Gln Thr Leu Leu Asp Arg
     1085                1090               1095

His Glu Ser Leu Arg Thr Ser Phe His Met Ile Glu Glu Gln Leu
     1100                1105               1110

Val Gln Lys Val His Glu Gln Val Ser Trp Lys Met Asp Met Lys
     1115                1120               1125

Thr Val Ser Ala Asn Asp Val Ser Arg Leu Lys Asp Ser Phe Val
     1130                1135               1140

Gln Pro Phe Asp Ile Ser Thr Ala Pro Leu Phe Arg Ala Ser Leu
     1145                1150               1155

Leu Thr Ile His Lys Asp Glu His Ile Leu Met Met Asp Val His
     1160                1165               1170

His Ile Val Gly Asp Gly Val Ser Thr Thr Ile Leu Phe Gln Glu
     1175                1180               1185

Leu Ile Gln Leu Tyr Gln Gly Gln Ala Leu Pro Glu Val Lys Val
     1190                1195               1200

His Tyr Lys Asp Tyr Ala Val Trp Gln Leu Ser Gln Gln Asp Arg
     1205                1210               1215

Leu Lys Glu Ser Glu Asn Phe Trp Leu Gln Gln Phe Ser Gly Glu
     1220                1225               1230

Leu Pro Val Leu Glu Leu Pro Thr Asp Tyr Ser Arg Pro Pro Ile
     1235                1240               1245

Arg Arg Leu Glu Gly Glu Tyr Val Ser Gln Ser Leu Arg Gly Asp
     1250                1255               1260
```

-continued

```
Leu His Glu Ser Val Lys Ala Phe Met Lys Asn His Glu Val Thr
1265                1270                1275

Leu Tyr Met Val Leu Leu Ala Thr Tyr Asn Val Leu Leu His Lys
1280                1285                1290

Tyr Thr Asn Gln His Asp Ile Ile Val Gly Thr Pro Val Ser Asp
1295                1300                1305

Arg Pro His Pro Asp Val Met Ser Thr Val Gly Met Phe Val Asn
1310                1315                1320

Thr Leu Ala Val Arg Asn Gln Leu Glu Ser Glu Gln Thr Phe Glu
1325                1330                1335

Lys Phe Leu Ala Asn Val Lys Asn Lys Met Leu Glu Val Tyr Gly
1340                1345                1350

His Gln Glu Tyr Pro Phe Glu Asp Val Ile Glu Lys Val Lys Val
1355                1360                1365

Gln Arg Asp Thr Ser Arg His Pro Leu Phe Asp Thr Met Phe Gly
1370                1375                1380

Val Gln Asn Leu Glu Ile Ser His Val Glu Leu Pro Asp Trp Gly
1385                1390                1395

Ile Glu Ala Leu Asp Ile Asp Trp Thr Asn Ser Lys Phe Asp Met
1400                1405                1410

Ser Trp Met Val Phe Glu Ala Asp Gly Leu Glu Ile Gly Val Glu
1415                1420                1425

Tyr Ser Thr Ser Leu Phe Glu Arg Asn Thr Ile Gln Arg Met Ile
1430                1435                1440

Gly His Phe Glu His Ile Ile Glu Gln Ile Met Glu Asn Pro Gln
1445                1450                1455

Ile Arg Leu Ala Asp Ile Gln Leu Thr Thr Glu Asp Glu Arg Ile
1460                1465                1470

Gln Ile Leu Glu Glu Phe Asn His Gln Pro Thr Lys Ile Thr Tyr
1475                1480                1485

Asp Gln Ala Ile Gln Asn Arg Phe Glu Glu Gln Ala Met Lys Thr
1490                1495                1500

Pro Asp Ala Val Ala Leu Val Tyr Lys Gly Gln Glu Leu Thr Tyr
1505                1510                1515

Arg Glu Leu Asn Gln Arg Ser Asn Gln Met Ala Arg Thr Leu Arg
1520                1525                1530

Glu His Gly Val Gly Arg Asp Gln Ile Ile Ala Val Met Ile Asn
1535                1540                1545

Arg Ser His Glu Leu Ile Ile Ser Ile Leu Ala Val Leu Lys Ala
1550                1555                1560

Gly Gly Ala Tyr Leu Pro Ile Asp Pro Thr Tyr Pro Leu Asp Arg
1565                1570                1575

Ile Glu His Met Leu Glu Asp Ser Gln Thr Ala Met Leu Leu Thr
1580                1585                1590

Gln Lys Glu Ile Gln Ile Pro Thr Gly Tyr Ser Gly Glu Val Leu
1595                1600                1605

Phe Val Asp Gln Ala Asp Ile Tyr His Glu Asp Ala Thr Asp Leu
1610                1615                1620

Ser Ser Met Asn Gln Pro Ala Asp Leu Ala Tyr Ile Ile Tyr Thr
1625                1630                1635

Ser Gly Ser Thr Gly Lys Ser Lys Gly Val Met Ile Glu His Arg
1640                1645                1650
```

-continued

Ser Leu His Asn Leu Ile His Ile Ser His Pro Tyr Lys Met Gly
1655                1660                1665

Ala Gly Ser Arg Val Leu Gln Phe Ala Ser Ser Phe Asp Ala
1670                1675                1680

Ser Val Ala Glu Ile Phe Pro Ala Leu Leu Thr Gly Ser Thr Leu
1685                1690                1695

Tyr Ile Glu Glu Lys Glu Glu Leu Leu Thr Asn Leu Val Pro Tyr
1700                1705                1710

Leu Leu Glu Asn Gln Ile Thr Thr Val Ala Leu Pro Pro Ser Leu
1715                1720                1725

Leu Arg Ser Val Pro Tyr Arg Glu Leu Pro Ala Leu Glu Cys Ile
1730                1735                1740

Val Ser Val Gly Glu Ala Cys Thr Phe Asp Ile Val Gln Thr Trp
1745                1750                1755

Gly Gln Asn Arg Thr Phe Ile Asn Gly Tyr Gly Pro Thr Glu Ser
1760                1765                1770

Thr Val Cys Ser Ala Phe Gly Val Val Thr Ala Glu Asp Lys Arg
1775                1780                1785

Ile Thr Ile Gly Lys Pro Phe Pro Asn Gln Lys Val Tyr Ile Ile
1790                1795                1800

Asn Glu Asn Gln Gln Leu Gln Pro Ile Gly Val Pro Gly Glu Leu
1805                1810                1815

Cys Ile Ala Gly Ala Gly Leu Ser Arg Gly Tyr Leu Asn Arg Pro
1820                1825                1830

Glu Leu Thr Gln Glu Lys Phe Val Asn Asn Pro Phe Ala Pro Gly
1835                1840                1845

Glu Arg Met Tyr Lys Thr Gly Asp Val Ala Arg Trp Leu Pro Asp
1850                1855                1860

Gly Asn Ile Glu Tyr Ala Gly Arg Met Asp Asp Gln Val Lys Val
1865                1870                1875

Arg Gly Asn Arg Val Glu Leu Gly Glu Val Thr Ser Gln Leu Leu
1880                1885                1890

Thr His Pro Ser Ile Thr Glu Ala Val Val Val Pro Ile Val Asp
1895                1900                1905

Thr His Gly Ala Thr Thr Leu Cys Ala Tyr Phe Ile Glu Asp Lys
1910                1915                1920

Glu Val Lys Val Asn Asp Leu Arg His His Leu Ala Lys Ala Leu
1925                1930                1935

Pro Glu Phe Met Ile Pro Thr Tyr Phe Ile Lys Val Asp His Ile
1940                1945                1950

Pro Leu Thr Gly Asn Gly Lys Val Asn Lys Gln Ala Leu Pro Asp
1955                1960                1965

Pro Ser Glu Phe Ile Ser Ala Gln Thr Gly His Glu Ile Val Ala
1970                1975                1980

Pro Ser Ser Gln Asp Glu Glu Ile Leu Val Gln Val Trp Glu Glu
1985                1990                1995

Val Leu Gln Phe Lys Pro Ile Gly Val Glu Asp Asn Phe Phe Glu
2000                2005                2010

Arg Gly Gly Asp Ser Ile Lys Ala Leu Gln Ile Val Ala Arg Leu
2015                2020                2025

Ser Lys Tyr Asn Arg Lys Leu Asp Ser Arg His Ile Phe Lys Asn
2030                2035                2040

Pro Thr Ile Ser Met Leu Ala Pro Tyr Leu Glu Gln Arg Gly Ala

-continued

```
              2045                2050                2055
Leu Ile Glu Gln Asp Ser Ile Glu Gly Glu Val Pro Leu Thr Pro
              2060                2065                2070
Ile Gln Ser Trp Phe Phe Glu Gln Pro Phe Val Tyr Pro His His
              2075                2080                2085
Phe Asn Gln Ser Met Leu Leu Pro Asn Glu Gln Gly Trp Asp Arg
              2090                2095                2100
Gln Arg Ile Glu Gln Ala Phe Thr Thr Ile Val Arg His His Asp
              2105                2110                2115
Ala Leu Arg Met Lys Tyr Gln Phe Arg Glu Lys Ile Ile Gln Glu
              2120                2125                2130
Asn Gln Gly Ile Glu Gly Glu Phe Phe Thr Leu His Glu Val Asp
              2135                2140                2145
Val Thr Lys Glu Arg Asp Trp Gln Met Arg Ile Glu Gln Glu Ala
              2150                2155                2160
Asn Gln Leu Gln Ala Ser Phe Asp Leu Thr Thr Gly Pro Leu Val
              2165                2170                2175
Lys Leu Gly Leu Tyr His Thr Ala Tyr Gly Asp Tyr Leu Leu Ile
              2180                2185                2190
Val Val His His Leu Leu Ile Asp Gly Val Ser Trp Arg Ile Leu
              2195                2200                2205
Leu Glu Asp Phe Gln Thr Leu Tyr Glu Gln Lys Gly Glu Leu Pro
              2210                2215                2220
Ala Lys Thr Thr Ser Phe Lys Ala Trp Ala Val Gln Leu Glu Gly
              2225                2230                2235
Tyr Ala Arg Ser Lys Lys Leu Gln Asp Glu Ala Ser Tyr Trp Lys
              2240                2245                2250
Gly Leu Leu Asn Lys Ser Ile Arg Glu Leu Pro Ala Asp Lys Glu
              2255                2260                2265
Ser Ser Asp Thr Phe Leu Phe Gly Asp Thr Lys Glu Val Gln Leu
              2270                2275                2280
Thr Phe Asp Ile Asn Glu Thr Gln Asp Leu Leu Thr Asp Ala His
              2285                2290                2295
His Ala Tyr Lys Thr Lys Ala Asp Asp Leu Leu Leu Ala Ala Leu
              2300                2305                2310
Val Leu Ser Ile Asn Glu Trp Thr Lys Gln Ser Asp Ile Ile Val
              2315                2320                2325
Asn Leu Glu Gly His Gly Arg Glu Thr Ile Gly Glu Gly Ile Asp
              2330                2335                2340
Leu Ser Arg Thr Ile Gly Trp Phe Thr Thr Ile Tyr Pro Val Leu
              2345                2350                2355
Phe Glu Val Glu Asn His Gln Leu Ser Ser Val Ile Lys His Val
              2360                2365                2370
Lys Glu Thr Leu Arg Asn Val Pro Asn Asn Gly Ile Gly Phe Gly
              2375                2380                2385
Ile Leu Gln His Met Ser His Ser Asp Val Ser Gln Ser Gln Leu
              2390                2395                2400
Ser Ser His His Ile Ser Phe Asn Tyr Leu Gly Gln Met Gly Glu
              2405                2410                2415
Asp Ser Ala Ser Gln Ser Glu Thr Asp Asn Gly Val Leu Ile Asn
              2420                2425                2430
Thr Gly Asp Gln Ile Ser Pro Met Asn Ala Asn Pro Gly Ser Leu
              2435                2440                2445
```

-continued

```
Asn Met Thr Cys Leu Val Met Asn Asn Thr Leu Leu Val Thr Phe
    2450                2455                2460

Asp Tyr Asn Pro Gln Arg Tyr Glu Gln Glu Thr Ile Gln Arg Leu
    2465                2470                2475

Ala Asp Arg Tyr Lys Ser Asn Leu Lys Ala Val Leu Asp His Cys
    2480                2485                2490

Val Gln Arg Glu Gln Thr Glu Arg Thr Pro Ser Asp Phe Ser Thr
    2495                2500                2505

Lys Lys Leu Ser Leu Glu Asp Leu Asp Asp Val Phe Ala Thr Leu
    2510                2515                2520

Lys Asn Leu
    2525

<210> SEQ ID NO 27
<211> LENGTH: 2491
<212> TYPE: PRT
<213> ORGANISM: Brevibacillus texasporus

<400> SEQUENCE: 27

Met Ile Asn Thr Ser Asp Val Lys Asp Ile Tyr Ser Leu Ser Pro Met
1               5                  10                  15

Gln Arg Gly Met Leu Phe His Thr Leu Lys Asp Lys Glu Asn Leu Ala
            20                  25                  30

Tyr Phe Asp Gln Thr Thr Phe Gln Ile Glu Gly Asp Ile Cys Val Glu
        35                  40                  45

Ser Leu Glu Lys Ser Phe Asn Glu Leu Ile Arg Lys Tyr Asp Val Leu
    50                  55                  60

Arg Thr Ile Phe Leu Tyr Gln Lys Leu Lys Glu Pro Met Gln Val Val
65                  70                  75                  80

Leu Lys Glu Arg Thr Ala Asn Ile His Tyr Glu Asp Phe Ser Met Lys
                85                  90                  95

Ser Glu Ser Asp Lys Ala Lys Ala Leu Arg Val Ala Lys Gln Arg Asp
            100                 105                 110

Arg Asp Glu Gly Phe Asp Leu Ser Arg Asp Ile Leu Met Arg Leu Ser
        115                 120                 125

Leu Leu Lys Val Ala Pro Asn Gln Tyr Glu Leu Val Ile Ser Ser His
    130                 135                 140

His Ile Ile Ile Asp Gly Trp Cys Thr Gly Ile Leu Tyr Gln Glu Leu
145                 150                 155                 160

Phe Tyr Phe Tyr Gln Cys Phe Val Ala Asn Gln Pro Ile Pro Ala Glu
                165                 170                 175

Lys Ser Ile Pro Tyr Ser Arg Tyr Ile Arg Trp Leu Glu Glu Gln Asp
            180                 185                 190

Glu Glu Glu Gly Lys Ala Tyr Trp Gly Glu Tyr Leu Gln Asp Phe Glu
        195                 200                 205

Gly Ala Ser Val Ile Pro Lys Gln Asn Ala Lys Gly Glu Lys Glu Val
    210                 215                 220

Cys Ser Ile Asp Lys Val Thr Phe His Phe Asp Lys Lys Leu Thr Glu
225                 230                 235                 240

Glu Leu Val Gln Val Ala Lys Thr Cys Gln Val Thr Ile Ser Thr Leu
                245                 250                 255

Phe Gln Thr Met Trp Gly Ile Leu Leu Gln Lys Tyr Asn Asn Ser Gln
            260                 265                 270

Glu Ala Ile Phe Gly Ser Val Ile Ser Gly Arg Ser Pro Glu Ile Pro
```

```
            275                 280                 285
Asp Val Glu Lys Ile Val Gly Ile Phe Ile Asn Thr Ile Pro Val Arg
    290                 295                 300
Ile Arg Thr Leu Asp Lys Gln Thr Phe Lys Glu Leu Leu Ile Gln Val
305                 310                 315                 320
Gln Glu Ala Ser Val Asn Ser Glu Lys Tyr Asn Tyr Leu Thr Leu Ala
                325                 330                 335
Asp Ile Gln Ala Val Thr Gly Ser Asn His Ala Leu Ile His His Ile
                340                 345                 350
Val Ala Phe Glu Asn Phe Pro Ile Ala Ser Asp Ser Phe Val Asp Ser
            355                 360                 365
Ser Asp Ser Asp Ser Glu Glu Leu Lys Val Val Asn Val Ile Asp Asp
370                 375                 380
His Glu Lys Thr Asn Phe Asp Phe Ser Val Gln Val Gln Leu Asp Thr
385                 390                 395                 400
Glu Leu Leu Val Lys Ile Ser Tyr Asn Gln His Leu Tyr His Arg Ser
                405                 410                 415
Phe Ile Glu Asn Ile Phe His His Leu Gln Gln Ile Ala Gly Ser Ile
                420                 425                 430
Thr His Asn Pro Asp Ile Gln Ile Asn Glu Ile Ala Ile Val Ser Lys
            435                 440                 445
Glu Glu Lys Lys Gln Leu Leu Arg Tyr Ser Thr Pro Ala Lys Ser Asp
            450                 455                 460
Phe Pro Met Asp Lys Thr Ile His Gln Leu Phe Glu Glu Gln Val Ser
465                 470                 475                 480
Arg Thr Pro Glu Gln Ile Ala Val Val Phe Lys Gly Glu Ser Phe Thr
                485                 490                 495
Tyr Arg Glu Leu Asn Glu Lys Ala Asn Gln Leu Ala Trp Val Leu Arg
                500                 505                 510
Lys Arg Glu Val Arg Pro Asn Glu Ile Val Ala Ile Met Ala Glu His
            515                 520                 525
Ser Leu Glu Met Leu Val Gly Val Ile Gly Thr Leu Lys Ala Gly Ala
            530                 535                 540
Ala Tyr Leu Pro Ile Asp Pro Ser Tyr Pro Glu Lys Arg Ile Ala His
545                 550                 555                 560
Met Leu Gln Asp Ser Lys Ala Glu Gln Leu Leu Ile Gln Pro His Leu
                565                 570                 575
Asn Met Pro Gln Asp Phe Lys Gly Ser Val Leu Trp Leu Thr Glu Glu
                580                 585                 590
Ser Trp Ala Lys Glu Ser Thr Thr Asp Leu Pro Leu Ala Thr Ser Ala
            595                 600                 605
Asn Asp Leu Ala Tyr Met Ile Tyr Thr Ser Gly Ser Thr Gly Leu Pro
            610                 615                 620
Lys Gly Val Met Val Glu His Gln Ala Leu Val Asn Leu Val Met Trp
625                 630                 635                 640
His Asn Glu Ala Phe Gly Val Thr Met Thr Asp Gln Cys Thr Lys Leu
                645                 650                 655
Ala Gly Phe Gly Phe Asp Ala Ser Val Trp Glu Thr Phe Pro Pro Leu
                660                 665                 670
Ile Gln Gly Ala Thr Leu His Val Leu Glu Glu Ser Arg Arg Gly Asp
            675                 680                 685
Ile Tyr Ala Leu His Glu Tyr Phe Glu Lys Asn Ala Ile Thr Ile Ser
            690                 695                 700
```

-continued

```
Phe Leu Pro Thr Gln Leu Ala Glu Gln Phe Met Glu Leu Thr Ser Ser
705                 710                 715                 720

Thr Leu Arg Val Leu Leu Ile Gly Gly Asp Arg Ala Gln Lys Val Lys
            725                 730                 735

Glu Thr Ser Tyr Gln Ile Ile Asn Asn Tyr Gly Pro Thr Glu Asn Thr
            740                 745                 750

Val Val Thr Thr Ser Gly Gln Leu His Pro Glu Gln Asp Val Phe Pro
            755                 760                 765

Ile Gly Lys Pro Ile Thr Asn His Ser Val Tyr Ile Leu Asp Gln Asn
770                 775                 780

Arg His Leu Gln Pro Ile Gly Ile Pro Gly Glu Leu Cys Val Ser Gly
785                 790                 795                 800

Ala Gly Leu Ala Arg Gly Tyr Leu Asn Gln Pro Glu Leu Thr Val Glu
            805                 810                 815

Arg Phe Val Asp Asn Pro Phe Val Pro Gly Glu Arg Met Tyr Arg Thr
            820                 825                 830

Gly Asp Leu Val Arg Trp Arg Ile Asp Gly Ser Ile Glu Tyr Leu Gly
            835                 840                 845

Arg Ile Asp Glu Gln Val Lys Ile Arg Gly Tyr Arg Ile Glu Leu Gly
850                 855                 860

Glu Ile Glu Thr Lys Leu Leu Glu His Pro Ser Ile Ser Glu Ala Leu
865                 870                 875                 880

Val Val Ala Arg Asn Asp Glu Gln Gly Tyr Thr Tyr Leu Cys Ala Tyr
            885                 890                 895

Val Val Ala Thr Gly Ala Trp Ser Val Ser Ser Leu Arg Glu His Leu
            900                 905                 910

Ile Glu Thr Leu Pro Glu Tyr Met Ile Pro Ala Tyr Met Met Glu Val
            915                 920                 925

Glu Lys Met Pro Leu Thr Ala Asn Gly Lys Ile Asp Lys Arg Ala Leu
            930                 935                 940

Pro Val Pro Asp Arg Gln Arg Met Asn Glu Tyr Val Ala Pro Ala Thr
945                 950                 955                 960

Glu Thr Glu Glu Lys Leu Val Leu Leu Phe Gln Glu Ile Leu Gly Leu
            965                 970                 975

Glu Arg Ile Gly Thr Lys Asp His Phe Phe Glu Leu Gly Gly His Ser
            980                 985                 990

Leu Lys Ala Met Met Leu Val Ser Arg Met His Lys Glu Leu Gly Val
            995                 1000                1005

Asp Val Gln Leu Asn Glu Met Phe Ala Arg Pro Thr Val Lys Asp
    1010                1015                1020

Leu Ser Ala Tyr Ile Asp Gln Met Asn Gly Ser Ala Tyr Thr Ala
    1025                1030                1035

Ile Gln Pro Val Glu Glu Gln Pro Tyr Tyr Pro Val Ser Phe Ala
    1040                1045                1050

Gln Arg Arg Met Tyr Val Val Gln Gln Met Arg Asp Ser Glu Thr
    1055                1060                1065

Thr Ser Tyr Asn Met Pro Phe Thr Phe Glu Leu Lys Gly Lys Leu
    1070                1075                1080

His Leu Asp Lys Leu Arg Glu Ala Leu Gln Ile Leu Val Leu Arg
    1085                1090                1095

His Glu Ser Leu Arg Thr Ser Phe His Met Ile Asp Glu Asn Leu
    1100                1105                1110
```

-continued

```
Val Gln Lys Val Asn Lys Asp Ile Ser Trp Asp Leu Glu Val Ile
1115                1120                1125

Glu Ala Gln Glu Ser Glu Ile Glu Val Lys Leu Glu Glu Phe Ile
1130                1135                1140

Arg Pro Phe His Leu Ser Glu Ala Pro Leu Phe Arg Ala Arg Leu
1145                1150                1155

Ile Cys Leu Asn Pro Gln His His Leu Leu Ser Leu Asp Met His
1160                1165                1170

His Ile Ile Ser Asp Gly Val Ser Met Asn Leu Phe Leu Gln Glu
1175                1180                1185

Phe Met Thr Leu Tyr Gln Gly Glu Ala Leu Pro Ala Leu Ser Ile
1190                1195                1200

Gln Tyr Lys Asp Tyr Ala Val Trp Gln Gln Ser Asp Lys Gln Arg
1205                1210                1215

Ala Arg Leu Lys Glu Gln Glu Lys Tyr Trp Leu His His Phe Ser
1220                1225                1230

Gly Glu Leu Pro Thr Leu Glu Leu Pro Thr Asp Phe Pro Arg Pro
1235                1240                1245

Ala Ile Gln Gln Phe Asp Gly Asp Glu Trp Ala Phe Glu Met Asn
1250                1255                1260

Ala Asp Leu Leu Ala Lys Val Lys Gln Ile Cys Ser Ser Gln Gly
1265                1270                1275

Thr Thr Leu Tyr Met Thr Leu Leu Ala Ala Tyr Gln Val Phe Leu
1280                1285                1290

Ala Arg Tyr Thr Gly Gln Glu Asp Ile Ile Val Gly Ser Pro Ile
1295                1300                1305

Ala Gly Arg Ser His Ala Asp Leu Glu Asn Met Ile Gly Met Phe
1310                1315                1320

Val Asn Thr Leu Ala Leu Arg Gly Lys Pro Lys Ala Asp Gln Ser
1325                1330                1335

Phe Leu Ser Tyr Leu Lys Gln Val Lys Glu Thr Val Phe Gln Ala
1340                1345                1350

Tyr Ala Asn Ala Glu Tyr Pro Phe Glu Glu Leu Ile Glu Lys Leu
1355                1360                1365

Asp Leu Glu Arg Asp Met Ser Arg His Pro Leu Phe Asp Thr Leu
1370                1375                1380

Phe Ser Leu Gln Asn Met Glu Ile Ser Glu Phe Gln Met Asn Asn
1385                1390                1395

Leu Glu Ile Phe Pro Tyr Glu Thr Gly Gln Lys Asn Ala Lys Phe
1400                1405                1410

Ala Leu Ser Trp Leu Ile Ala Glu Gly Glu Ser Leu Tyr Val Thr
1415                1420                1425

Ile Glu Tyr Ser Thr Lys Cys Phe Lys Arg Glu Thr Ile Lys Arg
1430                1435                1440

Met Ala Ser His Phe Glu Gln Leu Leu Ala Gln Ile Val Glu Gln
1445                1450                1455

Pro Glu Ala Arg Ile Gly Gln Leu Glu Leu Val Ala Asp Ala Glu
1460                1465                1470

Arg Lys Met Leu Leu Glu Asp Phe Asn Leu Thr Lys Val Asp Tyr
1475                1480                1485

Pro Arg Glu Lys Thr Ile Gln Glu Leu Phe Glu Glu Gln Val Asp
1490                1495                1500

Lys Asn Pro Asp Gln Ile Ala Leu Ile Cys Gly Glu Gln Gln Phe
```

-continued

```
              1505                1510                1515

Thr Tyr Glu Gln Leu Asn Val Lys Phe Asn Gln Leu Ala His Val
    1520                1525                1530

Leu Arg Arg Glu Gly Val Gln Pro Asn Gln Val Ile Gly Leu Ile
    1535                1540                1545

Thr Asp Arg Ser Leu Ser Met Ile Val Gly Ile Phe Gly Ile Ile
    1550                1555                1560

Lys Ala Gly Gly Gly Tyr Leu Pro Ile Asp Pro Thr Tyr Pro Thr
    1565                1570                1575

Glu Arg Ile Glu Tyr Met Leu Glu Asp Ser Gln Thr His Leu Leu
    1580                1585                1590

Leu Val Gln His Arg Asp Met Val Pro Ala Gly Tyr Gln Gly Glu
    1595                1600                1605

Val Leu Ile Ile Glu Asp Glu Ile Ser Arg Asp Glu Gln Val Ala
    1610                1615                1620

Asn Ile Glu Leu Ile Asn Gln Pro Gln Asp Leu Ala Tyr Val Met
    1625                1630                1635

Tyr Thr Ser Gly Ser Thr Gly Lys Pro Lys Gly Asn Leu Thr Thr
    1640                1645                1650

His Arg Asn Ile Ile Lys Thr Val Cys Asn Asn Gly Tyr Ile Glu
    1655                1660                1665

Ile Thr Thr Glu Asp Arg Leu Leu Gln Leu Ser Asn Tyr Ala Phe
    1670                1675                1680

Asp Gly Ser Thr Phe Asp Ile Phe Ser Ser Leu Leu His Gly Ala
    1685                1690                1695

Thr Leu Val Leu Val Pro Lys Glu Val Ile Leu Asn Pro Thr Asp
    1700                1705                1710

Leu Ile Thr Leu Ile Arg Glu Gln Gln Ile Thr Val Ser Phe Met
    1715                1720                1725

Thr Thr Ser Leu Phe Asn Ala Leu Val Glu Leu Asp Val Ser Ser
    1730                1735                1740

Phe Gln Asn Met Arg Lys Ile Ala Phe Gly Gly Glu Lys Ala Ser
    1745                1750                1755

Phe Lys His Val Glu Lys Ala Leu Asp Phe Leu Gly Asn Gly Arg
    1760                1765                1770

Leu Val Asn Gly Tyr Gly Pro Thr Glu Thr Thr Val Phe Ala Thr
    1775                1780                1785

Thr Tyr Thr Val Asp Glu Arg Ile Lys Glu Trp Gly Ile Ile Pro
    1790                1795                1800

Ile Gly Arg Pro Leu His Asn Thr Thr Val His Ile Leu Ser Ala
    1805                1810                1815

Asp Asp Lys Leu Gln Pro Ile Gly Val Ile Gly Glu Leu Cys Val
    1820                1825                1830

Ser Gly Glu Gly Leu Ala Arg Gly Tyr Leu Asn Leu Pro Glu Leu
    1835                1840                1845

Thr Met Glu Arg Phe Val Glu Asn Pro Phe Arg Pro Gly Glu Arg
    1850                1855                1860

Met Tyr Arg Thr Gly Asp Leu Ala Arg Trp Leu Pro Asp Gly Val
    1865                1870                1875

Leu Glu Tyr Val Gly Arg Lys Asp Glu Gln Val Lys Ile Arg Gly
    1880                1885                1890

His Arg Ile Glu Leu Ser Glu Ile Glu Thr Arg Ile Leu Glu His
    1895                1900                1905
```

-continued

```
Pro Ala Ile Ser Glu Thr Val Leu Leu Ala Lys Arg Asn Glu Gln
    1910                1915                1920

Gly Ser Ser Tyr Leu Cys Ala Tyr Ile Val Ala His Gly Gln Trp
    1925                1930                1935

Asn Ile Gln Glu Leu Arg Lys His Val Arg Asp Val Leu Pro Glu
    1940                1945                1950

His Met Val Pro Ser Tyr Phe Ile Gly Leu Asp Lys Leu Pro Leu
    1955                1960                1965

Thr Ser Asn Gly Lys Val Asp Lys Arg Ala Leu Pro Glu Pro Glu
    1970                1975                1980

Gly Ser Leu Gln Leu Thr Arg Glu Ile Val Ala Pro Arg Asn Glu
    1985                1990                1995

Ser Glu Lys Gln Leu Val Glu Ile Val Ala Glu Val Leu Gly Leu
    2000                2005                2010

Glu Ala Ser Glu Ile Ser Ile Thr Asp Asn Leu Phe Glu Leu Gly
    2015                2020                2025

Gly His Ser Leu Thr Ile Leu Arg Ile Leu Ala Lys Val His Thr
    2030                2035                2040

Cys Asn Trp Lys Leu Glu Met Lys Asp Phe Tyr Asn Cys Lys Asn
    2045                2050                2055

Leu Glu Glu Ile Ala Ser Lys Ala Thr Asp Met Gln Glu Asn Gln
    2060                2065                2070

Asn Leu Ser Gly Ser Gly Ser Val Phe Lys Lys Gly Gly Lys Lys
    2075                2080                2085

Ser Ile Pro Val Val Pro Val His Asp Arg Gln Lys Glu Met Glu
    2090                2095                2100

His Val Leu Leu Leu Gly Ser Thr Gly Phe Leu Gly Ile His Leu
    2105                2110                2115

Leu His Glu Leu Leu Gln Lys Thr Glu Ala Thr Ile Leu Cys Val
    2120                2125                2130

Ile Arg Ala Glu Asn Asp Glu Ala Ala Met Gln Arg Leu Arg Lys
    2135                2140                2145

Lys Ile Asp Phe Tyr Phe Thr Ser Gln Tyr Ser Ser Ser Gln Ile
    2150                2155                2160

Asp Glu Trp Phe Thr Arg Ile Gln Ile Ile His Gly Asp Ile Thr
    2165                2170                2175

Gln Ala Asn Phe Gly Leu Glu Ala Lys His Tyr Glu Ser Leu Gly
    2180                2185                2190

Ala Ile Val Asp Thr Val Ile His Thr Ala Ala Leu Val Lys His
    2195                2200                2205

Tyr Gly His Tyr Glu Glu Phe Glu Arg Ala Asn Val His Gly Thr
    2210                2215                2220

Gln Gln Val Val Thr Phe Cys Leu Asn Asn Lys Leu Pro Met His
    2225                2230                2235

Tyr Val Ser Thr Leu Ser Val Ser Gly Thr Thr Val Glu Glu Ala
    2240                2245                2250

Thr Glu Leu Val Glu Phe Thr Glu Lys Asp Phe Tyr Val Gly Gln
    2255                2260                2265

Asn Tyr Glu Ser Asn Val Tyr Leu Arg Ser Lys Phe Glu Ala Glu
    2270                2275                2280

Ala Val Leu Val Gly Gly Met Glu Asn Gly Leu Asp Ala Arg Ile
    2285                2290                2295
```

-continued

```
Tyr Arg Val Gly Asn Leu Thr Gly Arg Phe Gln Asp Gly Trp Phe
    2300                2305                2310

Gln Glu Asn Ile Asn Glu Asn Met Phe Tyr Leu Leu Ser Lys Ala
    2315                2320                2325

Phe Leu Glu Leu Gly Gly Phe Asp Gln Glu Ile Met Gln Gly Met
    2330                2335                2340

Val Asp Leu Thr Pro Ile Asp Ile Cys Ala Gln Ala Ile Ile His
    2345                2350                2355

Ile Ile Asn Ser Lys Gly Ile Glu Glu Arg Val Phe His Leu Gln
    2360                2365                2370

Asn Pro His Leu Val Thr Tyr Asp Asp Met Tyr Arg Val Phe Glu
    2375                2380                2385

Gly Leu Gly Phe Ser Arg Arg Val Gln Ser Arg Glu Asp Val Thr
    2390                2395                2400

Arg Glu Leu Asp Val Met Met Ser Gln Gly Asn Glu Lys Leu Phe
    2405                2410                2415

Leu Ala Gly Ile Leu Thr Thr Met Leu Asp Asp Val Glu Arg Ala
    2420                2425                2430

Glu Gln Phe Asn Val Ala Val Asp Ser Ser Arg Thr Met Gln Leu
    2435                2440                2445

Leu Glu Asp Thr Ser Phe Thr Tyr Pro Val Pro Asp Asp Glu Tyr
    2450                2455                2460

Leu Arg Lys Leu Ala Met His Met Ile Lys Val Gly Phe Val Thr
    2465                2470                2475

Pro Asn His Thr Val Ala Glu Lys Ile Gly Thr Ser Arg
    2480                2485                2490

<210> SEQ ID NO 28
<211> LENGTH: 240
<212> TYPE: PRT
<213> ORGANISM: Brevibacillus texasporus

<400> SEQUENCE: 28

Met Ala Val Ile Glu Leu Lys Asn Leu Thr Lys Lys Tyr Asn Glu Val
1               5                   10                  15

Tyr Ala Val Asp His Leu Asn Ile Glu Val Pro Gln Gly His Ile Tyr
                20                  25                  30

Ala Phe Leu Gly Ser Asn Gly Ala Gly Lys Thr Thr Thr Ile Lys Met
            35                  40                  45

Met Thr Gly Gln Leu Asn Pro Ser Glu Gly Glu Val Leu Phe Leu Gly
        50                  55                  60

Arg Asn Ile Trp Gln Asp Arg Glu Ala Arg Arg Ile Ala Gly Tyr Ala
65                  70                  75                  80

Pro Asp Val Pro Leu Leu His Glu Gly Leu Thr Val Arg Glu Met Val
                85                  90                  95

Arg Phe Val Gly Ala Leu Tyr Gly Ser Asp Glu Asp Leu Asn Lys Arg
            100                 105                 110

Val Asp Thr Leu Leu Glu His Phe Glu Leu Ala Asp Lys Ala Asp Gln
        115                 120                 125

Leu Ile Lys Glu Tyr Ser Leu Gly Met Lys Arg Lys Val Ser Ile Ala
    130                 135                 140

Cys Ala Leu Ile His Arg Pro Lys Ile Leu Leu Leu Asp Glu Val Thr
145                 150                 155                 160

Asn Gly Leu Asp Pro Lys Ala Thr Arg Glu Val Lys Asn Tyr Ile Arg
                165                 170                 175
```

```
His Phe Ala Lys Glu Glu Gly Gly Thr Val Phe Ile Thr Thr His Ile
            180             185                 190

Leu Asp Ile Val Glu Glu Leu Ala Asp Thr Ile Ser Ile Leu His Lys
        195             200                 205

Gly Lys Ile Lys Val Thr Gly Ser Met Glu Glu Leu Arg His Val Ala
    210             215                 220

Gly Asn Glu Glu Gly Arg Leu Glu Asp Ile Phe Leu Ser Ala Ile Glu
225             230             235                 240
```